US012673091B2

(12) United States Patent
Abbott et al.

(10) Patent No.: US 12,673,091 B2
(45) Date of Patent: Jul. 7, 2026

(54) ENGINEERED PROBIOTICS FOR EXPRESSION OF FIBER-SYNTHESIZING ENZYMES IN GUT

(71) Applicant: ZBiotics Company, San Francisco, CA (US)

(72) Inventors: Zachary D. Abbott, Millbrae, CA (US); John William Kidder Oliver, San Francisco, CA (US)

(73) Assignee: ZBiotics Company, San Francisco, CA (US)

( * ) Notice: Subject to any disclaimer, the term of this patent is extended or adjusted under 35 U.S.C. 154(b) by 535 days.

(21) Appl. No.: 18/030,658

(22) PCT Filed: Oct. 7, 2021

(86) PCT No.: PCT/US2021/053983
§ 371 (c)(1),
(2) Date: Apr. 6, 2023

(87) PCT Pub. No.: WO2022/076693
PCT Pub. Date: Apr. 14, 2022

(65) Prior Publication Data
US 2023/0372453 A1 Nov. 23, 2023

Related U.S. Application Data

(60) Provisional application No. 63/089,334, filed on Oct. 8, 2020.

(51) Int. Cl.
| | |
|---|---|
| *A61K 38/45* | (2006.01) |
| *A61K 35/742* | (2015.01) |
| *A61K 35/744* | (2015.01) |
| *A61K 35/745* | (2015.01) |
| *A61K 35/747* | (2015.01) |
| *A61K 38/47* | (2006.01) |
| *C12N 1/20* | (2006.01) |
| *C12N 9/10* | (2006.01) |
| *C12N 9/90* | (2006.01) |
| *C12N 15/75* | (2006.01) |

(52) U.S. Cl.
CPC ........... *A61K 38/45* (2013.01); *A61K 35/742* (2013.01); *A61K 35/744* (2013.01); *A61K 35/745* (2013.01); *A61K 35/747* (2013.01); *A61K 38/47* (2013.01); *C12N 1/20* (2013.01); *C12N 9/1055* (2013.01); *C12N 9/90* (2013.01); *C12N 15/75* (2013.01); *C12Y 204/0101* (2013.01); *C12Y 504/99011* (2013.01); *C12N 2800/101* (2013.01)

(58) Field of Classification Search
CPC ........ C12N 9/1055; C12N 1/20; C12N 1/205; C12Y 204/0101; A61K 38/45; A61K 35/742; A61K 35/744; A61K 35/745; A61K 38/47; A61K 35/74–747
See application file for complete search history.

(56) References Cited

U.S. PATENT DOCUMENTS

| | | | |
|---|---|---|---|
| 4,801,536 | A | 1/1989 | Stahl et al. |
| 5,160,742 | A | 11/1992 | Mazer et al. |
| 5,275,819 | A | 1/1994 | Amer et al. |
| 5,527,784 | A | 6/1996 | Ishihara |
| 5,800,821 | A | 9/1998 | Acheson et al. |
| 7,888,064 | B2 | 2/2011 | Berger et al. |
| 9,161,957 | B2 | 10/2015 | Smith et al. |
| 9,630,997 | B2 | 4/2017 | Hughes et al. |
| 9,782,351 | B2 | 10/2017 | Gill et al. |
| 9,987,224 | B2 | 6/2018 | Kovarik et al. |
| 10,548,844 | B2 | 2/2020 | Anselmo et al. |
| 10,849,938 | B2 | 12/2020 | Abbott |
| 11,696,932 | B2 | 7/2023 | Abbott |
| 11,975,033 | B2 | 5/2024 | Abbott |
| 2003/0031659 | A1 | 2/2003 | Farmer |
| 2007/0161031 | A1 | 7/2007 | Trinklein et al. |
| 2009/0022691 | A1 | 1/2009 | Moore et al. |

(Continued)

FOREIGN PATENT DOCUMENTS

| | | |
|---|---|---|
| CN | 101649323 A | 2/2010 |
| CN | 101985625 A | 3/2011 |

(Continued)

OTHER PUBLICATIONS

Biedendieck et al., "Export, purification, and activities of affinity tagged *Lactobacillus reuteri* levansucrase produced by *Bacillus megaterium*." Applied Microbiology and Biotechnology 74 (2007): 1062-1073.
Tang et al., "Isolation and characterization of levansucrase-encoding gene from *Bacillus amyloliquefaciens*." Gene 96 (1990): 89-93.
Seo et al., "An efficient plasmid vector for constitutive high-level expression of foreign genes in *Escherichia coli*." Biotechnol Lett (2009) 31:877-881.
"Blood Alcohol Content (BAC) Calculator" American Addiction Centers, www.alcohol.org/bac-calculator, pp. 1-2, (2019).
Amalaradjou et al., "Bioengineered probiotics, a strategic approach to control enteric infections." Bioengineered 4(6) (2013): 379-387.
Amidon et al., "Colon-targeted oral drug delivery systems: design trends and approaches." Aaps Pharmscitech 16 (2015): 731-741.

(Continued)

*Primary Examiner* — Thane Underdahl

(74) *Attorney, Agent, or Firm* — David E. Shore; Foley Hoag LLP

(57) ABSTRACT

The present disclosure provides solutions to various challenges in health, including health challenges related to high consumption of carbohydrate and/or low consumption of soluble fiber. The present disclosure provides, among other things, bacteria engineered for expression of a fiber-synthesizing enzyme, e.g., for expression of the enzyme in the gut (e.g., in the intestine). In particular embodiments, the present disclosure provides bacteria engineered for expression of a fiber-synthesizing enzyme that consumes carbohydrate in the process of synthesizing fiber, e.g., in the gut. The present disclosure further includes formulations of isolated fiber-synthesizing enzymes for administration to subjects.

75 Claims, 10 Drawing Sheets

Specification includes a Sequence Listing.

(56)            References Cited

U.S. PATENT DOCUMENTS

| | | | |
|---|---|---|---|
| 2009/0060894 A1 | 3/2009 | Somberg et al. | |
| 2010/0113423 A1 | 5/2010 | Mochly-Rosen et al. | |
| 2010/0285532 A1 | 11/2010 | Berger et al. | |
| 2011/0150855 A1 | 6/2011 | Joh et al. | |
| 2012/0034322 A1 | 2/2012 | Oda et al. | |
| 2012/0321718 A1 | 12/2012 | Manzo et al. | |
| 2013/0004475 A1 | 1/2013 | Hatanaka et al. | |
| 2013/0089535 A1 | 4/2013 | Yamashiro et al. | |
| 2013/0230557 A1* | 9/2013 | Datta | C12N 9/80 |
| | | | 424/93.2 |
| 2014/0065697 A1 | 3/2014 | Zhang et al. | |
| 2014/0134700 A1 | 5/2014 | Lu et al. | |
| 2014/0186436 A1 | 7/2014 | Yang et al. | |
| 2015/0087702 A1 | 3/2015 | Talalay et al. | |
| 2016/0074445 A1 | 3/2016 | Smith et al. | |
| 2016/0076044 A1 | 3/2016 | Remaut et al. | |
| 2016/0340665 A1 | 11/2016 | Falb et al. | |
| 2017/0267981 A1 | 9/2017 | Kralj et al. | |
| 2017/0319636 A1 | 11/2017 | Kim et al. | |
| 2018/0333441 A1 | 11/2018 | Chung | |
| 2019/0076489 A1 | 3/2019 | Abbott | |
| 2019/0224111 A1 | 7/2019 | Bianco-Peled et al. | |
| 2020/0345793 A1 | 11/2020 | Abbott | |
| 2021/0121506 A1 | 4/2021 | Abbott | |
| 2023/0372453 A1 | 11/2023 | Abbott et al. | |
| 2024/0316123 A1 | 9/2024 | Abbott | |

FOREIGN PATENT DOCUMENTS

| | | | | |
|---|---|---|---|---|
| CN | 102337280 A | 2/2012 | | |
| CN | 103114056 A | 5/2013 | | |
| CN | 103484482 B | 7/2015 | | |
| CN | 106222190 A | 12/2016 | | |
| CN | 106867930 A | 6/2017 | | |
| CN | 107815458 A | 3/2018 | | |
| CN | 108103081 A | 6/2018 | | |
| DE | 10106163 B4 | 3/2007 | | |
| EP | 0968719 A2 | 1/2000 | | |
| EP | 2235045 B1 | 10/2012 | | |
| EP | 4192969 A1 | 6/2023 | | |
| EP | 3954778 B1 * | 10/2023 | | C12P 19/04 |
| JP | H09168391 A | 6/1997 | | |
| JP | 2660520 B2 | 10/1997 | | |
| JP | 2013066446 A | 4/2013 | | |
| JP | 2014506466 A | 3/2014 | | |
| JP | 5881352 B2 | 3/2016 | | |
| KR | 20090101130 A | 9/2009 | | |
| KR | 20130092182 A | 8/2013 | | |
| KR | 20170094986 A | 8/2017 | | |
| KR | 101853603 B1 | 5/2018 | | |
| WO | WO-87/002385 A1 | 4/1987 | | |
| WO | WO-89/010967 A1 | 11/1989 | | |
| WO | WO-1992/018631 A1 | 10/1992 | | |
| WO | WO-01/27247 A2 | 4/2001 | | |
| WO | WO-2006/032693 A1 | 3/2006 | | |
| WO | WO-2015/023989 A1 | 2/2015 | | |
| WO | WO-2015/074054 A1 | 5/2015 | | |
| WO | WO-2016/075243 A1 | 5/2016 | | |
| WO | WO-2016/172341 A2 | 10/2016 | | |
| WO | WO-2016/201380 A9 | 2/2017 | | |
| WO | WO-2019/055707 A1 | 3/2019 | | |
| WO | WO-2020077010 A1 * | 4/2020 | | C12N 15/70 |
| WO | WO-2022/013269 A1 | 1/2022 | | |
| WO | WO-2022/076693 A1 | 4/2022 | | |

OTHER PUBLICATIONS

Ben-Yehuda et al., "RacA, a bacterial protein that anchors chromosomes to the cell poles." Science 299(5606) (2003): 532-536.
Calvo et al., "FlgM is secreted by the flagellar export apparatus in Bacillus subtilis." Journal of Bacteriology 197(1) (2015): 81-91.

Caramori et al., "Role of FlgM in sigma D-dependent gene expression in Bacillus subtilis." Journal of Bacteriology 178(11) (1996): 3113-3118.
Casula et al., "Bacillus probiotics: spore germination in the gastrointestinal tract." Applied and Environmental Microbiology 68(5) (2002): 2344-2352.
Chen et al., "Role of the sigmaD-dependent autolysins in Bacillus subtilis population heterogeneity." Journal of Bacteriology 191(18) (2009): 5775-5784.
Cross, "The world's first GMO probiotic is for sale; it's designed to prevent hangovers." Chemical and Engineering News, pp. 1-4, (2019).
Cutting et al., "Oral vaccine delivery by recombinant spore probiotics." International Reviews of Immunology 28(6) (2009): 487-505.
Duc et al., "Germination of the spore in the gastrointestinal tract provides a novel route for heterologous antigen delivery." Vaccine 21(27-30) (2003): 4215-4224.
Elshaghabee et al., "Bacillus as Potential Probiotics: Status, Concerns, and Future Perspectives." Frontiers in Microbiology, 8(1490):1-15, (2017).
Extended European Search Report for EP Application No. 18855675.7 dated Aug. 20, 2021.
Gibson et al., "Enzymatic assembly of DNA molecules up to several hundred kilobases." Nat Methods, 2009. 6(5): p. 343-5.
Gold et al., "Cloning and Expression of the Zymomonas mobilis "Production of Ethanol" Genes in Lactobacillus casei." Current Microbiology, 33:256-260, (1996).
Guttenplan et al., "The cell biology of peritrichous flagella in Bacillus subtilis." Mol Microbiol, 87(1):211-29.[000153] 4, (2013).
Ho et al., "Isolation and characterization of an aldehyde dehydrogenase encoded by the aldB gene of Escherichia coli." Journal of Bacteriology 187(3) (2005): 1067-1073.
Homann et al., "Microbially produced acetaldehyde from ethanol may increase the risk of colon cancer via folate deficiency." International Journal of Cancer 86(2) (2000): 169-173.
Hong et al., "The use of bacterial spore formers as probiotics." FEMS Microbiology Reviews 29 (2005): 813-835.
Hosoi et al., "Changes in Fecal Microflora Induced by Intubation of Mice with Bacillus Subtilis (Natto) Spores are Dependent upon Dietary Components." Can J Microbiol., [Abstract only], 45(1):59-66, (1999).
Hosseini, et. al., "Biological Containment of Genetically Modified Bacillus subtilis." Applied and Environmental Microbiology, 84(3):1-15, (2018).
Howland et al., "Are some drinkers resistant to hangover? A literature review." Current Drug Abuse Reviews 1 (2008): 42-46.
International Search Report and Written Opinion for International Application No. PCT/US18/50957 dated Feb. 5, 2019.
Invitation to Pay Additional Fee for International Application No. PCT/US18/50957 dated Nov. 30, 2018.
Jendrossek et al., "Three different proteins exhibiting NAD-dependent acetaldehyde dehydrogenase activity from Alcaligenes eutrophus." European Journal of Biochemistry 167.3 (1987): 541-548.
Jokelainen et al., "In vitro acetaldehyde formation by human colonic bacteria." Gut 35 (1994): 1271-1274.
Konkit et al., "Aldehyde dehydrogenase activity in Lactococcus chungangensis: Application in cream cheese to reduce aldehyde in alcohol metabolism." Journal of Dairy Science 99.3 (2016): 1755-1761.
Koo et al., "Cloning and characterization of the bifunctional alcohol/acetaldehyde dehydrogenase gene (adhE) in Leuconostoc mesenteroides isolated from kimchi." Biotechnol. Lett., 27(7):505-510 (2005).
Kullen et al., "Genetic modification of intestinal lactobacilli and bifidobacteria." Current Issues in Molecular Biology 2(2) (2000): 41-50.
Leser et. al., "Germination and outgrowth of Bacillus subtilis and Bacillus licheniformis spores in the gastrointestinal tract of pigs." Journal of Applied Microbiology, 104(2008):1025-1033, (2007).
Li et al., "Probiotics and alcoholic liver disease: treatment and potential mechanisms." Gastroenterology Research and Practice 2016 (2015): 5491465.

(56)     References Cited

OTHER PUBLICATIONS

Lu et al., "Alleviating acute alcoholic liver injury in mice with Bacillus subtilis co-expressing alcohol dehydrogenase and acetaldehyde dehydrogenase." Journal of Functional Foods, 49:342-350, (2018).

Lucchetti-Miganeh et. al., "The post-transcriptional regulator CsrA plays a central role in the adaptation of bacterial pathogens to different stages of infection in animal hosts." Microbiology 154: 16-29, (2008).

Lyu et al., "Heterologous expression of aldehyde dehydrogenase in Lactococcus lactis for acetaldehyde detoxification at low pH." Applied Biochemistry and Biotechnology 184 (2017): 570-581.

Macnab, "Genetics and biogenesis of bacterial flagella." Annu Rev Genet, 1992. 26: p. 131-58.

Mukherjee et al., "CsrA-FliW interaction governs flagellin homeostasis and a checkpoint on flagellar morphogenesis in Bacillus subtilis." Mol Microbiol, 2011. 82(2): p. 447-61.

Mukherjee et al., "The structure and regulation of flagella in Bacillus subtilis." Annual Review of Genetics 48 (2014): 319-340.

Nosova et. al., "Acetaldehyde Production and Metabolism by Human Indigenous and Probiotic Lactobacillus and Bifidobacterium Strains" Alcohol and Alcoholism 35(6):561-568, (2000).

Olmos et al., "Bacillus subtilis a potential probiotic bacterium to formulate functional feeds for aquaculture." J. Microb. Biochem. Technol 6(7) (2014): 361-365.

Oshiro et al., "Robust stoichiometry of FliW-CsrA governs flagellin homeostasis and cytoplasmic organization in Bacillus subtilis." MBio 10(3) (2019).

Partial European Search Report for EP Application No. 18855675.7 dated May 3, 2021.

Rodríguez-Zavala et al., "Characterization of E. coli tetrameric aldehyde dehydrogenases with atypical properties compared to other aldehyde dehydrogenases." Protein Science 15(6) (2006): 1387-1396.

Rubio et al., "Transcytosis of Bacillus subtilis extracellular vesicles through an in vitro intestinal epithelial cell model." Scientific Reports 10 (2020): 3120.

Salaspuro, "Microbial metabolism of ethanol and acetaldehyde and clinical consequences." Addict Biol, 2(1):35-46, (1997).

Schrader et al., "NAD (P)-dependent aldehyde dehydrogenases induced during growth of Ralstonia eutropha strain Bo on tetrahydrofurfuryl alcohol." Journal of Bacteriology 183(24) (2001): 7408-7411.

Sorokulova, "Modern Status and Perspectives of Bacillus Bacteria as Probiotics" Journal of Probiotics and Health, 1(4):2-5, (2013).

Sprince et al., "Protective action of ascorbic acid and sulfur compounds against acetaldehyde toxicity: implications in alcoholism and smoking." Agents Actions, [Abstract only], 5(2):164-173, (1975).

Supplementary European Search Report for EP Application No. 21878541.8 dated Oct. 9, 2024.

Suva et. al., "Novel insight on probiotic Bacillus subtilis: Mechanism of action and clinical applications." Journal of Current Research in Scientific Medicine, 2(2):65-72, (2016).

Szmigiel et al., "The influence of Bacillus subtilis 87Y isolated from Eisenia fetida on the growth of pathogenic and probiotic microorganisms." (2019).

Tam et al., "The intestinal life cycle of Bacillus subtilis and close relatives." Journal of Bacteriology 188(7) (2006): 2692-2700.

Vakulskas et al., "Regulation of bacterial virulence by Csr (Rsm) systems." Microbial Mol Biol Rev, 79(2):193-224, (2015).

Vogt et al., "Mouse intestinal microbiota reduction favors local intestinal immunity triggered by antigens displayed in Bacillus subtilis biofilm." Microbial Cell Factories, 17:187, (2018).

Wall et al., "Hangover Symptoms in Asian Americans with Variations in the Aldehyde Dehydrogenase (ALDH2) Gene." Journal of Studies on Alchol, 61(1):13, 7 pages, (2000).

Wang et al., "Effects of beverages on alcohol metabolism: Potential health benefits and harmful impacts." International Journal of Molecular Sciences 17(354) (2016).

Yakhnin et al., "CsrA of Bacillus subtilis regulates translation initiation of the gene encoding the flagellin protein (hag) by blocking ribosome binding." Mol Microbiol, 2007. 64(6): p. 1605-20.

Yao et al., "Acetaldehyde detoxification using resting cells of recombinant Escherichia coli overexpressing acetaldehyde dehydrogenase." Applied Biochemistry and Biotechnology 172 (2014): 2030-2040.

Yurina et al., "Live bacterial vectors-a promising DNA vaccine delivery system." Medical Sciences 6(2) (2018): 27.

Zhu et al., "Isolation of strong constitutive promoters from Lactococcus lactis subsp. lactis N8." FEMS Microbiology Letters 362 (2015): fnv107.

Abid, Y., et. al., Isolation and structural characterization of levan produced by probiotic Bacillus tequilensis-GM from Tunisian fermented goat milk, Internation Journal of Biological Macromolecules, 133:786-794, (2019).

Adamberg, K., et al., Levan enhances Associated Growth of Bacteroides, Escherichia, Streptococcus and Faecalibacterium in Fecal Microbiota, Plos One, (2012), <https://journals.plos.org/plosone/article?id=10.1371/journal.pone.0144042>, retrieved on Dec. 2, 2015.

Anwar, M.A., et. al., Inulin and levan synthesis by probiotic Lactobacillus gasseri strains: characterization of three novel fructansucrase enzymes and their fructan products, 156(Pt4): 1264-1274, (2010).

Anwar, M.A., et. al., The Probiotic Lactobacillus johnsonii NCC 533 Produces High-Molecular-Mass Inulin from Sucrose by Using an Inulosucrase Enzyme, 74(11): 3426-3433, (2008).

Bai, et al., Engineered butyrate-producing bacteria prevents high fat diet-induced obesity in mice, Microb Cell Fact, 19(94):1-13, (2020).

Dahech, I., et. al., Oral administration of levan polysaccharide reduces the alloxan-induced oxidative stress in rats, 1;49(5): 942-947, (2011).

Davis, L.M.G., et. al., A dose dependent impact of prebiotic galactooligosaccharides on the intestinal microbiota of healthy adults, Int. J. Food Microbiol, 144(2):285-292, (2010).

Desai, M.S. et al., A Dietary Fiber-Deprived Gut Microbiota Degrades the Colonic Mucus Barrier and Enhances Pathogen Susceptibility, Cell, 167(5):1339-1353.e21 (2016).

Dong, Y. et al., Total, insoluble, and soluble dietary fiber intake and insulin resistance and blood pressure in adolescents, Eur. J. Clin. Nutr., 73(8):1172-1178 (2019).

Earle, K.A. et al., Quantitative Imaging of Gut Microbiota Spatial Organization, Cell Host Microbe, 18(4):478-488 (2015).

Geel-Schutten, G.H.V., et al., Biochemical and Structural Characterization of the Glucan and Fructan Exopolysaccharides Synthesized by the Lactobacillus reuteri Wild-Type Strain and by Mutant Strains, Applied and Environmental Microbiology, 65(7):3008-3014, (1999).

González-Garcinuño, A., et. al., Effect of bacteria type and sucrose concentration on levan yield and its molecular weight, 91, (2017).

Gu, Y., et. al., Improvement of levan production in Bacillus amyloliquefaciens through metabolic optimization of regulatory elements, Applied genetics and olecular biotechnology, 101: 4163-4174, (2017).

Guiziou, S. et al., A part toolbox to tune genetic expression in Bacillus subtilis, Nucleic Acids Res., 44(15):7495-7508 (2016).

Hamdy, A.A. et. al., Possible correlation between levansucrase production and probiotic activity of Bacillus sp. isolated from honey and honey bee, World J. Microbiol Biotechnol, 33(4):69, (2017).

Hamdy, A.A., et. al., In vivo assessment of possible probiotic propertis of Bacillus subtilis and prebiotic properties of levan, Biocatalysis and Agricultural Biotechnology, 13:190-197, (2018).

International Search Report, International Application No. PCT/US2021/053983, 4 pages, Feb. 2, 2022.

Kim, H.J. et al., A randomized controlled trial of a probiotic, VSL#3, on gut transit and symptoms in diarrhoea-predominant irritable bowel syndrome, Aliment. Pharmacol. Ther., 17(7):895-904 (2003).

Korakli, M., et. al., Metabolism by bifidobacteria and lactic acid bacteria of polysaccharides from wheat and rye, and exopolysaccharides produced by Lactobacillus sanfranciscensis, Society for applied microbiology, (2002).

(56) References Cited

OTHER PUBLICATIONS

Liu, Q., et. al., Efficient biosynthesis of levan from sucrose by a novel levansucrase from Brenneria goodwinii, 10(157): 1732-1740, (2017).

Marlett, J.A and Cheung, T.F., Database and quick methods of assessing typical dietary fiber intakes using data for 228 commonly consumed foods, J. Am. Diet Assoc., 97(10):1139-1148 (1997).

Parnell, W. et al., Exploring the relationship between sugars and obesity, Public Health Nutr., 11(8):860-866 (2008).

Porras-Dominguez, J.R., et. al., Levan-type fructooligosaccharides synthesis by a levansucrase-endolevanase fusion enzyme (LevB1SacB) 177:40-48, (2017).

Schmidt, K. et al., Prebiotic intake reduces the waking cortisol response and alters emotional bias in healthy volunteers, Psychopharmacology (Berl), 232(10):1793-1801 (2015).

Townsend, G.E. et al., Dietary sugar silences a colonization factor in a mammalian gut symbiont, PNAS USA, 116(1):233-238 (2019).

Van Hijum, S.A.F.T., et al., Purification of a novel fructosyltransferase from *Lactobacillus reuteri* strain 121 and characterzation of the levan produced, FEMS Microbiology Letters 205, pp. 323-328, (2001).

Van Hijum, S.A.F.T., et. al., Characterization of a Novel Fructosyltransferase from Lactobacillus reuteri That Synthesizes High-Molecular-Weight Inulin and Inulin Oligosaccharides, Applied and Environmental Microbiology, 68(9):4390-4398, (2002).

Wei, Q. et al., Natto Characteristics as Affected by Steaming Time, Bacillus Strain, and Fermentation Time, J. Food Sci., 66(1):167-173 (2001).

Written Opinion, International Application No. PCT/US2021/053983, 7 pages, Feb. 2, 2022.

Kumar et al., "In vitro comparism of the extracellular secretion of inulosucrase enzyme in potential probiotic *Escherichia coli* 16 and BL-21." Advanced Research Journal of Biotechnology 12.45, 64-70 pgs, (2013).

* cited by examiner

|  | Gomphrena marginata | Gomphrena macrocephala (Shiomi et al. 1996) | Chromohalobacter salexigens (Husseiny et al. 2015) | Bacillus licheniformis (Dahech et al. 2013) | ZB423 (ZBIOTICS) | Pfaffia glomerata (Caleffi et al., 2015) |
|---|---|---|---|---|---|---|
|  | Levan | Levan | Levan | Levan | Levan | Inulin |
| C-1 | 60.3 | 60.6 | 60.7 | 59.7 | 59.96 | 63.7 |
| C-2 | 104.6 | 104.9 | 105 | 104.1 | 104.25 | 106.1 |
| C-3 | 76.7 | 76.9 | 77.1 | 76.1 | 76.35 | 79.8 |
| C-4 | 75.7 | 75.9 | 76 | 75.1 | 75.24 | 77.2 |
| C-5 | 80.7 | 81 | 81.1 | 80.2 | 80.31 | 83.9 |
| C-6 | 63.8 | 64.1 | 64.1 | 63.3 | 63.42 | 65 |

Fig. 7

SEQUENCE LISTING

```
<160> NUMBER OF SEQ ID NOS: 85

<210> SEQ ID NO 1
<211> LENGTH: 1876
<212> TYPE: PRT
<213> ORGANISM: Saccharomyces cerevisiae

<400> SEQUENCE: 1

Met Asn Thr Asp Gln Gln Pro Tyr Gln Gly Gln Thr Asp Tyr Thr Gln
1               5                   10                  15

Gly Pro Gly Asn Gly Gln Ser Gln Glu Gln Asp Tyr Asp Gln Tyr Gly
            20                  25                  30

Gln Pro Leu Tyr Pro Ser Gln Ala Asp Gly Tyr Tyr Asp Pro Asn Val
        35                  40                  45

Ala Ala Gly Thr Glu Ala Asp Met Tyr Gly Gln Gln Pro Pro Asn Glu
    50                  55                  60

Ser Tyr Asp Gln Asp Tyr Thr Asn Gly Glu Tyr Tyr Gly Gln Pro Pro
65                  70                  75                  80

Asn Met Ala Ala Gln Asp Gly Glu Asn Phe Ser Asp Phe Ser Ser Tyr
                85                  90                  95

Gly Pro Pro Gly Thr Pro Gly Tyr Asp Ser Tyr Gly Gly Gln Tyr Thr
            100                 105                 110

Ala Ser Gln Met Ser Tyr Gly Glu Pro Asn Ser Ser Gly Thr Ser Thr
```

-continued

```
                115                 120                 125

Pro Ile Tyr Gly Asn Tyr Asp Pro Asn Ala Ile Ala Met Ala Leu Pro
    130                 135                 140

Asn Glu Pro Tyr Pro Ala Trp Thr Ala Asp Ser Gln Ser Pro Val Ser
145                 150                 155                 160

Ile Glu Gln Ile Glu Asp Ile Phe Ile Asp Leu Thr Asn Arg Leu Gly
                165                 170                 175

Phe Gln Arg Asp Ser Met Arg Asn Met Phe Asp His Phe Met Val Leu
                180                 185                 190

Leu Asp Ser Arg Ser Ser Arg Met Ser Pro Asp Gln Ala Leu Leu Ser
                195                 200                 205

Leu His Ala Asp Tyr Ile Gly Gly Asp Thr Ala Asn Tyr Lys Lys Trp
    210                 215                 220

Tyr Phe Ala Ala Gln Leu Asp Met Asp Asp Glu Ile Gly Phe Arg Asn
225                 230                 235                 240

Met Ser Leu Gly Lys Leu Ser Arg Lys Ala Arg Lys Ala Lys Lys Lys
                245                 250                 255

Asn Lys Lys Ala Met Glu Glu Ala Asn Pro Glu Asp Thr Glu Glu Thr
                260                 265                 270

Leu Asn Lys Ile Glu Gly Asp Asn Ser Leu Glu Ala Ala Asp Phe Arg
                275                 280                 285

Trp Lys Ala Lys Met Asn Gln Leu Ser Pro Leu Glu Arg Val Arg His
    290                 295                 300

Ile Ala Leu Tyr Leu Leu Cys Trp Gly Glu Ala Asn Gln Val Arg Phe
305                 310                 315                 320

Thr Ala Glu Cys Leu Cys Phe Ile Tyr Lys Cys Ala Leu Asp Tyr Leu
                325                 330                 335

Asp Ser Pro Leu Cys Gln Gln Arg Gln Glu Pro Met Pro Glu Gly Asp
                340                 345                 350

Phe Leu Asn Arg Val Ile Thr Pro Ile Tyr His Phe Ile Arg Asn Gln
                355                 360                 365

Val Tyr Glu Ile Val Asp Gly Arg Phe Val Lys Arg Glu Arg Asp His
    370                 375                 380

Asn Lys Ile Val Gly Tyr Asp Asp Leu Asn Gln Leu Phe Trp Tyr Pro
385                 390                 395                 400

Glu Gly Ile Ala Lys Ile Val Leu Glu Asp Gly Thr Lys Leu Ile Glu
                405                 410                 415

Leu Pro Leu Glu Glu Arg Tyr Leu Arg Leu Gly Asp Val Val Trp Asp
                420                 425                 430

Asp Val Phe Phe Lys Thr Tyr Lys Glu Thr Arg Thr Trp Leu His Leu
                435                 440                 445

Val Thr Asn Phe Asn Arg Ile Trp Val Met His Ile Ser Ile Phe Trp
    450                 455                 460

Met Tyr Phe Ala Tyr Asn Ser Pro Thr Phe Tyr Thr His Asn Tyr Gln
465                 470                 475                 480

Gln Leu Val Asp Asn Gln Pro Leu Ala Ala Tyr Lys Trp Ala Ser Cys
                485                 490                 495

Ala Leu Gly Gly Thr Val Ala Ser Leu Ile Gln Ile Val Ala Thr Leu
                500                 505                 510

Cys Glu Trp Ser Phe Val Pro Arg Lys Trp Ala Gly Ala Gln His Leu
                515                 520                 525

Ser Arg Arg Phe Trp Phe Leu Cys Ile Ile Phe Gly Ile Asn Leu Gly
    530                 535                 540
```

-continued

```
Pro Ile Ile Phe Val Phe Ala Tyr Asp Lys Asp Thr Val Tyr Ser Thr
545             550             555             560

Ala Ala His Val Val Ala Ala Val Met Phe Phe Val Ala Val Ala Thr
                565             570             575

Ile Ile Phe Phe Ser Ile Met Pro Leu Gly Gly Leu Phe Thr Ser Tyr
                580             585             590

Met Lys Lys Ser Thr Arg Arg Tyr Val Ala Ser Gln Thr Phe Thr Ala
        595             600             605

Ala Phe Ala Pro Leu His Gly Leu Asp Arg Trp Met Ser Tyr Leu Val
        610             615             620

Trp Val Thr Val Phe Ala Ala Lys Tyr Ser Glu Ser Tyr Tyr Phe Leu
625             630             635             640

Val Leu Ser Leu Arg Asp Pro Ile Arg Ile Leu Ser Thr Thr Ala Met
                645             650             655

Arg Cys Thr Gly Glu Tyr Trp Trp Gly Ala Val Leu Cys Lys Val Gln
                660             665             670

Pro Lys Ile Val Leu Gly Leu Val Ile Ala Thr Asp Phe Ile Leu Phe
        675             680             685

Phe Leu Asp Thr Tyr Leu Trp Tyr Ile Ile Val Asn Thr Ile Phe Ser
        690             695             700

Val Gly Lys Ser Phe Tyr Leu Gly Ile Ser Ile Leu Thr Pro Trp Arg
705             710             715             720

Asn Ile Phe Thr Arg Leu Pro Lys Arg Ile Tyr Ser Lys Ile Leu Ala
                725             730             735

Thr Thr Asp Met Glu Ile Lys Tyr Lys Pro Lys Val Leu Ile Ser Gln
                740             745             750

Val Trp Asn Ala Ile Ile Ile Ser Met Tyr Arg Glu His Leu Leu Ala
        755             760             765

Ile Asp His Val Gln Lys Leu Leu Tyr His Gln Val Pro Ser Glu Ile
        770             775             780

Glu Gly Lys Arg Thr Leu Arg Ala Pro Thr Phe Phe Val Ser Gln Asp
785             790             795             800

Asp Asn Asn Phe Glu Thr Glu Phe Phe Pro Arg Asp Ser Glu Ala Glu
                805             810             815

Arg Arg Ile Ser Phe Phe Ala Gln Ser Leu Ser Thr Pro Ile Pro Glu
                820             825             830

Pro Leu Pro Val Asp Asn Met Pro Thr Phe Thr Val Leu Thr Pro His
        835             840             845

Tyr Ala Glu Arg Ile Leu Leu Ser Leu Arg Glu Ile Ile Arg Glu Asp
        850             855             860

Asp Gln Phe Ser Arg Val Thr Leu Leu Glu Tyr Leu Lys Gln Leu His
865             870             875             880

Pro Val Glu Trp Glu Cys Phe Val Lys Asp Thr Lys Ile Leu Ala Glu
                885             890             895

Glu Thr Ala Ala Tyr Glu Gly Asn Glu Asn Glu Ala Glu Lys Glu Asp
                900             905             910

Ala Leu Lys Ser Gln Ile Asp Asp Leu Pro Phe Tyr Cys Ile Gly Phe
        915             920             925

Lys Ser Ala Ala Pro Glu Tyr Thr Leu Arg Thr Arg Ile Trp Ala Ser
        930             935             940

Leu Arg Ser Gln Thr Leu Tyr Arg Thr Ile Ser Gly Phe Met Asn Tyr
945             950             955             960
```

Ser Arg Ala Ile Lys Leu Leu Tyr Arg Val Glu Asn Pro Glu Ile Val
            965                 970                 975

Gln Met Phe Gly Gly Asn Ala Glu Gly Leu Glu Arg Glu Leu Glu Lys
            980                 985                 990

Met Ala Arg Arg Lys Phe Lys Phe  Leu Val Ser Met Gln  Arg Leu Ala
        995                 1000                1005

Lys Phe  Lys Pro His Glu Leu  Glu Asn Ala Glu Phe  Leu Leu Arg
    1010                1015                1020

Ala Tyr  Pro Asp Leu Gln Ile  Ala Tyr Leu Asp Glu  Glu Pro Pro
    1025                1030                1035

Leu Thr  Glu Gly Glu Glu Pro  Arg Ile Tyr Ser Ala  Leu Ile Asp
    1040                1045                1050

Gly His  Cys Glu Ile Leu Asp  Asn Gly Arg Arg Arg  Pro Lys Phe
    1055                1060                1065

Arg Val  Gln Leu Ser Gly Asn  Pro Ile Leu Gly Asp  Gly Lys Ser
    1070                1075                1080

Asp Asn  Gln Asn His Ala Leu  Ile Phe Tyr Arg Gly  Glu Tyr Ile
    1085                1090                1095

Gln Leu  Ile Asp Ala Asn Gln  Asp Asn Tyr Leu Glu  Glu Cys Leu
    1100                1105                1110

Lys Ile  Arg Ser Val Leu Ala  Glu Phe Glu Glu Leu  Asn Val Glu
    1115                1120                1125

Gln Val  Asn Pro Tyr Ala Pro  Gly Leu Arg Tyr Glu  Glu Gln Thr
    1130                1135                1140

Thr Asn  His Pro Val Ala Ile  Val Gly Ala Arg Glu  Tyr Ile Phe
    1145                1150                1155

Ser Glu  Asn Ser Gly Val Leu  Gly Asp Val Ala Ala  Gly Lys Glu
    1160                1165                1170

Gln Thr  Phe Gly Thr Leu Phe  Ala Arg Thr Leu Ser  Gln Ile Gly
    1175                1180                1185

Gly Lys  Leu His Tyr Gly His  Pro Asp Phe Ile Asn  Ala Thr Phe
    1190                1195                1200

Met Thr  Thr Arg Gly Gly Val  Ser Lys Ala Gln Lys  Gly Leu His
    1205                1210                1215

Leu Asn  Glu Asp Ile Tyr Ala  Gly Met Asn Ala Met  Leu Arg Gly
    1220                1225                1230

Gly Arg  Ile Lys His Cys Glu  Tyr Tyr Gln Cys Gly  Lys Gly Arg
    1235                1240                1245

Asp Leu  Gly Phe Gly Thr Ile  Leu Asn Phe Thr Thr  Lys Ile Gly
    1250                1255                1260

Ala Gly  Met Gly Glu Gln Met  Leu Ser Arg Glu Tyr  Tyr Tyr Leu
    1265                1270                1275

Gly Thr  Gln Leu Pro Val Asp  Arg Phe Leu Thr Phe  Tyr Tyr Ala
    1280                1285                1290

His Pro  Gly Phe His Leu Asn  Asn Leu Phe Ile Gln  Leu Ser Leu
    1295                1300                1305

Gln Met  Phe Met Leu Thr Leu  Val Asn Leu Ser Ser  Leu Ala His
    1310                1315                1320

Glu Ser  Ile Met Cys Ile Tyr  Asp Arg Asn Lys Pro  Lys Thr Asp
    1325                1330                1335

Val Leu  Val Pro Ile Gly Cys  Tyr Asn Phe Gln Pro  Ala Val Asp
    1340                1345                1350

Trp Val  Arg Arg Tyr Thr Leu  Ser Ile Phe Ile Val  Phe Trp Ile

-continued

```
        1355                 1360                 1365

Ala Phe  Val Pro Ile Val Val  Gln Glu Leu Ile Glu  Arg Gly Leu
        1370                 1375                 1380

Trp Lys  Ala Thr Gln Arg Phe  Phe Cys His Leu Leu  Ser Leu Ser
        1385                 1390                 1395

Pro Met  Phe Glu Val Phe Ala  Gly Gln Ile Tyr Ser  Ser Ala Leu
        1400                 1405                 1410

Leu Ser  Asp Leu Ala Ile Gly  Gly Ala Arg Tyr Ile  Ser Thr Gly
        1415                 1420                 1425

Arg Gly  Phe Ala Thr Ser Arg  Ile Pro Phe Ser Ile  Leu Tyr Ser
        1430                 1435                 1440

Arg Phe  Ala Gly Ser Ala Ile  Tyr Met Gly Ala Arg  Ser Met Leu
        1445                 1450                 1455

Met Leu  Leu Phe Gly Thr Val  Ala His Trp Gln Ala  Pro Leu Leu
        1460                 1465                 1470

Trp Phe  Trp Ala Ser Leu Ser  Ser Leu Ile Phe Ala  Pro Phe Val
        1475                 1480                 1485

Phe Asn  Pro His Gln Phe Ala  Trp Glu Asp Phe Phe  Leu Asp Tyr
        1490                 1495                 1500

Arg Asp  Tyr Ile Arg Trp Leu  Ser Arg Gly Asn Asn  Gln Tyr His
        1505                 1510                 1515

Arg Asn  Ser Trp Ile Gly Tyr  Val Arg Met Ser Arg  Ala Arg Ile
        1520                 1525                 1530

Thr Gly  Phe Lys Arg Lys Leu  Val Gly Asp Glu Ser  Glu Lys Ala
        1535                 1540                 1545

Ala Gly  Asp Ala Ser Arg Ala  His Arg Thr Asn Leu  Ile Met Ala
        1550                 1555                 1560

Glu Ile  Ile Pro Cys Ala Ile  Tyr Ala Ala Gly Cys  Phe Ile Ala
        1565                 1570                 1575

Phe Thr  Phe Ile Asn Ala Gln  Thr Gly Val Lys Thr  Thr Asp Asp
        1580                 1585                 1590

Asp Arg  Val Asn Ser Val Leu  Arg Ile Ile Ile Cys  Thr Leu Ala
        1595                 1600                 1605

Pro Ile  Ala Val Asn Leu Gly  Val Leu Phe Phe Cys  Met Gly Met
        1610                 1615                 1620

Ser Cys  Cys Ser Gly Pro Leu  Phe Gly Met Cys Cys  Lys Lys Thr
        1625                 1630                 1635

Gly Ser  Val Met Ala Gly Ile  Ala His Gly Val Ala  Val Ile Val
        1640                 1645                 1650

His Ile  Ala Phe Phe Ile Val  Met Trp Val Leu Glu  Ser Phe Asn
        1655                 1660                 1665

Phe Val  Arg Met Leu Ile Gly  Val Val Thr Cys Ile  Gln Cys Gln
        1670                 1675                 1680

Arg Leu  Ile Phe His Cys Met  Thr Ala Leu Met Leu  Thr Arg Glu
        1685                 1690                 1695

Phe Lys  Asn Asp His Ala Asn  Thr Ala Phe Trp Thr  Gly Lys Trp
        1700                 1705                 1710

Tyr Gly  Lys Gly Met Gly Tyr  Met Ala Trp Thr Gln  Pro Ser Arg
        1715                 1720                 1725

Glu Leu  Thr Ala Lys Val Ile  Glu Leu Ser Glu Phe  Ala Ala Asp
        1730                 1735                 1740

Phe Val  Leu Gly His Val Ile  Leu Ile Cys Gln Leu  Pro Leu Ile
        1745                 1750                 1755
```

-continued

```
Ile Ile  Pro Lys Ile Asp Lys  Phe His Ser Ile Met  Leu Phe Trp
    1760              1765              1770

Leu Lys  Pro Ser Arg Gln Ile  Arg Pro Pro Ile Tyr  Ser Leu Lys
    1775              1780              1785

Gln Thr  Arg Leu Arg Lys Arg  Met Val Lys Lys Tyr  Cys Ser Leu
    1790              1795              1800

Tyr Phe  Leu Val Leu Ala Ile  Phe Ala Gly Cys Ile  Ile Gly Pro
    1805              1810              1815

Ala Val  Ala Ser Ala Lys Ile  His Lys His Ile Gly  Asp Ser Leu
    1820              1825              1830

Asp Gly  Val Val His Asn Leu  Phe Gln Pro Ile Asn  Thr Thr Asn
    1835              1840              1845

Asn Asp  Thr Gly Ser Gln Met  Ser Thr Tyr Gln Ser  His Tyr Tyr
    1850              1855              1860

Thr His  Thr Pro Ser Leu Lys  Thr Trp Ser Thr Ile  Lys
    1865              1870              1875

<210> SEQ ID NO 2
<211> LENGTH: 5631
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgaatacgg accaacaacc atatcaaggc caaacagact acacgcaagg tcctgggaac      60
gggcaatccc aggaacaaga ctacgatcag tatggccagc cattgtatcc gagccaggcc     120
gatgggtatt atgatccgaa tgtggcagcg ggaacggagg cagatatgta cggacaacaa     180
cccccgaatg agtcgtatga tcaagactat actaatggcg aatactatgg ccaaccgcct     240
aatatggcgg cgcaggatgg cgaaaatttt tcggactttt caagttacgg tccgccgggc     300
acaccggggt acgattcata tggcggccaa tataccgcaa gccaaatgtc ttatggcgag     360
ccgaacagct caggcacatc aaccccgatt tacggaaatt acgaccctaa cgcaattgcc     420
atggctctgc cgaatgaacc atatcccgca tggacggctg atagccagag tccggtcagt     480
attgaacaaa ttgaagatat ttttattgat ttgacgaacc ggttaggatt tcagcgggat     540
agcatgcgga atatgtttga tcattttatg gttctgcttg actcacggtc cagcagaatg     600
tcacctgatc aagccttatt atcattacac gccgactaca ttggaggaga tacagcaaac     660
tacaaaaagt ggtatttcgc ggcgcagtta gatatggatg atgagatcgg gtttcgtaat     720
atgtctctcg aaaactgag caggaaagca aggaaggcaa aaaaaaagaa taaaaaggcg     780
atggaggagg cgaatccgga agatacagag gagacactga ataagatcga aggcgacaat     840
tctttagaag ccgcagattt ccgttggaag gcaaaaatga accagttgag tccactggaa     900
cgagttcgac atatcgcgct gtatctttta tgctggggtg aggctaacca agtccggttc     960
accgccgaat gtttatgttt tatttacaaa tgtgccttag actaccttga ctctcctctg    1020
tgccaacaac gccaggaacc gatgcccgaa ggcgacttct aaaccgcgt gattacgccg    1080 atttatcatt tcattcgcaa tcaagtgtat gaaatcgttg atggacgttt tgttaaacgc    1140
gaacgcgatc ataataaaat cgttggctac gatgatctca accaacttttt ttggtacccg    1200 gaaggtattg ctaaaattgt attagaagac ggcacgaaac tcattgagtt accgttggag    1260
gaaagatact tacgccttgg cgacgtggtc tgggacgatg tttttttttaa aacctacaaa    1320
```

-continued

```
gaaacacgta cgtggttaca tcttgtaacg aattttaaca gaatttgggt aatgcatatc    1380
tccatttttt ggatgtactt tgcctacaat agccctacct tttatacaca taactaccag    1440
cagttagtcg acaatcaacc gctggccgca tacaaatggg cgtcctgtgc tttaggggc    1500 acagttgcga gcttaataca gatcgtagca acactgtgcg aatggagctt cgttccgaga    1560
aaatgggcgg gcgctcagca tttgtcacgc cgtttctggt ttctttgtat catcttcggt    1620
atcaacctgg gtccgattat atttgttttt gcttacgaca aagataccgt ctattctact    1680
gcagcccatg tagttgcagc agtaatgttc tttgtggcgg tagcgactat tatttttttt    1740
tcaatcatgc ctctgggcgg cctgttcacc tcgtatatga agaaatcgac acgacgctat    1800
gtagcatcgc aaacatttac agccgcgttt gccccgctgc atgggcttga ccgttggatg    1860
tcatatctgg tctgggtgac cgtattcgca gccaaatatt ccgaaagtta ttactttctt    1920
gtcttatctt tgcgagatcc gattcgtatc ttaagtacga cagcaatgag atgtacgggg    1980
gagtattggt ggggcgccgt tctttgtaaa gttcagccga aaatcgtctt gggactggtg    2040
attgcgacag actttatttt attttttctt gatacatatt tgtggtatat tatcgtgaat    2100
actatttttt ctgttggaaa atcattttat ctgggaatct cgattctgac gccttggcgc    2160
aacatcttta cacgccttcc taaaagaatc tatagtaaaa ttttggccac aaccgatatg    2220
gaaatcaaat ataaaccgaa ggtgcttatt agtcaggtgt ggaatgctat tattatatcg    2280
atgtatcgcg aacatctttt agcaatcgac catgttcaaa agttgctgta tcaccaggtt    2340
ccttcagaga tcgaaggaaa gaggacgttg agggcgccca cctttttcgt gagtcaagat    2400
gataacaact ttgaaacaga atttttttcca agggactccg aggccgaaag acggatttct    2460 tttttttgcac aatctttatc tacaccaatc ccggaacctc ttccagtcga caatatgccg    2520
acgtttacag tgctcacacc ccactatgcc gaaagaatcc tcttaagcct gagggaaata    2580
atccgagagg atgatcagtt ttctcgtgtt acgctgctgg agtatttaaa acaattacat    2640
cctgttgagt gggagtgctt cgtgaaggat acgaaaattt tggcagaaga gacggctgct    2700
tatgaaggca atgaaaacga agctgaaaaa gaagacgcgc tcaagtcaca gatagatgat    2760
ctcccttttt attgcatagg ctttaaatct gcggccccgg aatatacgct tcgcacaaga    2820
atatgggcat ctttaagatc ccaaacgtta taccggacca ttagtggatt tatgaactat    2880
tctcgggcaa ttaaactttt gtatagagtg gaaaacccgg aaattgtaca aatgttcggc    2940
ggaaatgctg aaggcctgga gagggaactc gaaaaaatgg ctcgcaggaa atttaaattt    3000
ctggtttcca tgcaacgcct tgcgaaattc aaaccccatg aattagagaa tgccgaattt    3060
ctgttgaggg catatccgga cttgcaaata gcataccttg atgaagaacc gccactgacg    3120
gaaggtgaag agccgagaat atattctgca cttattgacg gacactgcga gatccttgac    3180
aatggccgac gtaggcctaa atttagagtc caactttctg gaaacccgat tcttggtgat    3240
ggaaagtctg ataatcaaaa ccatgcgttg atcttctatc ggggagaata tattcaactt    3300
atagatgcaa atcaggataa ctatcttgag gagtgcctga aaattcggtc tgttctggct    3360
gagtttgagg aacttaacgt tgaacaggtg aatccctacg caccgggact cagatatgag    3420
gaacagacaa ccaaccaccc agtcgctatc gtaggcgcac gcgaatacat attctcagag    3480
aattccggtg tattaggcga cgtcgccgcc ggtaaagaac aaacgttcgg caccttgttt    3540
gcgcggacgc tctctcaaat tgggggaaaa ctgcattacg gacatcctga tttttattaat    3600 gcaacgttta tgacaacgcg aggaggagtg agtaaagctc agaaaggcct tcatttaaat    3660
```

```
gaagacattt atgccggcat gaatgcgatg ttgaggggcg gcagaataaa acattgtgaa     3720
tattatcagt gtggaaaagg tcgggattta ggattcggaa caatccttaa ttttacgacc     3780
aaaatcggcg ctggtatggg cgagcaaatg ttatcacgag agtattatta tcttggaacg     3840
caattaccgg ttgatcgatt cttgaccttt tactatgctc atccgggttt tcatcttaac     3900
aatctgttta ttcaactgtc cctgcaaatg ttcatgctga cgcttgtaaa tttgtcatct     3960
ctggcccatg aatcgatcat gtgtatctac gatcgcaata aaccaaagac agatgtgctg     4020
gtaccgatcg gctgctataa tttccaaccg gctgtggact gggtaagacg atatacactt     4080
tccatattta ttgtcttctg gatcgctttt gtacccattg tcgttcagga gcttattgaa     4140
cgcggcttgt ggaaagcgac tcaaagattc ttttgccatc ttttatccct ctctccaatg     4200
tttgaggtct tcgcgggtca aatttattct tcagcgctgc ttagcgactt ggctattggc     4260
ggcgcgaggt atatctcaac aggtcgcggg tttgctacgt cccgtatacc tttttcgatc     4320
ctctattcaa gatttgcagg cagcgctatt tacatgggcg cacgatctat gttaatgttg     4380
ttatttggaa cagttgctca ttggcaggcg ccacttcttt ggttctgggc atccttgtca     4440
tcattaatct tcgcgccgtt cgtttttaat ccgcatcaat ttgcctggga agatttttt     4500 ttagattatc gggattacat tcgctggctg agccgaggaa ataaccagta tcatcgtaat     4560
tcatggattg gttacgtacg aatgtctcgt gcccgtatta caggctttaa aagaaagctc     4620
gtcggcgacg aatccgaaaa agcagcggga gatgcaagcc gagcccatcg tactaacctg     4680
atcatggctg aaattatccc gtgcgctatc tatgcggcag ggtgtttcat agcgttcacg     4740
tttataaacg ctcagacagg cgtaaagaca accgacgatg accgcgtcaa ttcggttctg     4800
aggatcatca tatgtaccct tgcaccgatt gccgtgaatt tgggagtgct tttctttgt     4860 atgggtatgt catgctgcag cggtcctta ttcggtatgt gttgcaagaa gacaggctcc     4920
gttatggctg gtattgcaca cggtgttgct gtgattgttc atattgcgtt ctttatcgtg     4980
atgtgggtac tggagtcttt caattttgtt cgcatgctta ttggtgtggt gacatgtatt     5040
cagtgtcagc gcttgatctt tcactgcatg acggcactga tgctgactcg agaatttaaa     5100
aacgaccacg cgaatacagc cttttggacg ggcaaatggt atggcaaagg aatgggatat     5160
atggcctgga cccagccgag tagagaattg acggcaaaag tcattgaact tagtgaattt     5220
gcagcagatt tcgtattggg tcacgttatt ctgatctgtc agttaccact gatcatcatc     5280
cccaaaatcg acaagtttca ctcaattatg ctcttctggc tgaaaccatc acgtcagatc     5340
cgtcccccta tctatagtct caaacaaacg agattgagaa aaagaatggt taaaaaatat     5400
tgcagccttt actttttggt cttggccatt tttgcggggt gtatcatcgg ccccgctgta     5460
gcatcagcca agatccataa acacatcggt gattccttag atggagtcgt acataatctt     5520
ttccaaccga taaataccac aaacaatgac acgggcagtc agatgtcaac ttaccagagt     5580
cactactata ctcatacgcc gtccttaaaa acctggtcca caattaagta a             5631
```

<210> SEQ ID NO 3
<211> LENGTH: 1950
<212> TYPE: PRT
<213> ORGANISM: Arabidopsis thaliana

<400> SEQUENCE: 3

```
Met Ala Gln Arg Arg Glu Pro Asp Pro Pro Pro Gln Arg Arg Ile
1               5                   10                  15

Leu Arg Thr Gln Thr Val Gly Ser Leu Gly Glu Ala Met Leu Asp Ser
        20                  25                  30
```

```
Glu Val Val Pro Ser Ser Leu Val Glu Ile Ala Pro Ile Leu Arg Val
        35                  40                  45

Ala Asn Glu Val Glu Ala Ser Asn Pro Arg Val Ala Tyr Leu Cys Arg
    50                  55                  60

Phe Tyr Ala Phe Glu Lys Ala His Arg Leu Asp Pro Thr Ser Ser Gly
65                  70                  75                  80

Arg Gly Val Arg Gln Phe Lys Thr Ala Leu Leu Gln Arg Leu Glu Arg
                85                  90                  95

Glu Asn Glu Thr Thr Leu Ala Gly Arg Gln Lys Ser Asp Ala Arg Glu
                100                 105                 110

Met Gln Ser Phe Tyr Gln His Tyr Tyr Lys Lys Tyr Ile Gln Ala Leu
            115                 120                 125

Leu Asn Ala Ala Asp Lys Ala Asp Arg Ala Gln Leu Thr Lys Ala Tyr
        130                 135                 140

Gln Thr Ala Ala Val Leu Phe Glu Val Leu Lys Ala Val Asn Gln Thr
145                 150                 155                 160

Glu Asp Val Glu Val Ala Asp Glu Ile Leu Glu Thr His Asn Lys Val
                165                 170                 175

Glu Glu Lys Thr Gln Ile Tyr Val Pro Tyr Asn Ile Leu Pro Leu Asp
            180                 185                 190

Pro Asp Ser Gln Asn Gln Ala Ile Met Arg Leu Pro Glu Ile Gln Ala
            195                 200                 205

Ala Val Ala Ala Leu Arg Asn Thr Arg Gly Leu Pro Trp Thr Ala Gly
        210                 215                 220

His Lys Lys Lys Leu Asp Glu Asp Ile Leu Asp Trp Leu Gln Ser Met
225                 230                 235                 240

Phe Gly Phe Gln Lys Asp Asn Val Leu Asn Gln Arg Glu His Leu Ile
                245                 250                 255

Leu Leu Leu Ala Asn Val His Ile Arg Gln Phe Pro Lys Pro Asp Gln
            260                 265                 270

Gln Pro Lys Leu Asp Asp Arg Ala Leu Thr Ile Val Met Lys Lys Leu
        275                 280                 285

Phe Arg Asn Tyr Lys Lys Trp Cys Lys Tyr Leu Gly Arg Lys Ser Ser
    290                 295                 300

Leu Trp Leu Pro Thr Ile Gln Gln Glu Val Gln Gln Arg Lys Leu Leu
305                 310                 315                 320

Tyr Met Gly Leu Tyr Leu Leu Ile Trp Gly Glu Ala Ala Asn Leu Arg
            325                 330                 335

Phe Met Pro Glu Cys Leu Cys Tyr Ile Tyr His His Met Ala Phe Glu
            340                 345                 350

Leu Tyr Gly Met Leu Ala Gly Ser Val Ser Pro Met Thr Gly Glu His
            355                 360                 365

Val Lys Pro Ala Tyr Gly Gly Glu Asp Glu Ala Phe Leu Gln Lys Val
        370                 375                 380

Val Thr Pro Ile Tyr Gln Thr Ile Ser Lys Glu Ala Lys Arg Ser Arg
385                 390                 395                 400

Gly Gly Lys Ser Lys His Ser Val Trp Arg Asn Tyr Asp Asp Leu Asn
                405                 410                 415

Glu Tyr Phe Trp Ser Ile Arg Cys Phe Arg Leu Gly Trp Pro Met Arg
            420                 425                 430

Ala Asp Ala Asp Phe Phe Cys Gln Thr Ala Glu Glu Leu Arg Leu Glu
        435                 440                 445
```

-continued

```
Arg Ser Glu Ile Lys Ser Asn Ser Gly Asp Arg Trp Met Gly Lys Val
    450             455             460

Asn Phe Val Glu Ile Arg Ser Phe Trp His Ile Phe Arg Ser Phe Asp
465             470             475             480

Arg Leu Trp Ser Phe Tyr Ile Leu Cys Leu Gln Ala Met Ile Val Ile
            485             490             495

Ala Trp Asn Gly Ser Gly Glu Leu Ser Ala Ile Phe Gln Gly Asp Val
            500             505             510

Phe Leu Lys Val Leu Ser Val Phe Ile Thr Ala Ala Ile Leu Lys Leu
        515             520             525

Ala Gln Ala Val Leu Asp Ile Ala Leu Ser Trp Lys Ala Arg His Ser
    530             535             540

Met Ser Leu Tyr Val Lys Leu Arg Tyr Val Met Lys Val Gly Ala Ala
545             550             555             560

Ala Val Trp Val Val Val Met Ala Val Thr Tyr Ala Tyr Ser Trp Lys
            565             570             575

Asn Ala Ser Gly Phe Ser Gln Thr Ile Lys Asn Trp Phe Gly Gly His
            580             585             590

Ser His Asn Ser Pro Ser Leu Phe Ile Val Ala Ile Leu Ile Tyr Leu
            595             600             605

Ser Pro Asn Met Leu Ser Ala Leu Leu Phe Leu Phe Pro Phe Ile Arg
    610             615             620

Arg Tyr Leu Glu Arg Ser Asp Tyr Lys Ile Met Met Leu Met Met Trp
625             630             635             640

Trp Ser Gln Pro Arg Leu Tyr Ile Gly Arg Gly Met His Glu Ser Ala
            645             650             655

Leu Ser Leu Phe Lys Tyr Thr Met Phe Trp Ile Val Leu Leu Ile Ser
            660             665             670

Lys Leu Ala Phe Ser Tyr Tyr Ala Glu Ile Lys Pro Leu Val Gly Pro
        675             680             685

Thr Lys Asp Ile Met Arg Ile His Ile Ser Val Tyr Ser Trp His Glu
    690             695             700

Phe Phe Pro His Ala Lys Asn Asn Leu Gly Val Val Ile Ala Leu Trp
705             710             715             720

Ser Pro Val Ile Leu Val Tyr Phe Met Asp Thr Gln Ile Trp Tyr Ala
            725             730             735

Ile Val Ser Thr Leu Val Gly Gly Leu Asn Gly Ala Phe Arg Arg Leu
            740             745             750

Gly Glu Ile Arg Thr Leu Gly Met Leu Arg Ser Arg Phe Gln Ser Ile
        755             760             765

Pro Gly Ala Phe Asn Asp Cys Leu Val Pro Gln Asp Asn Ser Asp Asp
    770             775             780

Thr Lys Lys Lys Arg Phe Arg Ala Thr Phe Ser Arg Lys Phe Asp Gln
785             790             795             800

Leu Pro Ser Ser Lys Asp Lys Glu Ala Ala Arg Phe Ala Gln Met Trp
            805             810             815

Asn Lys Ile Ile Ser Ser Phe Arg Glu Glu Asp Leu Ile Ser Asp Arg
            820             825             830

Glu Met Glu Leu Leu Leu Val Pro Tyr Trp Ser Asp Pro Asp Leu Asp
            835             840             845

Leu Ile Arg Trp Pro Pro Phe Leu Leu Ala Ser Lys Ile Pro Ile Ala
    850             855             860

Leu Asp Met Ala Lys Asp Ser Asn Gly Lys Asp Arg Glu Leu Lys Lys
```

-continued

```
865                 870                 875                 880
Arg Leu Ala Val Asp Ser Tyr Met Thr Cys Ala Val Arg Glu Cys Tyr
                885                 890                 895
Ala Ser Phe Lys Asn Leu Ile Asn Tyr Leu Val Val Gly Glu Arg Glu
                900                 905                 910
Gly Gln Val Ile Asn Asp Ile Phe Ser Lys Ile Asp Glu His Ile Glu
                915                 920                 925
Lys Glu Thr Leu Ile Thr Glu Leu Asn Leu Ser Ala Leu Pro Asp Leu
            930                 935                 940
Tyr Gly Gln Phe Val Arg Leu Ile Glu Tyr Leu Leu Glu Asn Arg Glu
945                 950                 955                 960
Glu Asp Lys Asp Gln Ile Val Ile Val Leu Leu Asn Met Leu Glu Leu
                965                 970                 975
Val Thr Arg Asp Ile Met Glu Glu Glu Val Pro Ser Leu Leu Glu Thr
                980                 985                 990
Ala His Asn Gly Ser Tyr Val Lys  Tyr Asp Val Met Thr  Pro Leu His
            995                 1000                1005
Gln Gln  Arg Lys Tyr Phe Ser  Gln Leu Arg Phe Pro  Val Tyr Ser
    1010                1015                1020
Gln Thr  Glu Ala Trp Lys Glu  Lys Ile Lys Arg Leu  His Leu Leu
    1025                1030                1035
Leu Thr  Val Lys Glu Ser Ala  Met Asp Val Pro Ser  Asn Leu Glu
    1040                1045                1050
Ala Arg  Arg Arg Leu Thr Phe  Phe Ser Asn Ser Leu  Phe Met Asp
    1055                1060                1065
Met Pro  Pro Ala Pro Lys Ile  Arg Asn Met Leu Ser  Phe Ser Val
    1070                1075                1080
Leu Thr  Pro Tyr Phe Ser Glu  Asp Val Leu Phe Ser  Ile Phe Gly
    1085                1090                1095
Leu Glu  Gln Gln Asn Glu Asp  Gly Val Ser Ile Leu  Phe Tyr Leu
    1100                1105                1110
Gln Lys  Ile Phe Pro Asp Glu  Trp Thr Asn Phe Leu  Glu Arg Val
    1115                1120                1125
Lys Cys  Gly Asn Glu Glu Glu  Leu Arg Ala Arg Glu  Asp Leu Glu
    1130                1135                1140
Glu Glu  Leu Arg Leu Trp Ala  Ser Tyr Arg Gly Gln  Thr Leu Thr
    1145                1150                1155
Lys Thr  Val Arg Gly Met Met  Tyr Tyr Arg Lys Ala  Leu Glu Leu
    1160                1165                1170
Gln Ala  Phe Leu Asp Met Ala  Lys Asp Glu Glu Leu  Leu Lys Gly
    1175                1180                1185
Tyr Lys  Ala Leu Glu Leu Thr  Ser Glu Glu Ala Ser  Lys Ser Gly
    1190                1195                1200
Gly Ser  Leu Trp Ala Gln Cys  Gln Ala Leu Ala Asp  Met Lys Phe
    1205                1210                1215
Thr Phe  Val Val Ser Cys Gln  Gln Tyr Ser Ile His  Lys Arg Ser
    1220                1225                1230
Gly Asp  Gln Arg Ala Lys Asp  Ile Leu Arg Leu Met  Thr Thr Tyr
    1235                1240                1245
Pro Ser  Ile Arg Val Ala Tyr  Ile Asp Glu Val Glu  Gln Thr His
    1250                1255                1260
Lys Glu  Ser Tyr Lys Gly Thr  Glu Glu Lys Ile Tyr  Tyr Ser Ala
    1265                1270                1275
```

```
Leu Val Lys Ala Ala Pro Gln  Thr Lys Pro Met Asp  Ser Ser Glu
    1280            1285            1290

Ser Val Gln Thr Leu Asp Gln  Leu Ile Tyr Arg Ile  Lys Leu Pro
    1295            1300            1305

Gly Pro Ala Ile Leu Gly Glu  Gly Lys Pro Glu Asn  Gln Asn His
    1310            1315            1320

Ala Ile Ile Phe Thr Arg Gly  Glu Gly Leu Gln Thr  Ile Asp Met
    1325            1330            1335

Asn Gln Asp Asn Tyr Met Glu  Glu Ala Phe Lys Met  Arg Asn Leu
    1340            1345            1350

Leu Gln Glu Phe Leu Glu Lys  His Gly Gly Val Arg  Cys Pro Thr
    1355            1360            1365

Ile Leu Gly Leu Arg Glu His  Ile Phe Thr Gly Ser  Val Ser Ser
    1370            1375            1380

Leu Ala Trp Phe Met Ser Asn  Gln Glu Asn Ser Phe  Val Thr Ile
    1385            1390            1395

Gly Gln Arg Val Leu Ala Ser  Pro Leu Lys Val Arg  Phe His Tyr
    1400            1405            1410

Gly His Pro Asp Ile Phe Asp  Arg Leu Phe His Leu  Thr Arg Gly
    1415            1420            1425

Gly Ile Cys Lys Ala Ser Lys  Val Ile Asn Leu Ser  Glu Asp Ile
    1430            1435            1440

Phe Ala Gly Phe Asn Ser Thr  Leu Arg Glu Gly Asn  Val Thr His
    1445            1450            1455

His Glu Tyr Ile Gln Val Gly  Lys Gly Arg Asp Val  Gly Leu Asn
    1460            1465            1470

Gln Ile Ser Met Phe Glu Ala  Lys Ile Ala Asn Gly  Asn Gly Glu
    1475            1480            1485

Gln Thr Leu Ser Arg Asp Leu  Tyr Arg Leu Gly His  Arg Phe Asp
    1490            1495            1500

Phe Phe Arg Met Leu Ser Cys  Tyr Phe Thr Thr Ile  Gly Phe Tyr
    1505            1510            1515

Phe Ser Thr Met Leu Thr Val  Leu Thr Val Tyr Val  Phe Leu Tyr
    1520            1525            1530

Gly Arg Leu Tyr Leu Val Leu  Ser Gly Leu Glu Glu  Gly Leu Ser
    1535            1540            1545

Ser Gln Arg Ala Phe Arg Asn  Asn Lys Pro Leu Glu  Ala Ala Leu
    1550            1555            1560

Ala Ser Gln Ser Phe Val Gln  Ile Gly Phe Leu Met  Ala Leu Pro
    1565            1570            1575

Met Met Met Glu Ile Gly Leu  Glu Arg Gly Phe His  Asn Ala Leu
    1580            1585            1590

Ile Glu Phe Val Leu Met Gln  Leu Gln Leu Ala Ser  Val Phe Phe
    1595            1600            1605

Thr Phe Gln Leu Gly Thr Lys  Thr His Tyr Tyr Gly  Arg Thr Leu
    1610            1615            1620

Phe His Gly Gly Ala Glu Tyr  Arg Gly Thr Gly Arg  Gly Phe Val
    1625            1630            1635

Val Phe His Ala Lys Phe Ala  Glu Asn Tyr Arg Phe  Tyr Ser Arg
    1640            1645            1650

Ser His Phe Val Lys Gly Ile  Glu Leu Met Ile Leu  Leu Leu Val
    1655            1660            1665
```

```
Tyr Gln Ile Phe Gly Gln Ser Tyr Arg Gly Val Val Thr Tyr Ile
    1670                1675                1680

Leu Ile Thr Val Ser Ile Trp Phe Met Val Val Thr Trp Leu Phe
    1685                1690                1695

Ala Pro Phe Leu Phe Asn Pro Ser Gly Phe Glu Trp Gln Lys Ile
    1700                1705                1710

Val Asp Asp Trp Thr Asp Trp Asn Lys Trp Ile Tyr Asn Arg Gly
    1715                1720                1725

Gly Ile Gly Val Pro Pro Glu Lys Ser Trp Glu Ser Trp Trp Glu
    1730                1735                1740

Lys Glu Leu Glu His Leu Arg His Ser Gly Val Arg Gly Ile Thr
    1745                1750                1755

Leu Glu Ile Phe Leu Ala Leu Arg Phe Phe Ile Phe Gln Tyr Gly
    1760                1765                1770

Leu Val Tyr His Leu Ser Thr Phe Lys Gly Lys Asn Gln Ser Phe
    1775                1780                1785

Trp Val Tyr Gly Ala Ser Trp Phe Val Ile Leu Phe Ile Leu Leu
    1790                1795                1800

Ile Val Lys Gly Leu Gly Val Gly Arg Arg Arg Phe Ser Thr Asn
    1805                1810                1815

Phe Gln Leu Leu Phe Arg Ile Ile Lys Gly Leu Val Phe Leu Thr
    1820                1825                1830

Phe Val Ala Ile Leu Ile Thr Phe Leu Ala Leu Pro Leu Ile Thr
    1835                1840                1845

Ile Lys Asp Leu Phe Ile Cys Met Leu Ala Phe Met Pro Thr Gly
    1850                1855                1860

Trp Gly Met Leu Leu Ile Ala Gln Ala Cys Lys Pro Leu Ile Gln
    1865                1870                1875

Gln Leu Gly Ile Trp Ser Ser Val Arg Thr Leu Ala Arg Gly Tyr
    1880                1885                1890

Glu Ile Val Met Gly Leu Leu Leu Phe Thr Pro Val Ala Phe Leu
    1895                1900                1905

Ala Trp Phe Pro Phe Val Ser Glu Phe Gln Thr Arg Met Leu Phe
    1910                1915                1920

Asn Gln Ala Phe Ser Arg Gly Leu Gln Ile Ser Arg Ile Leu Gly
    1925                1930                1935

Gly Gln Arg Lys Asp Arg Ser Ser Lys Asn Lys Glu
    1940                1945                1950
```

```
<210> SEQ ID NO 4
<211> LENGTH: 5850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggcacaac gcagggaacc ggacccgcca cccccgcagc gtagaatatt gcggacgcaa      60
acggttggct ctctgggaga agccatgctt gattctgagg tcgttccttc atcacttgtc     120
gaaatagcgc caattttacg cgtcgcaaac gaagtagaag cttcaaatcc gcgtgtcgct     180
tacttatgta gattctacgc atttgaaaaa gctcaccgac ttgatccaac ctcttcaggc     240
cgcggagtta gacaatttaa gacggcattg cttcaacggt tagagcgtga gaacgaaacc     300
acattggcgg gaagacaaaa aagcgacgcg cgagagatgc aaagttttta ccagcattac     360
```

-continued

```
tacaaaaaat acattcaagc gttactgaat gcagcggaca aggcagatcg ggcgcaactt    420
acaaaagcgt accagacagc tgcagtcctt tttgaagtgc ttaaagctgt caatcagact    480
gaagacgtcg aagttgccga tgaaattctg gagacacaca ataaagtcga ggagaaaacg    540
cagatttatg tgcctataa cattcttccc ttagatcctg acagccaaaa tcaggccatt    600
atgcgcttgc cagaaattca ggcggctgtc gccgcactgc gcaacactcg tggtttacct    660
tggacagcag gacacaaaaa gaaattggat gaggatattc ttgattggct gcaatcgatg    720
ttcggttttc aaaaagataa tgtgctcaat caaagagaac atctgatttt gcttctggct    780
aacgttcata tccgccaatt cccgaagcct gatcagcagc caaaacttga cgaccgggct    840
cttacgattg taatgaaaaa gttatttcgg aattacaaga agtggtgcaa gtatcttggt    900
cgcaagtcat ccctttggct ccctacaatt caacaggaag tgcaacagcg taaattactt    960
tatatggggc tctacttgtt aatatgggga gaagccgcga atcttcgctt tatgccggaa    1020
tgtctgtgct atatctatca ccatatggca ttcgagttgt atgggatgtt agcaggcagc    1080
gtgtctccga tgactggcga acacgttaag cctgcatatg gaggggagga cgaagccttt    1140
ttacagaagg tcgtcacgcc aatttatcaa actatttcta aagaagcaaa aagatcaaga    1200
ggaggaaaaa gcaaacatag cgtgtggcgg aactatgatg atctcaatga gtattttggg    1260
agtattcggt gttttcggct tggctggccc atgcgcgcgg atgctgattt ttttgtcaa    1320 acagctgaag aattgaggtt agagagaagc gagattaaat cgaatagcgg ggatcgttgg    1380
atggggaaag taaactttgt agagattaga tcattttggc acatttttag atcttttgat    1440
agattgtggt cctttacat actgtgcttg caagcgatga ttgtaatcgc ttggaatggc    1500
tcgggtgaat tgtcggcgat ttttcaagga gatgtatttt tgaaggtgct ctctgtcttt    1560
attaccgcgg cgatcctgaa gctggcgcaa gccgttctcg atattgccct gtcctggaag    1620
gcgcgtcatt cgatgagcct gtatgttaaa cttcgttacg tcatgaaagt gggtgctgcg    1680
gcagtttggg tcgtcgttat ggcggtaaca tacgcatatt catggaaaaa cgcgtctggc    1740
ttctcccaga ccattaagaa ctggttcggc ggacattcac ataattcccc gtcactcttt    1800
attgtggcta tcctgattta tctgagccct aacatgttgt cagcacttct ttttctcttc    1860
ccgtttatcc gtcggtattt ggaacgatct gattacaaaa tcatgatgct tatgatgtgg    1920
tggtcccagc cacgactgta tatcggaagg gggatgcatg aatcagctct gtctctgttt    1980
aaatacacta tgttttggat tgttctgctg atttcgaaac ttgccttttc gtattacgcg    2040
gaaattaaac ccctcgtagg cccgacaaaa gacattatgc gaattcatat tagtgtttat    2100
tcgtggcatg agtttttttcc acatgcaaaa aacaatctgg gtgtagtcat tgcactttgg    2160
tcacccgtca tcctggtata tttcatggac acacaaattt ggtacgctat cgtctccacc    2220
ctggtgggag gcttaaacgg tgcttttaga cgtttagggg agatcagaac attaggtatg    2280
ttacgttcgc gcttccagag tatcccaggt gcatttaatg attgtcttgt cccgcaggac    2340
aactccgacg acactaaaaa aaagcgcttt agagcaactt ttagtcggaa atttgatcag    2400
cttccatcat caaaggacaa agaggcggca agattcgcac aaatgtggaa taaaatcatt    2460
tcaagttttc gtgaagaaga cctgatttca gaccgggaaa tggaactttt gcttgtacct    2520
tactggagtg atcctgattt ggacctgatc aggtggccgc cgtttttatt agcatccaaa    2580
attcctatcg cgctggacat ggctaaagac tctaacggta aggaccgtga actcaaaaag    2640
agactcgccg ttgattccta tatgacctgt gcagtccgtg aatgctacgc gtctttcaaa    2700
```

-continued

```
aatttaatta attatttagt tgttggagaa cgcgaagggc aagtcattaa tgatatcttt    2760
tcaaagatcg atgaacatat agaaaaagag accttaatta cagaacttaa tttgagcgcg    2820
ctgcccgatt tatacggaca attcgtgaga cttattgaat atctgctgga aaatcgggaa    2880
gaggataaag atcagattgt tatagtctta ttaaatatgc tggaattggt aacgcgggac    2940
attatggagg aagaagttcc gtctttgtta gaaacggctc ataatggatc ttacgttaag    3000
tatgatgtga tgacaccact ccatcagcag cgtaaatatt ttagtcaact gcggtttccg    3060
gtttacagcc aaacggaggc gtggaaagag aaaatcaaac gactgcattt gctgttgacg    3120
gtcaaagaat cggcaatgga cgtaccgtca aacttggaag cgcgaagaag attaaccttc    3180
ttttctaatt cactgttcat ggatatgcct cctgcaccga aaattcgtaa tatgttatca    3240
ttttcagtct taactccgta tttctctgaa gatgtccttt ttagcatctt cggccttgaa    3300
cagcagaatg aagatggagt gtccattctt ttctatcttc aaaaaatttt tccggatgaa    3360
tggaccaatt ttttagagcg ggtcaaatgc ggcaatgagg aagaactgcg ggcccgtgaa    3420
gatcttgaag aagaattgcg actttgggcc tcatatagag gtcaaacact gacaaaaaca    3480
gtacgtggga tgatgtatta tagaaaagct ctggaactgc aggcattttt agacatggct    3540
aaagatgaag aattattaaa aggttacaaa gctctggagc ttacatccga ggaagcgagt    3600
aagagcggag gttctttgtg ggctcaatgt caagcgttgg ctgacatgaa gttcaccttc    3660
gttgtttctt gccaacaata tagtattcat aagcgtagcg gtgatcaaag agcgaaggat    3720
atccttcggt tgatgacaac gtatccgagc atccgagttg catatataga cgaggtagag    3780
caaacgcaca aagagtccta taaaggcacg gaagaaaaga tatattactc tgctcttgtg    3840
aaagccgctc cacagacaaa gccgatggat tcttcagaaa gcgtacaaac attggatcag    3900
ttgatttacc gtatcaaact tccggggcca gcaatcctgg gagaaggcaa accggaaaat    3960
cagaatcacg caatcatttt cacaagaggc gaaggccttc aaacaatcga tatgaatcag    4020
gataattata tggaagaagc tttcaaaatg cgcaatctgt tacaggaatt ccttgaaaaa    4080
catggaggcg ttagatgccc tacaatcctg ggccttcgcg aacacatttt tactggcagt    4140
gtcagctctt tagcgtggtt tatgtccaac caagaaaact catttgtcac tataggccag    4200
agagtcttag cgagccctct gaaagtacgc tttcactatg gtcatccgga tattttttgat    4260 agattgtttc accttaccag gggtgggatt tgtaaagcct ctaaggtcat caacctcagc    4320
gaagacatct ttgctggctt taacagcaca cttcgcgaag gcaatgtcac ccaccatgaa    4380
tatattcaag ttggtaaggg acgtgatgtg gggttgaatc aaatctcgat gtttgaagcg    4440
aaaattgcca atggcaatgg agaacaaacc ttgtcccggg atctttaccg gttgggtcat    4500
cgtttcgatt tctttcgtat gctttcttgc tattttacca cgattgggtt ttattttttct    4560 accatgttga ccgtcctgac tgtatacgtc ttcctgtatg ggcggctgta tcttgtcctg    4620
agcggtctgg aagaaggact tagctcccaa cgggcctttc gcaacaacaa gcctttagaa    4680
gccgcacttg catcacaaag ttttgttcag atcggatttt taatggcatt gcctatgatg    4740
atggaaattg ggctcgaaag gggttttcac aatgctttaa tagaatttgt gcttatgcaa    4800
ttgcagcttg catccgtatt ctttactttt caattaggaa ccaagactca ctactatgga    4860
aggacattat ttcacggcgg agcagagtat agaggcacag gccgtggatt tgtcgtgttt    4920
catgcgaaat ttgccgaaaa ttatcggttc tattctaggt ctcattttgt caaaggcatc    4980
gagctgatga tccttctttt ggtctatcaa atcttcggtc aatcatatag gggtgtagtg    5040
acatacatcc ttatcactgt aagcatatgg tttatggttg tgacgtggct gtttgcgcct    5100
```

-continued

```
tttctgttta accccagtgg atttgaatgg cagaagatcg tggatgactg gaccgattgg      5160
aacaaatgga tctataatcg cggcggcatt ggggttccac cggagaaatc ttgggagtca      5220
tggtgggaaa aagaactgga acacctccgc catagcggag tccgggggaat tacattggaa      5280 attttccttg cgcttcgctt tttcatcttt cagtacgggc ttgtctacca tctcagcaca      5340
tttaaaggca aaaaccagtc attttgggtc tacggggcct catggtttgt cattctgttt      5400
attttgttaa ttgtaaaagg tttgggcgtt ggacggcgcc gctttctac taatttccag        5460 ctgcttttcc gcatcattaa aggtctcgtt ttcttaacgt tcgttgcaat tctgattact      5520
tttctggcac tgccgctgat aaccataaag gatttattta tctgtatgct tgcatttatg      5580
cctacggggt ggggtatgct tctgatagct caggcgtgca aaccgctgat ccagcaactg      5640
ggaatctggt cttccgtcag aaccttagca cgggggtacg aaatcgttat gggcctgtta       5700
ctgtttaccc cagtggcatt tcttgcgtgg tttccgtttg taagcgaatt ccaaacgcgc      5760
atgctgttta tcaggcgtt ttctcgcggg ttgcaaatta gccgcatttt aggcggccaa       5820
cggaaggata ggagcagcaa aaataaggag                                        5850
```

<210> SEQ ID NO 5
<211> LENGTH: 952
<212> TYPE: PRT
<213> ORGANISM: Oryza sativa

<400> SEQUENCE: 5

```
Met Ala Pro Ala Val Ala Gly Gly Gly Arg Arg Asn Asn Glu Gly
1               5                   10                  15

Val Asn Gly Asn Ala Ala Ala Pro Ala Cys Val Cys Gly Phe Pro Val
            20                  25                  30

Cys Ala Cys Ala Gly Ala Ala Ala Val Ala Ser Ala Ala Ser Ser Ala
        35                  40                  45

Asp Met Asp Ile Val Ala Ala Gly Gln Ile Gly Ala Val Asn Asp Glu
    50                  55                  60

Ser Trp Val Ala Val Asp Leu Ser Asp Ser Asp Asp Ala Pro Ala Ala
65              70                  75                  80

Gly Asp Val Gln Gly Ala Leu Asp Asp Arg Pro Val Phe Arg Thr Glu
                85                  90                  95

Lys Ile Lys Gly Val Leu Leu His Pro Tyr Arg Val Leu Ile Phe Val
            100                 105                 110

Arg Leu Ile Ala Phe Thr Leu Phe Val Ile Trp Arg Ile Glu His Lys
        115                 120                 125

Asn Pro Asp Ala Met Trp Leu Trp Val Thr Ser Ile Ala Gly Glu Phe
    130                 135                 140

Trp Phe Gly Phe Ser Trp Leu Leu Asp Gln Leu Pro Lys Leu Asn Pro
145             150                 155                 160

Ile Asn Arg Val Pro Asp Leu Ala Val Leu Arg Arg Arg Phe Asp His
                165                 170                 175

Ala Asp Gly Thr Ser Ser Leu Pro Gly Leu Asp Ile Phe Val Thr Thr
            180                 185                 190

Ala Asp Pro Ile Lys Glu Pro Ile Leu Ser Thr Ala Asn Ser Ile Leu
        195                 200                 205

Ser Ile Leu Ala Ala Asp Tyr Pro Val Asp Arg Asn Thr Cys Tyr Leu
    210                 215                 220

Ser Asp Asp Ser Gly Met Leu Leu Thr Tyr Glu Ala Met Ala Glu Ala
225             230                 235                 240
```

-continued

```
Ala Lys Phe Ala Thr Leu Trp Val Pro Phe Cys Arg Lys His Ala Ile
            245                 250                 255

Glu Pro Arg Gly Pro Glu Ser Tyr Phe Glu Leu Lys Ser His Pro Tyr
            260                 265                 270

Met Gly Arg Ala Gln Glu Glu Phe Val Asn Asp Arg Arg Arg Val Arg
            275                 280                 285

Lys Glu Tyr Asp Asp Phe Lys Ala Arg Ile Asn Gly Leu Glu His Asp
        290                 295                 300

Ile Lys Gln Arg Ser Asp Ser Tyr Asn Ala Ala Ala Gly Val Lys Asp
305                 310                 315                 320

Gly Glu Pro Arg Ala Thr Trp Met Ala Asp Gly Ser Gln Trp Glu Gly
            325                 330                 335

Thr Trp Ile Glu Gln Ser Glu Asn His Arg Lys Gly Asp His Ala Gly
            340                 345                 350

Ile Val Leu Val Leu Leu Asn His Pro Ser His Ala Arg Gln Leu Gly
            355                 360                 365

Pro Pro Ala Ser Ala Asp Asn Pro Leu Asp Phe Ser Gly Val Asp Val
        370                 375                 380

Arg Leu Pro Met Leu Val Tyr Val Ala Arg Glu Lys Arg Pro Gly Cys
385                 390                 395                 400

Asn His Gln Lys Lys Ala Gly Ala Met Asn Ala Leu Thr Arg Ala Ser
            405                 410                 415

Ala Val Leu Ser Asn Ser Pro Phe Ile Leu Asn Leu Asp Cys Asp His
            420                 425                 430

Tyr Ile Asn Asn Ser Gln Ala Leu Arg Ala Gly Ile Cys Phe Met Leu
            435                 440                 445

Gly Arg Asp Ser Asp Thr Val Ala Phe Val Gln Phe Pro Gln Arg Phe
        450                 455                 460

Glu Gly Val Asp Pro Thr Asp Leu Tyr Ala Asn His Asn Arg Ile Phe
465                 470                 475                 480

Phe Asp Gly Thr Leu Arg Ala Leu Asp Gly Leu Gln Gly Pro Ile Tyr
            485                 490                 495

Val Gly Thr Gly Cys Leu Phe Arg Arg Ile Thr Leu Tyr Gly Phe Glu
            500                 505                 510

Pro Pro Arg Ile Asn Val Gly Gly Pro Cys Phe Pro Arg Leu Gly Gly
            515                 520                 525

Met Phe Ala Lys Asn Arg Tyr Gln Lys Pro Gly Phe Glu Met Thr Lys
            530                 535                 540

Pro Gly Ala Lys Pro Val Ala Pro Pro Pro Ala Ala Thr Val Ala Lys
545                 550                 555                 560

Gly Lys His Gly Phe Leu Pro Met Pro Lys Lys Ala Tyr Gly Lys Ser
            565                 570                 575

Asp Ala Phe Ala Asp Thr Ile Pro Arg Ala Ser His Pro Ser Pro Tyr
            580                 585                 590

Ala Ala Glu Ala Ala Val Ala Ala Asp Glu Ala Ala Ile Ala Glu Ala
            595                 600                 605

Val Met Val Thr Ala Ala Ala Tyr Glu Lys Lys Thr Gly Trp Gly Ser
            610                 615                 620

Asp Ile Gly Trp Val Tyr Gly Thr Val Thr Glu Asp Val Val Thr Gly
625                 630                 635                 640

Tyr Arg Met His Ile Lys Gly Trp Arg Ser Arg Tyr Cys Ser Ile Tyr
            645                 650                 655
```

-continued

```
Pro His Ala Phe Ile Gly Thr Ala Pro Ile Asn Leu Thr Glu Arg Leu
            660                 665                 670

Phe Gln Val Leu Arg Trp Ser Thr Gly Ser Leu Glu Ile Phe Phe Ser
            675                 680                 685

Arg Asn Asn Pro Leu Phe Gly Ser Thr Phe Leu His Pro Leu Gln Arg
        690                 695                 700

Val Ala Tyr Ile Asn Ile Thr Thr Tyr Pro Phe Thr Ala Leu Phe Leu
705                 710                 715                 720

Ile Phe Tyr Thr Thr Val Pro Ala Leu Ser Phe Val Thr Gly His Phe
                725                 730                 735

Ile Val Gln Arg Pro Thr Thr Met Phe Tyr Val Tyr Leu Ala Ile Val
                740                 745                 750

Leu Gly Thr Leu Leu Ile Leu Ala Val Leu Glu Val Lys Trp Ala Gly
            755                 760                 765

Val Thr Val Phe Glu Trp Phe Arg Asn Gly Gln Phe Trp Met Thr Ala
            770                 775                 780

Ser Cys Ser Ala Tyr Leu Ala Ala Val Leu Gln Val Val Thr Lys Val
785                 790                 795                 800

Val Phe Arg Arg Asp Ile Ser Phe Lys Leu Thr Ser Lys Leu Pro Ala
                805                 810                 815

Gly Asp Glu Lys Lys Asp Pro Tyr Ala Asp Leu Tyr Val Val Arg Trp
                820                 825                 830

Thr Trp Leu Met Ile Thr Pro Ile Ile Ile Leu Val Asn Ile Ile
            835                 840                 845

Gly Ser Ala Val Ala Phe Ala Lys Val Leu Asp Gly Glu Trp Thr His
            850                 855                 860

Trp Leu Lys Val Ala Gly Gly Val Phe Phe Asn Phe Trp Val Leu Phe
865                 870                 875                 880

His Leu Tyr Pro Phe Ala Lys Gly Ile Leu Gly Lys His Gly Lys Thr
                885                 890                 895

Pro Val Val Val Leu Val Trp Trp Ala Phe Thr Phe Val Ile Thr Ala
                900                 905                 910

Val Leu Tyr Ile Asn Ile Pro His Ile His Gly Pro Gly Arg His Gly
            915                 920                 925

Ala Ala Ser Pro Ser His Gly His His Ser Ala His Gly Thr Lys Lys
            930                 935                 940

Tyr Asp Phe Thr Tyr Ala Trp Pro
945                 950
```

```
<210> SEQ ID NO 6
<211> LENGTH: 2859
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggcgccgg ctgtcgcggg aggcggtggc cgtcgaaata atgaaggagt caacggcaac      60
gccgcagctc cagcctgcgt atgcggcttt ccggtttgcg catgcgccgg ggctgccgct     120
gttgctagtg cggcctcttc cgctgatatg gacattgtgg cggccggcca gatcggcgcg     180
gtcaacgacg aatcatgggt cgccgtcgat ctgagcgata gtgacgacgc cccggcggcg     240
ggtgatgtac aaggcgctct cgatgaccgt ccggtgttta gaacagagaa aattaaaggc     300
gttctccttc acccgtatag agtgcttatt tttgtacggc tgatcgcgtt tacgctttc      360
```

```
gtcatctgga ggatagagca taagaacccg gatgcgatgt ggctgtgggt tacatctata    420
gcaggtgaat tttggtttgg tttttcttgg cttcttgatc agctcccgaa acttaatcct    480
ataaacagag ttccagactt ggctgtattg cggagacgat tcgatcatgc ggatggtact    540
tcgtcattac ccggactgga tatcttcgtt acaacagctg atccaattaa agagcctatt    600
ttgagcactg cgaacagtat cctgtcaatt ttagctgccg attatccggt tgatcggaac    660
acatgttatc ttagcgatga ttcaggaatg ctgctcacat atgaagcaat ggctgaggca    720
gctaaatttg ccacattatg ggtgccgttt tgtcgtaaac atgctattga gccgagggga    780
ccggaaagct attttgaatt aaaatctcat ccttatatgg gtagggcaca ggaagaattt    840
gttaacgatc gtcgaagggt aaggaaagaa tatgatgatt ttaaagcacg gattaacggc    900
ttagaacacg atatcaaaca acgctcagat tcatacaacg cggcagcagg tgttaaagac    960
ggggaaccac gtgctacatg gatggcagat ggctcacagt gggaagggac atggatcgaa   1020
caatcggaaa atcatcgaaa aggcgatcac gcaggtatg tgcttgttct gttaaatcat   1080
ccttcacatg cacgtcaatt aggaccaccg gcaagcgcag ataatccttt ggacttttcc   1140
ggagttgacg ttaggttacc tatgcttgta tacgtagccc gtgaaaaacg gcccggatgc   1200
aaccaccaaa aaaaagcggg agcaatgaac gcgttgacgc gcgcttccgc ggtcctcagc   1260
aattctccgt ttatacttaa tctggactgc gatcactaca ttaacaactc acaagcgctt   1320
cgtgcaggga tatgctttat gttgggacgt gatagtgaca cagtggcttt cgtgcaattt   1380
ccgcaaagat ttgaaggcgt agatccgacc gacctgtacg caaaccacaa tagaattttt   1440
tttgatggta ccctgagagc tttagatggg ttacaggggc cgatttatgt tggtacgggc   1500
tgcttgttta gacgcataac cttatatggt ttcgaaccgc cgagaatcaa tgttggtggc   1560
ccctgctttc ctcgcctcgg tgggatgttt gccaagaatc ggtatcagaa gcctggcttc   1620
gagatgacta agccgggagc gaaacccgtt gcacctccac cggctgctac agtagccaag   1680
gggaagcatg gctttttacc gatgccgaaa aaagcgtatg ggaaaagcga cgcatttgcg   1740
gatacaattc ctagagcgtc acaccctagt ccgtatgccg ccgaagcagc tgttgccgcc   1800
gacgaggctg caattgccga agcggtgatg gtcacagctg ccgcttatga gaaaaagacg   1860
ggttgggggt cagacatcgg ctgggtttac ggaacagtta cagaggatgt cgttactgga   1920
tatagaatgc acatcaaagg ctggcggtca cgctactgta gcatctaccc gcatgcattc   1980
atcggtaccg ctccgattaa tttgacagaa cgactgtttc aagtcttacg ctggagcaca   2040
ggatctttgg aaatcttctt ctctagaaat aatccgttat tcggtagcac attcctccat   2100
ccattgcaga gggttgcgta tattaatatc accacctatc catttactgc actgtttctt   2160
attttttata caacagtccc ggcgctgtct tttgtcacgg tcacttcat tgtacaacgc   2220 ccgacaacga tgttttacgt gtatctcgca atagtactgg gcacgctgct gatcttagcc   2280
gtcttagaag ttaagtgggc tggggtaacg gtattcgaat ggttccgcaa cggacaattt   2340
tggatgacgg catcttgttc agcttatttta gctgctgtcc ttcaagtcgt tacgaaggtt   2400
gtgtttcgcc gggacatttc gtttaaactg acatcgaaat tgcccgctgg ggatgaaaag   2460
aaagatccat atgcggatct ttacgtcgtg cggtggacct ggttaatgat tacgccgatc   2520
attatcatcc tcgttaacat catcggctct gcagtcgcgt tcgctaaagt gcttgatgga   2580
gaatggaccc attggttaaa agtggcgggc ggcgtctttt ttaacttctg ggtcttgttt   2640
catttatacc ctttcgcaaa gggaatttta ggcaagcatg ggaaaacgcc tgttgtggtc   2700
```

```
ctggtttggt gggctttcac ctttgttatt acagcggttc tttacatcaa catccctcat      2760
atccatgggc cgggaagaca tggcgccgca agcccgtctc atggacatca ttctgcacat      2820
ggcacaaaaa aatatgattt cacgtacgca tggccataa                           2859
```

<210> SEQ ID NO 7
<211> LENGTH: 276
<212> TYPE: PRT
<213> ORGANISM: Saccharomyces cerevisiae

<400> SEQUENCE: 7

```
Met Arg Leu Gln Arg Asn Ser Ile Ile Cys Ala Leu Val Phe Leu Val
1               5                   10                  15

Ser Phe Val Leu Gly Asp Val Asn Ile Val Ser Pro Ser Ser Lys Ala
            20                  25                  30

Thr Phe Ser Pro Ser Gly Gly Thr Val Ser Val Pro Val Glu Trp Met
        35                  40                  45

Asp Asn Gly Ala Tyr Pro Ser Leu Ser Lys Ile Ser Thr Phe Thr Phe
    50                  55                  60

Ser Leu Cys Thr Gly Pro Asn Asn Asn Ile Asp Cys Val Ala Val Leu
65                  70                  75                  80

Ala Ser Lys Ile Thr Pro Ser Glu Leu Thr Gln Asp Asp Lys Val Tyr
                85                  90                  95

Ser Tyr Thr Ala Glu Phe Ala Ser Thr Leu Thr Gly Asn Gly Gln Tyr
            100                 105                 110

Tyr Ile Gln Val Phe Ala Gln Val Asp Gly Gln Gly Tyr Thr Ile His
        115                 120                 125

Tyr Thr Pro Arg Phe Gln Leu Thr Ser Met Gly Gly Val Thr Ala Tyr
    130                 135                 140

Thr Tyr Ser Ala Thr Thr Glu Pro Thr Pro Gln Thr Ser Ile Gln Thr
145                 150                 155                 160

Thr Thr Thr Asn Asn Ala Gln Ala Thr Thr Ile Asp Ser Arg Ser Phe
                165                 170                 175

Thr Val Pro Tyr Thr Lys Gln Thr Gly Thr Ser Arg Phe Ala Pro Met
            180                 185                 190

Gln Met Gln Pro Asn Thr Lys Val Thr Ala Thr Thr Trp Thr Arg Lys
        195                 200                 205

Phe Ala Thr Ser Ala Val Thr Tyr Tyr Ser Thr Phe Gly Ser Leu Pro
    210                 215                 220

Glu Gln Ala Thr Thr Ile Thr Pro Gly Trp Ser Tyr Thr Ile Ser Ser
225                 230                 235                 240

Gly Val Asn Tyr Ala Thr Pro Ala Ser Met Pro Ser Asp Asn Gly Gly
                245                 250                 255

Trp Tyr Lys Pro Ser Lys Arg Leu Ser Leu Ser Ala Arg Lys Ile Asn
            260                 265                 270

Met Arg Lys Val
        275
```

<210> SEQ ID NO 8
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

-continued

```
atgcggcttc aacgtaacag tatcatttgt gccttagttt ttttagtatc ttttgtcttg      60
ggtgatgtca acattgtgtc gccgtcaagc aaagctacat tttctccaag tggcggcaca     120
gtgtccgttc ctgtcgaatg gatggacaac ggagcttatc cgagcctttc aaaaatttct     180
acatttacat ttagtctgtg cacgggtcca aataataata ttgattgtgt tgctgtcctg     240
gcaagtaaaa taacgcctag cgaattaact caggatgaca aagtttattc ttatacggct     300
gaatttgctt caacgttgac cgggaatggt caatactata tccaagtatt tgcccaggta     360
gatggccaag gctacacaat ccattacacg ccgcggttcc agctcacgtc aatggggggc     420
gtgacagcgt acacatatag tgcaacgacc gaacctacac cccagactag tattcaaaca     480
acaacgacaa ataatgcgca ggcaactacc atagattccc ggtccttcac agtcccttat     540
actaaacaaa cgggcacttc acgctttgcg cctatgcaga tgcagccgaa tactaaagtg     600
accgcgacaa cgtggacgag gaaattcgcc acctcagcag ttacctatta ctctactttt     660
ggatcgttgc ctgaacaagc aacaacaatt acacccggct ggtcgtatac tatatcaagc     720
ggggtaaact atgcgacacc tgctagtatg cctagcgata acggaggttg gtataagcca     780
agcaaacgat tgagcctttc agcgcggaaa attaacatgc gaaaagtttg a             831
```

<210> SEQ ID NO 9
<211> LENGTH: 584
<212> TYPE: PRT
<213> ORGANISM: Paraburkholderia acidophila

<400> SEQUENCE: 9

```
Met Leu Met Lys Arg Leu Phe Ala Ala Ser Leu Met Leu Ala Phe Ser
1               5                   10                  15

Ser Val Ser Ser Val Arg Ala Glu Glu Ala Val Lys Pro Gly Ala Pro
            20                  25                  30

Trp Trp Lys Ser Ala Val Phe Tyr Gln Val Tyr Pro Arg Ser Phe Lys
        35                  40                  45

Asp Thr Asn Gly Asp Gly Ile Gly Asp Phe Lys Gly Leu Thr Glu Lys
    50                  55                  60

Leu Asp Tyr Leu Lys Gly Leu Gly Ile Asp Ala Ile Trp Ile Asn Pro
65                  70                  75                  80

His Tyr Ala Ser Pro Asn Thr Asp Asn Gly Tyr Asp Ile Ser Asp Tyr
                85                  90                  95

Arg Glu Val Met Lys Glu Tyr Gly Thr Met Glu Asp Phe Asp Arg Leu
            100                 105                 110

Met Ala Glu Leu Lys Lys Arg Gly Met Arg Leu Met Val Asp Val Val
        115                 120                 125

Ile Asn His Ser Ser Asp Gln His Glu Trp Phe Lys Ser Ser Arg Ala
    130                 135                 140

Ser Lys Asp Asn Pro Tyr Arg Asp Tyr Tyr Phe Trp Arg Asp Gly Lys
145                 150                 155                 160

Asp Gly His Glu Pro Asn Asn Tyr Pro Ser Phe Phe Gly Gly Ser Ala
                165                 170                 175

Trp Glu Lys Asp Pro Val Thr Gly Gln Tyr Tyr Leu His Tyr Phe Gly
            180                 185                 190

Arg Gln Gln Pro Asp Leu Asn Trp Asp Thr Pro Lys Leu Arg Glu Glu
        195                 200                 205

Leu Tyr Ala Met Leu Arg Phe Trp Leu Asp Lys Gly Val Ser Gly Met
    210                 215                 220

Arg Phe Asp Thr Val Ala Thr Tyr Ser Lys Thr Pro Gly Phe Pro Asp
```

-continued

```
225                 230                 235                 240

Leu Thr Pro Glu Gln Met Lys Asn Phe Ala Glu Ala Tyr Thr Gln Gly
                245                 250                 255

Pro Asn Leu His Arg Tyr Leu Gln Glu Met His Glu Lys Val Phe Asp
                260                 265                 270

His Tyr Asp Ala Val Thr Ala Gly Glu Ile Phe Gly Ala Pro Leu Asn
                275                 280                 285

Gln Val Pro Leu Phe Ile Asp Ser Arg Arg Lys Glu Leu Asp Met Ala
                290                 295                 300

Phe Thr Phe Asp Leu Ile Arg Tyr Asp Arg Ala Leu Asp Arg Trp His
305                 310                 315                 320

Thr Ile Pro Arg Thr Leu Ala Asp Phe Arg Gln Thr Ile Asp Lys Val
                325                 330                 335

Asp Ala Ile Ala Gly Glu Tyr Gly Trp Asn Thr Phe Phe Leu Gly Asn
                340                 345                 350

His Asp Asn Pro Arg Ala Val Ser His Phe Gly Asp Asp Arg Pro Gln
                355                 360                 365

Trp Arg Glu Ala Ser Ala Lys Ala Leu Ala Thr Val Thr Leu Thr Gln
                370                 375                 380

Arg Gly Thr Pro Phe Ile Phe Gln Gly Asp Glu Leu Gly Met Thr Asn
385                 390                 395                 400

Tyr Pro Phe Lys Thr Leu Gln Asp Phe Asp Asp Ile Glu Val Lys Gly
                405                 410                 415

Phe Phe Gln Asp Tyr Val Glu Thr Gly Lys Ala Thr Ala Glu Glu Leu
                420                 425                 430

Leu Thr Asn Val Ala Leu Thr Ser Arg Asp Asn Ala Arg Thr Pro Phe
                435                 440                 445

Gln Trp Asp Asp Ser Ala Asn Ala Gly Phe Thr Thr Gly Lys Pro Trp
                450                 455                 460

Leu Lys Val Asn Pro Asn Tyr Thr Glu Ile Asn Ala Ala Arg Glu Ile
465                 470                 475                 480

Gly Asp Pro Lys Ser Val Tyr Ser Phe Tyr Arg Asn Leu Ile Ser Ile
                485                 490                 495

Arg His Glu Thr Pro Ala Leu Ser Thr Gly Ser Tyr Arg Asp Ile Asp
                500                 505                 510

Pro Ser Asn Ala Asp Val Tyr Ala Tyr Thr Arg Ser Gln Asp Gly Glu
                515                 520                 525

Thr Tyr Leu Val Val Val Asn Phe Lys Ala Glu Pro Arg Ser Phe Thr
                530                 535                 540

Leu Pro Asp Gly Met His Ile Ala Glu Thr Leu Ile Glu Ser Ser Ser
545                 550                 555                 560

Pro Ala Ala Pro Ala Ala Gly Ala Ala Ser Leu Glu Leu Gln Pro Trp
                565                 570                 575

Gln Ser Gly Ile Tyr Lys Val Lys
                580
```

<210> SEQ ID NO 10
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

-continued

```
atgctgatga agagattatt cgcggccagc ttaatgctgg ccttcagttc agtatcaagt          60
gttagagcag aggaagcagt aaaacctgga gcgccgtggt ggaagtcagc agttttttat         120
caagtttatc ctaggagttt taaggataca aatggtgatg ggattggcga ctttaagggt         180
cttacggaga aacttgacta tcttaaaggc cttggaatcg atgcgatctg gataaatcct         240
cattatgcat cccctaacac ggataatggc tatgatatta gcgactatcg tgaagtaatg         300
aaagagtatg ggacgatgga ggatttcgac cggctgatgg cggagctgaa aaaacgcggc         360
atgcgcctta tggtagatgt agtgatcaac cattcatctg atcagcacga atggttcaaa         420
tcctctcgtg ccagtaaaga taatccgtat cgtgattact attttttggcg tgatggaaaa         480 gacggtcatg aacctaataa ttatccttct ttcttcggcg gctcagcatg ggaaaaggat         540
ccggttaccg ggcaatacta tctccattac ttcggaagac agcagccaga cttgaactgg         600
gatacaccga aactgcggga ggagctgtat gcgatgcttc gtttctggct ggataaaggc         660
gtctctggaa tgcggtttga tacggtggcc acatattcta aaacgccggg atttccggac         720
ctgacgcctg agcagatgaa aaactttgcc gaagcttata cccagggtcc gaacctccac         780
cggtatctgc aagaaatgca tgaaaaagtg tttgatcatt atgacgcggt caccgctggg         840 gagattttg gcgcgccgct taaccaagtt ccgctgtttta ttgattcaag aagaaaagag         900
cttgatatgg ctttcacttt cgacttgatt agatacgacc gtgctttaga ccggtggcat         960
acaattccgc gcacgttagc tgatttccgt cagacgatcg acaaggtgga tgccatagcc        1020
ggcgaatacg gctggaatac attttttcttg gggaaccatg acaaccctcg cgcagtgagc        1080
cattttggtg acgatagacc tcagtggaga gaagcgagcg ctaaagcact cgccacagtc        1140
acgctgaccc agcgcggcac gccttttatt tttcaagggg atgaattagg gatgacgaat        1200 tacccttta aaacgcttca ggattttgat gacatcgaag tcaaaggatt cttccaagac        1260
tatgttgaaa cagggaaagc tactgctgaa gagctttga caaacgttgc gcttacgtca        1320
agggataatg cccgaacgcc ttttcaatgg gacgatagtg caaatgcggg atttaccacc        1380
ggcaagccat ggctgaaagt taacccgaat tacaccgaaa tcaatgccgc gcgtgaaatt        1440
ggagatccca gagcgtcta tagctttttat agaaacctga tttctatacg tcacgaaaca        1500
ccggcgttgt caactgggtc ctatcgagac attgatccta gcaacgccga tgtgtacgcg        1560
tatacgcggt cacaggacgg agagacatat ttggtagtcg ttaattttaa ggcagagccc        1620
cggtctttta ccttaccgga tggtatgcat attgcggaaa cactgattga gtcctcttcc        1680
ccggcggctc cggcagccgg cgcagcctct ctggagctcc agccgtggca gagtggtatt        1740
tacaaggtta aataa                                                         1755
```

<210> SEQ ID NO 11
<211> LENGTH: 797
<212> TYPE: PRT
<213> ORGANISM: Lactobacillus johnsonii

<400> SEQUENCE: 11

```
Met Leu Glu Asn Lys Asn His Lys Lys Ile Ser Leu Ser Gly Lys Ser
1               5                   10                  15

Leu Leu Met Gly Thr Leu Ser Thr Ala Ala Ile Val Leu Ser Ala Ser
            20                  25                  30

Thr Ala Asn Ala Ala Thr Ile Asn Ala Asp Asn Val Asn Glu Asn Gln
        35                  40                  45

Thr Val Glu Val Thr Ala Ser Ser Val Asn Asn Glu Asn Asn Lys Gln
    50                  55                  60
```

```
Val Thr Glu Lys Asp Ser Ala Asp Lys Ser Thr Ser Asp Val Ala Glu
65              70                  75                  80

Asp Ala Asn Thr Lys Lys Ser Asn Glu Asn Thr Glu Thr Thr Glu Lys
                85                  90                  95

Asn Thr Gln Thr Val Val Thr Asn Ala Pro Val Ser Asp Val Lys Asn
            100                 105                 110

Thr Asn Thr Val Thr Ala Glu Thr Pro Val Asp Lys Val Val Asn Asn
            115                 120                 125

Ser Asp Gln Lys Thr Thr Asn Ala Ala Thr Thr Asp Thr Lys Lys Asp
    130                 135                 140

Asp Val Lys Gln Val Glu Lys Lys Asp Ser Val Asp Lys Thr Asn Ala
145                 150                 155                 160

Glu Glu Asn Lys Asp Ser Ser Val Lys Pro Ala Glu Asn Ala Thr Lys
                165                 170                 175

Ala Glu Leu Lys Gly Gln Val Lys Asp Ile Val Glu Glu Ser Gly Val
            180                 185                 190

Asp Thr Ser Lys Leu Thr Asn Asp Gln Ile Asn Glu Leu Asn Lys Ile
            195                 200                 205

Asn Phe Ser Lys Glu Ala Lys Ser Gly Thr Gln Leu Thr Tyr Asn Asp
    210                 215                 220

Phe Lys Lys Ile Ala Lys Thr Leu Ile Glu Gln Asp Ala Arg Tyr Ala
225                 230                 235                 240

Ile Pro Phe Phe Asn Ala Ser Lys Ile Lys Asn Met Pro Ala Ala Lys
                245                 250                 255

Thr Leu Asp Ala Gln Ser Gly Lys Val Glu Asp Leu Glu Ile Trp Asp
            260                 265                 270

Ser Trp Pro Val Gln Asp Ala Lys Thr Gly Tyr Val Ser Asn Trp Asn
            275                 280                 285

Gly Tyr Gln Leu Val Ile Gly Met Met Gly Val Pro Asn Val Asn Asp
    290                 295                 300

Asn His Ile Tyr Leu Leu Tyr Asn Lys Tyr Gly Asp Asn Asp Phe Asn
305                 310                 315                 320

His Trp Lys Asn Ala Gly Pro Ile Phe Gly Leu Gly Thr Pro Val Ile
                325                 330                 335

Gln Gln Trp Ser Gly Ser Ala Thr Leu Asn Lys Asp Gly Ser Ile Gln
            340                 345                 350

Leu Tyr Tyr Thr Lys Val Asp Thr Ser Asp Asn Asn Thr Asn His Gln
            355                 360                 365

Lys Leu Ala Ser Ala Thr Val Tyr Leu Asn Leu Glu Lys Asp Gln Asp
    370                 375                 380

Lys Ile Ser Ile Ala His Val Asp Asn Asp His Ile Val Phe Glu Gly
385                 390                 395                 400

Asp Gly Tyr His Tyr Gln Thr Tyr Asp Gln Trp Lys Glu Thr Asn Lys
                405                 410                 415

Gly Ala Asp Asn Ile Ala Met Arg Asp Ala His Val Ile Asp Asp Asp
            420                 425                 430

Asn Gly Asn Arg Tyr Leu Val Phe Glu Ala Ser Thr Gly Thr Glu Asn
            435                 440                 445

Tyr Gln Gly Asp Asp Gln Ile Tyr Gln Trp Leu Asn Tyr Gly Gly Thr
    450                 455                 460

Asn Lys Asp Asn Leu Gly Asp Phe Phe Gln Ile Leu Ser Asn Ser Asp
465                 470                 475                 480
```

-continued

```
Ile Lys Asp Arg Ala Lys Trp Ser Asn Ala Ala Ile Gly Ile Ile Lys
            485                 490                 495

Leu Asn Asp Asp Val Lys Asn Pro Ser Val Ala Lys Val Tyr Ser Pro
            500                 505                 510

Leu Ile Ser Ala Pro Met Val Ser Asp Glu Ile Glu Arg Pro Asp Val
            515                 520                 525

Val Lys Leu Gly Asn Lys Tyr Tyr Leu Phe Ala Ala Thr Arg Leu Asn
        530                 535                 540

Arg Gly Ser Asn Asp Asp Ala Trp Met Ala Thr Asn Lys Ala Val Gly
545                 550                 555                 560

Asp Asn Val Ala Met Ile Gly Tyr Val Ser Asp Asn Leu Thr His Gly
                565                 570                 575

Tyr Val Pro Leu Asn Glu Ser Gly Val Val Leu Thr Ala Ser Val Pro
            580                 585                 590

Ala Asn Trp Arg Thr Ala Thr Tyr Ser Tyr Tyr Ala Val Pro Val Glu
            595                 600                 605

Gly Arg Asp Asp Gln Leu Leu Ile Thr Ser Tyr Ile Thr Asn Arg Gly
        610                 615                 620

Glu Val Ala Gly Lys Gly Met His Ala Thr Trp Ala Pro Ser Phe Leu
625                 630                 635                 640

Leu Gln Ile Asn Pro Asp Asn Thr Thr Thr Val Leu Ala Lys Met Thr
                645                 650                 655

Asn Gln Gly Asp Trp Ile Trp Asp Asp Ser Ser Glu Asn Pro Asp Met
                660                 665                 670

Met Gly Val Leu Glu Lys Asp Ala Pro Asn Ser Ala Ala Leu Pro Gly
            675                 680                 685

Glu Trp Gly Lys Pro Val Asp Trp Asp Leu Ile Gly Gly Tyr Asn Leu
        690                 695                 700

Lys Pro His Gln Pro Val Thr Pro Ile Pro Asn Val Pro Thr Thr Pro
705                 710                 715                 720

Glu Thr Pro Thr Thr Pro Asp Lys Pro Glu Val Pro Thr Thr Pro Glu
                725                 730                 735

Val Pro Thr Thr Pro Glu Thr Pro Thr Pro Glu Ala Pro Lys Asn Pro
            740                 745                 750

Val Lys Lys Thr Ser Gln Ser Lys Leu Pro Lys Ala Gly Asp Lys Asn
            755                 760                 765

Ser Phe Ala Ala Val Val Leu Gly Ala Val Ser Ser Ile Leu Gly Ala
            770                 775                 780

Val Gly Leu Thr Gly Val Ser Lys Arg Lys Arg Asn Asn
785                 790                 795
```

```
<210> SEQ ID NO 12
<211> LENGTH: 2394
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgttagaaa acaagaatca taagaagatt agccttagtg gaaaatcact tttgatggga       60
actttatcaa cagccgctat tgtactgagc gccagcacag caaacgctgc aacaattaat      120
gcagataacg ttaacgaaaa tcaaaccgtt gaagtaacgg catcctccgt gaataacgaa      180
aataataagc aggtgactga aaaagatagc gcggataaat caacttcaga cgttgccgag      240
```

```
gacgccaaca caaaaaaatc taatgaaaac acagaaacga cagagaaaaa tacacaaact      300
gttgtaacaa acgctccggt gagtgatgta aagaacacga atacggttac agcagaaaca      360
ccggttgata aggtggttaa caactctgac cagaaaacaa ctaatgcagc gacaacagat      420
acaaaaaaag acgacgtgaa acaagtagag aaaaaagatt ccgtggataa gaccaacgct      480
gaagaaaata aggactcctc agtaaagcct gctgaaaacg ctacaaaggc agaattgaaa      540
gggcaggtaa aagatatcgt tgaggaaagc ggagtcgaca cgagtaaact taccaatgat      600
caaattaacg agctgaacaa aattaacttt agcaagagg caaaaagcgg aacgcaattg       660
acatataatg attttaaaaa gatcgccaaa acccttattg aacaagatgc ccgctatgcc      720
atcccttttt ttaatgcaag taaaattaaa aatatgccag cagctaaaac actcgacgca      780
caaagcggca aagtggaaga tcttgaaatt tgggattctt ggccggtgca ggacgcgaaa      840
acgggctacg tgagtaactg gaatgggtac cagctggtca ttggaatgat gggagttccg      900
aatgtcaacg ataatcatat ttacctcctg tataataaat atggtgacaa cgactttaat      960
cattggaaaa acgcgggccc tattttcggc ctgggaacac cagtgatcca acaatggtcc      1020
ggatcagcca cacttaataa agacggatcg atacagcttt actacactaa ggtagacaca      1080
agcgataata atacaaatca tcaaaaactg gccagtgcta cagtctactt aaatttggaa      1140
aaagatcaag acaagataag tattgcacac gtggataatg accacatcgt gtttgaagga      1200
gacggttacc actatcagac atacgatcaa tggaaggaaa ccaataaagg cgcagacaat      1260
atcgcaatgc gcgatgcaca cgtcatagac gacgataacg ggaatcgcta tctcgtgttc      1320
gaagcgagta ccggaacaga aaactatcag ggtgatgacc agatttatca atggttgaat      1380
tatggaggca ctaacaaaga taaccttggt gactttttc aaatcttaag caactcagat       1440
atcaaagatc gcgcaaaatg gtccaatgca gccatcggca tcattaaatt aaatgatgat      1500
gtcaagaatc cttctgtcgc caaggtctat tcaccgttga tttcagcgcc tatggtatct      1560
gatgagatcg aacggccgga tgtcgtgaag ttaggaaata aatattatct gtttgctgcc      1620
acgcggttaa acagaggcag caacgatgat gcttggatgg caacaaacaa agcagtgggg      1680
gacaatgtgg caatgattgg gtatgtatct gacaacctta cccatggcta tgtaccgctt      1740
aatgaatctg gagtagtcct taccgcgtca gttcctgcga attggcgcac ggccacctac      1800
tcttattatg cggtccctgt cgaagggcgc gatgatcaat tgctgatcac atcttatatt      1860
accaatagag gtgaggttgc cggtaaagga atgcatgcca cgtgggcacc cagctttttg      1920
cttcagatca acccggacaa tacgaccaca gttctggcaa agatgacgaa ccaggggggac      1980 tggatatggg acgatagcag tgaaaaccct gacatgatgg gcgtattaga aaaagacgcc      2040
cctaattcag cagcactccc gggcgagtgg ggcaaaccag ttgactggga tctgattggt      2100
gggtacaacc tcaaaccaca tcaacctgtc acacctatac cgaacgtgcc aactacgccg      2160
gaaacaccta caacgcctga taaaccagaa gtaccaacta ccccagaagt cccgacaaca      2220
ccggaaacac cgaccccgga agcccctaaa aaccctgtca aaaagacgtc acagtcgaaa      2280
cttcctaaag cgggtgataa gaattctttt gccgcggttg ttttaggggc agtctcaagc      2340
attctgggcg ccgtgggcct cacgggcgtt tctaaaagaa aacgtaacaa ttaa           2394
```

<210> SEQ ID NO 13
<211> LENGTH: 783
<212> TYPE: PRT
<213> ORGANISM: Oryza sativa
<400> SEQUENCE: 13

-continued

```
Met Ala Pro Asn Leu Ser Lys Ala Lys Asp Asp Leu Ile Gly Asp Val
1               5                   10                  15

Val Ala Val Asp Gly Leu Ile Lys Pro Pro Arg Phe Thr Leu Lys Gly
                20                  25                  30

Lys Asp Leu Ala Val Asp Gly His Pro Phe Leu Leu Asp Val Pro Ala
            35                  40                  45

Asn Ile Arg Leu Thr Pro Ala Ser Thr Leu Val Pro Asn Ser Asp Val
        50                  55                  60

Pro Ala Ala Ala Ala Gly Ser Phe Leu Gly Phe Asp Ala Pro Ala Ala
65                  70                  75                  80

Lys Asp Arg His Val Val Pro Ile Gly Lys Leu Arg Asp Thr Arg Phe
                85                  90                  95

Met Ser Ile Phe Arg Phe Lys Val Trp Trp Thr Thr His Trp Val Gly
            100                 105                 110

Thr Asn Gly Arg Asp Val Glu Asn Glu Thr Gln Met Met Ile Leu Asp
        115                 120                 125

Gln Ser Gly Thr Lys Ser Ser Pro Thr Gly Pro Arg Pro Tyr Val Leu
    130                 135                 140

Leu Leu Pro Ile Val Glu Gly Pro Phe Arg Ala Cys Leu Glu Ser Gly
145                 150                 155                 160

Lys Ala Glu Asp Tyr Val His Met Val Leu Glu Ser Gly Ser Ser Thr
                165                 170                 175

Val Arg Gly Ser Val Phe Arg Ser Ala Val Tyr Leu His Ala Gly Asp
            180                 185                 190

Asp Pro Phe Asp Leu Val Lys Asp Ala Met Arg Val Val Arg Ala His
        195                 200                 205

Leu Gly Thr Phe Arg Leu Met Glu Glu Lys Thr Pro Pro Pro Ile Val
    210                 215                 220

Asp Lys Phe Gly Trp Cys Thr Trp Asp Ala Phe Tyr Leu Lys Val His
225                 230                 235                 240

Pro Glu Gly Val Trp Glu Gly Val Arg Arg Leu Ala Asp Gly Gly Cys
                245                 250                 255

Pro Pro Gly Leu Val Leu Ile Asp Asp Gly Trp Gln Ser Ile Cys His
            260                 265                 270

Asp Asp Asp Asp Leu Gly Ser Gly Ala Glu Gly Met Asn Arg Thr Ser
        275                 280                 285

Ala Gly Glu Gln Met Pro Cys Arg Leu Ile Lys Phe Gln Glu Asn Tyr
    290                 295                 300

Lys Phe Arg Glu Tyr Lys Gly Gly Met Gly Gly Phe Val Arg Glu Met
305                 310                 315                 320

Lys Ala Ala Phe Pro Thr Val Glu Gln Val Tyr Val Trp His Ala Leu
            325                 330                 335

Cys Gly Tyr Trp Gly Gly Leu Arg Pro Gly Ala Pro Gly Leu Pro Pro
            340                 345                 350

Ala Lys Val Val Ala Pro Arg Leu Ser Pro Gly Leu Gln Arg Thr Met
            355                 360                 365

Glu Asp Leu Ala Val Asp Lys Ile Val Asn Asn Gly Val Gly Leu Val
    370                 375                 380

Asp Pro Arg Arg Ala Arg Glu Leu Tyr Glu Gly Leu His Ser His Leu
385                 390                 395                 400

Gln Ala Ser Gly Ile Asp Gly Val Lys Val Asp Val Ile His Leu Leu
            405                 410                 415
```

-continued

```
Glu Met Val Cys Glu Glu Tyr Gly Gly Arg Val Glu Leu Ala Lys Ala
        420             425             430

Tyr Phe Ala Gly Leu Thr Glu Ser Val Arg Arg His Phe Asn Gly Asn
        435             440             445

Gly Val Ile Ala Ser Met Glu His Cys Asn Asp Phe Met Leu Leu Gly
        450             455             460

Thr Glu Ala Val Ala Leu Gly Arg Val Gly Asp Asp Phe Trp Cys Thr
465             470             475             480

Asp Pro Ser Gly Asp Pro Asp Gly Thr Phe Trp Leu Gln Gly Cys His
            485             490             495

Met Val His Cys Ala Tyr Asn Ser Leu Trp Met Gly Ala Phe Ile His
            500             505             510

Pro Asp Trp Asp Met Phe Gln Ser Thr His Pro Cys Ala Ala Phe His
            515             520             525

Ala Ala Ser Arg Ala Val Ser Gly Gly Pro Val Tyr Val Ser Asp Ala
        530             535             540

Val Gly Cys His Asp Phe Asp Leu Leu Arg Arg Leu Ala Leu Pro Asp
545             550             555             560

Gly Thr Ile Leu Arg Cys Glu Arg Tyr Ala Leu Pro Thr Arg Asp Cys
            565             570             575

Leu Phe Ala Asp Pro Leu His Asp Gly Lys Thr Met Leu Lys Ile Trp
            580             585             590

Asn Val Asn Lys Phe Ser Gly Val Leu Gly Ala Phe Asn Cys Gln Gly
            595             600             605

Gly Gly Trp Ser Arg Glu Ala Arg Arg Asn Met Cys Ala Ala Gly Phe
        610             615             620

Ser Val Pro Val Thr Ala Arg Ala Ser Pro Ala Asp Val Glu Trp Ser
625             630             635             640

His Gly Gly Gly Gly Asp Arg Phe Ala Val Tyr Phe Val Glu Ala
            645             650             655

Arg Lys Leu Gln Leu Leu Arg Arg Asp Glu Ser Val Glu Leu Thr Leu
        660             665             670

Glu Pro Phe Thr Tyr Glu Leu Leu Val Val Ala Pro Val Arg Ala Ile
        675             680             685

Val Ser Pro Glu Leu Gly Ile Gly Phe Ala Pro Ile Gly Leu Ala Asn
        690             695             700

Met Leu Asn Ala Gly Gly Ala Val Gln Gly Phe Glu Ala Ala Arg Lys
705             710             715             720

Asp Gly Asp Val Ala Ala Glu Val Ala Val Lys Gly Ala Gly Glu Met
            725             730             735

Val Ala Tyr Ser Ser Ala Arg Pro Arg Leu Cys Lys Val Asn Gly Gln
            740             745             750

Asp Ala Glu Phe Lys Tyr Glu Asp Gly Ile Val Thr Val Asp Val Pro
            755             760             765

Trp Thr Gly Ser Ser Lys Lys Leu Ser Arg Val Glu Tyr Phe Tyr
        770             775             780
```

<210> SEQ ID NO 14
<211> LENGTH: 2352
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

-continued

```
atggctccga atctgagtaa agcaaaggac gatttaattg gagacgtcgt cgcagtggat      60
ggccttatca aacctcctcg gtttacactc aaaggaaaag acctcgccgt tgatggtcac     120
ccgtttctgc tggacgtgcc ggcgaatatc cggttaacac cagcatcaac tcttgtccca     180
aactcggatg ttccggctgc agctgctggg agctttcttg gcttcgatgc acccgcggca     240
aaagatcgtc atgtcgttcc gattgggaaa ctgcgcgata caagatttat gtctatcttt     300
cgttttaaag tctggtggac gacacattgg gttgggacaa atggacggga tgtagagaac     360
gagacccaga tgatgatctt ggatcagtcc ggaacaaagt ctagcccgac tggaccgcgc     420
ccgtatgttc tgcttcttcc gatcgtcgaa ggcccgttta gagcctgttt agaatcgggg     480
aaagccgaag attatgtcca tatggtgctg gaaagtgggt ctagcaccgt acgtggttca     540
gtgtttagaa gcgctgtgta tcttcatgct ggcgatgacc cttttgattt ggtgaaagat     600
gcaatgcgcg tcgtacgtgc gcatttagga acgttccggt tgatggagga aaagacaccg     660
cctccgatcg ttgataagtt tggctggtgc acctgggatg cctttatttt aaaggtacat     720
ccagaaggag tgtgggaagg agtacggaga ttagcagatg gcggctgccc accggggctg     780
gtattaattg acgatggatg gcaatcgatt tgccatgatg atgacgatct tggctcagga     840
gctgaaggaa tgaacagaac aagcgcgggc gagcaaatgc cttgtaggct tattaaattt     900
caggaaaact ataaattcag ggaatacaaa ggtggcatgg gaggcttcgt gcgtgagatg     960
aaagcagcat ttccgaccgt ggagcaagtc tatgtttggc acgcactgtg cggatattgg    1020
ggaggtctcc gtccgggtgc accgggtctg ccgccagcaa aagtggtagc accgcgattg    1080
tccccgggct tacagcggac gatggaagat cttgcggtag ataaaattgt taacaatggc    1140
gtgggccttg tggatcctcg cagagctaga gaactgtatg aaggccttca ttcccacctc    1200
caggccagcg gtatagatgg agtgaaagta gatgttatac accttcttga gatggtttgc    1260
gaggaatacg gggggagagt agaattggct aaagcgtatt tcgcaggact cactgagtca    1320
gttcggaggc attttaacgg aaatggtgtc attgcgtcaa tggagcactg caacgatttt    1380
atgctgctgg gtacagaagc tgtagcatta ggccgggtgg gagatgattt ctggtgtaca    1440
gatccgtctg gtgacccaga tggtacgttc tggttacagg gatgccacat ggtacactgt    1500
gcgtataata gtttatggat gggcgccttt atacatccgg actgggacat gtttcaatct    1560
acacacccct gcgcggcgtt ccatgctgcg agcagagccg tctccggtgg accagtctat    1620
gtatcagatg cggttggctg ccatgatttc gatctgcttc gtaggctcgc actgccggat    1680
ggcacaattt tgcgttgcga acgctatgca ctgccgacaa gagattgtct ttttgcggat    1740
cccttgcatg atggcaaaac aatgttgaaa atatggaacg taaacaaatt ttcaggagtt    1800
ttaggagcat ttaattgcca gggcggagga tggtcacgcg aagctcgtcg caacatgtgc    1860
gcggctggtt ttagtgttcc ggtgactgct cgggcttcac ctgcagacgt tgagtggtca    1920
cacggaggcg tggtggagga tcgtttttgcc gtttatttcg tggaggctcg caaacttcaa    1980
ttactgcgtc gcgacgaaag cgtggaactg acattagaac cgtttacata tgagctgtta    2040
gtcgtggccc ccgtgagagc tatcgtgtca ccagaattag gtatcggctt cgcaccgatt    2100
ggcctcgcta atatgctgaa cgccggcggg gcggttcagg gttttgaagc cgcccgtaag    2160
gatggagatg tggctgctga ggtggctgtc aaagggcgg gtgaaatggt cgcatactct    2220
agtgcgagac caaggttatg caaggtaaac ggacaggacg ccgaatttaa atatgaagac    2280
ggaattgtca cagtagacgt cccttggaca ggatcctcca aaaaacttag cagggtagaa    2340
```

-continued

```
tatttctatt ag                                                                        2352
```

<210> SEQ ID NO 15
<211> LENGTH: 584
<212> TYPE: PRT
<213> ORGANISM: Gluconacetobacter diazotrophicus

<400> SEQUENCE: 15

```
Met Ala His Val Arg Arg Lys Val Ala Thr Leu Asn Met Ala Leu Ala
1               5                   10                  15

Gly Ser Leu Leu Met Val Leu Gly Ala Gln Ser Ala Leu Ala Gln Gly
                20                  25                  30

Asn Phe Ser Arg Gln Glu Ala Ala Arg Met Ala His Arg Pro Gly Val
                35                  40                  45

Met Pro Arg Gly Gly Pro Leu Phe Pro Gly Arg Ser Leu Ala Gly Val
        50                  55                  60

Pro Gly Phe Pro Leu Pro Ser Ile His Thr Gln Gln Ala Tyr Asp Pro
65                  70                  75                  80

Gln Ser Asp Phe Thr Ala Arg Trp Thr Arg Ala Asp Ala Leu Gln Ile
                85                  90                  95

Lys Ala His Ser Asp Ala Thr Val Ala Ala Gly Gln Asn Ser Leu Pro
                100                 105                 110

Ala Gln Leu Thr Met Pro Asn Ile Pro Ala Asp Phe Pro Val Ile Asn
                115                 120                 125

Pro Asp Val Trp Val Trp Asp Thr Trp Thr Leu Ile Asp Lys His Ala
        130                 135                 140

Asp Gln Phe Ser Tyr Asn Gly Trp Glu Val Ile Phe Cys Leu Thr Ala
145                 150                 155                 160

Asp Pro Asn Ala Gly Tyr Gly Phe Asp Asp Arg His Val His Ala Arg
                165                 170                 175

Ile Gly Phe Phe Tyr Arg Arg Ala Gly Ile Pro Ala Ser Arg Arg Pro
                180                 185                 190

Val Asn Gly Gly Trp Thr Tyr Gly Gly His Leu Phe Pro Asp Gly Ala
                195                 200                 205

Ser Ala Gln Val Tyr Ala Gly Gln Thr Tyr Thr Asn Gln Ala Glu Trp
        210                 215                 220

Ser Gly Ser Ser Arg Leu Met Gln Ile His Gly Asn Thr Val Ser Val
225                 230                 235                 240

Phe Tyr Thr Asp Val Ala Phe Asn Arg Asp Ala Asn Ala Asn Asn Ile
                245                 250                 255

Thr Pro Pro Gln Ala Ile Ile Thr Gln Thr Leu Gly Arg Ile His Ala
                260                 265                 270

Asp Phe Asn His Val Trp Phe Thr Gly Phe Thr Ala His Thr Pro Leu
                275                 280                 285

Leu Gln Pro Asp Gly Val Leu Tyr Gln Asn Gly Ala Gln Asn Glu Phe
        290                 295                 300

Phe Asn Phe Arg Asp Pro Phe Thr Phe Glu Asp Pro Lys His Pro Gly
305                 310                 315                 320

Val Asn Tyr Met Val Phe Glu Gly Asn Thr Ala Gly Gln Arg Gly Val
                325                 330                 335

Ala Asn Cys Thr Glu Ala Asp Leu Gly Phe Arg Pro Asn Asp Pro Asn
                340                 345                 350

Ala Glu Thr Leu Gln Glu Val Leu Asp Ser Gly Ala Tyr Tyr Gln Lys
        355                 360                 365
```

-continued

```
Ala Asn Ile Gly Leu Ala Ile Ala Thr Asp Ser Thr Leu Ser Lys Trp
    370             375             380

Lys Phe Leu Ser Pro Leu Ile Ser Ala Asn Cys Val Asn Asp Gln Thr
385             390             395             400

Glu Arg Pro Gln Val Tyr Leu His Asn Gly Lys Tyr Tyr Ile Phe Thr
            405             410             415

Ile Ser His Arg Thr Thr Phe Ala Ala Gly Val Asp Gly Pro Asp Gly
            420             425             430

Val Tyr Gly Phe Val Gly Asp Gly Ile Arg Ser Asp Phe Gln Pro Met
            435             440             445

Asn Tyr Gly Ser Gly Leu Thr Met Gly Asn Pro Thr Asp Leu Asn Thr
    450             455             460

Ala Ala Gly Thr Asp Phe Asp Pro Ser Pro Asp Gln Asn Pro Arg Ala
465             470             475             480

Phe Gln Ser Tyr Ser His Tyr Val Met Pro Gly Gly Leu Val Glu Ser
            485             490             495

Phe Ile Asp Thr Val Glu Asn Arg Arg Gly Gly Thr Leu Ala Pro Thr
            500             505             510

Val Arg Val Arg Ile Ala Gln Asn Ala Ser Ala Val Asp Leu Arg Tyr
            515             520             525

Gly Asn Gly Gly Leu Gly Gly Tyr Gly Asp Ile Pro Ala Asn Arg Ala
    530             535             540

Asp Val Asn Ile Ala Gly Phe Ile Gln Asp Leu Phe Gly Gln Pro Thr
545             550             555             560

Ser Gly Leu Ala Ala Gln Ala Ser Thr Asn Asn Ala Gln Val Leu Ala
            565             570             575

Gln Val Arg Gln Phe Leu Asn Gln
            580
```

```
<210> SEQ ID NO 16
<211> LENGTH: 423
<212> TYPE: PRT
<213> ORGANISM: Zymomonas mobilis

<400> SEQUENCE: 16

Met Leu Asn Lys Ala Gly Ile Ala Glu Pro Ser Leu Trp Thr Arg Ala
1               5               10              15

Asp Ala Met Lys Val His Thr Asp Asp Pro Thr Ala Thr Met Pro Thr
            20              25              30

Ile Asp Tyr Asp Phe Pro Val Met Thr Asp Lys Tyr Trp Val Trp Asp
            35              40              45

Thr Trp Pro Leu Arg Asp Ile Asn Gly Gln Val Val Ser Phe Gln Gly
    50              55              60

Trp Ser Val Ile Phe Ala Leu Val Ala Asp Arg Thr Lys Tyr Gly Trp
65              70              75              80

His Asn Arg Asn Asp Gly Ala Arg Ile Gly Tyr Phe Tyr Ser Arg Gly
            85              90              95

Gly Ser Asn Trp Ile Phe Gly Gly His Leu Leu Lys Asp Gly Ala Asn
            100             105             110

Pro Arg Ser Trp Glu Trp Ser Gly Cys Thr Ile Met Ala Pro Gly Thr
            115             120             125

Ala Asn Ser Val Glu Val Phe Phe Thr Ser Val Asn Asp Thr Pro Ser
    130             135             140

Glu Ser Val Pro Ala Gln Cys Lys Gly Tyr Ile Tyr Ala Asp Asp Lys
145             150             155             160
```

-continued

```
Ser Val Trp Phe Asp Gly Phe Asp Lys Val Thr Asp Leu Phe Gln Ala
            165             170             175

Asp Gly Leu Tyr Tyr Ala Asp Tyr Ala Glu Asn Asn Phe Trp Asp Phe
            180             185             190

Arg Asp Pro His Val Phe Ile Asn Pro Glu Asp Gly Lys Thr Tyr Ala
            195             200             205

Leu Phe Glu Gly Asn Val Ala Met Glu Arg Gly Thr Val Ala Val Gly
    210             215             220

Glu Glu Glu Ile Gly Pro Val Pro Pro Lys Thr Glu Thr Pro Asp Gly
225             230             235             240

Ala Arg Tyr Cys Ala Ala Ala Ile Gly Ile Ala Gln Ala Leu Asn Glu
            245             250             255

Ala Arg Thr Glu Trp Lys Leu Leu Pro Pro Leu Val Thr Ala Phe Gly
            260             265             270

Val Asn Asp Gln Thr Glu Arg Pro His Val Val Phe Gln Asn Gly Leu
    275             280             285

Thr Tyr Leu Phe Thr Ile Ser His His Ser Thr Tyr Ala Asp Gly Leu
    290             295             300

Ser Gly Pro Asp Gly Val Tyr Gly Phe Val Ser Glu Asn Gly Ile Phe
305             310             315             320

Gly Pro Tyr Glu Pro Leu Asn Gly Ser Gly Leu Val Leu Gly Asn Pro
            325             330             335

Ser Ser Gln Pro Tyr Gln Ala Tyr Ser His Tyr Val Met Thr Asn Gly
            340             345             350

Leu Val Thr Ser Phe Ile Asp Thr Ile Pro Ser Ser Asp Pro Asn Val
            355             360             365

Tyr Arg Tyr Gly Gly Thr Leu Ala Pro Thr Ile Lys Leu Glu Leu Val
    370             375             380

Gly His Arg Ser Phe Val Thr Glu Val Lys Gly Tyr Gly Tyr Ile Pro
385             390             395             400

Pro Gln Ile Glu Trp Leu Ala Glu Asp Glu Ser Ser Asn Ser Ala Ala
            405             410             415

Ala Leu Ser Leu Leu Asn Lys
            420
```

```
<210> SEQ ID NO 17
<211> LENGTH: 489
<212> TYPE: PRT
<213> ORGANISM: Clostridium acetobutylicum

<400> SEQUENCE: 17
```

```
Met Asn Lys Leu Lys Ile Val Lys Cys Ile Leu Ile Gly Ser Met Ile
1               5               10              15

Cys Ser Gly Ile Ile Thr Gln Gln Thr Phe Ala Ser Thr Asn Asp Met
            20              25              30

Asn Tyr Lys Glu Thr Tyr Gly Val Ser His Ile Thr Arg Tyr Asn Met
            35              40              45

Ser Lys Ile Pro Met Glu Gln Asn Asp Leu Lys Phe Lys Val Pro Gln
    50              55              60

Phe Asn Ala Ser Thr Leu Lys Asn Ile Ala Ser Ala Lys Gly Tyr Asp
65              70              75              80

Lys Asn Gly Asn Leu Ile Asp Leu Asp Val Trp Asp Ser Trp Pro Leu
            85              90              95

Gln Asn Gly Asp Gly Thr Val Ala Asn Tyr His Gly Tyr His Ile Val
```

```
                    100                 105                 110

Phe Ala Leu Ala Gly Asp Pro Lys Asn Gln Asp Asp Thr Ser Ile Tyr
            115                 120                 125

Met Phe Tyr Gln Lys Ile Gly Glu Asn Ser Ile Asp Ser Trp Lys Asn
            130                 135                 140

Ala Gly Lys Val Phe Lys Asp Ser Asp Lys Tyr Val Ala Asn Asp Pro
145                 150                 155                 160

Tyr Leu Lys Tyr Gln Thr Gln Glu Trp Ser Gly Ser Ala Thr Leu Thr
                    165                 170                 175

Ser Asp Gly Gln Val Arg Leu Phe Tyr Thr Asp Phe Ser Gly Val Ala
                    180                 185                 190

Lys Asp Gly Gly Thr Asp Ala Ser Asn Gln Val Ile Thr Thr Thr Gln
            195                 200                 205

Val Asn Leu Ser Gln Pro Asp Ser Asn Thr Ile Asn Ile Asp Ser Val
            210                 215                 220

Ser Asp His Lys Ser Val Phe Asp Gly Gly Asn Gly Thr Ile Tyr Gln
225                 230                 235                 240

Asn Val Gln Gln Phe Ile Asp Glu Gly Lys Trp Ser Ser Gly Asp Asn
                    245                 250                 255

His Thr Leu Arg Asp Pro His Tyr Val Glu Asp Asn Gly Arg Lys Tyr
                    260                 265                 270

Leu Val Phe Glu Ala Asn Thr Gly Thr Asn Asp Gly Tyr Gln Gly Asp
                    275                 280                 285

Thr Ser Leu Leu Asn Lys Ala Phe Tyr Gly Arg Ser Gln Ser Phe Phe
            290                 295                 300

Lys Thr Glu Lys Asp Gln Leu Leu Ile Asp Thr Asn Lys Lys His Asp
305                 310                 315                 320

Ala Ser Leu Ala Asn Gly Ala Leu Gly Ile Ile Glu Leu Asn Asn Asp
                    325                 330                 335

Tyr Thr Leu Lys Lys Glu Met Lys Pro Leu Ile Ala Ser Asn Thr Val
            340                 345                 350

Thr Asp Glu Ile Glu Arg Ala Asn Val Phe Lys Met Asn Gly Arg Trp
            355                 360                 365

Tyr Leu Phe Thr Asp Ser Arg Gly Ser Lys Met Thr Ile Asn Gly Ile
            370                 375                 380

Ser Ser Lys Asp Ile Tyr Met Leu Gly Phe Ser Ser Asn Ser Leu Thr
385                 390                 395                 400

Gly Pro Tyr Lys Pro Leu Asn Lys Thr Gly Leu Val Leu Asn Leu Asn
                    405                 410                 415

Leu Asp Pro Thr Asp Leu Thr Phe Thr Tyr Ser His Phe Ala Val Pro
                    420                 425                 430

Gln Thr Asn Gly Lys Asn Val Val Ile Thr Ser Tyr Ile Thr Asn Arg
            435                 440                 445

Gly Met Tyr Ser Asp His His Ser Ser Phe Ala Pro Ser Phe Leu Leu
            450                 455                 460

Asn Ile Lys Gly Thr Lys Thr Ser Val Ile Ser Asn Ser Ile Leu Gln
465                 470                 475                 480

Gln Gly Gln Leu Thr Ile Asp Asn Tyr
                    485
```

<210> SEQ ID NO 18
<211> LENGTH: 473
<212> TYPE: PRT
<213> ORGANISM: Bacillus subtilis

```
<400> SEQUENCE: 18

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
            85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
            165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
            245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
            325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
            355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
```

```
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470
```

<210> SEQ ID NO 19
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atgaacataa agaagtttgc gaagcaggcg acagtattaa cgttcaccac ggcactcttg        60
gctgggggcg caacccaggc ttttgctaaa gagaccaacc agaagccgta taaggaaacg       120
tatgggattt cccacattac aagacatgat atgctgcaga tcccagaaca acagaaaaac       180
gaaaaatacc aagtcccgga atttgattct tcgaccatta aaaacatttc ctcagctaaa       240
gggctggacg tatgggattc ttggcccctt cagaatgcag atggaactgt tgccaattac       300
catggctatc atattgtctt tgcgctggcg ggggatccga aaaacgcaga tgatacgtcc       360
atctacatgt tttaccaaaa agtaggggaa acaagcattg attcctggaa aaacgctggc       420
cgcgtcttca aggattcaga caaatttgat gcgaatgata gtatactgaa agatcagacg       480
caagagtgga gcggttccgc aactttcacg agcgacggaa aaatccgtct gttctacacc       540
gattttagcg gcaagcatta cgggaagcag actctgacga cggcccaagt caatgtatct       600
gcatcggact cttccctgaa tattaacgga gttgaagatt acaaatctat atttgacggt       660
gatggcaaaa cctaccaaaa cgtccagcag ttcatagacg aaggcaatta tagttcaggg       720
gacaatcata ctttacgtga cccacattat gtcgaagata aaggacataa atatctggtt       780
tttgaggcga cactggcac agaggacggg tatcaggggg aagagtccct gttcaataaa       840
gcttattacg gcaagtcaac atcttttttt cgccaagaat cacaaaagct gctgcaatca       900
gataagaaaa ggactgctga gttagcgaac ggcgcattag gcatgattga actgaatgac       960
gactacacac ttaaaaaagt tatgaaacca ttaattgcgt cgaacaccgt tactgatgaa      1020
attgaaaggg cgaatgtttt taagatgaac gggaaatggt atctctttac ggatagtcgc      1080
ggatcaaaga tgaccatcga tggtatcacg tccaatgaca tttacatgct tggatatgtt      1140
agcaattcct taactggacc ttataaaccg cttaacaaaa caggcttggt actgaaaatg      1200
gatttggatc caaatgacgt cacatttaca tactctcatt tcgctgttcc gcaggcaaag      1260
ggcaacaatg ttgtgattac atcttatatg accaaccgcg ctttttatgc ggataagcaa      1320
tcaaccttcg caccatcatt cctgcttaac atcaagggca aaaaaacgag cgtagtcaaa      1380
gattctatct tggaacaggg tcagctgacg gtcaacaaat aa                         1422
```

<210> SEQ ID NO 20
<211> LENGTH: 1422
<212> TYPE: DNA
<213> ORGANISM: Artificial Sequence
<220> FEATURE:

-continued

<223> OTHER INFORMATION: Description of Artificial Sequence: Synthetic
    polynucleotide

<400> SEQUENCE: 20

```
atgaacatca aaaagtttgc aaaacaagca acagtattaa cctttactac cgcactgctg      60
gcaggaggcg caactcaagc gtttgcgaaa gaaacgaacc aaaagccata taaggaaaca     120
tacggcattt cccatattac acgccatgat atgctgcaaa tccctgaaca gcaaaaaaat     180
gaaaaatatc aagttcctga attcgattcg tccacaatta aaaatatctc ttctgcaaaa     240
ggcctggacg tttgggacag ctggccatta caaaacgctg acggcactgt cgcaaactat     300
cacggctacc acatcgtctt tgcattagcc ggagatccta aaaatgcgga tgacacatcg     360
atttacatgt tctatcaaaa agtcggcgaa acttctattg acagctggaa aaacgctggc     420
cgcgtcttta aagacagcga caaattcgat gcaaatgatt ctatcctaaa agaccaaaca     480
caagaatggt caggttcagc cacatttaca tctgacggaa aaatccgttt attctacact     540
gatttctccg gtaaacatta cggcaaacaa acactgacaa ctgcacaagt taacgtatca     600
gcatcagaca gctctttgaa catcaacggt gtagaggatt ataaatcaat ctttgacggt     660
gacggaaaaa cgtatcaaaa tgtacagcag ttcatcgatg aaggcaacta cagctcaggc     720
gacaaccata cgctgagaga tcctcactac gtagaagata aaggccacaa atacttagta     780
tttgaagcaa acactggaac tgaagatggc taccaaggcg aagaatcttt atttaacaaa     840
gcatactatg gcaaaagcac atcattcttc cgtcaagaaa gtcaaaaact tctgcaaagc     900
gataaaaaac gcacggctga gttagcaaac ggcgctctcg gtatgattga gctaaacgat     960
gattacacac tgaaaaaagt gatgaaaccg ctgattgcat ctaacacagt aacagatgaa    1020
attgaacgcg cgaacgtctt taaaatgaac ggcaaatggt acctgttcac tgactcccgc    1080
ggatcaaaaa tgacgattga cggcattacg tctaacgata tttacatgct tggttatgtt    1140
tctaattctt taactggccc atacaagccg ctgaacaaaa ctggccttgt gttaaaaatg    1200
gatcttgatc ctaacgatgt aacctttact tactcacact tcgctgtacc tcaagcgaaa    1260
ggaaacaatg tcgtgattac aagctatatg acaaacagag gattctacgc agacaaacaa    1320
tcaacgtttg cgccaagctt cctgctgaac atcaaaggca agaaaacatc tgttgtcaaa    1380
gacagcatcc ttgaacaagg acaattaaca gttaacaaat aa                       1422
```

<210> SEQ ID NO 21
<211> LENGTH: 473
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 21

```
Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80
```

-continued

Gly Leu Asp Val Trp Asp Ser Trp Pro Leu Gln Asn Ala Asp Gly Thr
                    85                  90                  95

Val Ala Asn Tyr His Gly Tyr His Ile Val Phe Ala Leu Ala Gly Asp
                100                 105                 110

Pro Lys Asn Ala Asp Asp Thr Ser Ile Tyr Met Phe Tyr Gln Lys Val
                115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
                180                 185                 190

Thr Thr Ala Gln Val Asn Val Ser Ala Ser Asp Ser Ser Leu Asn Ile
                195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
                260                 265                 270

Gly Glu Glu Ser Leu Phe Asn Lys Ala Tyr Tyr Gly Lys Ser Thr Ser
                275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
                340                 345                 350

Trp Tyr Leu Phe Thr Asp Ser Arg Gly Ser Lys Met Thr Ile Asp Gly
                355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
                435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 22
<211> LENGTH: 915
<212> TYPE: DNA

<213> ORGANISM: Bacillus subtilis

<400> SEQUENCE: 22
atgagaatta accacaatat tgcagcgctt aacacactga accgtttgtc ttcaaacaac      60
agtgcgagcc aaaagaacat ggagaaactt tcttcaggtc ttcgcatcaa ccgtgcggga     120
gatgacgcag caggtcttgc gatctctgaa aaaatgagag acaaatcag aggtcttgaa      180 atggcttcta aaaactctca agacggaatc tctcttatcc aaacagctga gggtgcatta     240
actgaaactc atgcgatcct tcaacgtgtt cgtgagctag ttgttcaagc tggaaacact     300
ggaactcagg acaaagcaac tgatttgcaa tctattcaag atgaaatttc agctttaaca     360
gatgaaatcg atggtatttc aaatcgtaca gaattcaatg gtaagaaatt gctcgatggc     420
acttacaaag ttgacacagc tactcctgca aatcaaaaga acttggtatt ccaaatcgga     480
gcaaatgcta cacagcaaat ctctgtaaat attgaggata tgggtgctga cgctcttgga     540
attaaagaag ctgatggttc aattgcagct cttcattcag ttaatgatct tgacgtaaca     600
aaattcgcag ataatgcagc agatactgct gatatcggtt tcgatgctca attgaaagtt     660
gttgatgaag cgatcaacca agtttcttct caacgtgcta agcttggtgc ggtacaaaat     720
cgtctagagc acacaattaa caacttaagc gcttctggtg aaaacttgac agctgctgag     780
tctcgtatcc gtgacgttga catggctaaa gagatgagcg aattcacaaa gaacaacatt     840
ctttctcagg cttctcaagc tatgcttgct caagcaaacc aacagccgca aaacgtactt     900
caattattac gttaa                                                      915

<210> SEQ ID NO 23
<211> LENGTH: 273
<212> TYPE: DNA
<213> ORGANISM: Bacillus subtilis

<400> SEQUENCE: 23
ggaattgacg ccccaaagca tattgatatt cacaggaaag aaatttactt gaccattcag      60
gaagaaaata accgtgcagc agcgttatcc agcgatgtga tctccgcatt atcctcacaa     120
aaaaagtgag gatttttta tttttgtatt aacaaaatca gagacaatcc gatattaatg     180
atgtagccgg gaggaggcgc aaaaagactca gccagttaca aaataagggc acaaggacgt     240
gccttaacaa catattcagg gaggaacaaa aca                                  273

<210> SEQ ID NO 24
<211> LENGTH: 12
<212> TYPE: DNA
<213> ORGANISM: Bacillus subtilis

<400> SEQUENCE: 24
gcacaaggac gt                                                          12

<210> SEQ ID NO 25
<211> LENGTH: 13
<212> TYPE: DNA
<213> ORGANISM: Bacillus subtilis

<400> SEQUENCE: 25
attcagggag gaa                                                         13

<210> SEQ ID NO 26
<211> LENGTH: 8
<212> TYPE: DNA
<213> ORGANISM: Bacillus subtilis -continued

```
<400> SEQUENCE: 26 agggagga                                                                  8

<210> SEQ ID NO 27
<211> LENGTH: 225
<212> TYPE: DNA
<213> ORGANISM: Bacillus subtilis

<400> SEQUENCE: 27
atgctagttt tatcgcggaa aataaacgaa gcgattcaaa taggtgctga tattgaagta      60
aaagtgattg cggttgaagg ggatcaagtg aagcttggaa ttgacgcccc aaagcatatt     120
gatattcaca ggaaagaaat ttacttgacc attcaggaag aaaataaccg tgcagcagcg     180
ttatccagcg atgtgatctc cgcattatcc tcacaaaaaa agtga                     225

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taagggcaca aggacgtgcc tta                                               23

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcacaagaac gt                                                           12

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atttagggag gaa                                                          13

<210> SEQ ID NO 31
<211> LENGTH: 267
<212> TYPE: DNA
<213> ORGANISM: Bacillus subtilis

<400> SEQUENCE: 31
atgaaaatca atcaatttgg aacacaatcc gttaatccat atcaaaaaaa ttatgataag      60
caagcggtgc aaaaaactgt tgcacaacct caagataaaa ttgaaatttc atcacaggct     120
aaagaaatgc aacatgcatc cgacgcagtc actggttcac gacaggaaaa aattgcgcag     180
cttaaagcgc aaattgaaaa cgggtcatac aaagtagacg caaatcatat tgcgaaaaat     240
atgattaatt tttataaaaa gcaataa                                         267
```

185

186

```
<210> SEQ ID NO 32
<211> LENGTH: 765
<212> TYPE: DNA
<213> ORGANISM: Bacillus subtilis

<400> SEQUENCE: 32
atgcaatcct tgaattatga agatcaggtg ctttggacgc gctggaaaga gtggaaagat        60
cctaaagccg gtgacgactt aatgcgccgt tacatgccgc ttgtcacata tcatgtaggc       120
agaatttctg tcggactgcc gaaatcagtg cataaagacg atcttatgag ccttggtatg       180
cttggtttat atgatgccct tgaaaaattt gaccccagcc gggacttaaa atttgatacc       240
tacgcctcgt ttagaattcg cggcgcaatc atagacgggc ttcgtaaaga agattggctg       300
cccagaacct cgcgcgaaaa aacaaaaaag gttgaagcag caattgaaaa gcttgaacag       360
cggtatcttc ggaatgtatc gcccgcggaa attgcagagg aactcggaat gacggtacag       420
gatgtcgtgt caacaatgaa tgaaggtttt tttgcaaatc tgctgtcaat tgatgaaaag       480
ctccatgatc aagatgacgg ggaaaacatt caagtcatga tcagagatga caaaaatgtt       540
ccgcctgaag aaaagattat gaaggatgaa ctgattgcac agcttgcgga aaaaattcac       600
gaactctctg aaaaagaaca gctggttgtc agtttgttct acaaagagga gttgacactg       660
acagaaatcg gacaagtatt aaatctttct acgtcccgca tatctcagat ccattcaaag       720
gcattattta aattaaagaa tctgctggaa aaagtgatac aataa                      765

<210> SEQ ID NO 33
<211> LENGTH: 474
<212> TYPE: PRT
<213> ORGANISM: Escherichia coli

<400> SEQUENCE: 33

Met Ser Arg Leu Val Val Val Ser Asn Arg Ile Ala Pro Pro Asp Glu
1               5                   10                  15

His Ala Ala Ser Ala Gly Gly Leu Ala Val Gly Ile Leu Gly Ala Leu
                20                  25                  30

Lys Ala Ala Gly Gly Leu Trp Phe Gly Trp Ser Gly Glu Thr Gly Asn
            35                  40                  45

Glu Asp Gln Pro Leu Lys Lys Val Lys Lys Gly Asn Ile Thr Trp Ala
        50                  55                  60

Ser Phe Asn Leu Ser Glu Gln Asp Leu Asp Glu Tyr Tyr Asn Gln Phe
65                  70                  75                  80

Ser Asn Ala Val Leu Trp Pro Ala Phe His Tyr Arg Leu Asp Leu Val
                85                  90                  95

Gln Phe Gln Arg Pro Ala Trp Asp Gly Tyr Leu Arg Val Asn Ala Leu
            100                 105                 110

Leu Ala Asp Lys Leu Leu Pro Leu Leu Gln Asp Asp Asp Ile Ile Trp
            115                 120                 125

Ile His Asp Tyr His Leu Leu Pro Phe Ala His Glu Leu Arg Lys Arg
        130                 135                 140

Gly Val Asn Asn Arg Ile Gly Phe Phe Leu His Ile Pro Phe Pro Thr
145                 150                 155                 160

Pro Glu Ile Phe Asn Ala Leu Pro Thr Tyr Asp Thr Leu Leu Glu Gln
                165                 170                 175

Leu Cys Asp Tyr Asp Leu Leu Gly Phe Gln Thr Glu Asn Asp Arg Leu
            180                 185                 190

Ala Phe Leu Asp Cys Leu Ser Asn Leu Thr Arg Val Thr Thr Arg Ser
            195                 200                 205
```

```
Ala Lys Ser His Thr Ala Trp Gly Lys Ala Phe Arg Thr Glu Val Tyr
    210                 215                 220

Pro Ile Gly Ile Glu Pro Lys Glu Ile Ala Lys Gln Ala Ala Gly Pro
225                 230                 235                 240

Leu Pro Pro Lys Leu Ala Gln Leu Lys Ala Glu Leu Lys Asn Val Gln
                245                 250                 255

Asn Ile Phe Ser Val Glu Arg Leu Asp Tyr Ser Lys Gly Leu Pro Glu
                260                 265                 270

Arg Phe Leu Ala Tyr Glu Ala Leu Leu Glu Lys Tyr Pro Gln His His
            275                 280                 285

Gly Lys Ile Arg Tyr Thr Gln Ile Ala Pro Thr Ser Arg Gly Asp Val
    290                 295                 300

Gln Ala Tyr Gln Asp Ile Arg His Gln Leu Glu Asn Glu Ala Gly Arg
305                 310                 315                 320

Ile Asn Gly Lys Tyr Gly Gln Leu Gly Trp Thr Pro Leu Tyr Tyr Leu
                325                 330                 335

Asn Gln His Phe Asp Arg Lys Leu Leu Met Lys Ile Phe Arg Tyr Ser
                340                 345                 350

Asp Val Gly Leu Val Thr Pro Leu Arg Asp Gly Met Asn Leu Val Ala
            355                 360                 365

Lys Glu Tyr Val Ala Ala Gln Asp Pro Ala Asn Pro Gly Val Leu Val
    370                 375                 380

Leu Ser Gln Phe Ala Gly Ala Ala Asn Glu Leu Thr Ser Ala Leu Ile
385                 390                 395                 400

Val Asn Pro Tyr Asp Arg Asp Glu Val Ala Ala Ala Leu Asp Arg Ala
                405                 410                 415

Leu Thr Met Ser Leu Ala Glu Arg Ile Ser Arg His Ala Glu Met Leu
                420                 425                 430

Asp Val Ile Val Lys Asn Asp Ile Asn His Trp Gln Glu Cys Phe Ile
            435                 440                 445

Ser Asp Leu Lys Gln Ile Val Pro Arg Ser Ala Glu Ser Gln Gln Arg
    450                 455                 460

Asp Lys Val Ala Thr Phe Pro Lys Leu Ala
465                 470
```

```
<210> SEQ ID NO 34
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atgtcccgtt tagtagtggt gtccaatcgt atcgcgccgc cggacgaaca tgctgcctca        60
gctggcggcc tggccgtagg aatcctgggc gccctcaagg cagctggagg attatggttc       120
ggctggtctg gcgagacagg aaatgaggat caaccactta agaaagtgaa aaaaggcaat       180
atcacatggg cttccttcaa cctcagcgag caagacctgg atgagtatta taaccagttt       240
agcaatgctg tgctttggcc ggcttttcat tacaggttag atttggttca gtttcaaaga       300
cccgcatggg atggatacct ccgagtgaat gcgttgttgg cagataaact tctcccgctc       360
cttcaggatg atgatattat ctggattcat gactaccatc ttctcccttt cgcccacgaa       420
ttgcgcaaac ggggcgtgaa caataggata ggttttttttt tgcacattcc ttttcccaca      480
```

```
ccggaaattt tcaacgcgct tccgacatac gatactttac ttgaacagct gtgtgattac      540
gatcttctcg gcttccaaac tgaaaatgac agacttgcct ttttggattg cctctcaaat      600
ttgacgaggg ttacgactag aagtgccaag agccatacag cgtgggaaa agcattcagg       660 acagaagttt atcctattgg gatcgagcct aaggaaattg cgaaacaagc ggcagggcca      720
ttacctccga aacttgcgca actcaaagcg gaattaaaga acgtacaaaa catttttagc      780
gtcgaaagac ttgattattc taagggtctc ccggaaagat tcttagccta cgaggcattg      840
cttgaaaaat atccacagca tcatgggaaa attcgttata cgcaaatcgc tccgactagc      900
agaggcgacg tccaagcgta tcaggacata cgccaccaac ttgaaaatga agcgggtaga      960
atcaatggca aatatggaca actggggtgg acacctcttt attacttgaa tcaacatttc      1020
gatagaaaat tgttgatgaa aatctttcgt tattctgacg tcggactggt gacaccgctg      1080
agagatggca tgaacttagt tgccaaggaa tatgtagctg cgcaagaccc tgctaatccg      1140
ggagtactgg tgctctcaca atttgcaggg gccgcgaatg aacttacatc agctctcatc      1200
gttaatccgt atgacaggga tgaagtcgca gcggcgcttg accgggctct tacaatgtcc      1260
ttagcggaga gaattagcag acatgctgaa atgctggatg tgattgtgaa gaacgatatc      1320
aatcattggc aagaatgttt catttctgac ttaaagcaaa ttgtcccgcg ttcagctgag      1380
tcacagcaac gggataaagt cgccacattt cccaaactgg cataa                      1425
```

```
<210> SEQ ID NO 35
<211> LENGTH: 310
<212> TYPE: PRT
<213> ORGANISM: Neisseria meningitidis

<400> SEQUENCE: 35

Met Asp Ile Val Phe Ala Ala Asp Asp Asn Tyr Ala Ala Tyr Leu Cys
1               5                   10                  15

Val Ala Ala Lys Ser Val Glu Ala Ala His Pro Asp Thr Glu Ile Arg
            20                  25                  30

Phe His Val Leu Asp Ala Gly Ile Ser Glu Ala Asn Arg Ala Ala Val
        35                  40                  45

Ala Ala Asn Leu Arg Gly Gly Asn Ile Arg Phe Ile Asp Val Asn
        50                  55                  60

Pro Glu Asp Phe Ala Gly Phe Pro Leu Asn Ile Arg His Ile Ser Ile
65                  70                  75                  80

Thr Thr Tyr Ala Arg Leu Lys Leu Gly Glu Tyr Ile Ala Asp Cys Asp
                85                  90                  95

Lys Val Leu Tyr Leu Asp Ile Asp Val Leu Val Arg Asp Ser Leu Lys
                100                 105                 110

Pro Leu Trp Asp Thr Asp Leu Gly Asp Asn Trp Leu Gly Ala Cys Ile
            115                 120                 125

Asp Leu Phe Val Glu Arg Gln Asn Ala Tyr Lys Gln Lys Ile Gly Met
        130                 135                 140

Ala Asp Gly Glu Tyr Tyr Phe Asn Ala Gly Val Leu Leu Ile Asn Leu
145                 150                 155                 160

Lys Lys Trp Arg Gln His Asp Ile Phe Lys Met Ala Cys Glu Trp Val
            165                 170                 175

Glu Gln Tyr Lys Asp Val Met Gln Tyr Gln Asp Gln Asp Ile Leu Asn
            180                 185                 190

Gly Leu Phe Lys Gly Gly Val Cys Tyr Ala Asn Ser Arg Phe Asn Phe
            195                 200                 205
```

```
Met Pro Thr Asn Asp Ala Phe Met Ala Asn Arg Phe Ala Ser Arg His
    210                 215                 220

Thr Asp Pro Leu Tyr Arg Asp Arg Thr Tyr Thr Ala Met Pro Val Ala
225                 230                 235                 240

Val Ser His Tyr Cys Gly Pro Ala Lys Pro Trp His Arg Asp Cys Thr
                245                 250                 255

Ala Trp Gly Ala Glu Arg Phe Thr Glu Leu Ala Gly Ser Leu Thr Ser
                260                 265                 270

Val Pro Glu Glu Trp Arg Gly Lys Leu Ala Val Pro His Arg Val Phe
                275                 280                 285

Pro Thr Lys Arg Met Leu Gln Arg Trp Arg Arg Lys Leu Ser Ala Arg
    290                 295                 300

Phe Leu Arg Lys Ile Tyr
305                 310
```

<210> SEQ ID NO 36
<211> LENGTH: 933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
atggatattg tatttgcggc agatgataat tatgctgcgt atctctgtgt tgccgccaaa        60
tccgtggaag ccgctcaccc cgatacagag atccggttcc atgtacttga cgctggcatt       120
tccgaagcaa accgggcagc agttgcagcc aatctccgcg gtggcggtaa tattcgtttt       180
atagatgtga acccggaaga ctttgccggc tttccattga atattcgcca tattagtata       240
acaacttacg cacgtctgaa acttggggag tacattgcgg attgtgacaa ggtactttat       300
ctcgatatag atgtacttgt gcgtgatagt cttaaaccgt tatgggatac agatcttgga       360
gataattggc ttggtgcatg catcgactta tttgtagaga gacaaaacgc ttataagcaa       420
aaaattggca tggctgacgg tgaatattac tttaacgcag gggtgctcct gattaacctt       480
aagaagtggc ggcaacacga tatcttcaaa atggcttgcg aatgggttga gcagtataag       540
gatgtaatgc agtaccagga ccaagacatc ctgaatggat tatttaaagg tggagtgtgt       600
tacgctaata gcagattcaa tttcatgccg accaatgatg ctttcatggc aaaccggttt       660
gcttcacgcc atacggaccc attgtataga gatagaacgt atacagcaat gcctgtggcc       720
gtttcgcatt attgtggtcc ggcgaaaccg tggcatcgcg attgcacagc atggggcgca       780
gaaagattta cagaacttgc aggaagtctg acatcagttc cggaggaatg gcgcggaaaa       840
cttgcggtgc ctcatcgggt gttcccgact aaacgtatgc tgcaaagatg gagacgcaaa       900
ctctccgctc gatttctgag aaaaatctat tga                                    933
```

<210> SEQ ID NO 37
<211> LENGTH: 293
<212> TYPE: PRT
<213> ORGANISM: Synechococcus elongatus

<400> SEQUENCE: 37

```
Met Ile Ile Val His Leu Cys Gly Gly Leu Gly Asn Gln Met Phe Gln
1               5                   10                  15

Tyr Ala Ala Gly Leu Ala Ala Ala His Arg Ile Gly Ser Glu Val Lys
                20                  25                  30

Phe Asp Thr His Trp Phe Asp Ala Thr Cys Leu His Gln Gly Leu Glu
```

-continued

```
            35                40                45
Leu Arg Arg Val Phe Gly Leu Glu Leu Pro Glu Pro Ser Ser Lys Asp
    50                55                60
Leu Arg Lys Val Leu Gly Ala Cys Val His Pro Ala Val Arg Arg Leu
65                70                75                80
Leu Ala Gly His Phe Leu His Gly Leu Arg Pro Lys Ser Leu Val Ile
                85                90                95
Gln Pro His Phe His Tyr Trp Thr Gly Phe Glu His Leu Pro Asp Asn
            100                105                110
Val Tyr Leu Glu Gly Tyr Trp Gln Ser Glu Arg Tyr Phe Ser Asn Ile
            115                120                125
Ala Asp Ile Ile Arg Gln Gln Phe Arg Phe Val Glu Pro Leu Asp Pro
    130                135                140
His Asn Ala Ala Leu Met Asp Glu Met Gln Ser Gly Val Ser Val Ser
145                150                155                160
Leu His Ile Arg Arg Gly Asp Tyr Phe Asn Asn Pro Gln Met Arg Arg
                165                170                175
Val His Gly Val Asp Leu Ser Glu Tyr Tyr Pro Ala Ala Val Ala Thr
            180                185                190
Met Ile Glu Lys Thr Asn Ala Glu Arg Phe Tyr Val Phe Ser Asp Asp
            195                200                205
Pro Gln Trp Val Leu Glu His Leu Lys Leu Pro Val Ser Tyr Thr Val
    210                215                220
Val Asp His Asn Arg Gly Ala Ala Ser Tyr Arg Asp Met Gln Leu Met
225                230                235                240
Ser Ala Cys Arg His His Ile Ile Ala Asn Ser Thr Phe Ser Trp Trp
                245                250                255
Gly Ala Trp Leu Asn Pro Arg Pro Asp Lys Val Val Ile Ala Pro Arg
            260                265                270
His Trp Phe Asn Val Asp Val Phe Asp Thr Arg Asp Leu Tyr Cys Pro
            275                280                285
Gly Trp Ile Val Leu
    290
```

<210> SEQ ID NO 38
<211> LENGTH: 882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
atgattattg tgcacctttg cggtggttta ggaaaccaga tgttccaata tgcggcaggc      60
cttgccgcgg cgcacagaat tggcagcgaa gttaaattcg atacgcattg gttcgatgcg     120
acatgtctgc atcagggttt agagttgcgc agagtttttg gtttggagct tccggaaccc     180
agttccaagg acctgagaaa agttttaggc gcttgcgttc atcctgcagt gagacggctt     240
ttggctggtc actttctgca tggcttacgg ccgaagtcgc tcgttatcca acccatttt      300 cactactgga cgggctttga acatttaccg gacaacgtat acttagaggg ctactggcag     360
tctgaaagat acttttcaaa tattgctgat attataagac aacagtttcg ttttgtcgaa     420
ccgttagatc cgcataatgc ggccctcatg gatgaaatgc agtccggggt tagtgtttca     480
cttcatattc gccgtggaga ctacttcaac aacccgcaaa tgcgtcgtgt ccacggcgta     540
```

-continued

```
gacttgagcg agtactaccc ggcggcagtc gcgacgatga tcgaaaaaac caacgcagaa      600
cggttttacg tgttttcaga tgacccacag tgggtattgg aacatctgaa actgcctgtt      660
tcttacaccg tggtggacca taaccgaggc gctgcctcgt atagggatat gcaacttatg      720
tctgcttgcc gacaccatat cattgcgaat tcaacattca gctggtgggg agcttggctt      780
aaccctcggc cggacaaggt cgtgatcgct ccacgccatt ggtttaacgt agatgtattc      840
gacacacgcg atttatattg cccagggtgg atagtactgt aa                        882
```

<210> SEQ ID NO 39
<211> LENGTH: 672
<212> TYPE: PRT
<213> ORGANISM: Geobacillus kaustophilus

<400> SEQUENCE: 39

```
Met Asn Val Leu Ser Ser Ile Cys Tyr Gly Gly Asp Tyr Asn Pro Glu
1               5                   10                  15

Gln Trp Pro Glu Glu Ile Trp Tyr Glu Asp Ala Lys Leu Met Gln Lys
            20                  25                  30

Ala Gly Val Asn Leu Val Ser Leu Gly Ile Phe Ser Trp Ser Lys Ile
        35                  40                  45

Glu Pro Ser Asp Gly Val Phe Asp Phe Glu Trp Leu Asp Lys Val Ile
    50                  55                  60

Asp Ile Leu Tyr Asp His Gly Val Tyr Ile Asn Leu Gly Thr Ala Thr
65                  70                  75                  80

Ala Thr Thr Pro Ala Trp Phe Val Lys Lys Tyr Pro Asp Ser Leu Pro
                85                  90                  95

Ile Asp Glu Ser Gly Val Ile Leu Ser Phe Gly Ser Arg Gln His Tyr
            100                 105                 110

Cys Pro Asn His Pro Gln Leu Ile Thr His Ile Lys Arg Leu Val Arg
        115                 120                 125

Ala Ile Ala Glu Arg Tyr Lys Asn His Pro Ala Leu Lys Met Trp His
    130                 135                 140

Val Asn Asn Glu Tyr Ala Cys His Val Ser Lys Cys Phe Cys Glu Asn
145                 150                 155                 160

Cys Ala Val Ala Phe Arg Lys Trp Leu Lys Glu Arg Tyr Lys Thr Ile
                165                 170                 175

Asp Glu Leu Asn Glu Arg Trp Gly Thr Asn Phe Trp Gly Gln Arg Tyr
            180                 185                 190

Asn His Trp Asp Glu Ile Asn Pro Pro Arg Lys Ala Pro Thr Phe Ile
        195                 200                 205

Asn Pro Ser Gln Glu Leu Asp Tyr Tyr Arg Phe Met Asn Asp Ser Ile
    210                 215                 220

Leu Lys Leu Phe Leu Thr Glu Lys Glu Ile Leu Arg Glu Val Thr Pro
225                 230                 235                 240

Asp Ile Pro Val Ser Thr Asn Phe Met Gly Ser Phe Lys Pro Leu Asn
                245                 250                 255

Tyr Phe Gln Trp Ala Gln His Val Asp Ile Val Thr Trp Asp Ser Tyr
            260                 265                 270

Pro Asp Pro Arg Glu Gly Leu Pro Ile Gln His Ala Met Met Asn Asp
        275                 280                 285

Leu Met Arg Ser Leu Arg Lys Gly Gln Pro Phe Ile Leu Met Glu Gln
    290                 295                 300

Val Thr Ser His Val Asn Trp Arg Asp Ile Asn Val Pro Lys Pro Pro
305                 310                 315                 320
```

```
Gly Val Met Arg Leu Trp Ser Tyr Ala Thr Ile Ala Arg Gly Ala Asp
            325                 330                 335

Gly Ile Met Phe Phe Gln Trp Arg Gln Ser Arg Ala Gly Ala Glu Lys
            340                 345                 350

Phe His Gly Ala Met Val Pro His Phe Leu Asn Glu Asn Asn Arg Ile
            355                 360                 365

Tyr Arg Glu Val Thr Gln Leu Gly Gln Glu Leu Lys Lys Leu Asp Cys
    370                 375                 380

Leu Val Gly Ser Arg Ile Lys Ala Glu Val Ala Ile Ile Phe Asp Trp
385                 390                 395                 400

Glu Asn Trp Trp Ala Val Glu Leu Ser Ser Lys Pro His Asn Lys Leu
            405                 410                 415

Arg Tyr Ile Pro Ile Val Glu Ala Tyr Tyr Arg Glu Leu Tyr Lys Arg
            420                 425                 430

Asn Ile Ala Val Asp Phe Val Arg Pro Ser Asp Asp Leu Thr Lys Tyr
            435                 440                 445

Lys Val Val Ile Ala Pro Met Leu Tyr Met Val Lys Glu Gly Glu Asp
    450                 455                 460

Glu Asn Leu Arg Gln Phe Val Ala Asn Gly Gly Thr Leu Ile Val Ser
465                 470                 475                 480

Phe Phe Ser Gly Ile Val Asp Glu Asn Asp Arg Val His Leu Gly Gly
            485                 490                 495

Tyr Pro Gly Pro Leu Arg Asp Ile Leu Gly Ile Phe Val Glu Glu Phe
            500                 505                 510

Val Pro Tyr Pro Glu Thr Lys Val Asn Lys Ile Tyr Ser Asn Asp Gly
            515                 520                 525

Glu Tyr Asp Cys Thr Thr Trp Ala Asp Ile Ile Arg Leu Glu Gly Ala
    530                 535                 540

Glu Pro Leu Ala Thr Phe Lys Gly Asp Trp Tyr Ala Gly Leu Pro Ala
545                 550                 555                 560

Val Thr Arg Asn Cys Tyr Gly Lys Gly Glu Gly Ile Tyr Val Gly Thr
            565                 570                 575

Tyr Pro Asp Ser Asn Tyr Leu Gly Arg Leu Leu Glu Gln Val Phe Ala
            580                 585                 590

Lys His His Ile Asn Pro Ile Leu Glu Val Ala Glu Asn Val Glu Val
            595                 600                 605

Gln Gln Arg Glu Thr Asp Glu Trp Lys Tyr Leu Ile Ile Ile Asn His
    610                 615                 620

Asn Asp Tyr Glu Val Thr Leu Ser Leu Pro Glu Asp Lys Ile Tyr Gln
625                 630                 635                 640

Asn Met Ile Asp Gly Lys Cys Phe Arg Gly Gly Glu Leu Arg Ile Gln
            645                 650                 655

Gly Val Asp Val Ala Val Leu Arg Glu His Asp Glu Ala Gly Lys Val
            660                 665                 670
```

```
<210> SEQ ID NO 40
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atgaacgttt tgtcgtctat ttgctacggt ggggattata acccggagca atggccggag      60
```

```
gagatctggt atgaagatgc taaattaatg caaaaagcgg gggtcaattt agtgagctta      120 ggcattttt cttggtctaa aatcgaaccg tctgatgggg tttttgactt tgaatggtta       180
gataaagtca ttgatatcct ttacgatcac ggcgtgtata ttaatctggg aacagcgacg      240
gctactactc cggcgtggtt tgtaaaaaag tatcctgatt cactcccgat cgatgaatcc      300
ggcgtcatct tatcttttgg ttctcggcaa cattattgcc cgaaccaccc tcaattgatc      360
acacatatta aacgtcttgt tcgggctatc gccaacgct ataaaaacca tccagcgctt       420
aagatgtggc acgtcaataa cgagtatgca tgtcatgtgt caaatgctt ttgcgagaat       480 tgtgctgtgg cgtttcgaaa atggttaaaa gaacgttata aacaatcga cgaacttaac       540 gaaagatggg ggactaattt ctggggccag agatataatc actgggacga aattaacccg      600
ccgcgaaaag caccgacatt catcaatcct agccaagaac ttgactatta tcgatttatg      660
aacgattcta tcctgaaact gttttttaaca gaaaaagaaa ttttaagaga agtgacacct      720
gacatccctg tctcaacaaa tttcatggga agcttcaagc cgttgaacta ttttcaatgg      780
gcacaacacg tggatattgt tacgtgggat tcttatccgg accctcgcga aggtcttccg      840
atccaacatg ccatgatgaa tgatttaatg cgttcactca ggaagggcca accgtttatt      900
ctgatggagc aggtaacaag ccatgtgaat tggagagata tcaacgtccc taaaccgcca      960
ggcgtaatga ggctgtggtc ctatgcaact attgcgcggg gagcagatgg cattatgttt     1020
tttcagtggc gtcaatcacg agctggggct gaaaaatttc acggagcgat ggtgccgcat     1080 ttttttaaatg aaaacaatag aatttatcgc gaagttacac agcttggaca ggaactgaag     1140
aaacttgatt gtttggtcgg gtcacgtata aaagccgaag tcgcgataat atttgattgg     1200
gaaaactggt gggccgtaga gttatcctcg aaaccacaca acaaactccg atacattccc     1260
attgttgaag catactatcg cgaactgtat aaaagaaata ttgcagtgga ttttgtgcgg     1320
ccatctgatg acttgacgaa gtataaggtt gtgatcgcac caatgttata tatggtaaaa     1380
gaaggcgaag atgaaaactt acgacaattc gtggctaatg gaggcacatt gatcgtctca     1440
ttctttagcg gaattgtgga cgaaaacgat cgcgttcatt taggcggtta tcctggccct     1500
ctccgcgata tccttggcat atttgttgag gagtttgtac cttacccaga aactaaggtg     1560
aataaaattt attccaacga tggggaatat gactgtacaa catgggcgga cattattcgt     1620
ttagaaggtg cggagccgtt agctaccttt aaaggcgatt ggtatgcggg cctgccagcg     1680
gtcacgagga attgctatgg taaaggcgaa ggtatttatg tgggcactta ccctgatagc     1740
aattatttag gcagactgtt ggaacaagtg tttgccaaac atcacattaa tcctatcctc     1800
gaagtggcgg agaatgtcga gtccaacag agggaaacag atgaatggaa atatctgatt     1860
attattaacc acaacgatta tgaagtaacc ctgtccttac cggaagataa gatctaccaa     1920
aatatgatag acggaaaatg ttttaggggc ggagagctgc gtatccaagg ggtggacgtt     1980
gcagtcttac gggaacacga cgaagcagga aaagtttaa                            2019
```

<210> SEQ ID NO 41
<211> LENGTH: 1737
<212> TYPE: PRT
<213> ORGANISM: Clostridium chauvoei

<400> SEQUENCE: 41

```
Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
```

-continued

```
                20                25                30

Ser Ala Ala Gly Asn Ser Val Ser Tyr Asp Gly Glu Arg Arg Val Asn
            35                40                45

Phe Asn Glu Asn Trp Arg Phe Gln Arg Glu Thr Asn Gly Ser Ile Ala
        50                55                60

Gly Ala Gln Asn Pro Gly Phe Asp Asp Ser Ser Trp Arg Lys Leu Asn
65                70                75                80

Leu Pro His Asp Trp Ser Ile Glu Leu Asp Phe Asn Lys Asn Ser Leu
                85                90                95

Ala Thr His Glu Gly Gly Tyr Leu Asp Gly Gly Ile Gly Trp Tyr Arg
            100               105               110

Lys Thr Phe Thr Ile Pro Glu Ser Met Lys Gly Lys Arg Ile Ser Leu
        115               120               125

Asp Phe Asp Gly Val Tyr Met Asn Ser Thr Thr Tyr Leu Asn Gly Glu
        130               135               140

Val Leu Gly Thr Tyr Pro Phe Gly Tyr Asn Ala Phe Ser Tyr Asp Ile
145               150               155               160

Ser Asp Lys Leu Tyr Lys Asp Gly Arg Ala Asn Val Leu Val Val Lys
            165               170               175

Val Asn Asn Thr Gln Pro Ser Ser Arg Trp Tyr Ser Gly Ser Gly Ile
            180               185               190

Tyr Arg Asn Val Tyr Leu Thr Val Thr Asp Pro Ile His Val Ala Arg
            195               200               205

Tyr Gly Thr Phe Val Thr Thr Pro Asn Leu Glu Lys Ser Ile Lys Glu
        210               215               220

Asp Arg Ala Asp Val Asn Ile Lys Thr Lys Ile Ser Asn Asp Ala Ala
225               230               235               240

Glu Ala Lys Gln Val Lys Ile Lys Ser Thr Ile Tyr Asp Gly Ala Gly
            245               250               255

Asn Thr Val Gln Thr Val Glu Thr Glu Glu Lys Thr Ala Ala Ala Gly
            260               265               270

Thr Val Thr Pro Phe Glu Gln Asn Thr Val Ile Lys Gln Pro Lys Leu
        275               280               285

Trp Ser Ile Asp Lys Pro Tyr Arg Tyr Asn Leu Val Thr Glu Val Ile
        290               295               300

Val Gly Gly Gln Thr Val Asp Thr Tyr Glu Thr Lys Phe Gly Val Arg
305               310               315               320

Tyr Phe Lys Phe Asp Glu Asn Glu Gly Phe Ser Leu Asn Gly Glu Tyr
            325               330               335

Met Lys Leu His Gly Val Ser Met His His Asp Leu Gly Ala Leu Gly
            340               345               350

Ala Ala Thr Asn Ala Arg Gly Val Glu Arg Gln Met Gln Ile Met Lys
            355               360               365

Asp Met Gly Val Asn Ala Ile Arg Val Thr His Asn Pro Ala Ser Pro
        370               375               380

Glu Leu Leu Glu Ala Ala Asn Lys Leu Gly Leu Phe Ile Ile Glu Glu
385               390               395               400

Ala Phe Asp Ser Trp Ala Gln Ser Lys Lys Pro Tyr Asp Tyr Gly Arg
            405               410               415

Phe Phe Asn Ala Trp Ala Glu His Asp Ile Lys Glu Met Val Asp Arg
            420               425               430

Gly Lys Asn Glu Pro Ala Ile Ile Met Trp Ser Ile Gly Asn Glu Ile
            435               440               445
```

-continued

```
Tyr Asp Thr Thr Asn Ala Ala Gly Val Glu Thr Ala Arg Asn Leu Val
    450             455             460

Gly Trp Val Lys Glu Ile Asp Thr Thr Arg Pro Thr Thr Ile Gly Glu
465             470             475             480

Asp Lys Thr Arg Gly Asp Lys Val Asn Val Thr Pro Ile Asn Ser Tyr
            485             490             495

Ile Lys Glu Ile Phe Asn Ile Val Asp Val Val Gly Leu Asn Tyr Ser
            500             505             510

Glu Asn Asn Tyr Asp Gly Tyr His Lys Gln Asn Pro Ser Trp Lys Leu
            515             520             525

Tyr Gly Ser Glu Thr Ser Ser Ala Thr Arg Ser Arg Gly Val Tyr Thr
    530             535             540

His Pro Tyr Gln Tyr Asn Gln Ser Thr Lys Tyr Ala Asp Leu Gln Gln
545             550             555             560

Ser Ser Tyr Asp Asn Asp Tyr Val Gly Trp Gly Arg Thr Ala Glu Asp
            565             570             575

Ala Trp Lys Tyr Asp Arg Asp Leu Lys His Ile Ala Gly Gln Phe Ile
            580             585             590

Trp Thr Gly Phe Asp Tyr Ile Gly Glu Pro Thr Pro Tyr Tyr Asn Ser
            595             600             605

Tyr Pro Ala Lys Ser Ser Tyr Phe Gly Ala Val Asp Thr Ala Gly Phe
    610             615             620

Pro Lys Asp Ile Phe Tyr Tyr Tyr Gln Ser Gln Trp Lys Lys Glu Pro
625             630             635             640

Met Val His Leu Leu Pro His Trp Asn Trp Lys Glu Gly Glu Lys Val
            645             650             655

Arg Val Leu Ala Tyr Thr Asn Ala Ser Lys Val Glu Leu Val Leu Asn
            660             665             670

Gly Glu Ser Leu Gly Glu Lys Asn Tyr Asp Asn Lys Gln Thr Ser Trp
            675             680             685

Gly Ala Pro Tyr Lys Glu Thr Lys Asp Gly Lys Thr Tyr Leu Glu Trp
    690             695             700

Ala Val Pro Phe Lys Pro Gly Lys Leu Glu Ala Val Ala Lys Asp Glu
705             710             715             720

Asn Gly Lys Val Ile Ala Arg Asp Gln Val Val Thr Ala Gly Glu Pro
            725             730             735

Ala Ser Val Arg Leu Thr Ala Asp Arg Lys Val Val Lys Ala Asp Gly
            740             745             750

Thr Asp Leu Ser Phe Ile Thr Ala Asp Ile Val Asp Ser Lys Gly Ile
            755             760             765

Val Val Pro Asp Ala Asp His Leu Ile Thr Phe Asn Val Thr Gly Gln
    770             775             780

Gly Glu Leu Ala Gly Val Asp Asn Gly Asn Ala Ser Ser Val Glu Arg
785             790             795             800

Tyr Lys Asp Asn Lys Arg Lys Ala Phe Ser Gly Lys Ala Leu Ala Ile
            805             810             815

Val Gln Ser Ser Lys Leu Ser Gly Lys Ile Thr Val His Ala Ser Val
            820             825             830

Ala Gly Leu Ser Ser Asp Ser Thr Ser Val Phe Thr Val Thr Pro Ala
            835             840             845

Asp His Asp Lys Lys Ile Val Ala Gly Ile Asp Asp Val Asn Leu Thr
    850             855             860
```

```
Val Asp Val Asn Glu Ala Pro Lys Leu Pro Ser Glu Ile Lys Val Tyr
865             870             875             880

Tyr Ser Asp Glu Ser Ala Ala Ala Lys Asn Val Thr Trp Asp Glu Val
                885             890             895

Asp Pro Lys Gln Tyr Ser Thr Val Gly Glu Phe Thr Val Glu Gly Ser
            900             905             910

Val Glu Gly Thr Ser Leu Lys Ala Lys Ala Phe Val Ile Val Lys Gly
        915             920             925

Ile Val Ala Val Lys Pro Tyr Ser Thr Ala Thr Lys Val Gly Val Gln
    930             935             940

Pro Val Leu Pro Glu Lys Ala Thr Leu Leu Tyr Ser Asp Gly Thr Thr
945             950             955             960

Lys Gly Ala Thr Val Thr Trp Asp Glu Ile Pro Glu Asp Lys Leu Ala
            965             970             975

Lys Glu Gly Arg Phe Thr Val Glu Gly Ser Val Glu Gly Thr Asp Leu
            980             985             990

Lys Ala Asn Val Tyr Val Arg Val  Thr Asn Glu Val Lys  Ser Val Asn
            995             1000            1005

Ile Met  Leu Gln Glu Gln Gly  Ser Ala Tyr Pro Lys  Leu Glu Ala
    1010            1015            1020

Thr Phe  Thr Asn Pro Ala Asp  Asn Leu Gln His Leu  Asn Asp Gly
    1025            1030            1035

Ile Lys  Ser Tyr Thr Asn Asn  Pro Val Asn Arg Trp  Thr Asn Trp
    1040            1045            1050

Thr Arg  Thr Pro Arg Asp Ala  Gly Asp Ser Ile Thr  Val Asn Phe
    1055            1060            1065

Gly Lys  Lys His Val Ile Asn  Asn Leu Asp Leu Phe  Val Phe Thr
    1070            1075            1080

Asp Ser  Gly Thr Val Val Pro  Glu Lys Ala Glu Val  Gln Tyr Trp
    1085            1090            1095

Asp Gly  Thr Ala Trp Lys Asp  Val Glu Asn Leu Thr  Gln Pro Ser
    1100            1105            1110

Pro Tyr  Val Val Glu Lys Asn  Glu Leu Thr Phe Asp  Ala Val Ala
    1115            1120            1125

Thr Glu  Lys Leu Lys Phe His  Leu Thr Pro Ser Val  Lys Gly Lys
    1130            1135            1140

Phe Leu  Ala Leu Thr Glu Ala  Glu Val Tyr Ala Asp  Gln Ile Val
    1145            1150            1155

Met Gly  Glu Thr Ala Lys Leu  Gln Ser Ile Thr Val  Asn Gly Lys
    1160            1165            1170

Ala Leu  Glu Gly Phe Asp His  Ala Lys Lys Asn Tyr  Glu Leu Val
    1175            1180            1185

Leu Pro  Tyr Gly Ser Glu Leu  Pro Lys Ile Glu Ala  Ala Ala Ala
    1190            1195            1200

Asp Asn  Ala Thr Val Thr Ile  Leu Pro Ala Phe Ser  Tyr Pro Gly
    1205            1210            1215

Thr Ala  Lys Leu Phe Val Thr  Ser Glu Asp Gly Lys  Val Thr Thr
    1220            1225            1230

Glu Tyr  Ser Ile Gly Val Ser  Thr Glu Glu Pro Lys  Leu Val Ser
    1235            1240            1245

Ala Glu  Leu Ser Ala Asp Lys  Thr Asn Val Met Glu  Asp Asp Ile
    1250            1255            1260

Ile Asp  Leu Lys Val Ile Gly  Leu Phe Glu Ser Lys  Glu Lys Ile
```

```
          1265                    1270                    1275

Asp Val Thr Asp Ser Gln Pro  Thr Tyr Glu Phe Asp  Gln Gln Ile
     1280                    1285                    1290

Ile Lys Ile Glu Gly Asn Lys  Leu Tyr Ala Leu Glu  Thr Gly Asn
     1295                    1300                    1305

Val Lys Val Lys Val Thr Val  Thr Tyr Lys Gly Val  Ser Val Thr
     1310                    1315                    1320

Thr Pro Ala Leu Glu Phe Thr  Ile Ala Lys Asn Pro  Ala Pro Lys
     1325                    1330                    1335

Tyr Ile Thr Ser Leu Glu Pro  Val Thr Val Val Val  Lys Lys Gly
     1340                    1345                    1350

Glu Ala Pro Glu Leu Pro Ala  Thr Val Val Ala His  Tyr Asn Arg
     1355                    1360                    1365

Gly Ile Pro Arg Asp Val Lys  Val Lys Trp Glu Arg  Ile Asn Pro
     1370                    1375                    1380

Ser Lys Tyr Gln Gln Leu Gly  Glu Phe Thr Val Ser  Gly Met Val
     1385                    1390                    1395

Glu Gly Thr Asp Ile Lys Ala  Gln Ala Lys Val Ile  Val Lys Gly
     1400                    1405                    1410

Ala Val Ala Val Glu Asp Ile  Arg Met Ala Val Leu  Leu Lys Gln
     1415                    1420                    1425

Met Pro Gln Leu Pro Gly Lys  Val Thr Val Tyr Tyr  Ser Asp Gly
     1430                    1435                    1440

Ala Glu Glu Gln Arg Ala Val  Lys Trp Glu Glu Ile  Pro Gln Glu
     1445                    1450                    1455

Glu Leu Glu Asn Val Gly Glu  Phe Lys Val Lys Gly  Asp Val Asn
     1460                    1465                    1470

Gly Val Lys Leu Lys Ala Thr  Ala Thr Ile Arg Val  Thr Asp Glu
     1475                    1480                    1485

Val Gly Gly Glu Gln Asn Ile  Ser Arg Ala Lys Asn  Gly Tyr Glu
     1490                    1495                    1500

Tyr Pro Lys Ala Glu Ala Ser  Phe Thr Asn Asn Gly  Pro Gly Ser
     1505                    1510                    1515

Ser Asp Arg Ile Glu Ala Ile  Asn Asp Asp Val Ile  Ser Tyr Glu
     1520                    1525                    1530

Ala Asn Pro His Asn Arg Trp  Thr Asn Trp Gln Pro  Val Pro Arg
     1535                    1540                    1545

Ala Gly Asp Trp Val Ser Ile  Thr Phe Gly Asp Tyr  Glu Pro Thr
     1550                    1555                    1560

Glu Tyr Asp Val Asp Ser Met  Glu Ile His Trp Phe  Ala Asp His
     1565                    1570                    1575

Gly Thr Ser Tyr Pro Glu Arg  Phe Gln Ile Glu Tyr  Lys Ser Gly
     1580                    1585                    1590

Asp Ser Trp Lys Glu Val Thr  Ser Leu Lys Ser Asp  Pro Ala Ser
     1595                    1600                    1605

Pro Ala Leu Gly Lys Ala Asn  Val Tyr Ser Phe Asp  Arg Val Lys
     1610                    1615                    1620

Thr Ser Ala Ile Arg Val Lys  Met Thr Ala Gln Ala  Gly Lys Ser
     1625                    1630                    1635

Leu Ala Ile Thr Glu Leu Lys  Val Phe Ser Lys Trp  Pro Lys Ala
     1640                    1645                    1650

Gly Thr Glu Pro Glu Val Thr  Asp Ile Lys Val Gly  Gly Lys Ser
     1655                    1660                    1665
```

```
Ile Leu  Glu Asp Phe Glu Gln  Lys Gly Asp His Tyr  Glu Val Thr
    1670              1675              1680

Ile Asp  Ala Gly Asp Ala Asn  Val Met Pro Lys Ile  Asn Val Lys
    1685              1690              1695

Ala Lys  Asp Gln Thr Ser Ile  Thr Ile Val Pro Ala  Val Thr Ser
    1700              1705              1710

Pro Ser  Thr Ala Lys Val Ile  Ala Lys Ser Glu Asp  Gly Lys Lys
    1715              1720              1725

Val Lys  Val Tyr Ser Ile His  Tyr Lys
    1730              1735
```

<210> SEQ ID NO 42
<211> LENGTH: 5214
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atgaagaaag cgatcagctg cgtttttctg atatctgcac tcatcttaag cagctttcaa      60
gtaccggtgc aggggcaagc gatgtctaaa actacgtcag cggccggaaa cagcgtttca     120
tacgatggtg aacggagagt taatttcaat gaaaattggc ggttccagcg ggaaaccaat     180
ggtagcattg caggtgcaca aaatccaggg tttgatgact cttcctggag aaagcttaat     240
ttaccgcatg actggagcat agaacttgat ttcaataaaa actcattggc gacgcacgaa     300 gggggggtatt tggacggcgg catcgggtgg taccgaaaaa cgttcaccat acctgaatca     360
atgaaaggca aagaatctc tctggatttc gatggtgtat atatgaactc aacaacatat     420
ttaaacgggg aggtattagg tacatatccg tttggctata cgccttttc ttacgacatt     480 tccgataaac tgtataaaga tggaagagcg aacgtgcttg tagtgaaggt caataatacg     540
caaccatcta gtcgatggta ttcaggaagc ggcatatatc gtaatgtgta tttaactgta     600
acggatccca ttcatgttgc gcggtatggc acatttgtca caacacctaa cttggagaaa     660
tcaattaaag aagatcgggc agacgtcaac attaaaacga aaatttctaa cgatgcggcg     720
gaagcaaaac aagtcaaaat caaatcaaca atatatgacg gagctggtaa cacagtacag     780
acggttgaaa cggaggaaaa aacagcagca gcaggtaccg taaccccgtt tgagcaaaac     840
acggtaataa aacagcctaa actgtggtcc atcgacaaac cgtaccgtta taacctggta     900
acggaggtta ttgttggcgg ccaaacggtg gatacttatg aaactaaatt cggagtcagg     960
tattttaagt ttgacgagaa tgaggggttt tctctgaacg gagagtacat gaagcttcat    1020
ggcgtctcca tgcatcacga tttaggagct ttaggcgcgg cgacaaacgc tagagggtt    1080 gaaaggcaga tgcagattat gaaagacatg ggagtcaatg ccatcagagt aacacataac    1140
ccggcaagcc ctgaacttct ggaagccgcg aacaagctcg gcctgtttat tattgaggaa    1200
gcttttgatt cgtgggctca gagtaagaaa ccctatgact atggaagatt tttcaatgcg    1260
tgggcggagc acgatataaa agaaatggtt gacagaggga aaaacgaacc cgcaatcatc    1320
atgtggagta ttgggaatga aatctatgat acgactaatg cagcgggcgt ggaaaccgcg    1380
aggaatcttg tgggctgggt caaagaaatt gacactacac ggcccacaac aatcggcgaa    1440
gacaagacta ggggcgacaa agtaaacgtg acgccaatta cagttatat caaagaaatt    1500 ttcaacattg ttgacgtagt tgggctgaac tactcggaaa caattatga tggatatcac    1560
```

-continued

```
aaacagaatc cctcttggaa actgtatgga tccgaaacaa gcagtgcgac aagatcaagg    1620
ggtgtttata cacacccata tcagtataac caatctacaa aatacgccga tctgcaacaa    1680
tcctcttatg acaacgacta tgttggctgg ggtagaacag cggaagacgc gtggaagtac    1740
gacagagatt tgaaacatat cgcgggacag tttatttgga cgggattcga ttacattggt    1800
gaaccaaccc cgtactataa tagctatcct gcgaaaagca gctacttcgg agcagtggat    1860
acagctggat tccctaaaga tatcttttac tattatcagt cgcaatggaa aaaggagccg    1920
atggtacatc ttcttccgca ttggaactgg aaggaaggag agaaggtcag agtactggcc    1980
tacaccaatg ctagcaaagt cgaacttgta ctgaatggcg aatccctcgg agagaaaaat    2040
tatgataata aacaaacgtc ctggggagct ccttataagg aaacaaaaga cggaaagaca    2100
tatctggaat gggcggtccc tttcaagcct ggcaaactgg aagccgtggc aaaagatgaa    2160
aacggcaagg taattgcaag agatcaagta gtgacggcgg gagagcccgc tagcgttaga    2220
ttgacagctg ataggaaagt tgtgaaagca gatggaacag atttaagctt tattaccgca    2280
gatatcgtag attctaaggg cattgttgtc ccggatgctg atcatttgat tacattcaat    2340
gtgactggac aaggagaact ggctggagta gataatggta atgcatcatc cgttgaacgg    2400
tacaaagata ataaaagaaa ggcctttttca ggtaaggcct tggcaatcgt acagtcatca    2460
aaacttagcg gtaaaatcac cgtacacgcc tcggttgcag gtctttcatc cgatagtaca    2520
agtgtcttca cagtcacacc ggcggatcac gataaaaaaa ttgtagcagg tattgacgat    2580
gtgaacctta cggttgacgt caacgaagcg ccaaaacttc cgtctgaaat taaagtctat    2640
tattcagacg aatctgcggc cgcgaaaaat gttacatggg atgaagtgga ccctaaacag    2700
tattctacag ttggcgagtt tacagtcgaa ggctcggttg agggcacaag cttaaaggcg    2760
aaagcgtttg tcatagttaa aggtatcgtc gccgttaaac cctattctac ggcgaccaaa    2820
gttggagttc aacctgtttt acctgagaaa gcaacattac tttatagcga tggcactact    2880
aaaggggcca cagtgacatg ggatgaaatc ccagaagata aattggcgaa agagggccgg    2940
tttacggtag aaggttcagt agagggcaca gacttgaaag cgaatgttta tgtgcgagtt    3000
acgaatgagg taaagtctgt taacattatg cttcaggagc agggcagcgc atatccaaag    3060
cttgaggcga cctttacaaa tccggcggac aatctgcagc acctgaatga tggtatcaaa    3120
tcttatacaa acaatccggt gaatagatgg acgaattgga caagaacacc aagggacgcg    3180
ggagacagta tcacggtgaa ctttgggaaa aaacacgtaa tcaacaatct tgacctttt    3240 gtatttacag atagtggtac ggttgtccct gagaaagctg aagttcaata ttgggatgga    3300
actgcctgga aagacgtaga gaatttaaca cagccttcac cgtacgttgt ggaaaaaaac    3360
gagttgactt tcgatgcagt cgcgacagaa aaattaaaat ttcatctgac accgtctgtc    3420
aaaggtaaat ttctggccct gacagaagca gaagtatacg cagaccagat tgtaatggga    3480
gaaacagcta aactccagtc cataacggtc aatggtaagg cactcgaagg gtttgatcat    3540
gcgaaaaaga attatgagct cgtactgccg tacgggtccg aattgcctaa gattgaagca    3600
gctgcggctg acaatgctac cgtgacgatt ttacctgcct tttcttatcc aggaacggcg    3660
aagttgttcg taacaagtga ggacggaaaa gttacaaccg aatatagcat tggcgtttcg    3720
actgaagagc caaagctggt ctcagctgag ttgagcgcag ataagaccaa tgtcatggaa    3780
gatgatataa ttgacctgaa agtgataggc ctctttgaga gcaaggaaaa gattgacgtc    3840
acagacagcc aaccaaccta cgagttcgac cagcaaatta taaagatcga aggaaataaa    3900
ttgtatgcgc tggaaaccgg taatgtcaaa gtaaaggtca ccgttactta taaaggagtc    3960
```

-continued

```
tctgttacga caccagccct tgaattcacg atcgcgaaga atcctgctcc gaaatatatt   4020
acatcgctcg agccagtcac agtagttgtg aaaaaaggcg aagctcccga actccctgcg   4080
actgttgtcg ctcattataa ccgcggtatc ccgcgggatg ttaaagttaa atgggaacgg   4140
ataaatccat caaagtacca acaattaggc gaatttaccg tttcgggaat ggtggaagga   4200
actgatatta aagcccaagc taaagtgata gtgaaaggag cagttgcagt agaggatatt   4260
agaatggcag tccttttgaa gcaaatgcct cagttacctg gaaaggttac ggtatactat   4320
agtgatggtg cggaagaaca acgagctgtt aaatgggagg agataccgca agaagaactt   4380
gaaaacgtgg gagaatttaa ggtgaaagga gatgttaatg gtgttaagct gaaagcaacc   4440
gcgaccatcc gggtaacgga tgaagtgggg ggagaacaga atatttcgcg ggcaaaaaat   4500
ggctatgagt acccgaaggc tgaggctagt tttacaaata atgggccggg gtctagcgac   4560
cgtattgagg ctatcaatga cgacgttatc tcatacgaag caaatccgca caacaggtgg   4620
accaactggc agccggtgcc tagagctggc gactgggtct ccattacctt tggtgattat   4680
gaaccaacag aatacgacgt tgactcgatg gaaatccatt ggtttgcgga ccacggaacc   4740
tcttacccag agaggtttca gatcgaatat aaaagcggag actcgtggaa agaagtcacg   4800
agcctgaaga gtgacccggc ctctccagcc ctgggaaaag ctaatgttta ttcattcgac   4860
cgtgtgaaga cctctgctat tagggtaaaa atgacagctc aggcgggtaa aagtcttgct   4920
attacggaat taaaagtctt ttcaaaatgg cctaaagcag gcaccgaacc tgaggtcacc   4980
gatatcaagt tggcggcaa atctatcctc gaagattttg aacaaaaagg cgaccattat   5040
gaagtgacaa ttgatgcggg tgatgcgaat gtaatgccga aaatcaatgt gaaagcgaag   5100
gatcaaacgt ctatcacaat cgtcccggcg gttactagtc cgtcaacggc aaaagtgatc   5160
gctaaatcgg aagatggcaa aaaagtgaaa gtatattcaa tacattataa ataa        5214
```

```
<210> SEQ ID NO 43
<211> LENGTH: 1550
<212> TYPE: PRT
<213> ORGANISM: Komagataeibacter xylinus

<400> SEQUENCE: 43

Met Pro Glu Val Arg Ser Ser Thr Gln Ser Glu Ser Gly Met Ser Gln
1               5                   10                  15

Trp Met Gly Lys Ile Leu Ser Ile Arg Gly Ala Gly Leu Thr Ile Gly
                20                  25                  30

Val Phe Gly Leu Cys Ala Leu Ile Ala Ala Thr Ser Val Thr Leu Pro
            35                  40                  45

Pro Glu Gln Gln Leu Ile Val Ala Phe Val Cys Val Val Ile Phe Phe
        50                  55                  60

Ile Val Gly His Lys Pro Ser Arg Arg Ser Gln Ile Phe Leu Glu Val
65                  70                  75                  80

Leu Ser Gly Leu Val Ser Leu Arg Tyr Leu Thr Trp Arg Leu Thr Glu
                85                  90                  95

Thr Leu Ser Phe Asp Thr Trp Leu Gln Gly Leu Leu Gly Thr Met Leu
                100                 105                 110

Leu Val Ala Glu Leu Tyr Ala Leu Met Met Leu Phe Leu Ser Tyr Phe
            115                 120                 125

Gln Thr Ile Ala Pro Leu His Arg Ala Pro Leu Pro Leu Pro Pro Asn
        130                 135                 140

Pro Asp Glu Trp Pro Thr Val Asp Ile Phe Val Pro Thr Tyr Asn Glu
```

-continued

```
145                150                155                    160

Glu Leu Ser Ile Val Arg Leu Thr Val Leu Gly Ser Leu Gly Ile Asp
                165                170                175

Trp Pro Pro Glu Lys Val Arg Val His Ile Leu Asp Asp Gly Arg Arg
                180                185                190

Pro Glu Phe Ala Ala Phe Ala Ala Glu Cys Gly Ala Asn Tyr Ile Ala
                195                200                205

Arg Pro Thr Asn Glu His Ala Lys Ala Gly Asn Leu Asn Tyr Ala Ile
        210                215                220

Gly His Thr Asp Gly Asp Tyr Ile Leu Ile Phe Asp Cys Asp His Val
225                230                235                240

Pro Thr Arg Ala Phe Leu Gln Leu Thr Met Gly Trp Met Val Glu Asp
                245                250                255

Pro Lys Ile Ala Leu Met Gln Thr Pro His His Phe Tyr Ser Pro Asp
                260                265                270

Pro Phe Gln Arg Asn Leu Ser Ala Gly Tyr Arg Thr Pro Pro Glu Gly
                275                280                285

Asn Leu Phe Tyr Gly Val Val Gln Asp Gly Asn Asp Phe Trp Asp Ala
        290                295                300

Thr Phe Phe Cys Gly Ser Cys Ala Ile Leu Arg Arg Thr Ala Ile Glu
305                310                315                320

Gln Ile Gly Gly Phe Ala Thr Gln Thr Val Thr Glu Asp Ala His Thr
                325                330                335

Ala Leu Lys Met Gln Arg Leu Gly Trp Ser Thr Ala Tyr Leu Arg Ile
                340                345                350

Pro Leu Ala Gly Gly Leu Ala Thr Glu Arg Leu Ile Leu His Ile Gly
                355                360                365

Gln Arg Val Arg Trp Ala Arg Gly Met Leu Gln Ile Phe Arg Ile Asp
        370                375                380

Asn Pro Leu Phe Gly Arg Gly Leu Ser Trp Gly Gln Arg Leu Cys Tyr
385                390                395                400

Leu Ser Ala Met Thr Ser Phe Leu Phe Ala Val Pro Arg Val Ile Phe
                405                410                415

Leu Ser Ser Pro Leu Ala Phe Leu Phe Phe Gly Gln Asn Ile Ile Ala
                420                425                430

Ala Ser Pro Leu Ala Leu Leu Ala Tyr Ala Ile Pro His Met Phe His
                435                440                445

Ala Val Gly Thr Ala Ser Lys Ile Asn Lys Gly Trp Arg Tyr Ser Phe
        450                455                460

Trp Ser Glu Val Tyr Glu Thr Thr Met Ala Leu Phe Leu Val Arg Val
465                470                475                480

Thr Ile Val Thr Leu Leu Ser Pro Ser Arg Gly Lys Phe Asn Val Thr
                485                490                495

Asp Lys Gly Gly Leu Leu Glu Lys Gly Tyr Phe Asp Leu Gly Ala Val
                500                505                510

Tyr Pro Asn Ile Ile Leu Gly Leu Ile Met Phe Gly Gly Leu Ala Arg
                515                520                525

Gly Val Tyr Glu Leu Ser Phe Gly His Leu Asp Gln Ile Ala Glu Arg
                530                535                540

Ala Tyr Leu Leu Asn Ser Ala Trp Ala Met Leu Ser Leu Ile Ile Ile
545                550                555                560

Leu Ala Ala Ile Ala Val Gly Arg Glu Thr Gln Gln Lys Arg Asn Ser
                565                570                575
```

-continued

```
His Arg Ile Pro Ala Thr Ile Pro Val Glu Val Ala Asn Ala Asp Gly
            580                 585                 590

Ser Ile Ile Val Thr Gly Val Thr Glu Asp Leu Ser Met Gly Gly Ala
            595                 600                 605

Ala Val Lys Met Ser Trp Pro Ala Lys Leu Ser Gly Pro Thr Pro Val
            610                 615                 620

Tyr Ile Arg Thr Val Leu Asp Gly Glu Glu Leu Ile Leu Pro Ala Arg
625                 630                 635                 640

Ile Ile Arg Ala Gly Asn Gly Arg Gly Ile Phe Ile Trp Thr Ile Asp
                645                 650                 655

Asn Leu Gln Gln Glu Phe Ser Val Ile Arg Leu Val Phe Gly Arg Ala
            660                 665                 670

Asp Ala Trp Val Asp Trp Gly Asn Tyr Lys Ala Asp Arg Pro Leu Leu
            675                 680                 685

Ser Leu Met Asp Met Val Leu Ser Val Lys Gly Leu Phe Arg Ser Ser
            690                 695                 700

Gly Asp Ile Val His Arg Ser Ser Pro Thr Lys Pro Leu Ala Gly Asn
705                 710                 715                 720

Ala Leu Ser Asp Asp Thr Asn Asn Pro Ser Arg Lys Glu Arg Val Leu
            725                 730                 735

Lys Gly Thr Val Lys Met Val Ser Leu Leu Ala Leu Leu Thr Phe Ala
            740                 745                 750

Ser Ser Ala Gln Ala Ala Ser Ala Pro Arg Ala Val Ala Ala Lys Ala
            755                 760                 765

Pro Ala His Gln Pro Glu Ala Ser Asp Leu Pro Pro Leu Pro Ala Leu
            770                 775                 780

Leu Pro Ala Thr Ser Gly Ala Ala Gln Ala Gly Ala Gly Asp Ala Gly
785                 790                 795                 800

Ala Asn Gly Pro Gly Ser Pro Thr Gly Gln Pro Leu Ala Ala Asp Ser
                805                 810                 815

Ala Asp Ala Leu Val Glu Asn Ala Glu Asn Thr Ser Asp Thr Ala Thr
            820                 825                 830

Val His Asn Tyr Thr Leu Lys Asp Leu Gly Ala Ala Gly Ser Ile Thr
            835                 840                 845

Met Arg Gly Leu Ala Pro Leu Gln Gly Ile Glu Phe Gly Ile Pro Ser
            850                 855                 860

Asp Gln Leu Val Thr Ser Ala Arg Leu Val Leu Ser Gly Ser Met Ser
865                 870                 875                 880

Pro Asn Leu Arg Pro Glu Thr Asn Ser Val Thr Met Thr Leu Asn Glu
                885                 890                 895

Gln Tyr Ile Gly Thr Leu Arg Pro Asp Pro Ala His Pro Thr Phe Gly
            900                 905                 910

Pro Met Ser Phe Glu Ile Asn Pro Ile Phe Phe Val Ser Gly Asn Arg
            915                 920                 925

Leu Asn Phe Asn Phe Ala Ser Gly Ser Lys Gly Cys Ser Asp Ile Thr
            930                 935                 940

Asn Asp Thr Leu Trp Ala Thr Ile Ser Gln Asn Ser Gln Leu Gln Ile
945                 950                 955                 960

Thr Thr Ile Ala Leu Pro Pro Arg Arg Leu Leu Ser Arg Leu Pro Gln
                965                 970                 975

Pro Phe Tyr Asp Lys Asn Val Arg Gln His Val Thr Val Pro Met Val
                980                 985                 990
```

```
Leu Ala Gln Thr Tyr Asp Pro Gln  Ile Leu Lys Ser Ala  Gly Ile Leu
        995              1000               1005

Ala Ser  Trp Phe Gly Lys Gln  Thr Asp Phe Leu Gly  Val Thr Phe
    1010              1015               1020

Pro Val  Ser Ser Thr Ile Pro  Gln Ser Gly Asn Ala  Ile Leu Ile
    1025              1030               1035

Gly Val  Ala Asp Glu Leu Pro  Thr Ser Leu Gly Arg  Pro Gln Val
    1040              1045               1050

Asn Gly  Pro Ala Val Leu Glu  Leu Pro Asn Pro Ser  Asp Ala Asn
    1055              1060               1065

Ala Thr  Ile Leu Val Val Thr  Gly Arg Asp Arg Asp  Glu Val Ile
    1070              1075               1080

Thr Ala  Ser Lys Gly Ile Ala  Phe Ala Ser Ala Pro  Leu Pro Thr
    1085              1090               1095

Asp Ser  His Met Asp Val Ala  Pro Val Asp Ile Ala  Pro Arg Lys
    1100              1105               1110

Pro Asn  Asp Ala Pro Ser Phe  Ile Ala Met Asp His  Pro Val Arg
    1115              1120               1125

Phe Gly  Asp Leu Val Thr Ala  Ser Lys Leu Gln Gly  Thr Gly Phe
    1130              1135               1140

Thr Ser  Gly Val Leu Ser Val  Pro Phe Arg Ile Pro  Pro Asp Leu
    1145              1150               1155

Tyr Thr  Trp Arg Asn Arg Pro  Tyr Lys Met Gln Val  Arg Phe Arg
    1160              1165               1170

Ser Pro  Ala Gly Glu Ala Lys  Asp Val Glu Lys Ser  Arg Leu Asp
    1175              1180               1185

Val Gly  Ile Asn Glu Val Tyr  Leu His Ser Tyr Pro  Leu Arg Glu
    1190              1195               1200

Thr His  Gly Leu Val Gly Ala  Val Leu Gln Gly Val  Gly Leu Ala
    1205              1210               1215

Arg Pro  Ala Ser Gly Met Gln  Val His Asp Leu Asp  Val Pro Pro
    1220              1225               1230

Trp Thr  Val Phe Gly Gln Asp  Gln Leu Asn Phe Tyr  Phe Asp Ala
    1235              1240               1245

Met Pro  Leu Ala Arg Gly Ile  Cys Gln Ser Gly Ala  Ala Asn Asn
    1250              1255               1260

Ala Phe  His Leu Gly Leu Asp  Pro Asp Ser Thr Ile  Asp Phe Ser
    1265              1270               1275

Arg Ala  His His Ile Ala Gln  Met Pro Asn Leu Ala  Tyr Met Ala
    1280              1285               1290

Thr Val  Gly Phe Pro Phe Thr  Thr Tyr Ala Asp Leu  Ser Gln Thr
    1295              1300               1305

Ala Val  Val Leu Pro Glu His  Pro Asn Ala Ala Thr  Val Gly Ala
    1310              1315               1320

Tyr Leu  Asp Leu Met Gly Phe  Met Gly Ala Ala Thr  Trp Tyr Pro
    1325              1330               1335

Val Ala  Gly Val Asp Ile Val  Ser Ala Asp His Val  Ser Asp Val
    1340              1345               1350

Ala Asp  Arg Asn Leu Leu Val  Ile Ser Thr Leu Ala  Thr Ser Gly
    1355              1360               1365

Glu Ile  Ala Pro Leu Leu Ser  Arg Ser Ser Tyr Glu  Val Ala Asp
    1370              1375               1380

Gly His  Leu Arg Thr Val Ser  His Ala Ser Ala Leu  Asp Asn Ala
```

```
          1385              1390              1395

Ile Lys  Ala Val Asp Asp Pro  Leu Thr Ala Phe Arg  Asp Arg Asp
    1400              1405              1410

Ser Lys  Pro Gln Asp Val Asp  Thr Pro Leu Thr Gly  Gly Val Gly
    1415              1420              1425

Ala Met  Ile Glu Ala Glu Ser  Pro Leu Thr Ala Gly  Arg Thr Val
    1430              1435              1440

Leu Ala  Leu Leu Ser Ser Asp  Gly Ala Gly Leu Asn  Asn Leu Leu
    1445              1450              1455

Gln Met  Leu Gly Glu Arg Lys  Lys Gln Ala Asn Ile  Gln Gly Asp
    1460              1465              1470

Leu Val  Val Ala His Gly Glu  Asp Leu Ser Ser Tyr  Arg Thr Ser
    1475              1480              1485

Pro Val  Tyr Thr Ile Gly Thr  Leu Pro Leu Trp Leu  Trp Pro Asp
    1490              1495              1500

Trp Tyr  Met His Asn Arg Pro  Val Arg Val Leu Leu  Val Gly Leu
    1505              1510              1515

Leu Gly  Cys Ile Leu Ile Val  Ser Val Leu Ala Arg  Ala Leu Ala
    1520              1525              1530

Arg His  Ala Thr Arg Arg Phe  Lys Gln Leu Glu Asp  Glu Arg Arg
    1535              1540              1545

Lys Ser
    1550
```

```
<210> SEQ ID NO 44
<211> LENGTH: 4653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atgccagagg tccgatcttc gacgcagtca gagagcggga tgtcccagtg gatgggaaaa      60
atcttatcaa taagaggggc aggactgacg ataggagtat ttggcctctg tgctcttata     120
gccgcgacaa gcgttacact tccacctgaa caacaactta ttgtggcgtt cgtctgtgtt     180
gtaatctttt ttatcgtcgg acacaagcca tcacggagat cgcaaatctt tctggaagta     240
ctttccggac ttgtctctct tcgctacctt acctggcggt taacggagac cctgtccttt     300
gatacctggt tacagggtct tctgggcacg atgttactgg tcgcggaatt atatgccctg     360
atgatgttat tcttgtcata cttccagaca atagcaccgc tgcatagagc gcccctccca     420
ctccccccga tcctgatga atggcctaca gtagatatat tcgtcccgac atacaatgag     480
gaactttcaa tcgtaagact gacagttttg gggagtttgg gaatagattg gccgccggaa     540
aaagttagag tacatatcct tgacgatggg aggcgtccag aatttgccgc ctttgcagcc     600
gagtgcggag caaactatat tgctagacct acaaatgagc atgcgaaagc tggaaattta     660
aattatgcga ttggccatac agacggggac tatatattaa ttttttgattg tgaccacgta     720 ccaacacgcg ctttcctgca gcttaccatg ggatggatgg ttgaagatcc aaaaatcgcg     780
cttatgcaaa ctccgcatca cttttacagc cctgacccat ccaacgcaa tttgtctgcg     840 gggtatagaa ctccgcctga aggcaactta ttttacggcg tagtgcagga tggaaatgat     900
ttctgggatg ctactttctt ctgcggtagc tgcgctattc ttagacggac agccatagaa     960
caaattgggg gattcgcgac gcagaccgta acggaggacg ctcatacagc ccttaaaatg    1020
```

-continued

```
caaagacttg gttggtcaac agcgtatttg agaataccat tggcaggtgg tcttgcgacg   1080
gaaagattaa tcctgcatat cggacaacgc gttcgttggg cacggggcat gctgcaaatc   1140
tttcgcatag ataacccgct ctttggacgc ggcttatcat gggggcagag gttgtgttat   1200
ttaagtgcca tgacctcctt tctttttgcc gtgccgcgtg ttattttttt aagttcacct   1260
ctggcctttc tgttttttgg acaaaacata attgctgcaa gccccttggc tttactggct   1320
tatgcgatcc cccatatgtt tcacgccgtt ggaactgcat ctaagatcaa taaaggttgg   1380
cgttattcgt tctggagtga agtgtacgag actacaatgg cgctgttcct ggtgcgtgtg   1440
accattgtca cactgctctc tcctagcaga ggcaagttta atgtgacaga caaagggggt   1500
ctgctcgaaa aaggttactt tgatcttgga gcggtatatc ctaatatcat tcttggcttg   1560
atcatgtttg gagggttggc gcgtggagta tacgaattgt cgtttggaca tcttgatcaa   1620
atcgccgaac gtgcttattt gctgaattca gcgtgggcaa tgttatcact tataatcatc   1680
ttagctgcga ttgcggtagg cagggagaca aacagaaaa gaaattctca caggattccg   1740
gccacaattc cggtcgaggt cgccaatgct gacggaagca taattgtcac aggagtcaca   1800
gaagatttgt ctatgggtgg agcggcagtt aaaatgagct ggccggcgaa gctgtccggc   1860
cctacgccgg tttatattag aacagtactg gatggggagg aattaatcct tcccgcgagg   1920
atcattaggg ctgggaacgg ccgaggcatt tttatctgga cgattgacaa tttgcagcaa   1980
gaattttctg tcatccgtct ggtattcggg cgtgccgatg cgtgggttga ctggggaaac   2040
tacaaagcag atcgtccgct gctgtcctta atggatatgg tgctctcggt taaaggactt   2100
tttcgttcca gcggcgatat tgttcatcga tcttctccta caaaaccgtt agcggggaat   2160
gccttgagtg acgatacaaa taaccctagc agaaaagaac gtgttttgaa aggaacggtg   2220
aagatggtat cactgcttgc actgttgaca ttcgcaagct cggcacaggc cgcttccgct   2280
cctagagcgg tggcagctaa ggctccggct catcaaccgg aagcttccga tctgcccccg   2340
ctgcctgcct tacttccggc gacaagcgga gcagcacaag caggcgccgg agacgcggga   2400
gcaaatggac cggggtctcc aaccggacaa ccccttgcgg cagattccgc agatgcgctt   2460
gttgagaatg ccgagaacac gtccgatacg gccacagttc acaattacac acttaaggac   2520
ctgggagctg ctggctccat tactatgagg ggactggcac ccctgcaggg aattgagttc   2580
ggcatcccaa gcgatcaact ggtaacctcg gctcgcctgg tactttcagg aagcatgtca   2640
cctaacctcc gaccggaaac gaattctgtt acaatgaccc tcaacgagca atatattggt   2700
acattgagac ctgacccagc acacccgacg tttgggccaa tgagtttcga aatcaatccg   2760 atttttttg tgtctggaaa cagattaaat ttcaatttcg cttcggggtc aaaaggctgc   2820
tctgacatta ctaatgacac gctctgggca acaatctcgc aaaatagtca actccagata   2880
acaacaattg cccttccccc gagaagattg ttaagcaggc tgccccaacc tttctatgat   2940
aaaaatgtac ggcaacatgt cacggtccct atggtacttg cccagaccta tgatccccag   3000
attcttaaga gcgcaggcat tctcgcttct tggtttggca agcagacaga ctttcttggt   3060
gtaacgtttc cggtttcttc aacgatcccg cagtccggaa acgcgatcct tatcggggtg   3120
gcggatgaat taccgacaag cttgggcagg cctcaagtta acggtccggc agtactggaa   3180
ttgccgaatc cttccgatgc taacgccaca atccttgttg tgaccgggcg tgatcgagat   3240
gaagtaatta cagccagcaa agggatcgct tttgcctcgg caccgcttcc tacgcgatagc  3300 catatggatg tcgcgccagt tgatatcgcc ccacgtaagc ctaatgatgc gcccagtttt   3360
```

```
atcgcaatgg atcatcctgt acggtttgga gacctcgtta cagcatccaa attacaaggc      3420
acagggttta cgtcaggcgt tttgagcgtt ccattccgga tccctcctga cttatacacc      3480
tggcggaatc gtccttacaa aatgcaagtt cgctttcgtt caccagcggg cgaagcgaaa      3540
gatgtggaaa aatctcggct tgatgtcgga atcaacgaag tttatttgca tagttatccc      3600
ttacgagaga cacacggcct ggtcggtgcc gttttacaag gggttggcct tgctagacca      3660
gcatctggta tgcaagtgca cgacctggat gtccctccat ggaccgtgtt tggacaagat      3720
caattaaatt tttattttga tgcgatgccg cttgctcggg ggatttgtca gtccggagca      3780
gcaaataatg cgttccatct gggattggac ccagactcta ctatagactt ttctcgggcc      3840
catcatatag cgcagatgcc taaccttgcg tacatggcaa ccgttggctt cccatttact      3900
acctatgccg atttgagcca gacagctgtc gtcctgccgg agcatcccaa tgcggcaaca      3960
gttggagctt atcttgacct gatggggttt atgggcgcgg ccacatggta tccggtggcg      4020
ggtgtggata ttgtcagtgc ggatcacgtt agcgatgtcg cggaccggaa tctccttgtt      4080
atttctacac tggctacatc tggtgagatc gcaccgcttc tttctcgttc cagctatgag      4140
gtagctgatg gacatttgcg taccgttagc catgctagcg cgttagataa cgctattaag      4200
gcagtggatg atcctttaac cgcctttaga gaccgggact caaaaccaca agacgtggat      4260
acgccactta ctggcggggt cggtgctatg atcgaagcag aatcaccgct caccgctgga      4320
cgtacggtgt tagcccttt gtcatccgat ggcgctggcc tgaataatct cttgcagatg      4380
ctgggcgaaa ggaaaaagca ggccaatata caaggggatc ttgttgtagc ccacggagaa      4440
gatttgtcat cctaccgtac atctccggtc tataccatcg gcacgctgcc attatggctg      4500
tggccggact ggtacatgca caatcggcca gtgagggtac ttcttgtggg gcttctgggt      4560
tgcattctca tagtttccgt gcttgcgcgc gctttagcta gacatgcgac tagacggttt      4620
aaacaactgg aggacgagag acgcaaatcg taa                                   4653
```

```
<210> SEQ ID NO 45
<211> LENGTH: 640
<212> TYPE: PRT
<213> ORGANISM: Zea mays

<400> SEQUENCE: 45

Met Ala Thr Pro Ser Ala Val Gly Ala Ala Cys Leu Leu Leu Ala Arg
1               5                   10                  15

Ala Ala Trp Pro Ala Ala Val Gly Asp Arg Ala Arg Pro Arg Arg Leu
            20                  25                  30

Gln Arg Val Leu Arg Arg Arg Cys Val Ala Glu Leu Ser Arg Glu Gly
        35                  40                  45

Pro Ala Pro Arg Pro Leu Pro Pro Ala Leu Leu Ala Pro Pro Leu Val
    50                  55                  60

Pro Gly Phe Leu Ala Pro Pro Ala Glu Pro Thr Gly Glu Pro Ala Ser
65                  70                  75                  80

Thr Pro Pro Pro Val Pro Asp Ala Gly Leu Gly Asp Leu Gly Leu Glu
                85                  90                  95

Pro Glu Gly Ile Ala Glu Gly Ser Ile Asp Asn Thr Val Val Val Ala
            100                 105                 110

Ser Glu Gln Asp Ser Glu Ile Val Val Gly Lys Glu Gln Ala Arg Ala
        115                 120                 125

Lys Val Thr Gln Ser Ile Val Phe Val Thr Gly Glu Ala Ser Pro Tyr
    130                 135                 140
```

Ala Lys Ser Gly Gly Leu Gly Asp Val Cys Gly Ser Leu Pro Val Ala
145                 150                 155                 160

Leu Ala Ala Arg Gly His Arg Val Met Val Met Pro Arg Tyr Leu
                165                 170                 175

Asn Gly Thr Ser Asp Lys Asn Tyr Ala Asn Ala Phe Tyr Thr Glu Lys
                180                 185                 190

His Ile Arg Ile Pro Cys Phe Gly Gly Glu His Glu Val Thr Phe Phe
                195                 200                 205

His Glu Tyr Arg Asp Ser Val Asp Trp Val Phe Val Asp His Pro Ser
        210                 215                 220

Tyr His Arg Pro Gly Asn Leu Tyr Gly Asp Lys Phe Gly Ala Phe Gly
225                 230                 235                 240

Asp Asn Gln Phe Arg Tyr Thr Leu Leu Cys Tyr Ala Ala Cys Glu Ala
                245                 250                 255

Pro Leu Ile Leu Glu Leu Gly Gly Tyr Ile Tyr Gly Gln Asn Cys Met
                260                 265                 270

Phe Val Val Asn Asp Trp His Ala Ser Leu Val Pro Val Leu Leu Ala
                275                 280                 285

Ala Lys Tyr Arg Pro Tyr Gly Val Tyr Lys Asp Ser Arg Ser Ile Leu
        290                 295                 300

Val Ile His Asn Leu Ala His Gln Gly Val Glu Pro Ala Ser Thr Tyr
305                 310                 315                 320

Pro Asp Leu Gly Leu Pro Pro Glu Trp Tyr Gly Ala Leu Glu Trp Val
                325                 330                 335

Phe Pro Glu Trp Ala Arg Arg His Ala Leu Asp Lys Gly Glu Ala Val
                340                 345                 350

Asn Phe Leu Lys Gly Ala Val Val Thr Ala Asp Arg Ile Val Thr Val
                355                 360                 365

Ser Lys Gly Tyr Ser Trp Glu Val Thr Thr Ala Glu Gly Gly Gln Gly
        370                 375                 380

Leu Asn Glu Leu Leu Ser Ser Arg Lys Ser Val Leu Asn Gly Ile Val
385                 390                 395                 400

Asn Gly Ile Asp Ile Asn Asp Trp Asn Pro Ala Thr Asp Lys Cys Ile
                405                 410                 415

Pro Cys His Tyr Ser Val Asp Asp Leu Ser Gly Lys Ala Lys Cys Lys
                420                 425                 430

Gly Ala Leu Gln Lys Glu Leu Gly Leu Pro Ile Arg Pro Asp Val Pro
        435                 440                 445

Leu Ile Gly Phe Ile Gly Arg Leu Asp Tyr Gln Lys Gly Ile Asp Leu
        450                 455                 460

Ile Gln Leu Ile Ile Pro Asp Leu Met Arg Glu Asp Val Gln Phe Val
465                 470                 475                 480

Met Leu Gly Ser Gly Asp Pro Glu Leu Glu Asp Trp Met Arg Ser Thr
                485                 490                 495

Glu Ser Ile Phe Lys Asp Lys Phe Arg Gly Trp Val Gly Phe Ser Val
                500                 505                 510

Pro Val Ser His Arg Ile Thr Ala Gly Cys Asp Ile Leu Leu Met Pro
                515                 520                 525

Ser Arg Phe Glu Pro Cys Gly Leu Asn Gln Leu Tyr Ala Met Gln Tyr
        530                 535                 540

Gly Thr Val Pro Val Val His Ala Thr Gly Gly Leu Arg Asp Thr Val
545                 550                 555                 560

Glu Asn Phe Asn Pro Phe Gly Glu Asn Gly Glu Gln Gly Thr Gly Trp

-continued

```
            565                 570                 575
Ala Phe Ala Pro Leu Thr Thr Glu Asn Met Leu Trp Thr Leu Arg Thr
            580                 585                 590

Ala Ile Ser Thr Tyr Arg Glu His Lys Ser Ser Trp Glu Gly Leu Met
        595                 600                 605

Lys Arg Gly Met Ser Lys Asp Phe Thr Trp Asp His Ala Ala Glu Gln
    610                 615                 620

Tyr Glu Gln Ile Phe Gln Trp Ala Phe Ile Asp Arg Pro Tyr Val Met
625                 630                 635                 640
```

```
<210> SEQ ID NO 46
<211> LENGTH: 1923
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggcgaccc cgtccgcagt gggcgcagcc tgcctttat tagcgcgcgc agcttggccg       60
gcagccgttg gagacagggc aagaccgcgg cgattacaac gcgtgttgcg gcggagatgt      120
gtagcagaac tttctcgtga agggccagca ccgaggcctt tacctcctgc cttgcttgcc      180
cccccgttag tacctggttt tctggcaccc ccagcgaaac caacaggcga accagcgagc      240
acgcctccgc cggttccgga cgctggactt ggcgacttgg gattagaacc tgaaggaatc      300
gcggaaggtt caatcgataa taccgtcgtg gtggcttctg aacaggatag tgagatcgta      360
gttgggaaag agcaggctcg cgcaaaagta acgcaatcaa ttgtattcgt aaccggcgag      420
gcaagcccct atgcgaaatc tggaggcctg ggcgatgttt gcggaagcct tccggttgcg      480
ttagctgcca gaggacatcg agtcatggtc gtcatgccgc ggtatctgaa cggaacgtca      540
gataaaaatt atgccaatgc cttctatacc gagaagcata tccggatccc ttgctttggt      600
ggcgaacacg aagtgacttt ttttcatgaa tatcgtgact cagtcgactg ggtttttgtc      660
gaccacccga gctatcatag accgggtaac ctgtacgggg ataaatttgg agcgtttggc      720
gataatcaat ccggtatac cttgctgtgt tatgccgcat gcgaagcccc tctcatcttg       780
gaactcggag gctatattta tggacaaaac tgtatgttcg tagtaaacga ttggcacgca      840
tcactcgtac cagtacttct cgcagcgaaa tatagaccgt atggcgttta caaagattcc      900
agatcaattt tagttattca caacttagct caccaaggcg tagaaccggc gtccacatat      960
ccagatcttg gattgccgcc agagtggtat ggagcgcttg aatgggtctt tcctgaatgg     1020
gctcgtcgac atgcgctgga taaaggtgaa gctgtcaatt ttctcaaagg tgctgtggtc     1080
actgccgaca gaattgtaac agtgagcaaa ggctattcct gggaagttac caccgctgag     1140
ggtggccaag ggctcaatga attgctgagc agccgtaaaa gtgttttgaa tggtatagtg     1200
aatggtatcg acatcaatga ttggaacccg gcaacagaca aatgtatccc ctgtcattac     1260
tccgtcgacg acctttcggg aaaagcaaag tgtaaaggcg cgcttcaaaa agagttgggc     1320
ttgccgatta daccggatgt gcctcttatt ggattcattg gccggttgga ttatcagaag     1380
ggaattgatc tgatccagct gattattccg gacttgatga gagaagatgt ccagtttgtg     1440
atgttgggct ccggcgatcc agaacttgaa gattggatgc ggagcaccga atcaatctt      1500 aaggataaat ttagaggatg ggtcgggttc tctgtgcctg tctcacatcg cattacggcg     1560
ggctgcgata tcctccttat gccttctcgg ttcgaaccgt gtggtttaaa tcaactttat     1620
```

```
gcgatgcagt acggcactgt gccggttgtt cacgcgactg gagggctgcg agatactgtt      1680
gagaatttta atccgtttgg agagaacggt gaacaaggaa caggatgggc cttcgcacca      1740
ctgactacgg agaacatgct gtggacactt agaacggcca tctctacgta tagggagcac      1800
aagtcctcgt gggagggact catgaaacgg ggaatgagta agatttcac ctgggatcac       1860 gctgcagaac aatatgagca aatctttcag tgggcgttta tcgatcgccc ctacgttatg      1920
tga                                                                     1923
```

<210> SEQ ID NO 47
<211> LENGTH: 899
<212> TYPE: PRT
<213> ORGANISM: Arabidopsis thaliana

<400> SEQUENCE: 47

```
Met Val Ser Leu Ser Asn Gln Thr Arg Phe Ser Phe His Pro Asn Asn
1               5                   10                  15

Leu Val Val Ser Glu Lys Arg Arg Leu Gly Ile Ser Gly Val Asn Phe
            20                  25                  30

Pro Arg Lys Ile Lys Leu Lys Ile Thr Cys Phe Ala Ala Glu Arg Pro
        35                  40                  45

Arg Gln Glu Lys Gln Lys Lys Lys Ser Gln Ser Gln Ser Thr Ser Asp
    50                  55                  60

Ala Glu Ala Gly Val Asp Pro Val Gly Phe Leu Thr Arg Leu Gly Ile
65                  70                  75                  80

Ala Asp Arg Ile Phe Ala Gln Phe Leu Arg Glu Arg His Lys Ala Leu
                85                  90                  95

Lys Asp Leu Lys Asp Glu Ile Phe Lys Arg His Phe Asp Phe Arg Asp
            100                 105                 110

Phe Ala Ser Gly Phe Glu Leu Leu Gly Met His Arg His Met Glu His
            115                 120                 125

Arg Val Asp Phe Met Asp Trp Gly Pro Gly Ser Arg Tyr Gly Ala Ile
        130                 135                 140

Ile Gly Asp Phe Asn Gly Trp Ser Pro Thr Glu Asn Ala Ala Arg Glu
145                 150                 155                 160

Gly Leu Phe Gly His Asp Asp Tyr Gly Tyr Trp Phe Ile Ile Leu Glu
                165                 170                 175

Asp Lys Leu Arg Glu Gly Glu Glu Pro Asp Glu Leu Tyr Phe Gln Gln
            180                 185                 190

Tyr Asn Tyr Val Asp Asp Tyr Asp Lys Gly Asp Ser Gly Val Ser Ala
        195                 200                 205

Glu Glu Ile Phe Gln Lys Ala Asn Asp Glu Tyr Trp Glu Pro Gly Glu
    210                 215                 220

Asp Arg Phe Ile Lys Asn Arg Phe Glu Val Pro Ala Lys Leu Tyr Glu
225                 230                 235                 240

Gln Met Phe Gly Pro Asn Ser Pro Gln Thr Leu Glu Glu Leu Gly Asp
                245                 250                 255

Ile Pro Asp Ala Glu Thr Arg Tyr Lys Gln Trp Lys Glu Glu His Lys
            260                 265                 270

Asp Asp Pro Pro Ser Asn Leu Pro Pro Cys Asp Ile Ile Asp Lys Gly
            275                 280                 285

Gln Gly Lys Pro Tyr Asp Ile Phe Asn Val Val Thr Ser Pro Glu Trp
        290                 295                 300

Thr Lys Lys Phe Tyr Glu Lys Glu Pro Pro Ile Pro Tyr Trp Leu Glu
305                 310                 315                 320
```

-continued

```
Thr Arg Lys Gly Arg Lys Ala Trp Leu Gln Lys Tyr Ile Pro Ala Val
            325                 330                 335

Pro His Gly Ser Lys Tyr Arg Leu Tyr Phe Asn Thr Pro Asp Gly Pro
            340                 345                 350

Leu Glu Arg Val Pro Ala Trp Ala Thr Tyr Val Gln Pro Glu Asp Glu
            355                 360                 365

Gly Lys Gln Ala Tyr Ala Ile His Trp Glu Pro Ser Pro Glu Ala Ala
        370                 375                 380

Tyr Lys Trp Lys Tyr Ser Lys Pro Lys Val Pro Glu Ser Leu Arg Ile
385                 390                 395                 400

Tyr Glu Cys His Val Gly Ile Ser Gly Ser Glu Pro Lys Val Ser Thr
                405                 410                 415

Phe Glu Glu Phe Thr Lys Lys Val Leu Pro His Val Lys Arg Ala Gly
                420                 425                 430

Tyr Asn Ala Ile Gln Leu Ile Gly Val Pro Glu His Lys Asp Tyr Phe
            435                 440                 445

Thr Val Gly Tyr Arg Val Thr Asn Phe Phe Ala Ala Ser Ser Arg Tyr
        450                 455                 460

Gly Thr Pro Asp Asp Phe Lys Arg Leu Val Asp Glu Ala His Gly Leu
465                 470                 475                 480

Gly Leu Leu Val Phe Leu Asp Ile Val His Ser Tyr Ala Ala Ala Asp
                485                 490                 495

Gln Met Val Gly Leu Ser Leu Phe Asp Gly Ser Asn Asp Cys Tyr Phe
                500                 505                 510

His Tyr Gly Lys Arg Gly His His Lys His Trp Gly Thr Arg Met Phe
            515                 520                 525

Lys Tyr Gly Asp Leu Asp Val Leu His Phe Leu Ile Ser Asn Leu Asn
        530                 535                 540

Trp Trp Ile Thr Glu Tyr Gln Val Asp Gly Tyr Gln Phe His Ser Leu
545                 550                 555                 560

Ala Ser Met Ile Tyr Thr His Asn Gly Phe Ala Ser Phe Asn Asn Asp
                565                 570                 575

Leu Asp Asp Tyr Cys Asn Gln Tyr Val Asp Arg Asp Ala Leu Met Tyr
                580                 585                 590

Leu Ile Leu Ala Asn Glu Ile Leu His Val Gln His Pro Asn Ile Ile
            595                 600                 605

Thr Ile Ala Glu Asp Ala Thr Tyr Tyr Pro Gly Leu Cys Glu Pro Val
        610                 615                 620

Ser Gln Gly Gly Leu Gly Phe Asp Tyr Tyr Val Asn Leu Ser Ala Ser
625                 630                 635                 640

Glu Met Trp Val Ser Leu Leu Asp Asn Val Pro Asp Asn Glu Trp Ser
                645                 650                 655

Met Ser Lys Ile Val Ser Thr Leu Val Ala Asn Lys Glu Tyr Ala Asp
            660                 665                 670

Lys Met Leu Ser Tyr Ala Glu Asn His Asn Gln Ser Ile Ser Gly Gly
            675                 680                 685

Arg Ser Phe Ala Glu Ile Leu Phe Gly Gly Val Asp Asn Gly Ser Pro
        690                 695                 700

Gly Gly Lys Glu Leu Leu Asp Arg Gly Ile Ser Leu His Lys Met Ile
705                 710                 715                 720

Arg Leu Ile Thr Phe Thr Ser Gly Gly Arg Ala Tyr Leu Asn Phe Met
            725                 730                 735
```

-continued

```
Gly Asn Glu Phe Gly His Pro Glu Arg Val Glu Phe Pro Thr Gln Ser
            740                 745                 750

Asn Asn Phe Ser Phe Ser Leu Ala Asn Arg Arg Trp Asp Leu Leu Glu
        755                 760                 765

Ser Gly Val His His His Leu Phe Ser Phe Asp Lys Glu Leu Met Asp
        770                 775                 780

Leu Asp Lys Ser Lys Gly Ile Leu Ser Arg Gly Leu Pro Ser Ile His
785                 790                 795                 800

His Val Asn Asp Ala Asn Met Val Ile Ser Phe Ser Arg Gly Pro Phe
                805                 810                 815

Leu Phe Ile Phe Asn Phe His Pro Ser Asn Ser Tyr Glu Lys Tyr Asp
            820                 825                 830

Val Gly Val Glu Glu Ala Gly Glu Tyr Thr Met Ile Leu Asn Ser Asp
        835                 840                 845

Glu Val Lys Tyr Gly Gly Gln Gly Ile Val Thr Glu Asp His Tyr Leu
    850                 855                 860

Gln Arg Ser Ile Ser Lys Arg Ile Asp Gly Gln Arg Asn Cys Leu Glu
865                 870                 875                 880

Val Phe Leu Pro Ser Arg Thr Ala Gln Val Tyr Lys Leu Thr Arg Ile
                885                 890                 895

Leu Arg Ile
```

```
<210> SEQ ID NO 48
<211> LENGTH: 2700
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atggtctctt tgtcgaatca gactagattt tctttccatc cgaataacct ggtcgtgagt      60
gagaaacgac gtttaggaat ctcgggcgtt aacttccctc gaaagattaa attaaaaatt     120
acatgctttg cagcggagag accgcgccaa gaaaagcaga agaaaaagtc acaatctcaa     180
agcacgtccg atgcggaagc aggagtagac ccggtgggct ttttaacacg cttgggcata     240
gcggatagga ttttttgcaca atttcttaga gaaagacata aggctcttaa agaccttaag    300
gacgaaatat ttaaacggca ttttgatttt cgggattttg catcaggctt cgaactgtta     360
ggaatgcaca ggcatatgga gcatcgggtt gattttatgg attggggacc gggatcacgg     420
tacggcgcaa ttattggtga ttttaacgga tggtctccaa cggagaatgc tgcgcgcgaa     480
ggcctctttg gccatgatga ctatggttat tggtttatta tacttgaaga taaattgaga    540
gaaggagagg agccggacga gttgtatttt caacaatata actatgttga tgactatgat    600
aaaggtgact caggcgtgtc ggctgaagaa attttccaaa aagcaaatga tgaatattgg    660
gagccgggtg aagataggtt tatcaaaaat agatttgaag tgccggctaa attatatgag    720
caaatgtttg gaccgaattc accgcaaaca ctggaggaat taggtgatat ccctgacgcg    780
gaaacaagat acaagcagtg gaagaagag cataaagatg atcctccatc taacctgccg     840
ccttgcgata ttattgataa aggtcaaggc aaaccgtatg atatctttaa tgttgttacg    900
tccccagaat ggacaaaaaa atttttatgag aaagaacccc cgatcccata ttggctggag    960
acacgtaaag gcagaaaggc gtggctccag aaatatatcc cggccgtccc ccacggctcc   1020
aagtaccgct tatacttcaa taccccggat ggaccattag aaagggttcc ggcttgggcg   1080
```

-continued

```
acctacgtac agccagaaga tgaaggcaaa caggcctatg ctattcattg ggaaccgagc      1140
ccggaggctg cctataaatg gaagtactca aaaccaaaag taccagaatc tttacggatt      1200
tatgaatgcc atgtggggat tagcggaagc gaaccgaaag taagcacttt tgaagagttt      1260
acaaaaaagg tgctgccgca cgtcaaacga gcgggatata acgcgatcca gttgatcggc      1320
gtgcctgagc ataaggatta ttttacggtc ggttatagag tgaccaactt tttcgcagca      1380
tcttcccgct acggtactcc tgacgatttt aaaagacttg tggatgaagc tcatgggctg      1440
ggtctcctgg tctttctgga tattgtccac tcatatgctg cggcggatca gatggttggg      1500
ctgagcttgt ttgacggttc caacgattgc tacttccact atgggaaacg tggccatcat      1560
aaacattggg ggaccagaat gttcaaatat ggcgaccttg atgtgcttca cttttttaatt      1620 tcaaacttaa attggtggat tacagaatac caggttgacg gatatcaatt ccacagcttg      1680
gcatcgatga tctatacaca taacgggttc gcaagtttca ataatgattt ggacgattat      1740
tgcaatcagt atgtagaccg ggatgccctt atgtacctga ttcttgcgaa cgaaatcctt      1800
catgttcagc atccgaacat cattactatt gcggaagatg caacatacta cccgggcctg      1860
tgcgaaccag tttcccaagg cggactggga tttgattatt atgtcaatct gtctgcatcc      1920
gaaatgtggg ttagcttact tgataacgtg cctgataatg agtggtcaat gtcaaaaatc      1980
gttagcacac tcgttgcaaa taaagaatac gctgacaaaa tgttatccta cgcagaaaat      2040
cataatcaga gtataagcgg tggtcggtca tttgccgaga tcttatttgg cggcgtggac      2100
aacggcagtc ccggcggtaa agagttatta gatagaggta tcagccttca caagatgatt      2160
cgcctgatta cttttacaag tggcggaaga gcttatttga acttcatggg aaacgagttc      2220
ggacatcctg aaagagtaga attcccaaca caatccaaca atttctcgtt cagcttagca      2280
aaccggcgat gggatctgct ggagagtggg gtacatcatc atttgttttc gtttgataaa      2340
gagctgatgg acctggataa aagcaaagga attctgagcc gaggacttcc gagcatccat      2400
catgttaatg acgcaaatat ggtcattagc ttttcccggg gccccttcct ttttatcttt      2460
aattttcacc cctcaaattc atatgaaaag tatgatgtcg gcgtcgagga ggcgggtgag      2520
tataccatga tcctcaactc agatgaggtg aaatatggtg gccaagggat agtaaccgaa      2580
gatcattatt tacaaaggtc tataagcaag aggatcgatg gacagagaaa ctgcttggag      2640 gtcttttttgc ccagtaggac agctcaggtg tacaagctta cacgaatcct tcgcatttga      2700
```

```
<210> SEQ ID NO 49
<211> LENGTH: 484
<212> TYPE: PRT
<213> ORGANISM: Bacillus subtilis

<400> SEQUENCE: 49

Met Lys Ile Leu Phe Ala Val Ser Glu Cys Thr Pro Phe Val Lys Ser
1               5                   10                  15

Gly Gly Leu Ala Asp Val Ala Gly Ala Leu Pro Lys Ala Leu Ala Arg
            20                  25                  30

Leu Gly Asn Glu Val Ala Val Met Leu Pro Lys Tyr Ser Gln Ile Pro
        35                  40                  45

Glu Pro Trp Lys Lys Arg Met Lys Lys Gln Ala Glu Cys Thr Val Ala
    50                  55                  60

Val Gly Trp Arg Gln Gln Tyr Cys Gly Ile Glu His Met Ala Glu Asn
65                  70                  75                  80

Asp Val Asn Tyr Tyr Phe Ile Asp Asn Glu Tyr Tyr Phe Asn Arg Asp
                85                  90                  95
```

-continued

```
Ser Leu Tyr Gly His Tyr Asp Asp Gly Glu Arg Phe Ala Phe Phe Ser
            100                 105                 110

Arg Ala Val Leu Glu Ala Ala Lys Val Val Asn Val Gln Ala Asp Ile
            115                 120                 125

Val His Thr His Asp Trp His Thr Ala Met Val Asn Tyr Leu Leu Lys
        130                 135                 140

Glu Glu Tyr Arg Lys His Pro Phe Tyr Glu Arg Met Lys Ser Val Leu
145                 150                 155                 160

Thr Ile His Asn Leu Gln Phe Gln Gly Ile Phe Pro Pro Asp Val Thr
                165                 170                 175

His Asp Leu Leu Gly Leu Glu Met Asp His Phe His Tyr Glu Arg Leu
                180                 185                 190

Glu Cys Asn Gly Phe Val Asn Phe Met Lys Ala Gly Ile Ile Ala Ala
            195                 200                 205

Asp His Val Thr Thr Val Ser Pro Thr Tyr Arg Asn Glu Ile Met Thr
        210                 215                 220

Pro Tyr Tyr Gly Glu Gln Leu Glu Gln Val Leu Gln Tyr Arg Glu Asp
225                 230                 235                 240

Asp Val Thr Gly Ile Leu Asn Gly Ile Asp Asp Thr Phe Tyr Gln Pro
                245                 250                 255

Lys Ser Asp Pro Tyr Ile Glu Ala Gln Tyr Asp Ser Gly Asp Leu Ala
                260                 265                 270

Cys Lys Leu Glu Asn Lys Thr Lys Leu Gln Gln Arg Met Gly Leu Pro
            275                 280                 285

Glu Lys Asn Asp Ile Pro Leu Ile Ser Met Val Thr Arg Leu Thr Lys
            290                 295                 300

Gln Lys Gly Leu Asp Leu Val Arg Arg Ile Met His Glu Leu Leu Glu
305                 310                 315                 320

Glu Gln Asp Ile Gln Leu Val Val Leu Gly Thr Gly Glu Arg Glu Phe
                325                 330                 335

Glu Asp Tyr Phe Arg Tyr Ala Glu Phe Ala Phe His Glu Lys Cys Arg
                340                 345                 350

Ala Tyr Ile Gly Phe Asp Glu Pro Leu Ala His Gln Ile Tyr Ala Gly
            355                 360                 365

Ser Asp Met Phe Leu Met Pro Ser Lys Phe Glu Pro Cys Gly Leu Gly
            370                 375                 380

Gln Leu Ile Ala Leu Gln Tyr Gly Ala Ile Pro Ile Val Arg Glu Thr
385                 390                 395                 400

Gly Gly Leu Tyr Asp Thr Val Arg Ala Tyr Gln Glu Glu Glu Gly Thr
                405                 410                 415

Gly Asn Gly Phe Thr Phe Ser Ala Phe Asn Ala His Asp Leu Lys Phe
            420                 425                 430

Thr Ile Glu Arg Ala Leu Ser Phe Tyr Cys Gln Gln Asp Val Trp Lys
        435                 440                 445

Ser Ile Val Lys Thr Ala Met Asn Ala Asp Tyr Ser Trp Gly Lys Ser
    450                 455                 460

Ala Lys Glu Tyr Gln Arg Ile Phe Glu Gln Val Thr Arg Ser Gly Arg
465                 470                 475                 480

Asp Val Leu Glu
```

<210> SEQ ID NO 50
<211> LENGTH: 1455
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 50
atgaagattt tgttcgcggt tagcgagtgc acacctttcg taaaatccgg cggattagcg      60
gacgttgcgg gtgctttacc gaaagcctta gcgcgccttg gaaatgaagt cgctgtgatg     120
ctgccgaaat atagtcaaat tccggaaccg tggaagaaaa gaatgaaaaa acaggcagaa     180
tgcacagttg cggtcggctg gcgccaacag tactgcggaa tcgaacatat ggctgagaat     240
gacgtgaact attattttat agataacgaa tattattttta acagagattc tctgtatgga     300
cactatgacg atggagagag gtttgcgttt tttagccggg ctgtgctcga gccgcgaaa     360 gtcgtgaatg tgcaggctga tatcgttcat acgcatgact ggcataccgc gatggtcaac     420
tatttgctga aagaagaata tcggaaacat ccgtttttatg agcgcatgaa aagcgttctt     480
acgattcata atctccaatt ccagggtatc tttccacccg atgtcacaca tgacctttta     540
ggcttagaaa tggatcattt ccattacgaa cgtttggaat gcaacggttt cgtgaatttt     600
atgaaggctg gaatcatcgc cgcagatcat gtgactacgg tctctcctac gtatcgtaat     660
gaaataatga cgccatatta tggtgaacag ctggagcagg ttcttcagta tcgcgaagat     720
gatgtcacgg gaattctgaa cggcattgat gacacgttct accaacctaa atcagaccca     780
tatattgaag cgcagtacga tagtggcgat cttgcctgca aattagaaaa taaaacaaag     840
ctgcaacaac gcatgggatt accagagaag aatgatatcc cgttaattttc aatggtaacc     900 agacttacga agcagaaggg cctggatttg gtcagacgga taatgcatga acttttagaa     960
gagcaggata tccagctggt cgtgctgggc accggagaaa gagaatttga ggattacttt    1020
cgctacgctg aatttgcgtt tcatgagaag tgccgcgcct acattggctt tgacgaaccc    1080
ttagcgcacc agatttacgc cggatcagat atgtttctca tgccgagcaa gtttgaacct    1140
tgtggacttg gccagctgat tgcattacaa tacggcgcca ttcctattgt acgggagacc    1200
ggaggcctgt atgacacagt gcgagcctat caggaagaag aaggtacagg caatggcttt    1260
acttttagtg cgtttaatgc acatgatctg aaattcacaa tagaaagagc tttaagcttt    1320
tattgtcaac aggatgtctg gaaatcaatc gtaaagaccg ctatgaatgc cgattattca    1380
tggggtaaat ctgcaaaaga gtaccaacgt atcttcgaac aagtgacacg gtctgggcgc    1440
gacgtccttg aataa                                                      1455

<210> SEQ ID NO 51
<211> LENGTH: 673
<212> TYPE: PRT
<213> ORGANISM: Arabidopsis thaliana

<400> SEQUENCE: 51

Met Ala Leu Lys Arg Gly Leu Ser Gly Val Asn Arg Ile Arg Gly Ser
1               5                   10                  15

Gly Gly Gly Ser Arg Ser Val Leu Val Leu Leu Ile Phe Phe Cys Val
                20                  25                  30

Phe Ala Pro Leu Cys Phe Phe Val Gly Arg Gly Val Tyr Ile Asp Ser
            35                  40                  45

Ser Asn Asp Tyr Ser Ile Val Ser Val Lys Gln Asn Leu Asp Trp Arg
        50                  55                  60

Glu Arg Leu Ala Met Gln Ser Val Arg Ser Leu Phe Ser Lys Glu Ile
65                  70                  75                  80

```
Leu Asp Val Ile Ala Thr Ser Thr Ala Asp Leu Gly Pro Leu Ser Leu
                85               90               95

Asp Ser Phe Lys Lys Asn Asn Leu Ser Ala Ser Trp Arg Gly Thr Gly
               100              105              110

Val Asp Pro Ser Phe Arg His Ser Glu Asn Pro Ala Thr Pro Asp Val
               115              120              125

Lys Ser Asn Asn Leu Asn Glu Lys Arg Asp Ser Ile Ser Lys Asp Ser
   130              135              140

Ile His Gln Lys Val Glu Thr Pro Thr Lys Ile His Arg Arg Gln Leu
145              150              155              160

Arg Glu Lys Arg Arg Glu Met Arg Ala Asn Glu Leu Val Gln His Asn
               165              170              175

Asp Asp Thr Ile Leu Lys Leu Glu Asn Ala Ala Ile Glu Arg Ser Lys
               180              185              190

Ser Val Asp Ser Ala Val Leu Gly Lys Tyr Ser Ile Trp Arg Arg Glu
               195              200              205

Asn Glu Asn Asp Asn Ser Asp Ser Asn Ile Arg Leu Met Arg Asp Gln
   210              215              220

Val Ile Met Ala Arg Val Tyr Ser Gly Ile Ala Lys Leu Lys Asn Lys
225              230              235              240

Asn Asp Leu Leu Gln Glu Leu Gln Ala Arg Leu Lys Asp Ser Gln Arg
               245              250              255

Val Leu Gly Glu Ala Thr Ser Asp Ala Asp Leu Pro Arg Ser Ala His
               260              265              270

Glu Lys Leu Arg Ala Met Gly Gln Val Leu Ala Lys Ala Lys Met Gln
               275              280              285

Leu Tyr Asp Cys Lys Leu Val Thr Gly Lys Leu Arg Ala Met Leu Gln
   290              295              300

Thr Ala Asp Glu Gln Val Arg Ser Leu Lys Lys Gln Ser Thr Phe Leu
305              310              315              320

Ala Gln Leu Ala Ala Lys Thr Ile Pro Asn Pro Ile His Cys Leu Ser
               325              330              335

Met Arg Leu Thr Ile Asp Tyr Tyr Leu Leu Ser Pro Glu Lys Arg Lys
               340              345              350

Phe Pro Arg Ser Glu Asn Leu Glu Asn Pro Asn Leu Tyr His Tyr Ala
               355              360              365

Leu Phe Ser Asp Asn Val Leu Ala Ala Ser Val Val Val Asn Ser Thr
   370              375              380

Ile Met Asn Ala Lys Asp Pro Ser Lys His Val Phe His Leu Val Thr
385              390              395              400

Asp Lys Leu Asn Phe Gly Ala Met Asn Met Trp Phe Leu Leu Asn Pro
               405              410              415

Pro Gly Lys Ala Thr Ile His Val Glu Asn Val Asp Glu Phe Lys Trp
               420              425              430

Leu Asn Ser Ser Tyr Cys Pro Val Leu Arg Gln Leu Glu Ser Ala Ala
               435              440              445

Met Arg Glu Tyr Tyr Phe Lys Ala Asp His Pro Thr Ser Gly Ser Ser
   450              455              460

Asn Leu Lys Tyr Arg Asn Pro Lys Tyr Leu Ser Met Leu Asn His Leu
465              470              475              480

Arg Phe Tyr Leu Pro Glu Val Tyr Pro Lys Leu Asn Lys Ile Leu Phe
               485              490              495
```

-continued

```
Leu Asp Asp Asp Ile Ile Val Gln Lys Asp Leu Thr Pro Leu Trp Glu
            500                 505                 510

Val Asn Leu Asn Gly Lys Val Asn Gly Ala Val Glu Thr Cys Gly Glu
        515                 520                 525

Ser Phe His Arg Phe Asp Lys Tyr Leu Asn Phe Ser Asn Pro His Ile
        530                 535                 540

Ala Arg Asn Phe Asn Pro Asn Ala Cys Gly Trp Ala Tyr Gly Met Asn
545                 550                 555                 560

Met Phe Asp Leu Lys Glu Trp Lys Lys Arg Asp Ile Thr Gly Ile Tyr
            565                 570                 575

His Lys Trp Gln Asn Met Asn Glu Asn Arg Thr Leu Trp Lys Leu Gly
            580                 585                 590

Thr Leu Pro Pro Gly Leu Ile Thr Phe Tyr Gly Leu Thr His Pro Leu
        595                 600                 605

Asn Lys Ala Trp His Val Leu Gly Leu Gly Tyr Asn Pro Ser Ile Asp
        610                 615                 620

Lys Lys Asp Ile Glu Asn Ala Ala Val Val His Tyr Asn Gly Asn Met
625                 630                 635                 640

Lys Pro Trp Leu Glu Leu Ala Met Ser Lys Tyr Arg Pro Tyr Trp Thr
            645                 650                 655

Lys Tyr Ile Lys Phe Asp His Pro Tyr Leu Arg Arg Cys Asn Leu His
            660                 665                 670

Glu
```

```
<210> SEQ ID NO 52
<211> LENGTH: 2022
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52 atggcccta agaggggct gagtggagtg aaccgtatca gaggatcagg aggaggcagc      60
cgttcagtcc tggttcttct tatctttttt tgcgtgttcg caccgttatg tttcttcgtt     120
ggtcgcggag tctatataga cagctcgaac gactactcaa ttgttagtgt aaagcagaat     180
ttagactgga gagagcgcct ggcaatgcaa tctgtaagat cattattctc gaaggaaatt     240
ttagatgtga tagccacgtc tacggcagac ttggggccgt tatctttaga tagcttcaaa     300
aagaacaatt tatcagctag ctggagaggc acgggcgttg accctagctt tcgccacagc     360
gaaaaccctg cgaccccgga tgttaagtca aacaatttaa atgaaaaaag agattctatt     420
tctaaagatt ccatccatca gaaggttgag acaccgacta aaatccaccg acgacaactt     480
cgtgagaaaa ggagagagat cgcgcgcgaat gaacttgtcc agcacaacga tgatacaatt    540
ttaaagttgg agaatgcagc cattgagcgt agtaaaagtg tagattctgc agtattagga     600
aaatactcaa tttggcgccg ggaaaatgaa aatgacaata gcgattctaa tatcaggctg     660
atgagggacc aggtcattat ggcacgcgta tattcgggca ttgcaaaatt aaaaaacaaa     720
aacgacttac ttcaagaact tcaggcgcgg cttaaggatt cccagagagt gctgggagaa     780
gctacatccg atgccgattt gccaaggagc gcgcacgaga aacttagagc gatgggtcaa     840
gttttggcta aagcgaaaat gcagctgtat gattgcaaat tagtcactgg taaactgaga     900
gcaatgttgc agacagcaga tgagcaggta cgaagcttaa aaaaacaatc aacgtttctt     960
gcacagcttg cagctaaaac aatacccaat ccaatccatt gtttatctat gagattgacc    1020
```

```
atagattatt accttttgtc tcccgagaag aggaagtttc cgcgatctga aaatctggaa   1080
aaccctaatc tgtatcatta cgctctgttc tcagacaatg ttttagcagc atctgttgtc   1140
gtaaatagca caatcatgaa tgcgaaggac ccgtctaaac atgtgttcca tcttgtcacg   1200
gataaactta actttggcgc catgaatatg tggtttcttc tgaatcctcc gggcaaagcc   1260
acaatccatg tggaaaatgt cgacgaattt aaatggctta actcctccta ttgcccggtt   1320
cttcggcagt tagaatcagc tgctatgaga gaatactatt ttaaagcgga tcatcctacg   1380
tccggcagca gcaatttaaa atacagaaat ccgaagtact tatctatgct taaccattta   1440
agattttatt taccggaagt ttatccgaaa cttaataaaa tcctgtttct cgacgatgac   1500
attattgttc aaaaagattt gactccgctt tgggaagtga acttaaatgg caaagtcaat   1560
ggggccgtgg agacttgcgg ggagtcattt catagatttg acaagtactt aaacttttct   1620
aacccgcaca ttgcacgtaa tttcaaccca aatgcatgtg gatgggcgta tggtatgaat   1680
atgtttgact aaaagaatg gaaaaaacgc gatataacag gaatttatca taagtggcaa   1740
aacatgaacg aaaacaggac actgtggaaa ctgggaacgt tgccgcctgg acttattacg   1800
ttttatgggt tgacgcaccc gcttaataaa gcctggcatg ttttaggact gggatataat   1860
cctagcattg acaagaaaga tattgaaaac gcggcggtag tgcattataa tgggaatatg   1920
aaaccgtggc ttgaactggc tatgtctaaa tatagaccgt actggacgaa atacattaaa   1980
tttgaccatc cgtatttacg acggtgcaac ctgcatgaat ag                     2022
```

```
<210> SEQ ID NO 53
<211> LENGTH: 397
<212> TYPE: PRT
<213> ORGANISM: Azorhizobium caulinodans

<400> SEQUENCE: 53

Met Ser Val Val Asp Val Ile Gly Leu Leu Ala Thr Ala Ala Tyr Val
1               5                   10                  15

Thr Leu Ala Ser Ala Tyr Lys Val Val Gln Phe Ile Asn Val Ser Ser
            20                  25                  30

Val Thr Asp Val Ala Gly Leu Glu Ser Asp Ala Leu Pro Leu Thr Pro
        35                  40                  45

Arg Val Asp Val Ile Val Pro Thr Phe Asn Glu Asn Ser Ser Thr Leu
    50                  55                  60

Leu Glu Cys Val Ala Ser Ile Cys Ala Gln Asp Tyr Arg Gly Pro Ile
65                  70                  75                  80

Thr Ile Val Val Val Asp Asp Gly Ser Thr Asn Lys Thr Ser Phe His
                85                  90                  95

Ala Val Cys Asp Lys Tyr Ala Ser Asp Glu Arg Phe Ile Phe Val Glu
            100                 105                 110

Leu Asp Gln Asn Lys Gly Lys Arg Ala Ala Gln Met Glu Ala Ile Arg
        115                 120                 125

Arg Thr Asp Gly Asp Leu Ile Leu Asn Val Asp Ser Asp Thr Val Ile
    130                 135                 140

Asp Lys Asp Val Val Thr Lys Leu Ala Ser Ser Met Arg Ala Pro Asn
145                 150                 155                 160

Val Gly Gly Val Met Gly Gln Leu Val Ala Lys Asn Arg Glu Arg Ser
                165                 170                 175

Trp Leu Thr Arg Leu Ile Asp Met Glu Tyr Trp Leu Ala Cys Asn Glu
            180                 185                 190
```

-continued

```
Glu Arg Ile Ala Gln Ser Arg Phe Gly Ser Val Met Cys Cys Cys Gly
        195                 200                 205

Pro Cys Ala Met Tyr Arg Arg Ser Ala Ile Thr Pro Leu Leu Ala Glu
        210                 215                 220

Tyr Glu His Gln Thr Phe Leu Gly Arg Pro Ser Asn Phe Gly Glu Asp
225                 230                 235                 240

Arg His Leu Thr Ile Leu Met Leu Lys Ala Gly Phe Arg Thr Gly Tyr
                245                 250                 255

Val Pro Gly Ala Val Ala Arg Thr Leu Val Pro Asp Gly Leu Ala Pro
                260                 265                 270

Tyr Leu Arg Gln Gln Leu Arg Trp Ala Arg Ser Thr Tyr Arg Asp Thr
                275                 280                 285

Ala Leu Ala Leu Arg Ile Lys Lys Asn Leu Ser Lys Tyr Ile Thr Phe
                290                 295                 300

Glu Ile Cys Ala Gln Asn Leu Gly Thr Ala Leu Leu Leu Val Met Thr
305                 310                 315                 320

Met Ile Ser Leu Ser Leu Thr Thr Ser Gly Ser Gln Thr Pro Val Ile
                325                 330                 335

Ile Leu Gly Val Val Val Gly Met Ser Ile Ile Arg Cys Cys Ser Val
                340                 345                 350

Ala Leu Ile Ala Lys Asp Phe Arg Phe Leu Tyr Phe Ile Val His Ser
                355                 360                 365

Ala Leu Asn Val Leu Ile Leu Thr Pro Leu Lys Leu Tyr Ala Leu Leu
                370                 375                 380

Thr Ile Arg Asp Ser Arg Trp Leu Ser Arg Glu Ser Ser
385                 390                 395
```

```
<210> SEQ ID NO 54
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgtcagtgg tcgacgtaat tggccttctg gccaccgccg cctatgtgac cctggcttcc      60
gcgtacaaag tagtccaatt tatcaatgtc tctagcgtga ctgacgtagc aggccttgag     120
agtgatgccc tcccgcttac accgcgcgta gatgtaatcg tgcccacgtt taatgaaaat     180
tcttccacgc tgttagaatg cgtcgcaagc atttgtgcgc aagactacag aggcccaatc     240
accattgtgg tggtagacga cggctcgact aataaaacta gctttcacgc agtttgcgac     300
aaatatgcgt cggatgagcg cttcatcttc gtcgaacttg atcagaacaa ggggaaacgc     360
gctgcacaga tggaggcaat cgccggacg gacggcgatc ttatcttgaa tgtcgattct     420
gataccgtga tcgacaagga tgttgttacg aaacttgctt cgagcatgcg cgcaccaaac     480
gtgggtggag tgatgggca actggttgcc aaaaatcggg aacgatcatg gctcacacgg     540
cttatcgata tggaatattg gttagcttgt aatgaggagc gcatcgctca aagccgcttt     600
ggttctgtca tgtgctgttg tggtccatgc gcgatgtaca gacgttctgc aatcacgcca     660
cttctggcgg aatacgaaca ccagacattc cttggacgac cgtctaattt tggcgaagat     720
cggcacttaa cgattttaat gttgaaagcg ggatttcgta cggggtatgt cccaggcgca     780
gtagctcgta cgttagttcc tgacggattg gctccttatt tgcgtcaaca acttcggtgg     840
gcccggagca cataccgtga tacagctctg gcattgcgta ttaaaaagaa cttatcaaaa     900
```

```
tatatcacat ttgaaatctg cgcgcaaaat ctgggtacgg cgcttttgct tgtgatgaca      960
atgatttcgt tatctcttac cacatcggga agtcaaaccc cggtaatcat tcttggagtt     1020
gtcgtcggca tgtcaatcat tagatgttgt tcggttgccc ttatcgctaa agatttaga     1080 tttctctatt ttattgtaca ttcggcgctt aatgtactga ttctcactcc gcttaaattg     1140
tacgctcttc ttaccattag agatagcaga tggttatcgc gcgaatcaag ctag          1194
```

<210> SEQ ID NO 55
<211> LENGTH: 29
<212> TYPE: PRT
<213> ORGANISM: Bacillus subtilis

<400> SEQUENCE: 55

```
Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala
            20                  25
```

<210> SEQ ID NO 56
<211> LENGTH: 30
<212> TYPE: PRT
<213> ORGANISM: Bacillus subtilis

<400> SEQUENCE: 56

```
Met Arg Lys Ser Leu Ile Thr Leu Gly Leu Ala Ser Val Ile Gly Thr
1               5                   10                  15

Ser Ser Phe Leu Ile Pro Phe Thr Ser Lys Thr Ala Ser Ala
            20                  25                  30
```

<210> SEQ ID NO 57
<211> LENGTH: 25
<212> TYPE: PRT
<213> ORGANISM: Bacillus subtilis

<400> SEQUENCE: 57

```
Met Lys Leu Arg Lys Val Leu Thr Gly Ser Val Leu Ser Leu Gly Leu
1               5                   10                  15

Leu Val Ser Ala Ser Pro Ala Phe Ala
            20                  25
```

<210> SEQ ID NO 58
<211> LENGTH: 30
<212> TYPE: PRT
<213> ORGANISM: Bacillus subtilis

<400> SEQUENCE: 58

```
Met Lys Arg Lys Leu Leu Ser Ser Leu Ala Ile Ser Ala Leu Ser Leu
1               5                   10                  15

Gly Leu Leu Val Ser Ala Pro Thr Ala Ser Phe Ala Ala Glu
            20                  25                  30
```

<210> SEQ ID NO 59
<211> LENGTH: 21
<212> TYPE: PRT
<213> ORGANISM: Bacillus subtilis

<400> SEQUENCE: 59

```
Met Lys Lys Val Met Leu Ala Thr Ala Leu Phe Leu Gly Leu Thr Pro
1               5                   10                  15

Ala Gly Ala Asn Ala
```

-continued

```
            20

<210> SEQ ID NO 60
<211> LENGTH: 24
<212> TYPE: PRT
<213> ORGANISM: Bacillus subtilis

<400> SEQUENCE: 60

Met Lys Arg Leu Cys Leu Trp Phe Thr Val Phe Ser Leu Phe Leu Val
1               5                   10                  15

Leu Leu Pro Gly Lys Ala Leu Gly
            20

<210> SEQ ID NO 61
<211> LENGTH: 24
<212> TYPE: PRT
<213> ORGANISM: Bacillus subtilis

<400> SEQUENCE: 61

Met Lys Lys Met Leu Met Leu Ala Phe Thr Phe Leu Leu Ala Leu Thr
1               5                   10                  15

Ile His Val Gly Glu Ala Ser Ala
            20

<210> SEQ ID NO 62
<211> LENGTH: 28
<212> TYPE: PRT
<213> ORGANISM: Bacillus subtilis

<400> SEQUENCE: 62

Met Phe Lys Lys Leu Leu Leu Ala Thr Ser Ala Leu Thr Phe Ser Leu
1               5                   10                  15

Ser Leu Val Leu Pro Leu Asp Gly His Ala Lys Ala
            20                  25

<210> SEQ ID NO 63
<211> LENGTH: 32
<212> TYPE: PRT
<213> ORGANISM: Bacillus subtilis

<400> SEQUENCE: 63

Met Lys Phe Val Lys Arg Arg Ile Ile Ala Leu Val Thr Ile Leu Met
1               5                   10                  15

Leu Ser Val Thr Ser Leu Phe Ala Leu Gln Pro Ser Ala Lys Ala Ala
            20                  25                  30

<210> SEQ ID NO 64
<211> LENGTH: 28
<212> TYPE: PRT
<213> ORGANISM: Bacillus subtilis

<400> SEQUENCE: 64

Met Lys Lys Val Leu Met Ala Phe Ile Ile Cys Leu Ser Leu Ile Leu
1               5                   10                  15

Ser Val Leu Ala Ala Pro Pro Ser Gly Ala Lys Ala
            20                  25

<210> SEQ ID NO 65
<211> LENGTH: 23
<212> TYPE: PRT
<213> ORGANISM: Bacillus subtilis

<400> SEQUENCE: 65
```

-continued

Met Lys Arg Phe Ile Leu Val Leu Ser Phe Leu Ser Ile Ile Val Ala
1               5                   10                  15

Tyr Pro Ile Gln Thr Asn Ala
            20

<210> SEQ ID NO 66
<211> LENGTH: 28
<212> TYPE: PRT
<213> ORGANISM: Bacillus subtilis

<400> SEQUENCE: 66

Met Lys Arg Met Ile Val Arg Met Thr Leu Pro Leu Leu Ile Val Cys
1               5                   10                  15

Leu Ala Phe Ser Ser Phe Ser Ala Ser Ala Arg Ala
            20                  25

<210> SEQ ID NO 67
<211> LENGTH: 28
<212> TYPE: PRT
<213> ORGANISM: Bacillus subtilis

<400> SEQUENCE: 67

Met Asn Ile Lys Lys Phe Ala Lys Gln Thr Val Leu Thr Phe Thr Thr
1               5                   10                  15

Ala Leu Leu Ala Gly Gly Ala Thr Gln Ala Phe Ala
            20                  25

<210> SEQ ID NO 68
<211> LENGTH: 28
<212> TYPE: PRT
<213> ORGANISM: Bacillus subtilis

<400> SEQUENCE: 68

Met Pro Tyr Leu Lys Arg Val Leu Leu Leu Leu Val Thr Gly Leu Phe
1               5                   10                  15

Met Ser Leu Phe Ala Val Thr Ala Thr Ala Ser Ala
            20                  25

<210> SEQ ID NO 69
<211> LENGTH: 28
<212> TYPE: PRT
<213> ORGANISM: Bacillus subtilis

<400> SEQUENCE: 69

Met Arg Lys Lys Arg Val Ile Thr Cys Val Met Ala Ala Ser Leu Thr
1               5                   10                  15

Leu Gly Ser Leu Leu Pro Ala Gly Tyr Ala Ser Ala
            20                  25

<210> SEQ ID NO 70
<211> LENGTH: 25
<212> TYPE: PRT
<213> ORGANISM: Bacillus subtilis

<400> SEQUENCE: 70

Met Lys Ile Arg Lys Ile Leu Leu Ser Ser Ala Leu Ser Phe Gly Met
1               5                   10                  15

Leu Ile Ser Ala Val Pro Ala Leu Ala
            20                  25

<210> SEQ ID NO 71

<211> LENGTH: 3075
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
atgaccatga ttacggattc actggccgtc gttttacaac gtcgtgactg ggaaaaccct     60
ggcgttaccc aacttaatcg ccttgcagca catccccctt tcgccagctg gcgtaatagc    120
gaagaggccc gcaccgatcg cccttcccaa cagttgcgca gcctgaatgg cgaatggcgc    180
tttgcctggt ttccggcacc agaagcggtg ccggaaagct ggctggagtg cgatcttcct    240
gaggccgata ctgtcgtcgt cccctcaaac tggcagatgc acggttacga tgcgcccatc    300
tacaccaacg tgacctatcc cattacggtc aatccgccgt ttgttcccac ggagaatccg    360
acgggttgtt actcgctcac atttaatgtt gatgaaagct ggctacagga aggccagacg    420
cgaattattt ttgatggcgt taactcggcg tttcatctgt ggtgcaacgg cgctgggtc     480 ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccgaaa    900
ctgtggagcg ccgaaatccc gaatctctat cgtgcggtgg ttgaactgca caccgccgac    960
ggcacgctga ttgaagcaga agcctgcgat gtcggtttcc gcgaggtgcg gattgaaaat   1020
ggtctgctgc tgctgaacgg caagccgttg ctgattcgag gcgttaaccg tcacgagcat   1080
catcctctgc atggtcaggt catggatgag cagacgatgg tgcaggatat cctgctgatg   1140
aagcagaaca actttaacgc cgtgcgctgt tcgcattatc cgaaccatcc gctgtggtac   1200
acgctgtgcg accgctacgg cctgtatgtg gtggatgaag ccaatattga aacccacggc   1260
atggtgccaa tgaatcgtct gaccgatgat ccgcgctggc taccggcgat gagcgaacgc   1320
gtaacgcgaa tggtgcagcg cgatcgtaat cacccgagtg tgatcatctg tcgctgggg    1380 aatgaatcag gccacggcgc taatcacgac gcgctgtatc gctggatcaa atctgtcgat   1440
ccttcccgcc cggtgcagta tgaaggcggc ggagccgaca ccacggccac cgatattatt   1500
tgcccgatgt acgcgcgcgt ggatgaagac cagcccttcc cggctgtgcc gaaatggtcc   1560
atcaaaaaat ggcttcgct  acctggagag acgcgcccgc tgatcctttg cgaatacgcc   1620
cacgcgatgg gtaacagtct ggcggtttc  gctaaatact ggcaggcgtt tcgtcagtat   1680
ccccgtttac agggcggctt cgtctgggac tgggtggatc agtcgctgat taaatatgat   1740
gaaaacggca acccgtggtc ggcttacggc ggtgattttg gcgatacgcc gaacgatcgc   1800
cagttctgta tgaacggtct ggtctttgcc gaccgcacgc cgcatccagc gctgacggaa   1860
gcaaaacacc agcagcagtt tttccagttc cgtttatccg ggcaaaccat cgaagtgacc   1920
agcgaatacc tgttccgtca tagcgataac gagctcctgc actggatggt ggcgctggat   1980
ggtaagccgc tggcaagcgg tgaagtgcct ctggatgtcg ctccacaagg taaacagttg   2040
attgaactgc ctgaactacc gcagccggag agcgccgggc aactctggct cacagtacgc   2100
```

```
gtagtgcaac cgaacgcgac cgcatggtca gaagccgggc acatcagcgc ctggcagcag    2160
tggcgtctgg cggaaaacct cagtgtgacg ctccccgccg cgtcccacgc catcccgcat    2220
ctgaccacca gcgaaatgga ttttttgcatc gagctgggta ataagcgttg gcaatttaac    2280
cgccagtcag gctttctttc acagatgtgg attggcgata aaaaacaact gctgacgccg    2340
ctgcgcgatc agttcacccg tgcaccgctg gataacgaca ttggcgtaag tgaagcgacc    2400
cgcattgacc ctaacgcctg ggtcgaacgc tggaaggcgg cgggccatta ccaggccgaa    2460
gcagcgttgt tgcagtgcac ggcagataca cttgctgatg cggtgctgat tacgaccgct    2520
cacgcgtggc agcatcaggg gaaaacctta tttatcagcc ggaaaaccta ccggattgat    2580
ggtagtggtc aaatggcgat taccgttgat gttgaagtgg cgagcgatac accgcatccg    2640
gcgcggattg gcctgaactg ccagctggcg caggtagcag agcgggtaaa ctggctcgga    2700
ttagggccgc aagaaaacta tcccgaccgc cttactgccg cctgtttttga ccgctgggat    2760 ctgccattgt cagacatgta taccccgtac gtcttcccga gcgaaaacgg tctgcgctgc    2820
gggacgcgcg aattgaatta tggcccacac cagtggcgcg cgacttcca gttcaacatc    2880 agccgctaca gtcaacagca actgatggaa accagccatc gccatctgct gcacgcggaa    2940
gaaggcacat ggctgaatat cgacggtttc catatgggga ttggtggcga cgactcctgg    3000
agcccgtcag tatcggcgga attccagctg agcgccggtc gctaccatta ccagttggtc    3060
tggtgtcaaa aataa                                                      3075
```

```
<210> SEQ ID NO 72
<211> LENGTH: 1024
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Glu Glu Ala Arg Thr Asp Arg Pro
            35                  40                  45

Ser Gln Gln Leu Arg Ser Leu Asn Gly Glu Trp Arg Phe Ala Trp Phe
        50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
                100                 105                 110

Pro Phe Val Pro Thr Glu Asn Pro Thr Gly Cys Tyr Ser Leu Thr Phe
            115                 120                 125

Asn Val Asp Glu Ser Trp Leu Gln Glu Gly Gln Thr Arg Ile Ile Phe
        130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
```

```
                     180                   185                   190

Ser Asp Gly Ser Tyr Leu Glu Asp Gln Asp Met Trp Arg Met Ser Gly
            195                   200                   205

Ile Phe Arg Asp Val Ser Leu Leu His Lys Pro Thr Thr Gln Ile Ser
        210                   215                   220

Asp Phe His Val Ala Thr Arg Phe Asn Asp Asp Phe Ser Arg Ala Val
225                   230                   235                   240

Leu Glu Ala Glu Val Gln Met Cys Gly Glu Leu Arg Asp Tyr Leu Arg
                245                   250                   255

Val Thr Val Ser Leu Trp Gln Gly Glu Thr Gln Val Ala Ser Gly Thr
                260                   265                   270

Ala Pro Phe Gly Gly Glu Ile Ile Asp Glu Arg Gly Gly Tyr Ala Asp
            275                   280                   285

Arg Val Thr Leu Arg Leu Asn Val Glu Asn Pro Lys Leu Trp Ser Ala
            290                   295                   300

Glu Ile Pro Asn Leu Tyr Arg Ala Val Val Glu Leu His Thr Ala Asp
305                   310                   315                   320

Gly Thr Leu Ile Glu Ala Glu Ala Cys Asp Val Gly Phe Arg Glu Val
                325                   330                   335

Arg Ile Glu Asn Gly Leu Leu Leu Leu Asn Gly Lys Pro Leu Leu Ile
            340                   345                   350

Arg Gly Val Asn Arg His Glu His His Pro Leu His Gly Gln Val Met
            355                   360                   365

Asp Glu Gln Thr Met Val Gln Asp Ile Leu Leu Met Lys Gln Asn Asn
        370                   375                   380

Phe Asn Ala Val Arg Cys Ser His Tyr Pro Asn His Pro Leu Trp Tyr
385                   390                   395                   400

Thr Leu Cys Asp Arg Tyr Gly Leu Tyr Val Val Asp Glu Ala Asn Ile
                405                   410                   415

Glu Thr His Gly Met Val Pro Met Asn Arg Leu Thr Asp Asp Pro Arg
            420                   425                   430

Trp Leu Pro Ala Met Ser Glu Arg Val Thr Arg Met Val Gln Arg Asp
            435                   440                   445

Arg Asn His Pro Ser Val Ile Ile Trp Ser Leu Gly Asn Glu Ser Gly
        450                   455                   460

His Gly Ala Asn His Asp Ala Leu Tyr Arg Trp Ile Lys Ser Val Asp
465                   470                   475                   480

Pro Ser Arg Pro Val Gln Tyr Glu Gly Gly Gly Ala Asp Thr Thr Ala
            485                   490                   495

Thr Asp Ile Ile Cys Pro Met Tyr Ala Arg Val Asp Glu Asp Gln Pro
            500                   505                   510

Phe Pro Ala Val Pro Lys Trp Ser Ile Lys Lys Trp Leu Ser Leu Pro
            515                   520                   525

Gly Glu Thr Arg Pro Leu Ile Leu Cys Glu Tyr Ala His Ala Met Gly
        530                   535                   540

Asn Ser Leu Gly Gly Phe Ala Lys Tyr Trp Gln Ala Phe Arg Gln Tyr
545                   550                   555                   560

Pro Arg Leu Gln Gly Gly Phe Val Trp Asp Trp Val Asp Gln Ser Leu
            565                   570                   575

Ile Lys Tyr Asp Glu Asn Gly Asn Pro Trp Ser Ala Tyr Gly Gly Asp
            580                   585                   590

Phe Gly Asp Thr Pro Asn Asp Arg Gln Phe Cys Met Asn Gly Leu Val
            595                   600                   605
```

```
Phe Ala Asp Arg Thr Pro His Pro Ala Leu Thr Glu Ala Lys His Gln
    610             615             620

Gln Gln Phe Phe Gln Phe Arg Leu Ser Gly Gln Thr Ile Glu Val Thr
625             630             635             640

Ser Glu Tyr Leu Phe Arg His Ser Asp Asn Glu Leu Leu His Trp Met
            645             650             655

Val Ala Leu Asp Gly Lys Pro Leu Ala Ser Gly Glu Val Pro Leu Asp
            660             665             670

Val Ala Pro Gln Gly Lys Gln Leu Ile Glu Leu Pro Glu Leu Pro Gln
        675             680             685

Pro Glu Ser Ala Gly Gln Leu Trp Leu Thr Val Arg Val Val Gln Pro
    690             695             700

Asn Ala Thr Ala Trp Ser Glu Ala Gly His Ile Ser Ala Trp Gln Gln
705             710             715             720

Trp Arg Leu Ala Glu Asn Leu Ser Val Thr Leu Pro Ala Ala Ser His
            725             730             735

Ala Ile Pro His Leu Thr Thr Ser Glu Met Asp Phe Cys Ile Glu Leu
            740             745             750

Gly Asn Lys Arg Trp Gln Phe Asn Arg Gln Ser Gly Phe Leu Ser Gln
            755             760             765

Met Trp Ile Gly Asp Lys Lys Gln Leu Leu Thr Pro Leu Arg Asp Gln
    770             775             780

Phe Thr Arg Ala Pro Leu Asp Asn Asp Ile Gly Val Ser Glu Ala Thr
785             790             795             800

Arg Ile Asp Pro Asn Ala Trp Val Glu Arg Trp Lys Ala Ala Gly His
            805             810             815

Tyr Gln Ala Glu Ala Ala Leu Leu Gln Cys Thr Ala Asp Thr Leu Ala
            820             825             830

Asp Ala Val Leu Ile Thr Thr Ala His Ala Trp Gln His Gln Gly Lys
        835             840             845

Thr Leu Phe Ile Ser Arg Lys Thr Tyr Arg Ile Asp Gly Ser Gly Gln
    850             855             860

Met Ala Ile Thr Val Asp Val Glu Val Ala Ser Asp Thr Pro His Pro
865             870             875             880

Ala Arg Ile Gly Leu Asn Cys Gln Leu Ala Gln Val Ala Glu Arg Val
            885             890             895

Asn Trp Leu Gly Leu Gly Pro Gln Glu Asn Tyr Pro Asp Arg Leu Thr
            900             905             910

Ala Ala Cys Phe Asp Arg Trp Asp Leu Pro Leu Ser Asp Met Tyr Thr
        915             920             925

Pro Tyr Val Phe Pro Ser Glu Asn Gly Leu Arg Cys Gly Thr Arg Glu
    930             935             940

Leu Asn Tyr Gly Pro His Gln Trp Arg Gly Asp Phe Gln Phe Asn Ile
945             950             955             960

Ser Arg Tyr Ser Gln Gln Gln Leu Met Glu Thr Ser His Arg His Leu
            965             970             975

Leu His Ala Glu Glu Gly Thr Trp Leu Asn Ile Asp Gly Phe His Met
            980             985             990

Gly Ile Gly Gly Asp Asp Ser Trp Ser Pro Ser Val Ser Ala Glu Phe
        995             1000            1005

Gln Leu Ser Ala Gly Arg Tyr His Tyr Gln Leu Val Trp Cys Gln
    1010            1015            1020
```

-continued

Lys

```
<210> SEQ ID NO 73
<211> LENGTH: 1992
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgagaaaac tgtatcatgg cgcttgctat tatccggaat tatgggatga agagacgatt        60
cagcaggaca ttgacatcat gcgtgaagtt ggcgtaaatg ttgtgcggat cggcgaattt       120
gcctggtcag tcatggaacc tgaagaagga aaaattgacg tcggtttttt caaagaaatc       180
atcgcccggc tgtatgatag cgggatcgaa acgattatgt gcacgccgac gcctaccccg       240
ccgatttggt tctcacatgg ccggcccgaa cgcatgcatg ccaatgaaaa aagagagatc       300
atggggcatg gctcccgtca gcatgcctgt acgaacaacc cgtatttccg aaaaaaagcc       360
gccatcatca ccacagccat cgccaaggag cttggccggc tcccggggct gatcggatgg       420
cagctagaca tgagtttaa atgccatgtt gcagaatgca tgtgtgagac atgcttgcgc       480
ctatggcatg actggctcaa aaatcgctac ggggtaattg agcgcttgaa tgaagcttgg       540
ggaaccgatg tgtggagcga gacctatcag acgtttgagc aagtcccgca gccgggaccg       600
gccccgtttc tgcatcatgc ctctctacgc actatgtatc agctgttttc gatggagatg       660
atcgcttcgt ttgcggatga acaggccaaa atcatccgct gctattcaga tgcgccgatc       720
acgcataacg gatcagtcat gttcagcgtg gacaatgagc gaatgtttca gaatctcgat       780
tttgcctcct atgacacgta cgcttcgcag gaaaacgcct ctgcctttt attgaactgt       840 gatttatgga gaaatctgaa acaagggcgc ccgtttttgga ttttggaaac gagtccgtcg       900
tatgccgcct cgcttgaaag ctccgcttac ccgcacgcag acgggtattt gcaggccgaa       960
gccgtatcgt cctacgcctt agggagccag gggtttttgct actggctatg gcgacagcag      1020
cgttcaggca gcgagatttc ccacggttcg gttctcagtg cctggggcga acccaccatc      1080
ggctatcaaa atgtgctggc ggttgagcgg gcaagaaagg aaatcgagcc tattattcta      1140
tcgactgaac ccgttcaagc cgaggcggcg atgacttact ctgacagagc aaaagcattt      1200
attaaaactg agcctcaccg gggactccgg catcgttcgc ttgtgacgca tttttatgaa      1260
cgtattctca cacggggat tcaccgtgac cttattccgg aaggcgctcc actggacggc      1320
tatcgcttgc tgtttacgcc atttgtgccg tatttgtctt ctgaatttat caaaaaagct      1380
tcggcattcg ctgaagcggg cggcatctgg atcaccgggc cgctgacagg aggacgcaca      1440
tgcgagcata ccattcatac cgattgcgga cttggcgaac ttgagaaaac gtcagggatc      1500
aaaacacttt ttacctttcc gatgaatgag aacgtgaata caggaaaagc gtttggcatc      1560
acggcgccgc tcggactgtg gagcgcggtg tttgacacag agagcggaaa cacccttggc      1620
acggttgaag caggaccggg ggcgggccat gcttttctga cggaacggaa ttacggcgag      1680
gggaaaattg tcatgctggg ctcgcttcca tccgggaaag aaggggatgc gatgctggaa      1740
gcgctcgtca ggcattatgc ggaggaagct gttatttcca gccggtcgga tgtgacaccc      1800
ggcacgatcg ttgccccgcg tataggcgaa aacggccttg tgtggatcgt tgtgaatatg      1860
gatggaaaag gcgggagcgt gacattgccg gaatcgggaa cggatttgtt gacgcaccgc      1920
ttggaaaagg cggggagact ggcggtcgga ccgcatgaat accgtgtgat tcaatttgac      1980
```
aatcacagct ga                                                                1992

<210> SEQ ID NO 74
<211> LENGTH: 663
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Arg Lys Leu Tyr His Gly Ala Cys Tyr Tyr Pro Glu Leu Trp Asp
1               5                   10                  15

Glu Glu Thr Ile Gln Gln Asp Ile Asp Ile Met Arg Glu Val Gly Val
            20                  25                  30

Asn Val Val Arg Ile Gly Glu Phe Ala Trp Ser Val Met Glu Pro Glu
        35                  40                  45

Glu Gly Lys Ile Asp Val Gly Phe Phe Lys Glu Ile Ile Ala Arg Leu
    50                  55                  60

Tyr Asp Ser Gly Ile Glu Thr Ile Met Cys Thr Pro Thr Pro Thr Pro
65                  70                  75                  80

Pro Ile Trp Phe Ser His Gly Arg Pro Glu Arg Met His Ala Asn Glu
                85                  90                  95

Lys Arg Glu Ile Met Gly His Gly Ser Arg Gln His Ala Cys Thr Asn
            100                 105                 110

Asn Pro Tyr Phe Arg Lys Lys Ala Ala Ile Ile Thr Thr Ala Ile Ala
        115                 120                 125

Lys Glu Leu Gly Arg Leu Pro Gly Leu Ile Gly Trp Gln Leu Asp Asn
    130                 135                 140

Glu Phe Lys Cys His Val Ala Glu Cys Met Cys Glu Thr Cys Leu Arg
145                 150                 155                 160

Leu Trp His Asp Trp Leu Lys Asn Arg Tyr Gly Val Ile Glu Arg Leu
                165                 170                 175

Asn Glu Ala Trp Gly Thr Asp Val Trp Ser Glu Thr Tyr Gln Thr Phe
            180                 185                 190

Glu Gln Val Pro Gln Pro Gly Pro Ala Pro Phe Leu His His Ala Ser
        195                 200                 205

Leu Arg Thr Met Tyr Gln Leu Phe Ser Met Glu Met Ile Ala Ser Phe
    210                 215                 220

Ala Asp Glu Gln Ala Lys Ile Ile Arg Cys Tyr Ser Asp Ala Pro Ile
225                 230                 235                 240

Thr His Asn Gly Ser Val Met Phe Ser Val Asp Asn Glu Arg Met Phe
                245                 250                 255

Gln Asn Leu Asp Phe Ala Ser Tyr Asp Thr Tyr Ala Ser Gln Glu Asn
            260                 265                 270

Ala Ser Ala Phe Leu Leu Asn Cys Asp Leu Trp Arg Asn Leu Lys Gln
        275                 280                 285

Gly Arg Pro Phe Trp Ile Leu Glu Thr Ser Pro Ser Tyr Ala Ala Ser
    290                 295                 300

Leu Glu Ser Ser Ala Tyr Pro His Ala Asp Gly Tyr Leu Gln Ala Glu
305                 310                 315                 320

Ala Val Ser Ser Tyr Ala Leu Gly Ser Gln Gly Phe Cys Tyr Trp Leu
                325                 330                 335

Trp Arg Gln Gln Arg Ser Gly Ser Glu Ile Ser His Gly Ser Val Leu
            340                 345                 350

```
Ser Ala Trp Gly Glu Pro Thr Ile Gly Tyr Gln Asn Val Leu Ala Val
        355             360             365

Glu Arg Ala Arg Lys Glu Ile Glu Pro Ile Ile Leu Ser Thr Glu Pro
        370             375             380

Val Gln Ala Glu Ala Ala Met Thr Tyr Ser Asp Arg Ala Lys Ala Phe
385             390             395             400

Ile Lys Thr Glu Pro His Arg Gly Leu Arg His Arg Ser Leu Val Thr
            405             410             415

His Phe Tyr Glu Arg Ile Leu Asn Thr Gly Ile His Arg Asp Leu Ile
            420             425             430

Pro Glu Gly Ala Pro Leu Asp Gly Tyr Arg Leu Leu Phe Thr Pro Phe
            435             440             445

Val Pro Tyr Leu Ser Ser Glu Phe Ile Lys Lys Ala Ser Ala Phe Ala
        450             455             460

Glu Ala Gly Gly Ile Trp Ile Thr Gly Pro Leu Thr Gly Gly Arg Thr
465             470             475             480

Cys Glu His Thr Ile His Thr Asp Cys Gly Leu Gly Glu Leu Glu Lys
            485             490             495

Thr Ser Gly Ile Lys Thr Leu Phe Thr Phe Pro Met Asn Glu Asn Val
            500             505             510

Asn Thr Gly Lys Ala Phe Gly Ile Thr Ala Pro Leu Gly Leu Trp Ser
        515             520             525

Ala Val Phe Asp Thr Glu Ser Gly Asn Thr Leu Gly Thr Val Glu Ala
        530             535             540

Gly Pro Gly Ala Gly His Ala Phe Leu Thr Glu Arg Asn Tyr Gly Glu
545             550             555             560

Gly Lys Ile Val Met Leu Gly Ser Leu Pro Ser Gly Lys Glu Gly Asp
            565             570             575

Ala Met Leu Glu Ala Leu Val Arg His Tyr Ala Glu Glu Ala Val Ile
            580             585             590

Ser Ser Arg Ser Asp Val Thr Pro Gly Thr Ile Val Ala Pro Arg Ile
        595             600             605

Gly Glu Asn Gly Leu Val Trp Ile Val Val Asn Met Asp Gly Lys Gly
        610             615             620

Gly Ser Val Thr Leu Pro Glu Ser Gly Thr Asp Leu Leu Thr His Arg
625             630             635             640

Leu Glu Lys Ala Gly Arg Leu Ala Val Gly Pro His Glu Tyr Arg Val
            645             650             655

Ile Gln Phe Asp Asn His Ser
            660
```

```
<210> SEQ ID NO 75
<211> LENGTH: 2061
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
atgtcaaagc ttgaaaaaac gcacgtaaca aaagcaaaat ttatgctcca tgggggagac        60
tacaaccccg atcagtggct ggatcggccc gatattttag ctgacgatat caaactgatg       120
aagctttctc atacgaatac gttttctgtc ggcatttttg catggagcgc acttgagccg       180
gaggagggcg tatatcaatt tgaatggctg gatgatattt ttgagcggat tcacagtata       240
```

-continued

```
ggcggccggg tcatattagc aacgccgagc ggagcccgtc cggcctggct gtcgcaaacc    300
tatccggaag ttttgcgcgt caatgcctcc cgcgtcaaac agctgcacgg cggaaggcac    360
aaccactgcc tcacatctaa agtctaccga gaaaaaacac ggcacatcaa ccgcttatta    420
gcagaacgat acggacatca cccggcgctg ttaatgtggc acatttcaaa cgaatacggg    480
ggagattgcc actgtgattt atgccagcat gctttccggg agtggctgaa atcgaaatat    540
gacaacagcc tcaagacatt gaaccatgcg tggtggaccc cttttttggag ccatacgttc    600 aatgactggt cacaaattga aagcccttcg ccgatcggtg aaaatggctt gcatggcctg    660
aatttagatt ggcgccggtt cgtcaccgat caaacgattt cgtttttatga aaatgaaatc    720 attccgctga aagaattgac gcctgatatc cctatcacaa cgaattttat ggctgacaca    780
ccggatttga tcccgtatca gggcctcgac tacagcaaat ttgcaaagca tgtcgatgcc    840
atcagctggg acgcttatcc tgtctggcac aatgactggg aaagcacagc tgatttggcg    900
atgaaggtcg gctttatcaa tgatctgtac cgaagcttga agcagcagcc cttcttatta    960
atggagtgta cgccaagcgc ggtcaattgg cataacgtca acaaggcaaa gcgcccgggc   1020
atgaatctgc tgtcatccat gcaaatgatt gcccacggct cggacagcgt tctctatttc   1080
caataccgca aatcacgggg gtcatcagaa aaattacacg gagcggttgt ggatcatgac   1140
aatagcccga agaaccgcgt ctttcaagaa gtggccaagg taggcgagac attggaacgg   1200
ctgtccgaag ttgtcggaac gaagaggccg gctcaaaccg cgattttata tgactgggaa   1260
aatcattggg cgctcgagga tgctcagggg tttgcgaagg cgacaaaacg ttatccgcaa   1320
acgcttcagc agcattaccg cacattctgg gaacacgata tccctgtcga cgtcatcacg   1380
aaagaacaag acttttcacc atataaactg ctgatcgtcc cgatgctgta tttaatcagc   1440
gaggacaccg tttcccgttt aaaagcgttt acggctgacg gcggcacctt agtcatgacg   1500
tatatcagcg gggttgtgaa tgagcatgac ttaacataca caggcggatg gcatccggat   1560
cttcaagcta tatttggagt tgagcctctt gaaacggaca ccctgtatcc gaaggatcga   1620
aacgctgtca gctaccgcag ccaaatatat gaaatgaagg attatgcaac cgtgattgat   1680
gtaaagacag cttcagtgga agcggtgtat caagaagatt tttatgcgcg cacgccagcg   1740
gtcacaagcc atgagtatca gcagggcaag gcgtatttta tcggcgcgcg tttggaggat   1800
caatttcagc gtgatttcta tgagggtctg atcacagacc tgtctctctc tccagttttt   1860
ccggttcggc acggaaaagg cgtctccgta caagcgaggc aggatcagga caatgattat   1920 attttttgtca tgaatttcac ggaagaaaaa cagctggtca cgtttgatca gagtgtgaag   1980
gacataatga caggagacat attgtcaggc gacctgacga tggaaaagta tgaagtgaga   2040
attgtcgtaa acacacatta g                                             2061
```

```
<210> SEQ ID NO 76
<211> LENGTH: 686
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ser Lys Leu Glu Lys Thr His Val Thr Lys Ala Lys Phe Met Leu
1               5                   10                  15

His Gly Gly Asp Tyr Asn Pro Asp Gln Trp Leu Asp Arg Pro Asp Ile
            20                  25                  30
```

Leu Ala Asp Asp Ile Lys Leu Met Lys Leu Ser His Thr Asn Thr Phe
35                    40                   45

Ser Val Gly Ile Phe Ala Trp Ser Ala Leu Glu Pro Glu Glu Gly Val
50                    55                   60

Tyr Gln Phe Glu Trp Leu Asp Asp Ile Phe Glu Arg Ile His Ser Ile
65                    70                   75                   80

Gly Gly Arg Val Ile Leu Ala Thr Pro Ser Gly Ala Arg Pro Ala Trp
85                   90                   95

Leu Ser Gln Thr Tyr Pro Glu Val Leu Arg Val Asn Ala Ser Arg Val
100                   105                  110

Lys Gln Leu His Gly Gly Arg His Asn His Cys Leu Thr Ser Lys Val
115                   120                  125

Tyr Arg Glu Lys Thr Arg His Ile Asn Arg Leu Leu Ala Glu Arg Tyr
130                   135                  140

Gly His His Pro Ala Leu Leu Met Trp His Ile Ser Asn Glu Tyr Gly
145                   150                  155                  160

Gly Asp Cys His Cys Asp Leu Cys Gln His Ala Phe Arg Glu Trp Leu
165                   170                  175

Lys Ser Lys Tyr Asp Asn Ser Leu Lys Thr Leu Asn His Ala Trp Trp
180                   185                  190

Thr Pro Phe Trp Ser His Thr Phe Asn Asp Trp Ser Gln Ile Glu Ser
195                   200                  205

Pro Ser Pro Ile Gly Glu Asn Gly Leu His Gly Leu Asn Leu Asp Trp
210                   215                  220

Arg Arg Phe Val Thr Asp Gln Thr Ile Ser Phe Tyr Glu Asn Glu Ile
225                   230                  235                  240

Ile Pro Leu Lys Glu Leu Thr Pro Asp Ile Pro Ile Thr Thr Asn Phe
245                   250                  255

Met Ala Asp Thr Pro Asp Leu Ile Pro Tyr Gln Gly Leu Asp Tyr Ser
260                   265                  270

Lys Phe Ala Lys His Val Asp Ala Ile Ser Trp Asp Ala Tyr Pro Val
275                   280                  285

Trp His Asn Asp Trp Glu Ser Thr Ala Asp Leu Ala Met Lys Val Gly
290                   295                  300

Phe Ile Asn Asp Leu Tyr Arg Ser Leu Lys Gln Gln Pro Phe Leu Leu
305                   310                  315                  320

Met Glu Cys Thr Pro Ser Ala Val Asn Trp His Asn Val Asn Lys Ala
325                   330                  335

Lys Arg Pro Gly Met Asn Leu Leu Ser Ser Met Gln Met Ile Ala His
340                   345                  350

Gly Ser Asp Ser Val Leu Tyr Phe Gln Tyr Arg Lys Ser Arg Gly Ser
355                   360                  365

Ser Glu Lys Leu His Gly Ala Val Val Asp His Asp Asn Ser Pro Lys
370                   375                  380

Asn Arg Val Phe Gln Glu Val Ala Lys Val Gly Glu Thr Leu Glu Arg
385                   390                  395                  400

Leu Ser Glu Val Val Gly Thr Lys Arg Pro Ala Gln Thr Ala Ile Leu
405                   410                  415

Tyr Asp Trp Glu Asn His Trp Ala Leu Glu Asp Ala Gln Gly Phe Ala
420                   425                  430

Lys Ala Thr Lys Arg Tyr Pro Gln Thr Leu Gln Gln His Tyr Arg Thr
435                   440                  445

Phe Trp Glu His Asp Ile Pro Val Asp Val Ile Thr Lys Glu Gln Asp

```
      450            455            460
Phe Ser Pro Tyr Lys Leu Leu Ile Val Pro Met Leu Tyr Leu Ile Ser
465            470            475            480

Glu Asp Thr Val Ser Arg Leu Lys Ala Phe Thr Ala Asp Gly Gly Thr
          485            490            495

Leu Val Met Thr Tyr Ile Ser Gly Val Val Asn Glu His Asp Leu Thr
          500            505            510

Tyr Thr Gly Gly Trp His Pro Asp Leu Gln Ala Ile Phe Gly Val Glu
      515            520            525

Pro Leu Glu Thr Asp Thr Leu Tyr Pro Lys Asp Arg Asn Ala Val Ser
      530            535            540

Tyr Arg Ser Gln Ile Tyr Glu Met Lys Asp Tyr Ala Thr Val Ile Asp
545            550            555            560

Val Lys Thr Ala Ser Val Glu Ala Val Tyr Gln Glu Asp Phe Tyr Ala
          565            570            575

Arg Thr Pro Ala Val Thr Ser His Glu Tyr Gln Gln Gly Lys Ala Tyr
          580            585            590

Phe Ile Gly Ala Arg Leu Glu Asp Gln Phe Gln Arg Asp Phe Tyr Glu
      595            600            605

Gly Leu Ile Thr Asp Leu Ser Leu Ser Pro Val Phe Pro Val Arg His
      610            615            620

Gly Lys Gly Val Ser Val Gln Ala Arg Gln Asp Gln Asp Asn Asp Tyr
625            630            635            640

Ile Phe Val Met Asn Phe Thr Glu Glu Lys Gln Leu Val Thr Phe Asp
          645            650            655

Gln Ser Val Lys Asp Ile Met Thr Gly Asp Ile Leu Ser Gly Asp Leu
          660            665            670

Thr Met Glu Lys Tyr Glu Val Arg Ile Val Val Asn Thr His
          675            680            685
```

<210> SEQ ID NO 77
<211> LENGTH: 1998
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
atgctcaaaa agcacgaaaa gttctactat ggcggtgatt ataatcctga acaatgggac      60
gaaagcgtct ggaaagagga tatgcgcttg atgaagaaag caggtgttaa ctatgtatcc     120
ataaacattt tctcttgggc acgtctccaa cctgatgaag aaacatatga tttttctacg     180
cttgataaaa taatggatat gctggctgaa aacggaattg tgctgacct ggctaccgcc      240 acggctgctc cgccggcctg gctgtcacgt aagtatcctg attctttgcc ggtcgacaaa     300
gatggctccc ggttcctgcc gggatctcgc aacactact gtccgaactc taaagactat      360
gctagactcg cagctaaatt ggtgagaaag atcgctgagc gctataaaag tcacccagca     420
ttagttatgt ggcatgtaaa caacgaatac ggctgccaca tatctgaatg ctactgcgat     480
aattgtaaaa agggttttca aacgtggctc aaggagaaat atggaacgat cgagaacttg     540
aataagagct ggagtaccga tttctggtca cagcgctact atgagtggga agaaatttgc     600
ctccctggaa aaacacctac ctttgcgaat ccaatgcagc agctcgatta taaggccttt     660
atggatgata gcctgttagc actgtataaa atggagcgtg acatactgaa aacttatacg     720
```

```
ccagacgtcc cagtcatgac gaatttaatg gggcttcata aaccagtgga cggctttcac    780
tgggctaagg agatggattt ggttacctgg gacgcgtatc ctgatccttt cgaggacatc    840
ccgtacgctc agttcatggc gcacgatctg acacgcagct tgaagaaaca acctttttct    900
ctcatggaac aggccgcggg ggccgtaaat tggcgcgcac agaacgctgt taaggcgcca    960
ggggttatgc gtttatggtc atacgaagca gcggcgcatg gtgctgacgg tataatgttt   1020
tttcaatggc gggcaagtca aggaggcgcg gaaaaatttc atagcgggat ggtaccgcat   1080
tcaggagatg aggagtctcg gaattttcgg gaggtcgtac agttaggaaa tgaacttaag   1140
aatttggaaa aagtaacggg aagtgcgtac gcgtccgacg tagcaatagt ttttgattgg   1200
aaaaactggt gggcgttgga actggacagt aagccgagct ctctggtcac ttatataaaa   1260
caactcctcc cgttctatcg ggttttgcac acgcagaaca taggtgtcga ctttatccat   1320
ccagatgaag ctatggatcg ctacaaggtg gtttttcgctc cggcgagcta ccgggtgaca   1380
aagacgtttg cagataaggt caaggcatac gtagagaacg gaggatattt cgcgacaaac   1440
ttcttcagcg ggatagctga tgagaatgaa cgtgtgtacc ttggaggtta cccaggcgct   1500
taccgtgaca tttttgggtat atatgtggaa gagtttgccc cgatgaaaaa aggagcggta   1560
catcagatcc ggactggata cggagatgct gcgatacgcg tgtgggaaga gaaaattcat   1620
ttgaaaggcg ccgaggcact cgcgtggttt aaggatggtt atctggccgg ctcaccggcg   1680
gtgaccgcac atcactgtgg caaaggcaaa gcatactata ttggcacaca gccagatgag   1740
caatacttat cctcactgct gaaggaaatt ctcaaggagg ctgacgttcg cccggccctc   1800
gatgctccgc gtggagtaga agtcgcggtt cgcaaaaacg gtcatgaaaa atttctcttc   1860
ttactgaacc atacagatca ggtgcaattc gtagatgccg gcggtactta tccagaactg   1920
atttacggtc gcaccgaagc cgaaaccgtg agactctcac cacgcgacgt gaaaatcctt   1980
caggtcatag agaaataa                                                  1998
```

<210> SEQ ID NO 78
<211> LENGTH: 665
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Leu Lys Lys His Glu Lys Phe Tyr Tyr Gly Gly Asp Tyr Asn Pro
1               5                   10                  15

Glu Gln Trp Asp Glu Ser Val Trp Lys Glu Asp Met Arg Leu Met Lys
            20                  25                  30

Lys Ala Gly Val Asn Tyr Val Ser Ile Asn Ile Phe Ser Trp Ala Arg
        35                  40                  45

Leu Gln Pro Asp Glu Glu Thr Tyr Asp Phe Ser Thr Leu Asp Lys Ile
    50                  55                  60

Met Asp Met Leu Ala Glu Asn Gly Ile Gly Ala Asp Leu Ala Thr Ala
65                  70                  75                  80

Thr Ala Ala Pro Pro Ala Trp Leu Ser Arg Lys Tyr Pro Asp Ser Leu
                85                  90                  95

Pro Val Asp Lys Asp Gly Ser Arg Phe Leu Pro Gly Ser Arg Gln His
            100                 105                 110

Tyr Cys Pro Asn Ser Lys Asp Tyr Ala Arg Leu Ala Ala Lys Leu Val
        115                 120                 125
```

```
Arg Lys Ile Ala Glu Arg Tyr Lys Ser His Pro Ala Leu Val Met Trp
    130                 135                 140

His Val Asn Asn Glu Tyr Gly Cys His Ile Ser Glu Cys Tyr Cys Asp
145                 150                 155                 160

Asn Cys Lys Lys Gly Phe Gln Thr Trp Leu Lys Glu Lys Tyr Gly Thr
                165                 170                 175

Ile Glu Asn Leu Asn Lys Ser Trp Ser Thr Asp Phe Trp Ser Gln Arg
                180                 185                 190

Tyr Tyr Glu Trp Glu Glu Ile Cys Leu Pro Gly Lys Thr Pro Thr Phe
                195                 200                 205

Ala Asn Pro Met Gln Gln Leu Asp Tyr Lys Ala Phe Met Asp Asp Ser
    210                 215                 220

Leu Leu Ala Leu Tyr Lys Met Glu Arg Asp Ile Leu Lys Thr Tyr Thr
225                 230                 235                 240

Pro Asp Val Pro Val Met Thr Asn Leu Met Gly Leu His Lys Pro Val
                245                 250                 255

Asp Gly Phe His Trp Ala Lys Glu Met Asp Leu Val Thr Trp Asp Ala
                260                 265                 270

Tyr Pro Asp Pro Phe Glu Asp Ile Pro Tyr Ala Gln Phe Met Ala His
    275                 280                 285

Asp Leu Thr Arg Ser Leu Lys Lys Gln Pro Phe Leu Leu Met Glu Gln
    290                 295                 300

Ala Ala Gly Ala Val Asn Trp Arg Ala Gln Asn Ala Val Lys Ala Pro
305                 310                 315                 320

Gly Val Met Arg Leu Trp Ser Tyr Glu Ala Ala Ala His Gly Ala Asp
                325                 330                 335

Gly Ile Met Phe Phe Gln Trp Arg Ala Ser Gln Gly Gly Ala Glu Lys
                340                 345                 350

Phe His Ser Gly Met Val Pro His Ser Gly Asp Glu Glu Ser Arg Asn
                355                 360                 365

Phe Arg Glu Val Val Gln Leu Gly Asn Glu Leu Lys Asn Leu Glu Lys
    370                 375                 380

Val Thr Gly Ser Ala Tyr Ala Ser Asp Val Ala Ile Val Phe Asp Trp
385                 390                 395                 400

Lys Asn Trp Trp Ala Leu Glu Leu Asp Ser Lys Pro Ser Ser Leu Val
                405                 410                 415

Thr Tyr Ile Lys Gln Leu Leu Pro Phe Tyr Arg Val Leu His Thr Gln
                420                 425                 430

Asn Ile Gly Val Asp Phe Ile His Pro Asp Glu Ala Met Asp Arg Tyr
                435                 440                 445

Lys Val Val Phe Ala Pro Ala Ser Tyr Arg Val Thr Lys Thr Phe Ala
    450                 455                 460

Asp Lys Val Lys Ala Tyr Val Glu Asn Gly Gly Tyr Phe Ala Thr Asn
465                 470                 475                 480

Phe Phe Ser Gly Ile Ala Asp Glu Asn Glu Arg Val Tyr Leu Gly Gly
                485                 490                 495

Tyr Pro Gly Ala Tyr Arg Asp Ile Leu Gly Ile Tyr Val Glu Glu Phe
                500                 505                 510

Ala Pro Met Lys Lys Gly Ala Val His Gln Ile Arg Thr Gly Tyr Gly
                515                 520                 525

Asp Ala Ala Ile Arg Val Trp Glu Glu Lys Ile His Leu Lys Gly Ala
    530                 535                 540

Glu Ala Leu Ala Trp Phe Lys Asp Gly Tyr Leu Ala Gly Ser Pro Ala
```

-continued

```
            545                 550                 555                 560

Val Thr Ala His His Cys Gly Lys Gly Lys Ala Tyr Tyr Ile Gly Thr
                565                 570                 575

Gln Pro Asp Glu Gln Tyr Leu Ser Ser Leu Leu Lys Glu Ile Leu Lys
            580                 585                 590

Glu Ala Asp Val Arg Pro Ala Leu Asp Ala Pro Arg Gly Val Glu Val
            595                 600                 605

Ala Val Arg Lys Asn Gly His Glu Lys Phe Leu Phe Leu Leu Asn His
        610                 615                 620

Thr Asp Gln Val Gln Phe Val Asp Ala Gly Gly Thr Tyr Pro Glu Leu
625                 630                 635                 640

Ile Tyr Gly Arg Thr Glu Ala Glu Thr Val Arg Leu Ser Pro Arg Asp
                645                 650                 655

Val Lys Ile Leu Gln Val Ile Glu Lys
            660                 665
```

<210> SEQ ID NO 79
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
atgtactatt taaaaaacac aaactttigg atgttcggtt tattcttttt cttttacttt      60
tttatcatgg gagcctactt cccgtttttc ccgatttggc tacatgacat caaccatatc     120
agcaaaagtg atacgggtat tattttigcc gctatttctc tgttctcgct attattccaa     180
ccgctgtttg gtctgctttc tgacaaactc gggctgcgca aatacctgct gtggattatt     240
accggcatgt tagtgatgtt tgcgccgttc tttattttta tcttcgggcc actgttacaa     300
tacaacattt tagtaggatc gattgttggt ggtatttatc taggcttttg ttttaacgcc     360
ggtgcgccag cagtagaggc atttattgag aaagtcagcc gtcgcagtaa tttcgaattt     420
ggtcgcgcgc ggatgtttgg ctgtgttggc tgggcgctgt gtgcctcgat tgtcggcatc     480
atgttcacca tcaataatca gtttgttttc tggctgggct ctggctgtgc actcatcctc     540
gccgttttac tcttttttcgc caaaacggat gcgccctctt ctgccacggt tgccaatgcg     600
gtaggtgcca accattcggc atttagcctt aagctggcac tggaactgtt cagacagcca     660
aaactgtggt ttttgtcact gtatgttatt ggcgtttcct gcacctacga tgtttttgac     720
caacagtttg ctaatttctt tacttcgttc tttgctaccg gtaacagggt acgcgggta     780 tttggctacg taacgacaat gggcgaatta cttaacgcct cgattatgtt ctttgcgcca     840
ctgatcatta atcgcatcgg tgggaaaaac gccctgctgc tggctggcac tattatgtct     900
gtacgtatta ttggctcatc gttcgccacc tcagcgctgg aagtggttat tctgaaaacg     960
ctgcatatgt ttgaagtacc gttcctgctg gtgggctgct ttaaatatat taccagccag    1020
tttgaagtgc gttttttcagc gacgattat ctggtctgtt tctgcttctt taagcaactg    1080
gcgatgattt ttatgtctgt actggcgggc aatatgtatg aaagcatcgg tttccagggc    1140
gcttatctgg tgctgggtct ggtggcgctg ggcttcacct taatttccgt gttcacgctt    1200
agcggccccg gccgcttttc cctgctgcgt cgtcaggtga atgaagtcgc ttaa          1254
```

<210> SEQ ID NO 80
<211> LENGTH: 417

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn His Ile Ser Lys Ser Asp Thr Gly Ile Ile
        35                  40                  45

Phe Ala Ala Ile Ser Leu Phe Ser Leu Leu Phe Gln Pro Leu Phe Gly
    50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
            85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Phe Gly Arg Ala Arg
    130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
            165                 170                 175

Ala Leu Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
        195                 200                 205

Ser Leu Lys Leu Ala Leu Glu Leu Phe Arg Gln Pro Lys Leu Trp Phe
    210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
            245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Ile Asn Arg Ile Gly Gly
        275                 280                 285

Lys Asn Ala Leu Leu Leu Ala Gly Thr Ile Met Ser Val Arg Ile Ile
    290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
            325                 330                 335

Ile Thr Ser Gln Phe Glu Val Arg Phe Ser Ala Thr Ile Tyr Leu Val
            340                 345                 350

Cys Phe Cys Phe Phe Lys Gln Leu Ala Met Ile Phe Met Ser Val Leu
        355                 360                 365

Ala Gly Asn Met Tyr Glu Ser Ile Gly Phe Gln Gly Ala Tyr Leu Val
    370                 375                 380
```

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala

<210> SEQ ID NO 81
<211> LENGTH: 1239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
atgaaaagta gtaagtcact ctactggaag ctttctgcgt atttcttctt tttcttcttt          60
acctggagct ctagttactc tctgttttcc atttggttgg gacaggagat aaagctgaat         120
ggctcagcca cggggctcat atttagtgtc aacgccatat tcgctctttg tatgcaacca         180
ttatacggat atatctccga cagaatcggc ctcaagaagc atattttatt ttttataagt         240
tgccttcttg tatttgttgg gccattctac atatttgtgt atgggccgtt attgcagtat         300
aatgtgctca taggtgccat tattggtggc ctgtacttgg gcgtggcatt tttggcagga         360
ataggcgcga tagaaacgta tattgagaag gtatctcgca agtacaagtt cgagtatgga         420
aagtctcgga tgtgggggag tcttggttgg ccgccgcga cgtttttttgc gggccaactt         480 ttcaatatca acccgcacat caattttttgg gtggccagcg tatccgctgt tatacttatg         540
gctataatct tctcagtaaa agttgaaatg agctcttatg aaatggagaa ggcagaatca         600
gtgcgtctcc gtgatgtagg taacttgttc ctcttaaagg aattctggtt tttcatgatc         660
tatgtcgtag gtgtaacatg tgtctatggg gtgtacgacc aacagttccc aatatactat         720
gcgtctttat tcccaaccga gtcaatcggt aatcaagtgt tcggttatct caatagtttc         780
caagtctttc tcgaggcagg gatgatgttc gccgcgccat ttattgttaa caaaataggc         840
gcgaagaatt ccttaatcct ggctggtttc ctcatgggct ttagaattat tggttccggg         900
ttggttgtgg gtcctatagg aatcagttct atgaagctta tacacgcgct tgaacttcct         960
ataatgctca tagccatttt taagtacctc gccgcgaatt ttgatacaag attatcatct        1020
attttgtacc tggttggctt ccaatttgcc agtcagattg gcgcctctgt cctctcccct        1080
atcgccggtg gcttgtatga ctcagtcgga tttagtcgca cttatctgat catgggtggg        1140
atggtacttg tttttaatgt tatttcaatg ttcacattgt tgaatagcaa aaagcataaa        1200
tttatccgga aggacgttca agaaaagact cagataatt                                1239

<210> SEQ ID NO 82
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Lys Ser Ser Lys Ser Leu Tyr Trp Lys Leu Ser Ala Tyr Phe Phe
1               5                   10                  15

Phe Phe Phe Phe Thr Trp Ser Ser Ser Tyr Ser Leu Phe Ser Ile Trp
                20                  25                  30

Leu Gly Gln Glu Ile Lys Leu Asn Gly Ser Ala Thr Gly Leu Ile Phe
        35                  40                  45

Ser Val Asn Ala Ile Phe Ala Leu Cys Met Gln Pro Leu Tyr Gly Tyr
        50                  55                  60

Ile Ser Asp Arg Ile Gly Leu Lys Lys His Ile Leu Phe Phe Ile Ser
65                  70                  75                  80

Cys Leu Leu Val Phe Val Gly Pro Phe Tyr Ile Phe Val Tyr Gly Pro
                85                  90                  95

Leu Leu Gln Tyr Asn Val Leu Ile Gly Ala Ile Ile Gly Gly Leu Tyr
                100                 105                 110

Leu Gly Val Ala Phe Leu Ala Gly Ile Gly Ala Ile Glu Thr Tyr Ile
                115                 120                 125

Glu Lys Val Ser Arg Lys Tyr Lys Phe Glu Tyr Gly Lys Ser Arg Met
        130                 135                 140

Trp Gly Ser Leu Gly Trp Ala Ala Ala Thr Phe Phe Ala Gly Gln Leu
145                 150                 155                 160

Phe Asn Ile Asn Pro His Ile Asn Phe Trp Val Ala Ser Val Ser Ala
                165                 170                 175

Val Ile Leu Met Ala Ile Ile Phe Ser Val Lys Val Glu Met Ser Ser
                180                 185                 190

Tyr Glu Met Glu Lys Ala Glu Ser Val Arg Leu Arg Asp Val Gly Asn
                195                 200                 205

Leu Phe Leu Leu Lys Glu Phe Trp Phe Phe Met Ile Tyr Val Val Gly
        210                 215                 220

Val Thr Cys Val Tyr Gly Val Tyr Asp Gln Gln Phe Pro Ile Tyr Tyr
225                 230                 235                 240

Ala Ser Leu Phe Pro Thr Glu Ser Ile Gly Asn Gln Val Phe Gly Tyr
                245                 250                 255

Leu Asn Ser Phe Gln Val Phe Leu Glu Ala Gly Met Met Phe Ala Ala
                260                 265                 270

Pro Phe Ile Val Asn Lys Ile Gly Ala Lys Asn Ser Leu Ile Leu Ala
        275                 280                 285

Gly Phe Leu Met Gly Phe Arg Ile Ile Gly Ser Gly Leu Val Val Gly
        290                 295                 300

Pro Ile Gly Ile Ser Ser Met Lys Leu Ile His Ala Leu Glu Leu Pro
305                 310                 315                 320

Ile Met Leu Ile Ala Ile Phe Lys Tyr Leu Ala Ala Asn Phe Asp Thr
                325                 330                 335

Arg Leu Ser Ser Ile Leu Tyr Leu Val Gly Phe Gln Phe Ala Ser Gln
        340                 345                 350

Ile Gly Ala Ser Val Leu Ser Pro Ile Ala Gly Gly Leu Tyr Asp Ser
        355                 360                 365

Val Gly Phe Ser Arg Thr Tyr Leu Ile Met Gly Gly Met Val Leu Val
        370                 375                 380

Phe Asn Val Ile Ser Met Phe Thr Leu Leu Asn Ser Lys Lys His Lys
385                 390                 395                 400

Phe Ile Arg Lys Asp Val Gln Glu Lys Thr Gln Ile Ile
                405                 410

<210> SEQ ID NO 83
<211> LENGTH: 1839
<212> TYPE: DNA
<213> ORGANISM: Artificial Sequence
<220> FEATURE:
<223> OTHER INFORMATION: Description of Artificial Sequence: Synthetic

```
       polynucleotide

<400> SEQUENCE: 83
atgaacatta agaagttcgc caagcaagca acggtgttaa cgtttacaac agcactgctg        60
gcaggcggag cgacacaggc ttttgcattg atgaaaagat tgttcgcggc ctcattaatg       120
ctcgcgttct cctctgtgtc gtccgttcgc gcggaagagg ccgtgaagcc gggagcacca       180
tggtggaaat ctgctgtgtt ttatcaggtg tacccgcggt ctttcaagga tacgaacggg       240
gatggaattg gagactttaa gggtctcacg gaaaagctgg attaccttaa ggggctgggc       300
attgacgcca tatggataaa ccctcattac gctagtccga acaccgataa tggttacgat       360
atctcagact atcgggaagt aatgaaagag tatggcacta tggaagactt tgaccggctt       420
atggcagaat tgaagaagag aggcatgagg ctgatggtgg acgtggtaat caaccactca       480
agcgatcagc acgaatggtt taagtcttct agggcatcca aagacaaccc ttaccgtgac       540
tactacttct ggcgcgacgg taaagatggc catgaaccga caattaccc gtcattcttc        600 ggcggatcgg cttgggagaa ggacccggta actggccagt attatcttca ctacttcggt       660
aggcagcaac cggatttgaa ctgggacaca cctaagttgc gtgaggagtt atacgcgatg       720
ctcagattct ggctggacaa aggtgtgtct ggcatgcgtt ttgacaccgt agcaacctac       780
tctaagacac cgggattccc ggatcttact cctgaacaga tgaagaattt tgcggaagca       840
tacactcagg gtcctaacct gcaccgatac ttacaagaaa tgcacgaaaa ggtctttgat       900
cactacgacg ctgtcacggc gggagagatc ttcggtgccc ctctcaacca agtaccgctt       960
ttcatcgaca gtcgccggaa ggaattagat atggccttca ctttcgactt aataagatac      1020
gatcgtgctc ttgacagatg gcacaccatt ccgaggacat tagctgattt ccgtcaaaca      1080
atcgataaag ttgacgcgat tgcaggcgag tacgggtgga acaccttctt cttaggaaac      1140
catgacaacc ctagagcagt gtcacatttc ggcgacgacc gcccacaatg gagagaggca      1200
agtgcgaagg cgctggctac cgtgacttta acacagcggg gaacaccgtt catcttccag      1260
ggagacgagc ttggaatgac caattaccca tttaagacac tgcaagactt tgatgacatc      1320
gaggttaagg gcttctttca agactacgtc gagactggta aggccacagc cgaggaatta      1380
ctgacaaacg tggccttgac tagtcgtgac aatgcgagaa cgcctttcca atgggatgac      1440
tcagctaacg ctggattcac aaccggcaag ccttggctca aggtcaatcc taactacaca      1500
gaaataaacg ctgcgcgcga gattgggggat cccaagtcag tctactcctt ctatcgcaac      1560
ctgatctcga tccgccatga gactcctgcc ctttcgaccg gatcgtatag agatatagac      1620
cccagtaatg cagatgtata cgcctatacg cgctcccaag acggagaaac ctacttggtg      1680
gtggtcaatt tcaaagccga gcctaggagt ttcaccttac cagacggtat gcatatcgcc      1740 gagacccta ttgagtcttc tagtccagct gcgcctgctg ccggtgcagc gagcttagag      1800
ttacaaccgt ggcaatcggg catctacaag gtgaagtag                             1839

<210> SEQ ID NO 84
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Asn Ile Lys Lys Phe Ala Lys Gln Ala Thr Val Leu Thr Phe Thr
1               5                   10                  15
```

```
Thr Ala Leu Leu Ala Gly Gly Ala Thr Gln Ala Phe Ala Leu Met Lys
         20                  25                  30

Arg Leu Phe Ala Ala Ser Leu Met Leu Ala Phe Ser Ser Val Ser Ser
         35                  40                  45

Val Arg Ala Glu Glu Ala Val Lys Pro Gly Ala Pro Trp Trp Lys Ser
         50                  55                  60

Ala Val Phe Tyr Gln Val Tyr Pro Arg Ser Phe Lys Asp Thr Asn Gly
65                  70                  75                  80

Asp Gly Ile Gly Asp Phe Lys Gly Leu Thr Glu Lys Leu Asp Tyr Leu
                 85                  90                  95

Lys Gly Leu Gly Ile Asp Ala Ile Trp Ile Asn Pro His Tyr Ala Ser
                 100                 105                 110

Pro Asn Thr Asp Asn Gly Tyr Asp Ile Ser Asp Tyr Arg Glu Val Met
         115                 120                 125

Lys Glu Tyr Gly Thr Met Glu Asp Phe Asp Arg Leu Met Ala Glu Leu
         130                 135                 140

Lys Lys Arg Gly Met Arg Leu Met Val Asp Val Val Ile Asn His Ser
145                 150                 155                 160

Ser Asp Gln His Glu Trp Phe Lys Ser Ser Arg Ala Ser Lys Asp Asn
                 165                 170                 175

Pro Tyr Arg Asp Tyr Tyr Phe Trp Arg Asp Gly Lys Asp Gly His Glu
                 180                 185                 190

Pro Asn Asn Tyr Pro Ser Phe Phe Gly Gly Ser Ala Trp Glu Lys Asp
         195                 200                 205

Pro Val Thr Gly Gln Tyr Tyr Leu His Tyr Phe Gly Arg Gln Gln Pro
         210                 215                 220

Asp Leu Asn Trp Asp Thr Pro Lys Leu Arg Glu Glu Leu Tyr Ala Met
225                 230                 235                 240

Leu Arg Phe Trp Leu Asp Lys Gly Val Ser Gly Met Arg Phe Asp Thr
                 245                 250                 255

Val Ala Thr Tyr Ser Lys Thr Pro Gly Phe Pro Asp Leu Thr Pro Glu
                 260                 265                 270

Gln Met Lys Asn Phe Ala Glu Ala Tyr Thr Gln Gly Pro Asn Leu His
         275                 280                 285

Arg Tyr Leu Gln Glu Met His Glu Lys Val Phe Asp His Tyr Asp Ala
         290                 295                 300

Val Thr Ala Gly Glu Ile Phe Gly Ala Pro Leu Asn Gln Val Pro Leu
305                 310                 315                 320

Phe Ile Asp Ser Arg Arg Lys Glu Leu Asp Met Ala Phe Thr Phe Asp
                 325                 330                 335

Leu Ile Arg Tyr Asp Arg Ala Leu Asp Arg Trp His Thr Ile Pro Arg
                 340                 345                 350

Thr Leu Ala Asp Phe Arg Gln Thr Ile Asp Lys Val Asp Ala Ile Ala
         355                 360                 365

Gly Glu Tyr Gly Trp Asn Thr Phe Phe Leu Gly Asn His Asp Asn Pro
         370                 375                 380

Arg Ala Val Ser His Phe Gly Asp Asp Arg Pro Gln Trp Arg Glu Ala
385                 390                 395                 400

Ser Ala Lys Ala Leu Ala Thr Val Thr Leu Thr Gln Arg Gly Thr Pro
                 405                 410                 415

Phe Ile Phe Gln Gly Asp Glu Leu Gly Met Thr Asn Tyr Pro Phe Lys
                 420                 425                 430
```

-continued

```
Thr Leu Gln Asp Phe Asp Asp Ile Glu Val Lys Gly Phe Phe Gln Asp
        435             440             445

Tyr Val Glu Thr Gly Lys Ala Thr Ala Glu Glu Leu Leu Thr Asn Val
        450             455             460

Ala Leu Thr Ser Arg Asp Asn Ala Arg Thr Pro Phe Gln Trp Asp Asp
465             470             475             480

Ser Ala Asn Ala Gly Phe Thr Thr Gly Lys Pro Trp Leu Lys Val Asn
                485             490             495

Pro Asn Tyr Thr Glu Ile Asn Ala Ala Arg Glu Ile Gly Asp Pro Lys
                500             505             510

Ser Val Tyr Ser Phe Tyr Arg Asn Leu Ile Ser Ile Arg His Glu Thr
        515             520             525

Pro Ala Leu Ser Thr Gly Ser Tyr Arg Asp Ile Asp Pro Ser Asn Ala
        530             535             540

Asp Val Tyr Ala Tyr Thr Arg Ser Gln Asp Gly Glu Thr Tyr Leu Val
545             550             555             560

Val Val Asn Phe Lys Ala Glu Pro Arg Ser Phe Thr Leu Pro Asp Gly
                565             570             575

Met His Ile Ala Glu Thr Leu Ile Glu Ser Ser Ser Pro Ala Ala Pro
                580             585             590

Ala Ala Gly Ala Ala Ser Leu Glu Leu Gln Pro Trp Gln Ser Gly Ile
        595             600             605

Tyr Lys Val Lys
        610
```

```
<210> SEQ ID NO 85
<211> LENGTH: 276
<212> TYPE: DNA
<213> ORGANISM: Bacillus subtilis

<400> SEQUENCE: 85
ggaattgacg ccccaaagca tattgatatt cacaggaaag aaatttactt gaccattcag        60
gaagaaaata accgtgcagc agcgttatcc agcgatgtga tctccgcatt atcctcacaa       120
aaaaagtgag gattttttta tttttgtatt aacaaaatca gagacaatcc gatattaatg       180
atgtagccgg gaggaggcgc aaaagactca gccagttaca aaataagggc acaaggacgt       240
gccttaacaa catattcagg gaggaacaaa acaatg                                  276
```

ENGINEERED PROBIOTICS FOR EXPRESSION OF FIBER-SYNTHESIZING ENZYMES IN GUT

PRIORITY APPLICATION

The present application claims the benefit of U.S. Provisional Patent Application No. 63/089,334, filed on Oct. 8, 2020, the content of which is hereby incorporated by reference herein in its entirety.

BACKGROUND

The microbiome is a complex collection of microbes that together impact many aspects of organismal health and function. For example, the microbiome can impact immunity, metabolism, and a variety of diseases. Microbes of the microbiome interact with host organisms through a variety of mechanisms, including microbial signaling, metabolite consumption, and small molecule production. Accordingly, the types and proportions of microbes and metabolites in the microbiome can have important impacts on health.

SUMMARY

Methods and compositions that modify the microbiome, e.g., by introducing new microbial functions or modifying existing microbial functions, can have important impacts on human health. The present disclosure provides solutions to various challenges in health and/or microbiome engineering. For example, the present disclosure recognizes that one challenge in human health is that many individuals consume daily diets that include carbohydrate such as monosaccharides and/or disaccharides, e.g., in excess of individual metabolic need. These consumed monosaccharides and/or disaccharides can have deleterious health effects in the gut (e.g., on the microbiome) and/or after digestion. To provide another example of a challenge in human health recognized by the present disclosure, many individuals consume daily diets that include too little fiber. Low consumption of fiber and/or low levels of gut fiber can have various deleterious health effects. The present disclosure provides solutions that simultaneously addresses harm caused by consumption of carbohydrates and harm caused by non-consumption of fiber.

The present disclosure provides, among other things, bacteria engineered for expression of a fiber-synthesizing enzyme, e.g., for expression of the enzyme in the gut (e.g., in intestine, e.g., in the small intestine and/or large intestine). In particular embodiments, the present disclosure provides bacteria engineered for expression of a fiber-synthesizing enzyme that consumes carbohydrate in the process of synthesizing fiber, e.g., in the gut. Those of skill in the art will appreciate that all references to gut herein include at least one or both of the small intestine and/or large intestine, as do references to intestine herein.

The present disclosure further provides, among other things, formulations for oral delivery of fiber-synthesizing enzymes, e.g., for delivery of fiber-synthesizing enzyme to gut (e.g., to intestine, e.g., to small intestine and/or large intestine). In various embodiments, the present disclosure provides a pill or sachet including isolated fiber-synthesizing enzyme.

In at least certain aspects, the present disclosure provides a method of decreasing the amount or concentration of a carbohydrate in the gut of a subject comprising administering to the subject a bacterium engineered to express a heterologous nucleic acid sequence encoding a fiber-synthesizing enzyme, wherein the fiber-synthesizing enzyme synthesizes fiber from a carbohydrate substrate.

In at least certain aspects, the present disclosure provides a method of increasing the amount or concentration of a fiber in the gut of a subject comprising administering to the subject a bacterium engineered to express a heterologous nucleic acid sequence encoding a fiber-synthesizing enzyme, wherein the fiber-synthesizing enzyme synthesizes fiber from a carbohydrate substrate.

In at least certain aspects, the present disclosure provides a method of treating a subject in need of decreased amount or concentration of a carbohydrate in the gut or increased amount or concentration of a fiber in the gut comprising administering to the subject a bacterium engineered to express a heterologous nucleic acid sequence encoding a fiber-synthesizing enzyme, wherein the fiber-synthesizing enzyme synthesizes fiber from a carbohydrate substrate.

In various embodiments, the subject is suffering from a condition positively correlated or associated with consumption of carbohydrate. In various embodiments, the subject is suffering from a condition negatively correlated or associated with consumption of fiber. In various embodiments, the subject is suffering from a condition selected from cardiovascular disease, heart disease, high blood pressure, high blood cholesterol, high blood glucose, diabetes, obesity, dysbiosis of the gut, inflammatory bowel disease, irritable bowel syndrome (IBS), diverticulitis, colorectal cancer, intestinal cancer, bloating, cramping, gas, hemorrhoids, and diarrhea.

In various embodiments, the fiber is a soluble fiber. In various embodiments, the synthesized fiber comprises glucose, fructose, galacturonic acid, N-acetyl-D-glucosamine, and/or galactose monomers. In various embodiments, the carbohydrate substrate is selected from one or more of UDP-glucose, UDP-galactose, UDP-fucose, ADP-$\alpha$-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose. In various embodiments, the synthesized fiber is a fructooligosaccharide and/or is selected from laminaribiose, callose, curdlan, oat beta-glucan, laminarin, pleuran, lentinan, yeast beta glucan, trehalulose, trehalose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin. In various embodiments, the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, a trehalose-6-phosphate synthase, an $\alpha$-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyltransferase, and a chitinoligosaccharide synthase. In various embodiments, the fiber-synthesizing enzyme is operatively linked with a secretion polypeptide.

In various embodiments, the bacterium is a spore-forming bacterium and/or is in a spore form. In various embodiments, the bacterium is a probiotic bacterium. In various embodiments, the bacterium is of a genus selected from *Bacillus, Bifidobacterium, Enterococcus, Escherichia, Lactobacillus, Lactococcus, Leuconostoc, Pediococcus,* and

*Streptococcus*, optionally wherein the bacterium is of the genus *Bacillus*, optionally wherein the bacterium is of the species *B. subtilis*. In various embodiments, the bacterium is of a strain characterized in that it does not colonize the gut.

In various embodiments, the method comprises administering the engineered bacterium to a subject that has consumed carbohydrate and/or the carbohydrate substrate within a preceding period, wherein the preceding period is a period of 24 hours 12 hours, 6 hours, 3 hours, or 1 hour. In various embodiments, the method comprises administering the engineered bacterium to a subject that has not consumed carbohydrate and/or the carbohydrate substrate. In various embodiments, the method comprises administering the engineered bacterium to a subject that has not consumed carbohydrate and/or the carbohydrate substrate within a preceding period, wherein the preceding period is a period of 24 hours 12 hours, 6 hours, 3 hours, or 1 hour. In various embodiments, the subject consumes carbohydrate and/or the carbohydrate substrate during a period subsequent to administration of the engineered bacterium, wherein the subsequent period is a period of 24 hours 12 hours, 6 hours, 3 hours, or 1 hour.

In various embodiments, the method prevents accumulation of sugar in the colon of the subject. In various embodiments, fiber-synthesizing enzymes and/or enzymes encoded by heterologous nucleic acid sequences comprised by the engineered bacterium consist of the fiber-synthesizing enzyme.

In various embodiments, the administration comprises oral administration of a composition comprising the engineered bacterium. In various embodiments, the administration comprises administration of about $10^4$ to about $10^{12}$ colony forming units of the engineered bacterium.

In various embodiments, the nucleic acid sequence encoding the expression product is operatively linked with a constitutive promoter. In various embodiments, the nucleic acid sequence encoding the expression product is operatively linked with a flagellin gene promoter. In various embodiments, the flagellin gene promoter comprises a mutation in a CsrA binding site, wherein the mutation in the CsrA binding site inhibits binding of CsrA to mRNA transcripts encoding the fiber-synthesizing enzyme but does not preclude expression of the fiber-synthesizing enzyme. In various embodiments, the engineered bacterium comprises a mutation of an endogenous flgM gene that reduces inhibition of a sigma factor by FlgM. In various embodiments, the flagellin gene promoter is a *B. subtilis* hag promoter. In various embodiments, the mutation in the CsrA binding site is a mutation in a *B. subtilis* hag promoter CsrA binding site selected from binding site 1 (BS1) and binding site 2 (BS2). In various embodiments, the mutation in the CsrA binding site is a mutation in the stem of the stem-loop secondary structure of BS1 or in the stem of the stem-loop secondary structure of BS2. In various embodiments, the mutation in the CsrA binding site is a mutation in the CsrA BS1 recognition sequence having the sequence AGGA. In various embodiments, the mutation in the CsrA binding site is a BS1 mutation according to SEQ ID NO: 29 or a BS2 mutation according to SEQ ID NO: 30. In various embodiments, the mutation in the CsrA binding site does not disrupt the Shine-Dalgarno sequence of the *B. subtilis* hag promoter. In various embodiments, the mutation of the endogenous flgM gene comprises deletion of all or a portion of the flgM gene. In various embodiments, the mutation of the endogenous flgM gene comprises a mutation in the sequence encoding the active site of flgM. In various embodiments, the mutation of the endogenous flgM gene comprises a mutation in the sequence encoding an amino acid that participates in binding of FlgM to SigD. In various embodiments, the mutation of the endogenous flgM gene alters a sequence that encodes an amino acid in the $3^{rd}$ helix or $4^{th}$ helix of FlgM at the C-terminal end of the FlgM protein. In various embodiments, the bacterium is of the species *B. subtilis* and the mutation of the endogenous flgM gene alters the amino acid sequence encoded by SEQ ID NO: 31 at an amino acid selected from I-58, K-62, I-65, G-68, D-73, and A-78. In various embodiments, the bacterium is of the species *B. subtilis* and the mutation of the endogenous flgM gene alters the amino acid sequence encoded by SEQ ID NO: 31 at an amino acid selected from I-3, G-7, S-10, V-11, A-40, K-41, M43, I-58, L-61, K-62, I-65, Y-70, K-71, V-72, D-73, A-74, H-76, I-77, A-78, N-80, M-81, I-82, N-83, F-84, Y-85, and K-86. In various embodiments, the mutation of the endogenous flgM gene reduces or eliminates FlgM biological activity. In various embodiments, the sigma factor is SigD.

In at least certain aspects, the present disclosure provides a bacterium engineered to express a heterologous nucleic acid sequence encoding a fiber-synthesizing enzyme, wherein the fiber-synthesizing enzyme synthesizes fiber from a carbohydrate substrate. In various embodiments, the fiber is a soluble fiber. In various embodiments, the synthesized fiber comprises glucose, fructose, galacturonic acid, N-acetyl-D-glucosamine, and/or galactose monomers. In various embodiments, the carbohydrate substrate is selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose. In various embodiments, the synthesized fiber is a fructooligosaccharide and/or is selected from laminaribiose, callose, curdlan, oat beta-glucan, laminarin, pleuran, lentinan, yeast beta glucan, trehalulose, trehalose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin. In various embodiments, the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, a trehalose-6-phosphate synthase, an α-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyltransferase, and a chitinoligosaccharide synthase. In various embodiments, the fiber-synthesizing enzyme is operatively linked with a secretion polypeptide. In various embodiments, the bacterium is a spore-forming bacterium and/or is in a spore form. In various embodiments, the bacterium is a probiotic bacterium. In various embodiments, the bacterium is of a genus selected from *Bacillus, Bifidobacterium, Enterococcus, Escherichia, Lactobacillus, Lactococcus, Leuconostoc, Pediococcus*, and *Streptococcus*, optionally wherein the bacterium is of the genus *Bacillus*, optionally wherein the bacterium is of the species *B. subtilis*. In various embodiments, the bacterium is of a strain characterized in that it does not colonize the gut. In various embodiments, fiber-synthesizing enzymes and/or enzymes encoded by heterologous nucleic acid sequences comprised by the engineered bacterium consist of the fiber-synthesizing enzyme.

In various embodiments, the nucleic acid sequence encoding the expression product is operatively linked with a constitutive promoter. In various embodiments, the nucleic acid sequence encoding the expression product is operatively linked with a flagellin gene promoter. In various embodiments, the flagellin gene promoter comprises a mutation in a CsrA binding site, wherein the mutation in the CsrA binding site inhibits binding of CsrA to mRNA transcripts encoding the fiber-synthesizing enzyme but does not preclude expression of the fiber-synthesizing enzyme. In various embodiments, the engineered bacterium comprises a mutation of an endogenous flgM gene that reduces inhibition of a sigma factor by FlgM. In various embodiments, the flagellin gene promoter is a B. subtilis hag promoter. In various embodiments, the mutation in the CsrA binding site is a mutation in a B. subtilis hag promoter CsrA binding site selected from binding site 1 (BS1) and binding site 2 (BS2). In various embodiments, the mutation in the CsrA binding site is a mutation in the stem of the stem-loop secondary structure of BS1 or in the stem of the stem-loop secondary structure of BS2. In various embodiments, the mutation in the CsrA binding site is a mutation in the CsrA BS1 recognition sequence having the sequence AGGA. In various embodiments, the mutation in the CsrA binding site is a BS1 mutation according to SEQ ID NO: 29 or a BS2 mutation according to SEQ ID NO: 30. In various embodiments, the mutation in the CsrA binding site does not disrupt the Shine-Dalgarno sequence of the B. subtilis hag promoter. In various embodiments, the mutation of the endogenous flgM gene comprises deletion of all or a portion of the flgM gene. In various embodiments, the mutation of the endogenous flgM gene comprises a mutation in the sequence encoding the active site of flgM. In various embodiments, the mutation of the endogenous flgM gene comprises a mutation in the sequence encoding an amino acid that participates in binding of FlgM to SigD. In various embodiments, the mutation of the endogenous flgM gene alters a sequence that encodes an amino acid in the $3^{rd}$ helix or $4^{th}$ helix of FlgM at the C-terminal end of the FlgM protein. In various embodiments, the bacterium is of the species B. subtilis and the mutation of the endogenous flgM gene alters the amino acid sequence encoded by SEQ ID NO: 31 at an amino acid selected from I-58, K-62, I-65, G-68, D-73, and A-78. In various embodiments, the bacterium is of the species B. subtilis and the mutation of the endogenous flgM gene alters the amino acid sequence encoded by SEQ ID NO: 31 at an amino acid selected from I-3, G-7, S-10, V-11, A-40, K-41, M43, I-58, L-61, K-62, I-65, Y-70, K-71, V-72, D-73, A-74, H-76, I-77, A-78, N-80, M-81, I-82, N-83, F-84, Y-85, and K-86. In various embodiments, the mutation of the endogenous flgM gene reduces or eliminates FlgM biological activity. In various embodiments, the sigma factor is SigD.

In at least certain aspects, the present disclosure provides a composition comprising the engineered bacterium of the present disclosure. In certain embodiments, the composition is formulated for oral administration. In some embodiments, the formulation comprises about $10^4$ to about $10^{12}$ colony forming units of the engineered bacterium. In various embodiments, the composition comprises a physiologically acceptable carrier. In various embodiments, the physiologically acceptable carrier is selected from a lactic acid fermented food, fermented dairy product, resistant starch, dietary fiber, carbohydrate, protein, glycosylated protein, water, capsule filler, and gummy material.

In at least certain aspects, the present disclosure provides a bacterial cell culture comprising the engineered bacterium of the present disclosure.

In at least certain aspects, the present disclosure provides a method of decreasing the amount or concentration of a carbohydrate in the gut of a subject comprising administering to the subject a composition comprising a fiber-synthesizing enzyme, wherein the fiber-synthesizing enzyme synthesizes fiber from a carbohydrate substrate. In various embodiments, the fiber synthesizing enzyme is an isolated fiber-synthesizing enzyme.

In at least certain aspects, the present disclosure provides a method of increasing the amount or concentration of a fiber in the gut of a subject comprising administering to the subject a composition comprising a fiber-synthesizing enzyme, wherein the fiber-synthesizing enzyme synthesizes fiber from a carbohydrate substrate. In various embodiments, the fiber synthesizing enzyme is an isolated fiber-synthesizing enzyme.

In at least certain aspects, the present disclosure provides a method of treating a subject in need of decreased amount or concentration of a carbohydrate in the gut or increased amount or concentration of a fiber in the gut comprising administering to the subject a composition comprising a fiber-synthesizing enzyme, wherein the fiber-synthesizing enzyme synthesizes fiber from a carbohydrate substrate. In various embodiments, the fiber synthesizing enzyme is an isolated fiber-synthesizing enzyme.

In various embodiments, the subject is suffering from a condition positively correlated or associated with consumption of carbohydrate. In various embodiments, the subject is suffering from a condition negatively correlated or associated with consumption of fiber. In various embodiments, the subject is suffering from a condition selected from cardiovascular disease, heart disease, high blood pressure, high blood cholesterol, high blood glucose, diabetes, obesity, dysbiosis of the gut, inflammatory bowel disease, irritable bowel syndrome (IBS), diverticulitis, colorectal cancer, intestinal cancer, bloating, cramping, gas, hemorrhoids, and diarrhea.

In various embodiments, the fiber is a soluble fiber. In various embodiments, the synthesized fiber comprises glucose, fructose, galacturonic acid, N-acetyl-D-glucosamine, and/or galactose monomers. In various embodiments, the carbohydrate substrate is selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose. In various embodiments, the synthesized fiber is a fructooligosaccharide and/or is selected from laminaribiose, callose, curdlan, oat beta-glucan, laminarin, pleuran, lentinan, yeast beta glucan, trehalulose, trehalose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin. In various embodiments, the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, a trehalose-6-phosphate synthase, an α-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyl-transferase, and a chitinoligosaccharide synthase.

In various embodiments, the method comprises administering the composition to a subject that has consumed carbohydrate and/or the carbohydrate substrate within a preceding period, wherein the preceding period is a period of 24 hours 12 hours, 6 hours, 3 hours, or 1 hour. In various embodiments, the method comprises administering the composition to a subject that has not consumed carbohydrate and/or the carbohydrate substrate. In various embodiments, the method comprises administering the composition to a subject that has not consumed carbohydrate and/or the carbohydrate substrate within a preceding period, wherein the preceding period is a period of 24 hours 12 hours, 6 hours, 3 hours, or 1 hour. In various embodiments, the subject consumes carbohydrate and/or the carbohydrate substrate during a period subsequent to administration of the composition, wherein the subsequent period is a period of 24 hours 12 hours, 6 hours, 3 hours, or 1 hour.

In various embodiments, the method prevents accumulation of sugar in the colon of the subject. In various embodiments, fiber-synthesizing enzymes comprising the composition and/or enzymes comprising the composition consist of the fiber-synthesizing enzyme. In various embodiments, the administration comprises oral administration of the composition.

In at least certain aspects, the present disclosure provides a composition comprising a fiber synthesizing enzyme, where the fiber-synthesizing enzyme synthesizes fiber from a carbohydrate substrate and the composition is formulated for oral administration. In various embodiments, the fiber is a soluble fiber. In various embodiments, the synthesized fiber comprises glucose, fructose, galacturonic acid, N-acetyl-D-glucosamine, and/or galactose monomers. In various embodiments, the carbohydrate substrate is selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose. In various embodiments, the synthesized fiber is a fructooligosaccharide and/or is selected from laminaribiose, callose, curdlan, oat beta-glucan, laminarin, pleuran, lentinan, yeast beta glucan, trehalulose, trehalose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin. In various embodiments, the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, a trehalose-6-phosphate synthase, an α-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyl-transferase, and a chitinoligosaccharide synthase. In various embodiments, fiber-synthesizing enzymes comprising the composition and/or enzymes comprising the composition consist of the fiber-synthesizing enzyme. In various embodiments, the composition comprises a physiologically acceptable carrier. In various embodiments, the physiologically acceptable carrier is selected from a lactic acid fermented food, fermented dairy product, resistant starch, dietary fiber, carbohydrate, protein, glycosylated protein, water, capsule filler, and gummy material.

Definitions

A, An, The: As used herein, "a", "an", and "the" refer to one or to more than one (i.e., to at least one) of the grammatical object of the article. By way of example, "an element" discloses embodiments of exactly one element and embodiments including more than one element.

About: As used herein, term "about", when used in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referenced value.

Administration: As used herein, the term "administration" typically refers to administration of a composition to a subject or system to achieve delivery of an agent that is, or is included in, the composition.

Associated with: Two events or entities are "associated" with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Between or From: As used herein, the term "between" refers to content that falls between indicated upper and lower, or first and second, boundaries, inclusive of the boundaries. Similarly, the term "from", when used in the context of a range of values, indicates that the range includes content that falls between indicated upper and lower, or first and second, boundaries, inclusive of the boundaries.

Binding: As used herein, the term "binding" refers to a non-covalent association between or among two or more agents. "Direct" binding involves physical contact between agents; indirect binding involves physical interaction by way of physical contact with one or more intermediate agents. Binding between two or more agents can occur and/or be assessed in any of a variety of contexts, including where interacting agents are studied in isolation or in the context of more complex systems (e.g., while covalently or otherwise associated with a carrier agents and/or in a biological system or cell).

Control expression or activity: As used herein, a first element (e.g., a protein, such as a transcription factor, or a nucleic acid sequence, such as promoter) "controls" or "drives" expression or activity of a second element (e.g., a protein or a nucleic acid encoding an agent such as a protein) if the expression or activity of the second element is wholly or partially dependent upon status (e.g., presence, absence, conformation, chemical modification, interaction, or other activity) of the first under at least one set of conditions. Control of expression or activity can be substantial control or activity, e.g., in that a change in status of the first element can, under at least one set of conditions, result in a change in expression or activity of the second element of at least 10% (e.g., at least 20%, 30%, 40%, 50%, 60%, 70%, 80%, 90%, 100%, 2-fold, 3-fold, 4-fold, 5-fold, 10-fold, 20-fold, 30-fold, 40-fold, 50-fold, 100-fold) as compared to a reference control.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of skill in the art appreciate that residues in a provided polypeptide or polynucleotide sequence are often designated (e.g., numbered or labeled) according to the scheme of a related reference sequence (even if, e.g., such designation does not reflect literal numbering of the provided sequence). By way of illustration, if a reference sequence includes a particular amino acid motif at positions 100-110, and a second related sequence includes the same motif at positions 110-120, the motif positions of the second related sequence can be said to "correspond to" positions 100-110 of the reference sequence. Those of skill in the art appreciate that corresponding positions can be readily identified, e.g., by alignment of sequences, and that such alignment is commonly accomplished by any of a variety of known tools, strategies, and/or algorithms, including without limitation software programs such as, for example, BLAST, CS-BLAST, CUDASW++, DIAMOND, FASTA, GGSEARCH/GL-SEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE.

Dosage form or unit dosage form: Those skilled in the art will appreciate that the term "dosage form" may be used to refer to a physically discrete unit of an agent (e.g., a therapeutic or diagnostic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total or free amount of a therapeutic composition or agent administered to a particular subject is determined by one or more attending physicians and may involve administration of multiple dosage forms.

Dosing regimen: As used herein, the term "dosing regimen" can refer to a set of one or more same or different unit doses administered to a subject, typically including a plurality of unit doses administration of each of which is separated from administration of the others by a period of time. In various embodiments, one or more or all unit doses of a dosing regimen may be the same or can vary (e.g., increase over time, decrease over time, or be adjusted in accordance with the subject and/or with a medical practitioner's determination). In various embodiments, one or more or all of the periods of time between each dose may be the same or can vary (e.g., increase over time, decrease over time, or be adjusted in accordance with the subject and/or with a medical practitioner's determination). In some embodiments, a given therapeutic agent has a recommended dosing regimen, which can involve one or more doses. Typically, at least one recommended dosing regimen of a marketed drug is known to those of skill in the art. In some embodiments, a dosing regimen is correlated with a desired or beneficial outcome when administered across a relevant population (i.e., is a therapeutic dosing regimen).

Engineered: As used herein, the term "engineered" refers to the aspect of having been manipulated by the hand of man. For example, a polynucleotide is considered to be "engineered" when two or more sequences, that are not linked together in that order in nature, are manipulated by the hand of man to be linked to one another in the engineered polynucleotide. Those of skill in the art will appreciate that an "engineered" nucleic acid or amino acid sequence can be a recombinant nucleic acid or amino acid sequence. In some embodiments, an engineered polynucleotide includes a coding sequence and/or a regulatory sequence that is found in nature operably linked with a first sequence but is not found in nature operably linked with a second sequence, which is in the engineered polynucleotide and operably linked in with the second sequence by the hand of man. In some embodiments, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution, deletion, or mating). As is common practice and is understood by those of skill in the art, progeny or copies, perfect or imperfect, of an engineered polynucleotide or cell are typically still referred to as "engineered" even though the direct manipulation was of a prior entity.

Excipient: As used herein, "excipient" refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

Expression: As used herein, "expression" refers individually and/or cumulatively to one or more biological process that result in production from a nucleic acid sequence of an encoded agent, such as a polypeptide. Expression specifically includes either or both of transcription and translation.

Fragment: As used herein, "fragment" refers a structure that is or includes a discrete portion of a reference agent (sometimes referred to as the "parent" agent). In some embodiments, a fragment lacks one or more moieties found in the reference agent. In some embodiments, a fragment is or includes one or more moieties found in the reference agent. In some embodiments, the reference agent is a polymer such as a polynucleotide or polypeptide. In some embodiments, a fragment of a polymer is or includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) of the reference polymer. In some embodiments, a fragment of a polymer is or includes at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the reference polymer. A fragment of a reference polymer is not necessarily identical to a corresponding portion of the reference polymer. For example, a fragment of a reference polymer can be a polymer having a sequence of residues having at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more identity to the reference polymer. A fragment may, or may not, be generated by physical fragmentation of a reference agent. In some instances a fragment is generated by physical fragmentation of a reference agent. In some instances, a fragment is not generated by physical fragmentation of a reference agent and can be instead, for example, produced by de novo synthesis or other means.

Gene or Transgene: As used herein, the term "gene" refers to a DNA sequence that is or includes coding sequence (i.e., a DNA sequence that encodes an expression product, such as an RNA product and/or a polypeptide product), optionally together with some or all of regulatory sequences that control expression of the coding sequence. In some embodiments, a gene includes non-coding sequence such as, without limitation, introns. In some embodiments, a gene may include both coding (e.g., exonic) and non-coding (e.g., intronic) sequences. In some embodiments, a gene includes a regulatory sequence that is a promoter. In some embodiments, a gene includes one or both of a (i) DNA nucleotides extending a predetermined number of nucleotides upstream of the coding sequence in a reference context, such as a source genome, and (ii) DNA nucleotides extending a predetermined number of nucleotides downstream of the coding sequence in a reference context, such as a source genome. In various embodiments, the predetermined number of nucleotides can be 500 bp, 1 kb, 2 kb, 3 kb, 4 kb, 5 kb, 10 kb, 20 kb, 30 kb, 40 kb, 50 kb, 75 kb, or 100 kb. As used herein, a "transgene" refers to a gene that is not endogenous or native to a reference context in which the gene is present or into which the gene may be placed by engineering.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Heterologous: As used herein, a first nucleic acid sequence is "heterologous" to a second nucleic acid sequence if the first nucleic acid sequence is not operatively linked with the second nucleic acid sequence in nature. By extension, a polypeptide is "heterologous" to an expression control sequence if it is encoded by nucleic acid sequence heterologous the promoter.

Identity: As used herein, the term "identity" refers to the overall relatedness between polymeric molecules, e.g., between nucleic acid molecules (e.g., DNA molecules and/ or RNA molecules) and/or between polypeptide molecules. Methods for the calculation of a percent identity as between two provided sequences are known in the art. Calculation of the percent identity of two nucleic acid or polypeptide sequences, for example, can be performed by aligning the two sequences (or the complement of one or both sequences) for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. The comparison of sequences and determination of percent identity between two sequences can be accomplished using a computational algorithm, such as BLAST (basic local alignment search tool).

"Improve," "increase," "inhibit," or "reduce": As used herein, the terms "improve", "increase", "inhibit", and "reduce", and grammatical equivalents thereof, indicate qualitative or quantitative difference from a reference.

Isolated: As used herein, "isolated" or "purified" can refer to a substance and/or entity that has been (a) separated from at least some of the components with which it was associated when initially produced (whether in nature and/or in an experimental setting), and/or (b) designed, produced, prepared, and/or manufactured by the hand of man. Isolated substances and/or entities may be separated from at least about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated substances and/ or entities are at least about 80%, about 85%, about 90%, about 91%, about 92%, about 93%, about 94%, about 95%, about 96%, about 97%, about 98%, about 99%, or more than about 99% pure. As used herein, a substance and/or entity is "pure" if it is substantially free of other components. In some embodiments, as will be understood by those skilled in the art, a substance and/or entity may still be considered "isolated" or "pure" after having been combined with certain other components such as, for example, one or more carriers or excipients (e.g., buffer, solvent, water, etc.); in such embodiments, percent isolation or purity of the substance and/or entity is calculated without including such carriers or excipients. To give but one example, in some embodiments, a biological polymer such as a polypeptide or polynucleotide that occurs in nature can be referred to as "isolated" when, (a) by virtue of its origin or source of derivation is not associated with some or all of the components with which it was associated in its native state in nature; (b) it is substantially free of other polypeptides or nucleic acids of the same species from the species that produces it in nature; (c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components (a) with which it is associated in nature; and/or (b) with which it was associated when initially produced.

Nucleic acid: As used herein, in its broadest sense, the term "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, the term nucleic acid refers to an individual nucleic acid residue (e.g., a nucleotide and/or nucleoside), and in some embodiments refers to an polynucleotide chain including a plurality of individual nucleic acid residues. A nucleic acid can be or include DNA, RNA, or a combinations thereof. A nucleic acid can include natural nucleic acid residues, nucleic acid analogs, and/or synthetic residues. In some embodiments, a nucleic acid includes natural nucleotides (e.g., adenosine, thymidine, guanosine, cytidine, uridine, deoxyadenosine, deoxythymidine, deoxy guanosine, and deoxycytidine). In some embodiments, a nucleic acid is or includes of one or more nucleotide analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid has a nucleotide sequence that encodes a functional gene product such as an RNA or protein. In some embodiments, a nucleic acid includes one or more introns. In some embodiments, a nucleic acid includes one or more genes. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid analog differs from a nucleic acid in that it does not utilize a phosphodiester backbone. For example, in some embodiments, a nucleic acid can include one or more peptide nucleic acids, which are known in the art and have peptide bonds instead of phosphodiester bonds in the backbone. Alternatively or additionally, in some embodiments, a nucleic acid has one or more phosphorothioate and/or 5'-N-phosphoramidite linkages rather than phosphodiester bonds. In some embodiments, a nucleic acid includes one or more modified sugars (e.g., 2'-fluororibose, ribose, 2'-deoxyribose, arabinose, and hexose) as compared with those in natural nucleic acids. In some embodiments, a nucleic acid is or includes at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues. In some embodiments, a nucleic acid is partly or wholly single stranded, or partly or wholly double stranded. In some embodiments a nucleic acid has a sequence including at least one element that encodes, or is the complement of a sequence that encodes, a polypeptide. In some embodiments, a nucleic acid has enzymatic activity.

Operably linked: As used herein, "operably linked" refers to the association of at least a first element and a second element such that the component elements are in a relationship permitting them to function in their intended manner. For example, a nucleic acid regulatory sequence is "operably linked" to a nucleic acid coding sequence if the regulatory sequence and coding sequence are associated in a manner that permits control of expression of the coding sequence by the regulatory sequence. In some embodiments, an "operably linked" regulatory sequence is directly or indirectly covalently associated with a coding sequence (e.g., in a single nucleic acid). In some embodiments, a regulatory sequence controls expression of a coding sequence in trans and inclusion of the regulatory sequence in the same nucleic acid as the coding sequence is not a requirement of operable linkage.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutically acceptable carrier: As used herein, the term "pharmaceutically acceptable carrier" refers to a pharmaceutically-acceptable material, composition, or vehicle, such as a liquid or solid filler, diluent, excipient, or solvent encapsulating material, that facilitates formulation of an agent (e.g., a pharmaceutical agent), modifies bioavailability of an agent, or facilitates transport of an agent from one organ or portion of a subject to another. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutical composition: As used herein, the term "pharmaceutical composition" refers to a composition in which a therapeutic agent is formulated together with one or more pharmaceutically acceptable carriers.

Polypeptide: As used herein, "polypeptide" refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may be or include of natural amino acids, non-natural amino acids, or both. In some embodiments, a polypeptide may be or include only natural amino acids or only non-natural amino acids. In some embodiments, a polypeptide can include D-amino acids, L-amino acids, or both. In some embodiments, a polypeptide may include only L-amino acids. In some embodiments, a polypeptide may include one or more pendant groups or other modifications, e.g., one or more amino acid side chains, e.g., at the polypeptide's N-terminus, at the polypeptide's C-terminus, at non-terminal amino acids, or at any combination thereof. In some embodiments, such pendant groups or modifications may be selected from acetylation, amidation, lipidation, methylation, phosphorylation, glycosylation, glycation, sulfation, mannosylation, nitrosylation, acylation, palmitoylation, prenylation, pegylation, etc., including combinations thereof. In some embodiments, a polypeptide may be cyclic, and/or may include a cyclic portion.

In some embodiments, the term "polypeptide" may be appended to a name of a reference polypeptide, activity, or structure to indicate a class of polypeptides that share a relevant activity or structure. For such classes, the present specification provides and/or those skilled in the art will be aware of exemplary polypeptides within the class whose amino acid sequences and/or functions are known. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that can in some embodiments be or include a characteristic sequence element) that shows very high sequence identity, often greater than 90% or even 95%, 96%, 97%, 98%, or 99%. Such a conserved region usually encompasses at least 3-4 and in some instances up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide can be or include a fragment of a parent polypeptide. In some embodiments, a useful polypeptide may be or include a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: The terms "prevent" and "prevention," as used herein in connection with the occurrence of a disease, disorder, or condition, refers to reducing the risk of developing the disease, disorder, or condition; delaying onset of the disease, disorder, or condition; delaying onset of one or more characteristics or symptoms of the disease, disorder, or condition; and/or to reducing the frequency and/or severity of one or more characteristics or symptoms of the disease, disorder, or condition. Prevention can refer to prevention in a particular subject or to a statistical impact on a population of subjects. Prevention can be considered to have occurred when onset of a disease, disorder, or condition has been delayed for a period of time that is predefined or understood by those of skill in the art.

Promoter: As used herein, a "promoter" or "promoter sequence" can be a DNA regulatory region that directly or indirectly (e.g., through promoter-bound proteins or substances) participates in initiation and/or processivity of transcription of a coding sequence. A promoter may, under suitable conditions, initiate transcription of a coding sequence upon binding of one or more transcription factors and/or regulatory moieties with the promoter. A promoter that participates in initiation of transcription of a coding sequence can be "operably linked" to the coding sequence. In certain instances, a promoter can be or include a DNA regulatory region that extends from a transcription initiation site (at its 3' terminus) to an upstream (5' direction) position such that the sequence so designated includes one or both of a minimum number of bases or elements necessary to initiate a transcription event. A promoter may be, include, or be operably associated with or operably linked to, expression control sequences such as enhancer and repressor sequences.

Reference: As used herein, "reference" refers to a standard or control relative to which a comparison is performed. For example, in some embodiments, an agent, sample, sequence, subject, animal, or individual, or population thereof, or a measure or characteristic representative thereof, is compared with a reference, an agent, sample, sequence, subject, animal, or individual, or population thereof, or a measure or characteristic representative thereof. In some embodiments, a reference is a measured value. In some embodiments, a reference is an established standard or expected value. In some embodiments, a reference is a historical reference. A reference can be quantitative of qualitative. Typically, as would be understood by those of skill in the art, a reference and the value to which it is compared represents measure under comparable conditions. Those of skill in the art will appreciate when sufficient similarities are present to justify reliance on and/or comparison. In some embodiments, an appropriate reference may be an agent, sample, sequence, subject, animal, or individual, or population thereof, under conditions those of skill in the art will recognize as comparable, e.g., for the purpose of assessing one or more particular variables (e.g., presence or absence of an agent or condition), or a measure or characteristic representative thereof.

Regulatory Sequence: As used herein in the context of expression of a nucleic acid coding sequence, a regulatory sequence is a nucleic acid sequence that controls expression of a coding sequence. In some embodiments, a regulatory sequence can control or impact one or more aspects of gene expression (e.g., cell-type-specific expression, inducible expression, etc.).

Risk: As used herein with respect to a disease, disorder, or condition, the term "risk" refers to the qualitative or quantitative probability (whether expressed as a percentage or otherwise) that a particular individual will develop the disease, disorder, or condition. In some embodiments, risk is expressed as a percentage. In some embodiments, a risk is a qualitative or quantitative probability that is equal to or greater than 0, 1, 2, 3, 4, 5, 6, 7, 8, 9, 10, 20, 30, 40, 50, 60, 70, 80, 90, or 100%. In some embodiments risk is expressed as a qualitative or quantitative level of risk relative to a reference risk or level or the risk of the same outcome attributed to a reference. In some embodiments, relative risk is increased or decreased in comparison to the reference sample by a factor of 1.1, 1.2, 1.3, 1.4, 1.5, 1.6, 1.7, 1.8, 1.9, 2, 3, 4, 5, 6, 7, 8, 9, 10, or more.

Subject: As used herein, the term "subject" refers to an organism, typically a mammal (e.g., a human, rat, or mouse). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject is not suffering from a disease, disorder or condition. In some embodiments, a subject does not display any symptom or characteristic of a disease, disorder, or condition. In some embodiments, a subject has one or more features characteristic of susceptibility to or risk of a disease, disorder, or condition. In some embodiments, a subject is a subject that has been tested for a disease, disorder, or condition, and/or to whom therapy has been administered. In some instances, a human subject can be interchangeably referred to as a "patient" or "individual."

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with, or presents a bio-marker status (e.g., a methylation status) associated with, development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For the avoidance of doubt, a delay in the onset of a particular symptom is considered one form of reducing the frequency of that symptom.

Therapeutically effective amount: As used herein, "thera-peutically effective amount" refers to an amount that pro-duces the desired effect for which it is administered. In some embodiments, the term refers to an amount that is sufficient, when administered to a population suffering from or sus-ceptible to a disease, disorder, and/or condition in accor-dance with a therapeutic dosing regimen, to treat the disease, disorder, and/or condition. In some embodiments, a thera-peutically effective amount is one that reduces the incidence and/or severity of, and/or delays onset of, one or more symptoms of the disease, disorder, and/or condition. Those of ordinary skill in the art will appreciate that a therapeuti-cally effective amount does not necessarily achieve success-ful treatment in every particular treated individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a par-ticular agent or therapy may be formulated and/or adminis-tered in a single dose. In some embodiments, a therapeuti-cally effective agent may be formulated and/or administered in a plurality of doses, for example, as part of a dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is admin-istered for the purpose of achieving any such result. In some embodiments, such treatment can be of a subject who does not exhibit signs of the relevant disease, disorder, or con-dition and/or of a subject who exhibits only early signs of the disease, disorder, or condition. Alternatively or additionally, such treatment can be of a subject who exhibits one or more established signs of the relevant disease, disorder and/or condition. In some embodiments, treatment can be of a subject who has been diagnosed as suffering from the relevant disease, disorder, and/or condition. In some embodiments, treatment can be of a subject known to have one or more susceptibility factors that are statistically cor-related with increased risk of development of the relevant disease, disorder, or condition.

Unit dose: As used herein, the term "unit dose" refers to an amount administered as a single dose and/or in a physi-cally discrete unit of a pharmaceutical composition. In many embodiments, a unit dose contains a predetermined quantity of an therapeutic agent. In some embodiments, a unit dose contains an entire single dose of the agent. In some embodi-ments, more than one unit dose is administered to achieve a total single dose. In some embodiments, administration of multiple unit doses is required, or expected to be required, in order to achieve an intended effect. A unit dose can be, for example, a volume of liquid (e.g., an acceptable carrier) containing a predetermined quantity of one or more thera-peutic agents, a predetermined amount of one or more therapeutic agents in solid form, a sustained release formu-lation or drug delivery device containing a predetermined amount of one or more therapeutic agents, etc. It will be appreciated that a unit dose can be present in a formulation that includes any of a variety of components in addition to the therapeutic agent(s). For example, acceptable carriers (e.g., pharmaceutically acceptable carriers), diluents, stabi-lizers, buffers, preservatives, etc., can be included. It will be appreciated by those skilled in the art, in many embodi-ments, a total appropriate daily dosage of a particular therapeutic agent can include a portion, or a plurality, of unit doses, and can be decided, for example, by a medical practitioner within the scope of sound medical judgment. In some embodiments, the specific effective dose level for any particular subject or organism can depend upon a variety of factors including the disorder being treated and the severity of the disorder; activity of specific therapeutic agent employed; specific composition employed; age, body weight, general health, sex and diet of the subject; time of administration, and rate of excretion of the specific thera-peutic agent employed; duration of the treatment; drugs and/or additional therapies used in combination or coinci-dental with specific compound(s) employed, and like factors well known in the medical arts.

A culture of ZB423 in production media containing sucrose was grown for 72 hours. The cell culture was then pelleted to remove cells and cold ethanol (1:1.5) was added to the supernatant. A white precipitate was observed and further purified by twice repeating dissolution in water and precipitation in cold ethanol followed by centrifugation to collect the pellet. The pellet was dried under vacuum for 24 hours before analysis. A separate industry standard for inulin was analyzed using the same HPAEC method. A strain of *Bacillus subtilis* PY79 that was not engineered to express SacB did not produce a precipitate or pellet from the supernatant and could not be analyzed. A) A chromatogram of 10 g of sample from the ZB423 pellet showing a degree of polymerization (DP) of around 50 B) An inulin standard run with the same HPAEC method and column for comparison showing a DP of around 14 consistent with plant inulin extracts.

Figure 4:
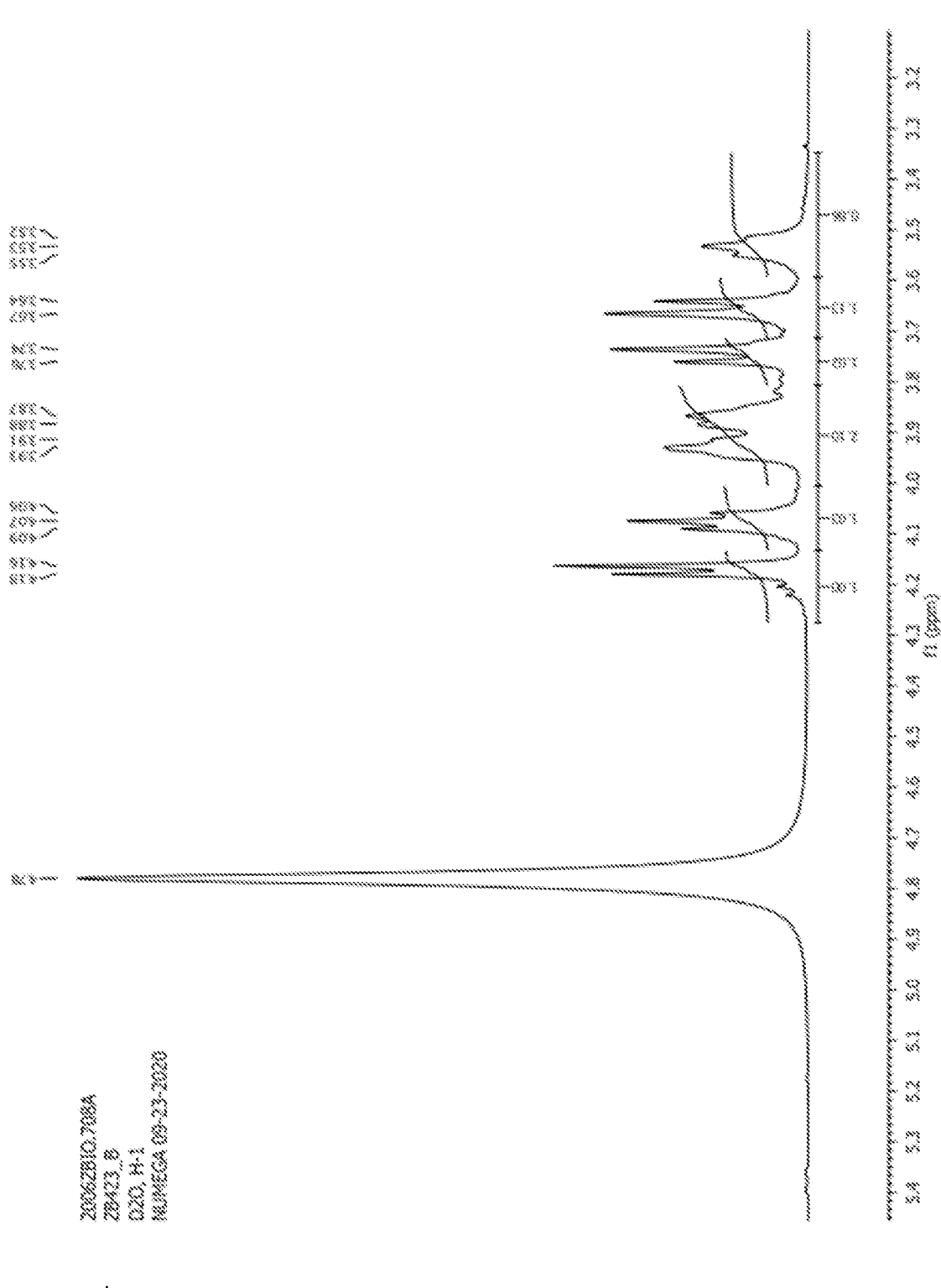

FIG. 4 1H-NMR spectra of Levan isolated from ZB423 culture. The spectra shows a solvent peak at 4.78 ppm; a doublet at 4.18, 4.16 ppm (integral: 1); a triplet at 4.09, 4.07, 4.06 ppm (integral: 1), two peaks with amorphous splitting at 3.93, 3.91, 3.88, 3.87 ppm (integral: 2), a doublet at 3.76, 3.74 ppm; a doublet at 3.67, 3.64 ppm; and a triplet at 3.55, 3.53, 3.52 ppm. Solvent was D2O.

Figure 5:
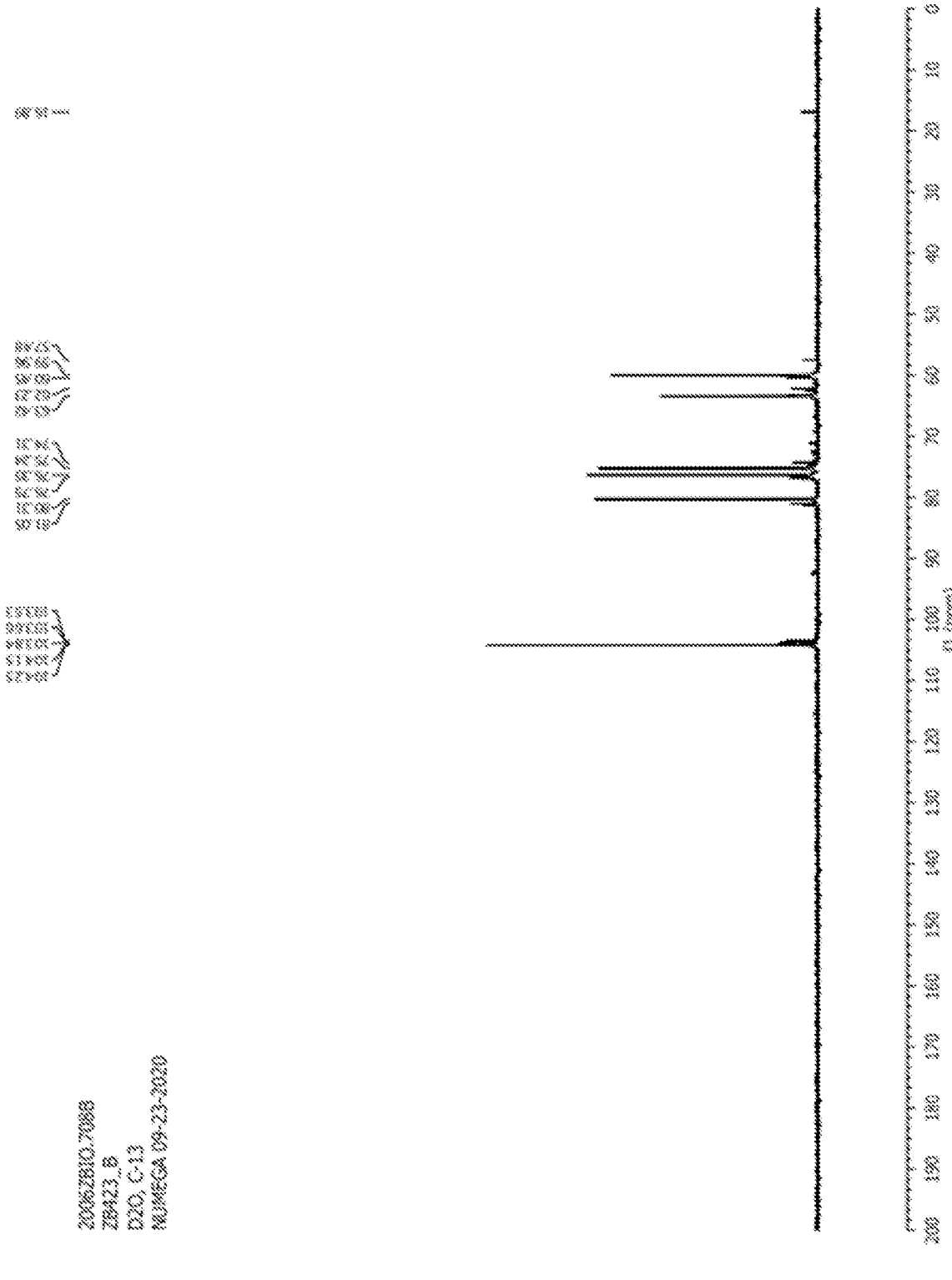

FIG. 5 13C-NMR Spectra of Levan isolated from ZB423 culture. The spectra shows peaks at 59.96, 104.25, 76.35, 75.24, 80.31, 63.42 ppm.

Figure 6:
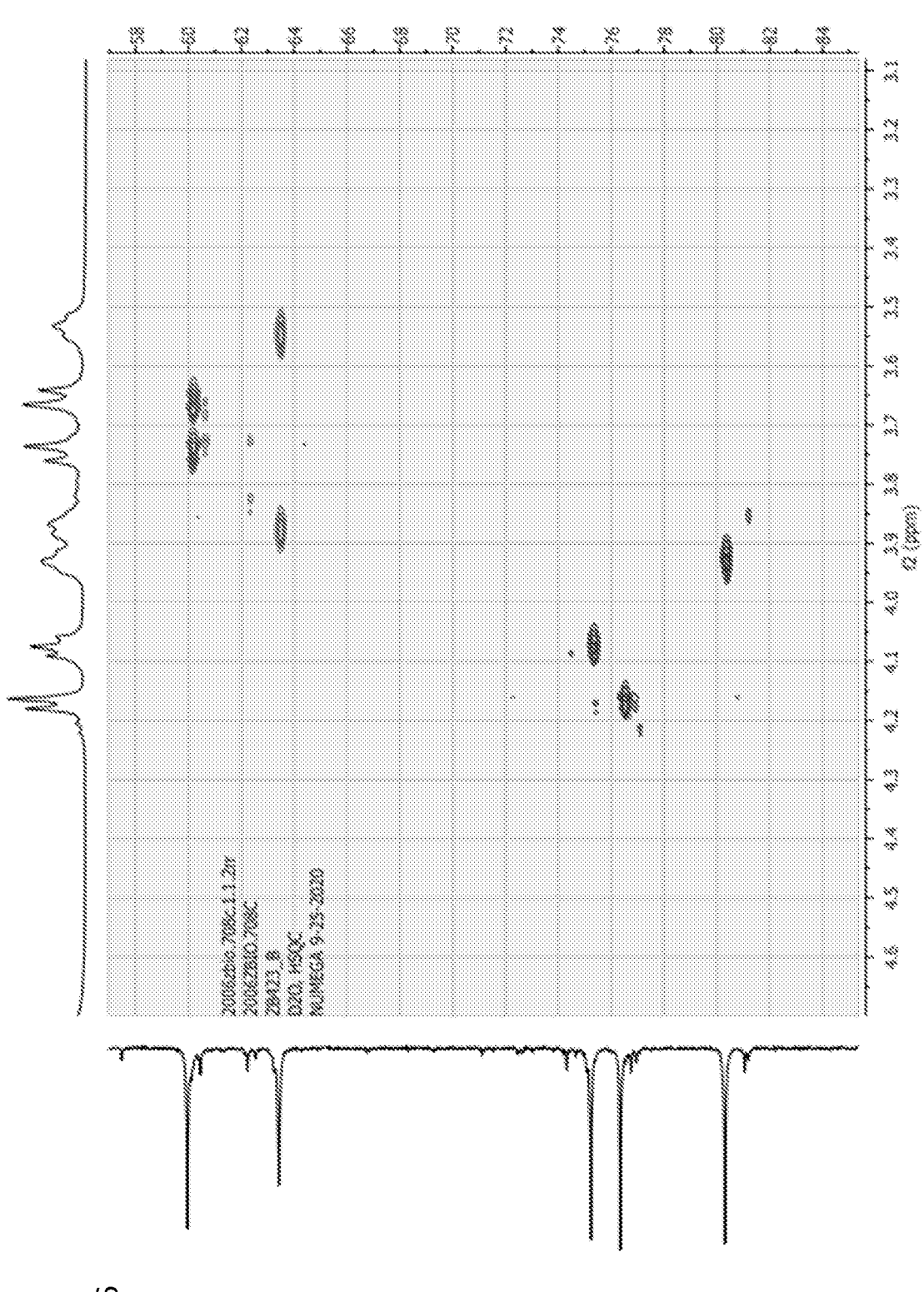

FIG. 6 HSQC-NMR Spectra of Levan isolated from ZB423 culture. This spectra shows the associations between 13C atoms and 1H NMR peaks. The result matches that analyzed previously for Levan from plant sources.

FIG. 7 Table of 13C-NMR chemical shifts for Levan isolated from ZB423 culture and comparison to literature.

Figure 8:
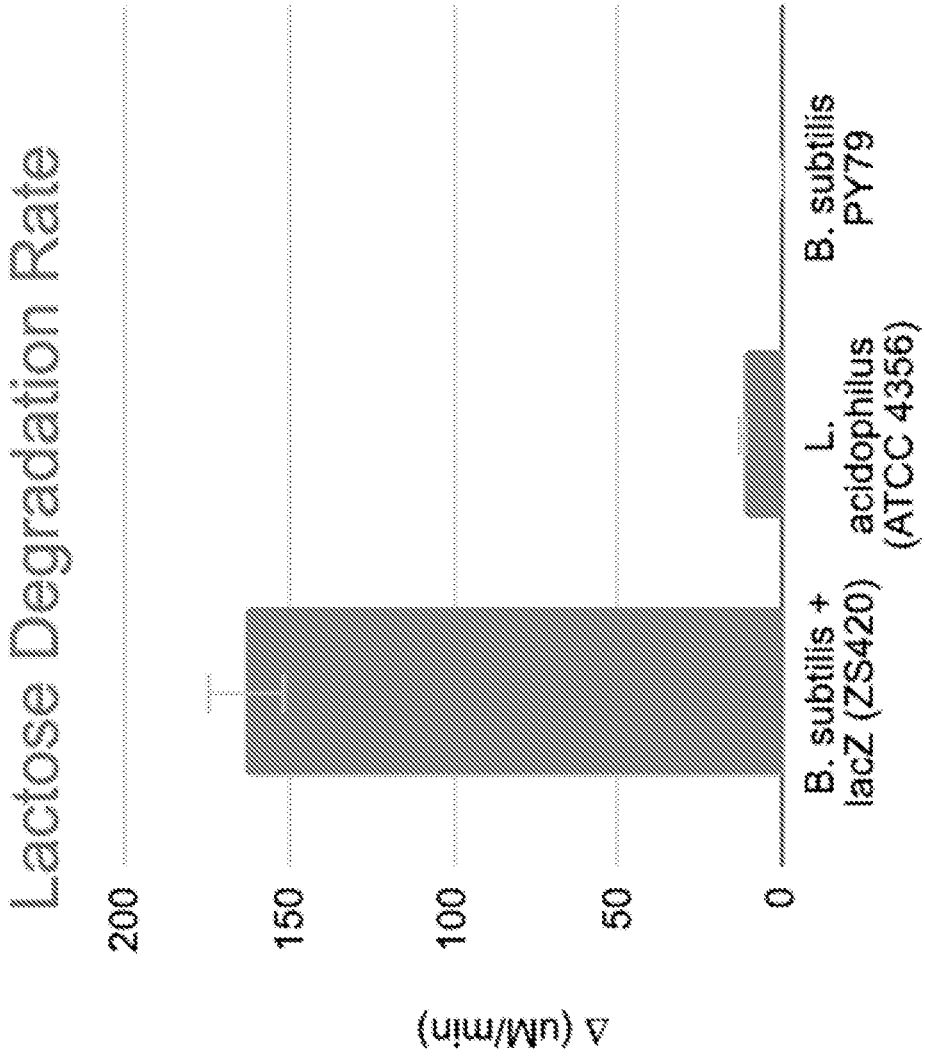

FIG. 8 Lactose degradation during transgalactosylation reactions in a culture of *B. subtilis* engineered with beta-galactosidase LacZ. Lactose is calculated from released glucose. The direct correlation between glucose accumulation and Lactose degradation is confirmed in control samples using purified lactase to effect complete Lactose degradation and correlating to released glucose.

Figure 9:
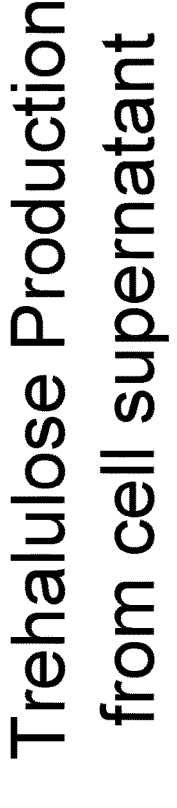
Figure 9:
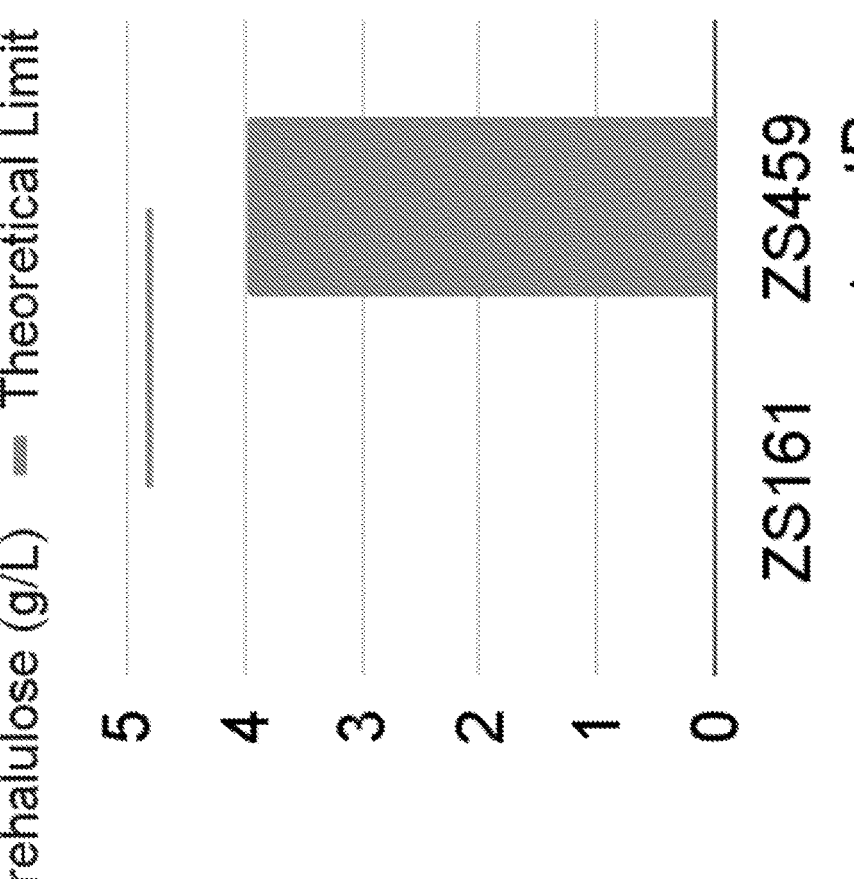

FIG. 9 Trehalulose production from cell supernatant (testing activity of secreted enzyme) isolated from culture broth of engineered strains of *Bacillus subtilis* PY79 with mutB (ZS459) or without mutB (ZS161) operably linked to the hag promoter in the expression locus. Trehalulose is calculated as the reduction in total sucrose. The theoretical limit is equal to the amount of sucrose added to the cell supernatant during the assay.

Figure 10:
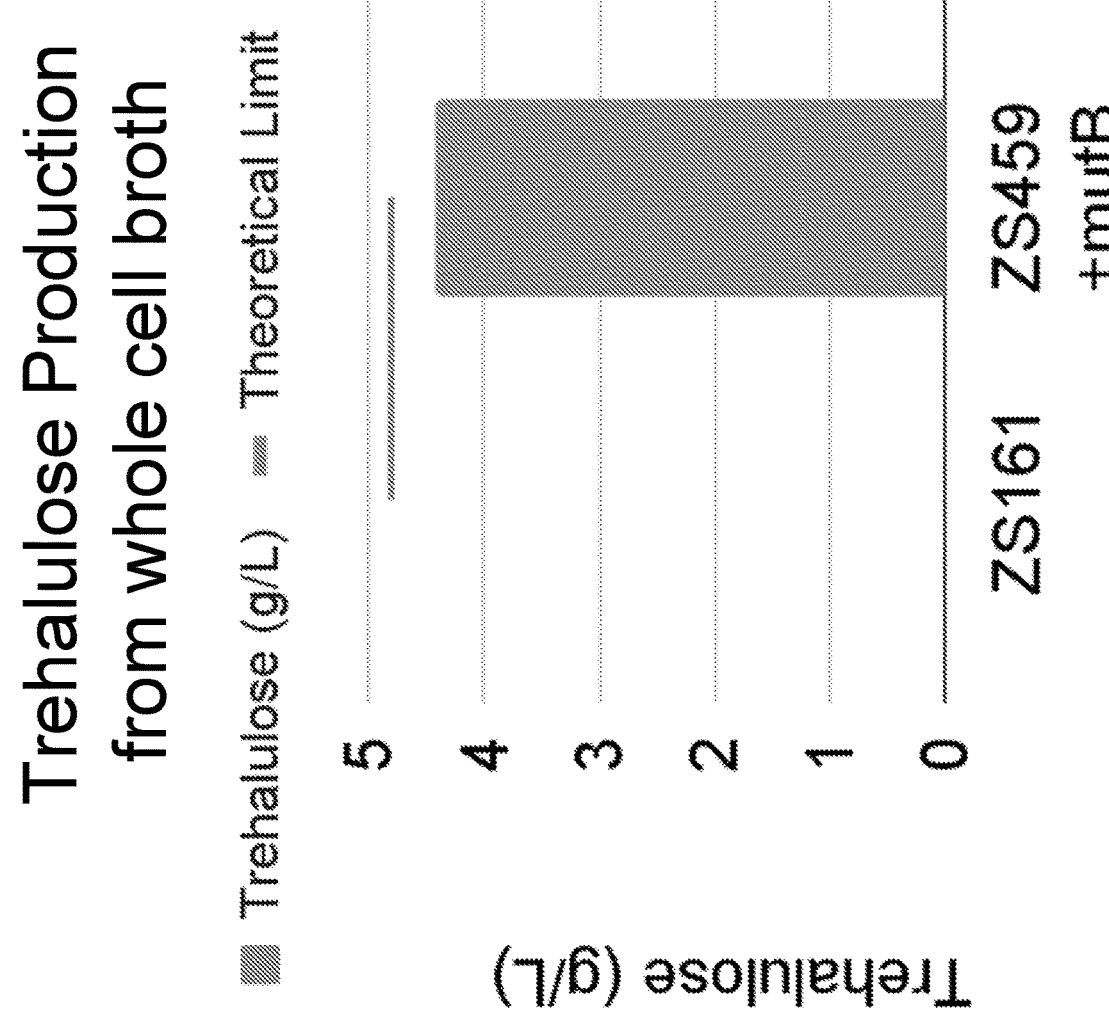

FIG. 10 Trehalulose production from whole cell broth (testing combined activity of intracellular and secreted enzyme) containing engineered strains of *Bacillus subtilis* PY79 with mutB (ZS459) or without mutB (ZS161) operably linked to the hag promoter in the expression locus. Trehalulose is calculated as the reduction in total sucrose. The theoretical limit is equal to the amount of sucrose added to the cell supernatant during the assay.

DETAILED DESCRIPTION

Metabolism and nutrition are complex areas in which many challenges have been identified. Functions of the gut (e.g., human gut) and gut microbiome (e.g., human gut microbiome) have been increasingly recognized, presenting new challenges in metabolism and nutrition. Certain of these challenges relate to the role of carbohydrates in human metabolism and nutrition. For instance, one function of the gut and/or gut microbiome is to digest carbohydrates, often into monosaccharides such as glucose, fructose, and galactose. Diets high in carbohydrates have been linked to, e.g., high blood pressure, heart disease, obesity, diabetes, high blood glucose and other health problems. Another important metabolic and nutritional challenge relates to soluble fiber. Soluble fiber can improve, e.g., gut health, and improve or reduce the risk of conditions such as high blood cholesterol, heart disease, obesity, diabetes, high blood glucose, and other health problems. Gut carbohydrates and gut soluble fiber can beneficially (e.g., therapeutically) or detrimentally impact the composition of the gut microbiome (e.g., the types and concentrations or amounts of the various microbes of the gut microbiome).

Those of skill in the art will appreciate that modern diets typically include concentrations and/or amounts of carbohydrate (e.g., monosaccharides and/or disaccharides and/or complex carbohydrate) that are in excess of nutritional requirements. Excess monosaccharides and/or disaccharides can in various instances result from consumption of monosaccharides, disaccharides, or complex carbohydrates, any and/or all of which are common in many modern diets. For instance, according to certain estimates, 5% of consumed sucrose can traverse the small intestine without being degraded and digested. Thus, from a typical carbohydrate source such as a can of soda, containing, e.g., 30 g of sucrose, as much as 1.5 g of sucrose can pass through the stomach and small intestine to reach the colon). Furthermore, sucrose in the intestine can be cleaved into glucose and fructose. While glucose can be rapidly absorbed through the intestinal lining, fructose is absorbed more slowly, resulting in accumulation of fructose in the colon. The present specification recognizes that agents that can increase certain generally beneficial microbiome processes, activities, and/or types of microbes, that can decrease certain generally deleterious microbiome processes, activities, and/or types of microbes, or that can promote a beneficial overall microbiome composition, are needed. Those of skill in the art will further appreciate that it is not necessary to articulate individual effects (e.g., on the composition of the gut microbiome) of an agent (e.g., to identify gut microbiome bacteria that are increased or decreased by delivery of the agent to the gut) to demonstrate and/or appreciate that the agent has a beneficial impact on health and/or the gut microbiome.

Those of skill in the art will further appreciate that modern diets typically include concentrations and/or amounts of fiber (e.g., soluble fiber) that are lower than the concentrations and/or amounts optimal for human health. Consumption of fiber (e.g., a high-fiber diet, e.g., a high-soluble fiber diet) helps maintain gut health. Fiber is commonly classified as soluble fiber, which can be dissolved in water to form a gel-like material, or insoluble fiber, which cannot be dissolved in water. Consumption of fiber (particularly soluble fiber) can help to maintain healthy body weight (e.g., to reduce or stabilize body weight), and/or to decrease risk of developing diabetes, heart disease, and/or some types of cancer (e.g., colorectal cancer and/or other gut or intestinal cancers). Consumption of fiber (particularly soluble fiber) can decrease risk of dying from cardiovascular disease and all cancers, causing and/or permitting increased longevity. Consumption of fiber (particularly soluble fiber) can decrease risk of developing hemorrhoids and/or small pouches in your colon (diverticular disease). Consumption of fiber (particularly soluble fiber) can decrease blood pressure and inflammation. Consumption of fiber (particularly soluble fiber) can slow absorption of glucose into blood and/or cause a decrease in blood glucose levels and/or stabilize blood glucose levels (e.g., decrease variation in blood glucose levels over time), e.g., in diabetic subjects.

Soluble fiber can help decrease blood cholesterol (e.g., total blood cholesterol concentration or amount), e.g., by decreasing low-density lipoprotein levels.

Gut carbohydrates and gut soluble fiber impact the composition of the gut microbiome. The gut microbiome typically includes trillions of microbes that contribute to, e.g., metabolism, nutrient and mineral absorption, synthesis of enzymes, vitamins and amino acids, and production of short-chain fatty acids (SCFAs). Microbes of the gut microbiome have tremendous potential to impact health (e.g., contribute to wellbeing or to disease) and/or physiology. Microbes of the gut microbiome can have metabolic activities that impact health of a host organism, protect a host organism against pathogens, educate the immune system of a host organism, and/or directly or indirectly affect many physiologic functions. The gut microbiome includes a variety of different types of microbes (e.g., a variety of different bacterial phyla, classes, orders, families, genera, species, and/or strains), each of which can be characterized by different metabolic characteristics. For example, different types of microbes may demonstrate increased or decreased growth under any of a variety of conditions, e.g., in the presence of carbohydrates or in the presence of fiber. Moreover, certain microbes are considered to be beneficial, certain microbes are considered to be harmful, and the overall composition of the gut microbiome (e.g., the relative amounts of different microbes in the gut microbiome) is considered to be an important factor in health.

Carbohydrate consumption and/or gut carbohydrate (e.g., consumption and/or excess of monosaccharides and/or disaccharides) can adversely impact the gut microbiome and/or cause various conditions associated with excess carbohydrate. Insufficient soluble fiber in the gut can also adversely impact the gut microbiome (e.g., gut microbiome composition and/or activity) and/or cause various conditions associated with insufficient fiber. Soluble fiber can also promote growth of health-promoting bacteria. Accordingly, carbohydrate consumption and/or insufficient fiber consumption can cause a disruption of the balance of microbiome strains (dysbiosis) of the gut microbiome, e.g., of the large intestine, e.g., by increasing the concentration or amount of Proteobacteria, decreasing the concentration or amount of Bacteroidetes, and/or causing an increase the ratio of Proteobacteria to Bacteroidetes. Dysbiosis of gut microbiota is associated with the pathogenesis of intestinal conditions (e.g. inflammatory bowel disease, and irritable bowel syndrome (IBS)), and extra-intestinal conditions (e.g, allergy, asthma, metabolic syndrome, cardiovascular disease, and obesity). Dysbiosis can include and/or present symptoms including bloating, cramping, gas, and diarrhea. Additionally, concentration and/or amount of Proteobacteria and/or Bacteroidetes, and/or the ratio thereof, can contribute to maintenance of immunological homeostasis and/or epithelial integrity in the intestinal mucosa. The genus Bacteroidetes has been associated with numerous health benefits, including the downregulation of inflammatory responses in the gut. Further to these impacts on the composition of the gut microbiome and functions thereof, sucrose and gut cleavage products glucose and fructose are known to have direct effects in silencing certain health-beneficial functions of gut microbiome bacteria such as *bacteroides.*

The present disclosure therefore recognizes a variety of distinct gut conditions (e.g., characterized by concentration or amount of one or more metabolites, e.g., increased or decreased relative to a reference) that benefit health and/or the gut microbiome. These target gut=conditions that benefit health and/or the gut microbiome can include any of one or more of (i) decrease in the concentration or amount of monosaccharides and/or disaccharides in the gut as compared to a reference and/or (ii) increase in the concentration or amount of gut fiber (e.g., gut soluble fiber) as compared to a reference, e.g., where the reference is a concentration or amount in the same subject at an earlier time, a concentration or amount identified as normal or healthy, a concentration or amount identified as abnormal or unhealthy, a concentration or amount representative of typical or healthy subjects, a concentration or amount representative of atypical or unhealthy subjects. The present disclosure further provides that decreasing the concentration or amount monosaccharides and/or disaccharides in the gut can be achieved, e.g., by competitive uptake of monosaccharides and/or disaccharides (e.g., sucrose) in the gut (e.g., in the small intestine and/or colon) by an alternative and/or beneficial process, and/or by removal of fructose produced from sucrose degradation in the gut (e.g., in the small intestine). The present disclosure further provides that the concentration or amount of gut fiber (e.g., gut soluble fiber) can be increased by synthesis in the gut of soluble fiber. The present disclosure further provides that these target gut nutrient conditions of reduced carbohydrate and increased fiber provide synergistic benefits to health and/or the gut microbiome, at least because monosaccharides and/or disaccharides can inhibit beneficial growth of the microbiome and/or of microbes thereof while soluble fiber promotes positive growth of the microbiome and/or of microbes thereof, and separately or additionally in some instances because low carbohydrate and high fiber can together modulate, decrease, and/or stabilize blood glucose levels. Moreover, methods and compositions of the present disclosure surprisingly and synergistically achieve both target gut nutrient conditions of decreased concentration or amount of gut monosaccharides and/or disaccharides and increased concentration or amount of fiber.

The present disclosure recognizes, among other things, at least two forms of synergy between carbohydrates (such as monosaccharides and/or disaccharides, including without limitation monosaccharides produced by digestion of complex carbohydrates) and soluble fiber: first, that soluble fiber in the gut can slow the digestion of carbohydrate (e.g., monosaccharides and/or disaccharides), and second that both carbohydrates (e.g., monosaccharides and/or disaccharides) and soluble fiber have profound impacts on the gut microbiome, the present disclosure including that reducing gut monosaccharides and/or disaccharides and increasing gut soluble fiber are independently and synergistically beneficial. The present disclosure provides compositions such as engineered bacteria, and methods of using the same, that benefit health by decreasing concentration and/or amount of gut monosaccharides and/or disaccharides and increasing gut soluble fiber, e.g., by enzymatic synthesis of fiber from substrates including carbohydrate (e.g., monosaccharides and/or disaccharides).

Various methods and compositions of the present disclosure include an engineered bacterium, such as a probiotic bacterium, that decreases amount and/or concentration of monosaccharides and/or disaccharides in the gut and increases amount and/or concentration of soluble fiber in the gut by enzymatically converting carbohydrate (e.g., monosaccharides and/or disaccharides) to soluble fiber. Enzymatic reactions that perform this function include but are not limited to oligofructose-synthases, which cleave sucrose and seclude fructose into a growing oligo-fructose chain which is not digestible by human enzymes in the intestinal tract. Accordingly, in certain exemplary embodiments, a composition or method of the present disclosure degrades sucrose and incorporates fructose into a fiber molecule. In certain particular methods and composition of the present disclosure, an engineered bacterium processes monosaccharides and/or disaccharides to produce levan fiber (e.g., by incorporating carbohydrate moieties into soluble fiber molecules).

Reducing Carbohydrate and Synthesizing Fiber

Compositions and methods of the present disclosure that decrease concentration or amount of gut carbohydrate (monosaccharides and/or disaccharides) and increase concentration or amount of gut fiber (e.g., soluble fiber) include enzymes that convert carbohydrate to fiber and further include engineered bacteria that encode and/or express enzymes that convert carbohydrate to fiber. The present disclosure includes the inventors' recognition that certain plant and bacterial enzymes participate in, catalyze, and/or cause reactions in which soluble indigestible fiber molecules are synthesized (e.g., directly) from substrates including one or more carbohydrates, e.g., by incorporating carbohydrate moieties into fiber molecules. Certain such reactions typically occur in non-therapeutic contexts and/or contexts that are not within a subject, e.g., during fermentation of food with soil bacteria, or during growth of plants in soil. Various bacteria and plants employ conversion of carbohydrates to fiber in producing energy storage molecules, structural molecules, and/or osmotic gradients. To the knowledge of the present inventors, none of these bacteria or plants, nor cells thereof, can, upon administration to a subject, cause incorporation of carbohydrate moieties consumed by the subject into fiber molecules, nor do so in therapeutically effective amounts (e.g., there is no therapeutically effective dosage of these bacteria or plants or cells thereof for synthesis in a subject of fiber molecules from consumed carbohydrates). The present disclosure reveals that introduction of such reactions into the context of the gut by administration to a subject of a bacterium engineered for such a reaction can decrease concentration or amount of gut monosaccharides and/or disaccharides while increasing gut soluble fiber.

Transgenes

The present disclosure includes engineered nucleic acids (transgenes) that encode and/or express a variety of exemplary enzymes that synthesize fiber from substrates including carbohydrate (fiber-synthesizing enzymes). Various fiber-synthesizing enzymes are known in the art, e.g., from studies of the conversion of carbohydrates to fibers in microorganisms (e.g., for use in a controlled fermentation context). For example, various fiber-synthesizing enzymes have been characterized, e.g., for sequence and/or fiber production characteristics in laboratory settings and systems such as *E. coli*.

In various embodiments, fiber-synthesizing enzymes of the present disclosure utilize a carbohydrate substrate selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose as a substrate in synthesizing a fiber that includes glucose, fructose, galacturonic acid, N-acetyl-D-glucosamine, and/or galactose monomers, e.g., wherein synthesized fibers include one or more of laminaribiose, callose, curdlan, oat beta-glucan, laminarin, pleuran, lentinan, yeast beta glucan, trehalulose, inulin, kestose, nystose, levan, raffinose, stachyose, and/or verbascose. In various embodiments, fiber-synthesizing enzymes of the present disclosure utilize UDP-glucose as a substrate in synthesizing fiber including glucose monomers, e.g., where synthesized fibers are or include one or more of laminaribiose, callose, curdlan, oat beta-glucan, laminarin, pleuran, lentinan, yeast beta glucan, and/or trehalulose. In various embodiments, fiber-synthesizing enzymes of the present disclosure utilize sucrose as a substrate in synthesizing fiber including fructose monomers, e.g., where synthesized fibers are or include inulin, kestose, nystose, and/or levan. In various embodiments, fiber-synthesizing enzymes of the present disclosure utilize sucrose and UDP-galactose as a substrate in synthesizing fiber including galactose monomers, e.g., where synthesized fibers are or include raffinose, stachyose, and/or verbascose.

Representative examples of fiber-synthesizing enzymes include a 1,3-beta-glucan synthase (e.g., 1,3-beta-glucan synthase component FKS1 or callose synthase 1), a 1,3;1,4-beta-D-glucan synthase (e.g., probable mixed-linked glucan synthase 6), a 1,6-beta-glucan synthase (e.g., Cell wall synthesis protein KRE9) a sucrose isomerase, a levansucrase, or a 1,6-alpha-galactosyltransferase (e.g., galactinol—sucrose galactosyltransferase). Representative examples of fiber-synthesizing enzymes include Levansucrase (sucrose 6-fructosyltransferase; beta-2,6-fructosyltransferase; beta-2,6-fructan:D-glucose 1-fructosyltransferase; EC 2.4.1.10); inulosucrase (sucrose:2,1-beta-D-fructan 1-beta-D-fructosyltransferase; sucrose 1-fructosyltransferase; EC 2.4.1.9); fructosyltransferase (2,1-fructan:2,1-fructan 1-fructosyltransferase; 1,2-beta-D-fructan 1(F)-fructosyltransferase; 1,2-beta-D-fructan:1,2-beta-D-fructan 1(F)-beta-D-fructosyltransferase; 1,2-beta-fructan 1(F)-fructosyltransferase; FFT; Fructan:fructan fructosyl transferase, EC 2.4.1.100); sucrose fructosyltransferase (SST; Sucrose 1(F)-fructosyltransferase; Sucrose-sucrose 1-fructosyltransferase; Sucrose:sucrose 1(F)-beta-D-fructosyltransferase; Sucrose:sucrose 1-fructosyltransferase; EC 2.4.1.99); Mutansucrase (EC 2.4.1.372); Sucrose—glucan glucosyltransferase (EC 2.4.1.4); Sucrose 6-glucosyltransferase (EC 2.4.1.5); Alpha-(1->2) branching sucrase (EC 2.4.1.373); Alternansucrase (Sucrose-1,6(3)-alpha-glucan 6(3)-alpha-glucosyltransferase; Sucrose:1,6-, 1,3-alpha-D-glucan 3-alpha- and 6-alpha-D-glucosyltransferase; EC 2.4.1.140); Sucrose—1,6-alpha-glucan 3(6)-alpha-glucosyltransferase (EC 2.4.1.125).

In one embodiment, a probiotic organism is engineered with a 2,1 beta fructosyltransferase (inulosucrase) to enable the synthesis of fructooligosaccharides (inulin, 1-kestose, 1-nystose) from consumed sucrose in the digestive tract. In another embodiment, a probiotic organism is engineered with a 2,6 beta fructosyltransferase (levanosucrase) to enable the synthesis of fructooligosaccharides (levan, 6-kestose, 6-nystose) from consumed sucrose in the digestive tract. In another embodiment, a probiotic organism is engineered with a galactosyltransferase specific to lactose (such as β(1→4) galactosyltransferase) to enable the synthesis of lactose terminal galactooligosaccharides (human milk oligosaccharides, galactooligosaccharides) from consumed lactose in the digestive tract. In another embodiment, a probiotic organism is engineered with a galactosyltransferase specific to galactinol (such as (α1→6) galactosyltransferase) to enable the synthesis of sucrose terminal galactooligosaccharides (raffinose, stachyose, verbascose) from consumed sucrose and glucose in the digestive tract, optionally with galactinol synthase, galactose isomerase, and membrane transporters to increase precursors and improve synthesis rates. In another embodiment, a probiotic organism is engineered with a β(1→3) glucan synthase (1,3-Betaglucan synthase) to enable the synthesis of beta-glucans (laminaribiose, callose, curdlan, oat beta-glucan) from consumed glucose or glucose produced from consumed sucrose in the digestive tract, optionally including fructose isomerase to enable synthesis from consumed fructose, optionally including a 1,4-beta-glucosyltransferase to enable synthesis of crosslinked polymers with improved prebiotic qualities from consumed sucrose and glucose in the digestive tract. In another embodiment, a probiotic organism is engineered with a β(1→3) glucan synthase (1,3-Beta-glucan synthase) is further engineered with a β(1→6) glucan synthase (1,6-Beta-glucan synthase) to create rare crosslinked prebiotic fibers (Laminarin/Pleuran/Lentinan/Yeast beta glucan) from consumed sucrose and glucose in the digestive tract. In another embodiment, a probiotic organism is engineered with a α(1→1) sucrose isomerase (trehalulose synthase) to enable the synthesis of rare prebiotic disaccharides (Trehalulose) from consumed glucose and fructose in the digestive tract. In another embodiment a probiotic organism is engineered with the pectin biosynthesis pathway to enable the synthesis of pectin and pectin-like polymers from consumed glucose and sucrose in the digestive tract.

Representative examples of fiber-synthesizing enzymes are further provided in the below table:

TABLE 1

| | | | | | |
|---|---|---|---|---|---|
| Exemplary fiber-synthesizing enzymes | | | | | |
| Enzyme(s) | Exemplary Gut Carbohydrate(s) Decreased (Enzyme Substrate(s)) | Fiber Monomer(s) | Fiber Monomer Linkage(s) | Product(s) (Common name(s)) | Exemplary Enzyme Sequences |
| 1,3-beta-glucan synthase | Glucose Sucrose Fructose (UDP-Glucose) | Glucose | β(1→3) | Laminaribiose Callose Curdlan | *Saccharomyces cerevisiae* FKS1 (1,3-beta-glucan synthase component) |
| | Glucose Sucrose Fructose (UDP-Glucose) | Glucose | β(1→3) | Callose | *Arabidopsis thaliana* (Mouse-ear cress) CALS1 (Callose synthase 1) |
| 1,3; 1,4-beta-D-glucan synthase | Glucose Sucrose Fructose (UDP-Glucose) | Glucose | β(1→3) β(1→4) | Oat beta-glucan | *Oryza sativa* subsp. *japonica* CSLF6 (Probable mixed-linked glucan synthase 6) |
| 1,3-beta-glucan synthase, 1,6-beta-glucan synthase | Glucose Sucrose Fructose (UDP-Glucose) | Glucose | β(1→3) β(1→6) | Laminarin Pleuran Lentinan Yeast beta glucan | *Saccharomyces cerevisiae* KRE9 (Cell wall synthesis protein KRE9) |
| Sucrose Isomerase, Trehalulose Synthase | Sucrose (Sucrose) | Glucose Fructose | α(1→1) | Trehalulose | *Pseudomonas mesoacidophila* MutB (Sucrose isomerase (Trehalulose synthase)) |
| Trehalose-6-phosphate synthase | Glucose Sucrose Fructose (UDP-Glucose, Glucose) | Glucose | α(1→1) | Trehalose | *Escherichia coli* (strain K12) otsA (Trehalose-6-phosphate synthase) |
| Inulinsucrase | Sucrose (Sucrose) | Fructose | β(2→1) | Inulin Kestose Nystose | *Lactobacillus johnsonii* InuJ (Inulosucrase) |
| Levansucrase | Sucrose (Sucrose) | Fructose | β(2→6) | Levan | *Bacillus subtilis* SacB (Levansucrase) |
| 1,6-alpha-galactosyltransferase | Lactose Glucose Sucrose Fructose (Galactinol) | Galactose | α(1→6) | Raffinose Stachyose Verbascose | *Oryza sativa* subsp. *japonica* RFS (Galactinol--sucrose galactosyltransferase) |
| α-1,4-galactosyltransferase | Lactose Glucose Sucrose Fructose (UDP-galactose) | Galactose | α(1→4) | Globotriose, Human milk oligosaccharides (HMOs) | *Neisseria meningitidis* lgtC (Alpha 1,4 galactosyltransferase) |
| Alpha-1,2-fucosyltransferase | Lactose Glucose Sucrose Fructose (GDP-fucose) | Fucose | α(1→2) | Human milk oligosaccharides (HMOs) | *Thermosynechococcus elongatus* tll0994 (Alpha-1,2-fucosyltransferase) |
| beta-galactosidase | Lactose (Lactose) | Galactose | β(1→3) | Human milk oligosaccharides (HMOs) | *Geobacillus kaustophilus* BgaB (Beta-galactosidase bgaB) |
| b-D-Galactosidase | Lactose (Lactose) | Galactose | β(1→4) | Human milk oligosaccharides (HMOs) | *Bacillus circulans* Bga (Beta-galactosidase) |

TABLE 1-continued

Exemplary fiber-synthesizing enzymes

| Enzyme(s) | Exemplary Gut Carbohydrate(s) Decreased (Enzyme Substrate(s)) | Fiber Monomer(s) | Fiber Monomer Linkage(s) | Product(s) (Common name(s)) | Exemplary Enzyme Sequences |
|---|---|---|---|---|---|
| cellulose synthase | Glucose Sucrose Fructose (UDP-Glucose) | Glucose | β(1→4) | Cellobiose/ Cellulose/ microcellulose/ Cotton | *Komagataeibacter xylinus* (Gluconacetobacter xylinus) AcsAB (Cellulose synthase 1) |
| maltose synthase, starch synthase | Glucose Sucrose Fructose (UDP-Glucose) | Glucose | α(1→4) | Maltose/ Amylose/Starch/ Glycogen | *Zea mays* (Maize) Ss1 (Starch synthase, chloroplastic/amyloplastic) |
| Starch-branching enzymE | Glucose Sucrose Fructose (UDP-Glucose) | Glucose | α(1→4), α(1→6) | Amylopectin/ Starch | *Arabidopsis thaliana* (Mouse-ear cress) SBE3 (1,4-alpha-glucan-branching enzyme 3, chloroplastic/amyloplastic) |
| Glycogen synthase | Glucose Sucrose Fructose (ADP-α-D-glucose) | Glucose | α(1→4) | Microbial Glycogen | *Bacillus subtilis* (strain 168) glgA (Glycogen synthase) |
| galacturonosyltransferase | Glucose Sucrose Fructose (UDP-α-D-galacturonate, various) | Galacturonic acid | α(1→4) | Pectin | *Arabidopsis thaliana* (Mouse-ear cress) GAUT1 (Polygalacturonate 4-alpha-galacturonosyltransferase) |
| Chitinoligosaccharide synthase | Glucose Sucrose Fructose (UDP-N-acetyl-alpha-D-glucosamine) | N-acetyl-D-glucosamine | β(1→4) | Chitin | *Azorhizobium caulinodans* nodC (N-acetylglucosaminyltransferase) |

In some embodiments, an FKS1 fiber-synthesizing enzyme has an amino acid sequence according to SEQ ID NO: 1 (UniProt Accession No. P38631). In various embodiments, a fiber-synthesizing enzyme has at least 80% identity to SEQ ID NO: 1, e.g., at least 80%, 85%, 90%, 95%, 96%, 97%, 98%, 99%, or 100% identity to SEQ ID NO: 1. The present disclosure further includes nucleic acid sequences encoding an FKS1 fiber-synthesizing enzyme. In certain embodiments, a nucleic acid sequence encoding an FKS1 fiber-synthesizing enzyme is a sequence engineered for expression in *B. subtilis*, e.g., a nucleic acid sequence having at least 80% identity to SEQ ID NO: 2, e.g., at least 80%, 85%, 90%, 95%, 96%, 97%, 98%, 99%, or 100% identity to SEQ ID NO: 2.

In some embodiments, a CALS1 fiber-synthesizing enzyme has an amino acid sequence according to SEQ ID NO: 3 (UniProt Accession No. Q9AUE0). In various embodiments, a fiber-synthesizing enzyme has at least 80% identity to SEQ ID NO: 3, e.g., at least 80%, 85%, 90%, 95%, 96%, 97%, 98%, 99%, or 100% identity to SEQ ID NO: 3. The present disclosure further includes nucleic acid sequences encoding a CALS1 fiber-synthesizing enzyme. In certain embodiments, a nucleic acid sequence encoding a CALS1 fiber-synthesizing enzyme is a sequence engineered for expression in *B. subtilis*, e.g., a nucleic acid sequence having at least 80% identity to SEQ ID NO: 4, e.g., at least 80%, 85%, 90%, 95%, 96%, 97%, 98%, 99%, or 100% identity to SEQ ID NO: 4.

In some embodiments, a CSLF6 fiber-synthesizing enzyme has an amino acid sequence according to SEQ ID NO: 5 (UniProt Accession No. Q84UP7). In various embodiments, a fiber-synthesizing enzyme has at least 80% identity to SEQ ID NO: 5, e.g., at least 80%, 85%, 90%, 95%, 96%, 97%, 98%, 99%, or 100% identity to SEQ ID NO: 5. The present disclosure further includes nucleic acid sequences encoding a CSLF6 fiber-synthesizing enzyme. In certain embodiments, a nucleic acid sequence encoding a CSLF6 fiber-synthesizing enzyme is a sequence engineered for expression in *B. subtilis*, e.g., a nucleic acid sequence having at least 80% identity to SEQ ID NO: 6, e.g., at least 80%, 85%, 90%, 95%, 96%, 97%, 98%, 99%, or 100% identity to SEQ ID NO: 6.

In some embodiments, a KRE9 fiber-synthesizing enzyme has an amino acid sequence according to SEQ ID NO: 7 (UniProt Accession No. P39005). In various embodiments, a fiber-synthesizing enzyme has at least 80% identity to SEQ ID NO: 7, e.g., at least 80%, 85%, 90%, 95%, 96%, 97%, 98%, 99%, or 100% identity to SEQ ID NO: 7. The present disclosure further includes nucleic acid sequences encoding a KRE9 fiber-synthesizing enzyme. In certain embodiments, a nucleic acid sequence encoding a KRE9 fiber-synthesizing enzyme is a sequence engineered for expression in *B. subtilis*, e.g., a nucleic acid sequence having at least 80% identity to SEQ ID NO: 8, e.g., at least 80%, 85%, 90%, 95%, 96%, 97%, 98%, 99%, or 100% identity to SEQ ID NO: 8.

In some embodiments, a MutB fiber-synthesizing enzyme has an amino acid sequence according to SEQ ID NO: 9 (UniProt Accession No. Q2PS28). In various embodiments, a fiber-synthesizing enzyme has at least 80% identity to SEQ ID NO: 9, e.g., at least 80%, 85%, 90%, 95%, 96%, 97%, 98%, 99%, or 100% identity to SEQ ID NO: 9. The present disclosure further includes nucleic acid sequences encoding a MutB fiber-synthesizing enzyme. In certain embodiments, a nucleic acid sequence encoding a MutB fiber-synthesizing enzyme is a sequence engineered for expression in *B. subtilis*, e.g., a nucleic acid sequence having at least 80% identity to SEQ ID NO: 10, e.g., at least 80%, 85%, 90%, 95%, 96%, 97%, 98%, 99%, or 100% identity to SEQ ID NO: 10.

In some embodiments, a otsA fiber-synthesizing enzyme has an amino acid sequence according to SEQ ID NO: 33 (UniProt Accession No. P31677). In various embodiments, a fiber-synthesizing enzyme has at least 80% identity to SEQ ID NO: 33, e.g., at least 80%, 85%, 90%, 95%, 96%, 97%, 98%, 99%, or 100% identity to SEQ ID NO: 33. The present disclosure further includes nucleic acid sequences encoding a MutB fiber-synthesizing enzyme. In certain embodiments, a nucleic acid sequence encoding a MutB fiber-synthesizing enzyme is a sequence engineered for expression in *B. subtilis*, e.g., a nucleic acid sequence having at least 80% identity to SEQ ID NO: 34, e.g., at least 80%, 85%, 90%, 95%, 96%, 97%, 98%, 99%, or 100% identity to SEQ ID NO: 34.

In some embodiments, an InuJ fiber-synthesizing enzyme has an amino acid sequence according to SEQ ID NO: 11 (UniProt Accession No. Q74K42). In various embodiments, a fiber-synthesizing enzyme has at least 80% identity to SEQ ID NO: 11, e.g., at least 80%, 85%, 90%, 95%, 96%, 97%, 98%, 99%, or 100% identity to SEQ ID NO: 11. The present disclosure further includes nucleic acid sequences encoding an InuJ fiber-synthesizing enzyme. In certain embodiments, a nucleic acid sequence encoding an InuJ fiber-synthesizing enzyme is a sequence engineered for expression in *B. subtilis*, e.g., a nucleic acid sequence having at least 80% identity to SEQ ID NO: 12, e.g., at least 80%, 85%, 90%, 95%, 96%, 97%, 98%, 99%, or 100% identity to SEQ ID NO: 12.

In some embodiments, an RFS fiber-synthesizing enzyme has an amino acid sequence according to SEQ ID NO: 13 (UniProt Accession No. Q5VQG4). In various embodiments, a fiber-synthesizing enzyme has at least 80% identity to SEQ ID NO: 13, e.g., at least 80%, 85%, 90%, 95%, 96%, 97%, 98%, 99%, or 100% identity to SEQ ID NO: 13. The present disclosure further includes nucleic acid sequences encoding an RFS fiber-synthesizing enzyme. In certain embodiments, a nucleic acid sequence encoding an RFS fiber-synthesizing enzyme is a sequence engineered for expression in *B. subtilis*, e.g., a nucleic acid sequence having at least 80% identity to SEQ ID NO:14, e.g., at least 80%, 85%, 90%, 95%, 96%, 97%, 98%, 99%, or 100% identity to SEQ ID NO: 14.

In some embodiments, a IgtC fiber-synthesizing enzyme has an amino acid sequence according to SEQ ID NO: 35 (UniProt Accession No. Q8KHJ3). In various embodiments, a fiber-synthesizing enzyme has at least 80% identity to SEQ ID NO: 35, e.g., at least 80%, 85%, 90%, 95%, 96%, 97%, 98%, 99%, or 100% identity to SEQ ID NO: 35. The present disclosure further includes nucleic acid sequences encoding a IgtC fiber-synthesizing enzyme. In certain embodiments, a nucleic acid sequence encoding a IgtC fiber-synthesizing enzyme is a sequence engineered for expression in *B. subtilis*, e.g., a nucleic acid sequence having at least 80% identity to SEQ ID NO: 36, e.g., at least 80%, 85%, 90%, 95%, 96%, 97%, 98%, 99%, or 100% identity to SEQ ID NO: 36.

In some embodiments, a tll0994 fiber-synthesizing enzyme has an amino acid sequence according to SEQ ID NO: 37 (UniProt Accession No. Q8DK72). In various embodiments, a fiber-synthesizing enzyme has at least 80% identity to SEQ ID NO: 37, e.g., at least 80%, 85%, 90%, 95%, 96%, 97%, 98%, 99%, or 100% identity to SEQ ID NO: 37. The present disclosure further includes nucleic acid sequences encoding a tll0994 fiber-synthesizing enzyme. In certain embodiments, a nucleic acid sequence encoding a tll0994 fiber-synthesizing enzyme is a sequence engineered for expression in *B. subtilis*, e.g., a nucleic acid sequence having at least 80% identity to SEQ ID NO: 38, e.g., at least 80%, 85%, 90%, 95%, 96%, 97%, 98%, 99%, or 100% identity to SEQ ID NO: 38.

In some embodiments, a BgaB fiber-synthesizing enzyme has an amino acid sequence according to SEQ ID NO: 39 (UniProt Accession No. P19668). In various embodiments, a fiber-synthesizing enzyme has at least 80% identity to SEQ ID NO: 39, e.g., at least 80%, 85%, 90%, 95%, 96%, 97%, 98%, 99%, or 100% identity to SEQ ID NO: 39. The present disclosure further includes nucleic acid sequences encoding a BgaB fiber-synthesizing enzyme. In certain embodiments, a nucleic acid sequence encoding a BgaB fiber-synthesizing enzyme is a sequence engineered for expression in *B. subtilis*, e.g., a nucleic acid sequence having at least 80% identity to SEQ ID NO: 40, e.g., at least 80%, 85%, 90%, 95%, 96%, 97%, 98%, 99%, or 100% identity to SEQ ID NO: 40.

In some embodiments, a Bga fiber-synthesizing enzyme has an amino acid sequence according to SEQ ID NO: 41 (UniProt Accession No. E5RWQ2). In various embodiments, a fiber-synthesizing enzyme has at least 80% identity to SEQ ID NO: 41, e.g., at least 80%, 85%, 90%, 95%, 96%, 97%, 98%, 99%, or 100% identity to SEQ ID NO: 41. The present disclosure further includes nucleic acid sequences encoding a Bga fiber-synthesizing enzyme. In certain embodiments, a nucleic acid sequence encoding a Bga fiber-synthesizing enzyme is a sequence engineered for expression in *B. subtilis*, e.g., a nucleic acid sequence having at least 80% identity to SEQ ID NO: 42, e.g., at least 80%, 85%, 90%, 95%, 96%, 97%, 98%, 99%, or 100% identity to SEQ ID NO: 42.

In some embodiments, a ScsAB fiber-synthesizing enzyme has an amino acid sequence according to SEQ ID NO: 43 (UniProt Accession No. P0CW87). In various embodiments, a fiber-synthesizing enzyme has at least 80% identity to SEQ ID NO: 43, e.g., at least 80%, 85%, 90%, 95%, 96%, 97%, 98%, 99%, or 100% identity to SEQ ID NO: 43. The present disclosure further includes nucleic acid sequences encoding a ScsAB fiber-synthesizing enzyme. In certain embodiments, a nucleic acid sequence encoding a ScsAB fiber-synthesizing enzyme is a sequence engineered for expression in *B. subtilis*, e.g., a nucleic acid sequence having at least 80% identity to SEQ ID NO: 44, e.g., at least 80%, 85%, 90%, 95%, 96%, 97%, 98%, 99%, or 100% identity to SEQ ID NO: 44.

In some embodiments, a Ss1 fiber-synthesizing enzyme has an amino acid sequence according to SEQ ID NO: 45 (UniProt Accession No. 049064). In various embodiments, a fiber-synthesizing enzyme has at least 80% identity to SEQ ID NO: 45, e.g., at least 80%, 85%, 90%, 95%, 96%, 97%, 98%, 99%, or 100% identity to SEQ ID NO: 45. The present disclosure further includes nucleic acid sequences encoding a Ss1 fiber-synthesizing enzyme. In certain embodiments, a nucleic acid sequence encoding a Ss1 fiber-synthesizing enzyme is a sequence engineered for expression in *B. subtilis*, e.g., a nucleic acid sequence having at least 80% identity to SEQ ID NO: 46, e.g., at least 80%, 85%, 90%, 95%, 96%, 97%, 98%, 99%, or 100% identity to SEQ ID NO: 46.

In some embodiments, a SBE3 fiber-synthesizing enzyme has an amino acid sequence according to SEQ ID NO: 47 (UniProt Accession No. D2WL32). In various embodiments, a fiber-synthesizing enzyme has at least 80% identity to SEQ ID NO: 47, e.g., at least 80%, 85%, 90%, 95%, 96%, 97%, 98%, 99%, or 100% identity to SEQ ID NO: 47. The present disclosure further includes nucleic acid sequences encoding a SBE3 fiber-synthesizing enzyme. In certain embodiments, a nucleic acid sequence encoding a SBE3 fiber-synthesizing enzyme is a sequence engineered for expression in *B. subtilis*, e.g., a nucleic acid sequence having at least 80% identity to SEQ ID NO: 48, e.g., at least 80%, 85%, 90%, 95%, 96%, 97%, 98%, 99%, or 100% identity to SEQ ID NO: 48.

In some embodiments, a HlgA fiber-synthesizing enzyme has an amino acid sequence according to SEQ ID NO: 49 (UniProt Accession No. P39125). In various embodiments, a fiber-synthesizing enzyme has at least 80% identity to SEQ ID NO: 49, e.g., at least 80%, 85%, 90%, 95%, 96%, 97%, 98%, 99%, or 100% identity to SEQ ID NO: 49. The present disclosure further includes nucleic acid sequences encoding a HlgA fiber-synthesizing enzyme. In certain embodiments, a nucleic acid sequence encoding a HlgA fiber-synthesizing enzyme is a sequence engineered for expression in *B. subtilis*, e.g., a nucleic acid sequence having at least 80% identity to SEQ ID NO: 50, e.g., at least 80%, 85%, 90%, 95%, 96%, 97%, 98%, 99%, or 100% identity to SEQ ID NO: 50.

In some embodiments, a GAUT1 fiber-synthesizing enzyme has an amino acid sequence according to SEQ ID NO: 51 (UniProt Accession No. Q9LE59). In various embodiments, a fiber-synthesizing enzyme has at least 80% identity to SEQ ID NO: 51, e.g., at least 80%, 85%, 90%, 95%, 96%, 97%, 98%, 99%, or 100% identity to SEQ ID NO: 51. The present disclosure further includes nucleic acid sequences encoding a GAUT1 fiber-synthesizing enzyme. In certain embodiments, a nucleic acid sequence encoding a GAUT1 fiber-synthesizing enzyme is a sequence engineered for expression in *B. subtilis*, e.g., a nucleic acid sequence having at least 80% identity to SEQ ID NO: 52, e.g., at least 80%, 85%, 90%, 95%, 96%, 97%, 98%, 99%, or 100% identity to SEQ ID NO: 52.

In some embodiments, a NodC fiber-synthesizing enzyme has an amino acid sequence according to SEQ ID NO: 53 (UniProt Accession No. Q07755). In various embodiments, a fiber-synthesizing enzyme has at least 80% identity to SEQ ID NO: 53, e.g., at least 80%, 85%, 90%, 95%, 96%, 97%, 98%, 99%, or 100% identity to SEQ ID NO: 53. The present disclosure further includes nucleic acid sequences encoding a NodC fiber-synthesizing enzyme. In certain embodiments, a nucleic acid sequence encoding a NodC fiber-synthesizing enzyme is a sequence engineered for expression in *B. subtilis*, e.g., a nucleic acid sequence having at least 80% identity to SEQ ID NO: 54, e.g., at least 80%, 85%, 90%, 95%, 96%, 97%, 98%, 99%, or 100% identity to SEQ ID NO: 54.

In some embodiments, a levansucrase fiber-synthesizing enzyme has an amino acid sequence according to SEQ ID NO: 15 (UniProt Accession No. Q43998), a levansucrase enzyme expressed by *Acetobacter diazotrophicus*, and/or a levansucrase enzyme encoded by *Acetobacter diazotrophicus* lsdA. In various embodiments, a fiber-synthesizing enzyme has at least 80% identity to SEQ ID NO: 15, e.g., at least 80%, 85%, 90%, 95%, 96%, 97%, 98%, 99%, or 100% identity to SEQ ID NO: 15.

In some embodiments, a levansucrase fiber-synthesizing enzyme has an amino acid sequence according to SEQ ID NO: 16 (UniProt Accession No. P0DJA3), a levansucrase enzyme expressed by *Zymomonas mobilis* subsp. *Mobilis*, and/or a levansucrase enzyme encoded by *Zymomonas mobilis* subsp. *mobilis* sacB. In various embodiments, a fiber-synthesizing enzyme has at least 80% identity to SEQ ID NO: 16, e.g., at least 80%, 85%, 90%, 95%, 96%, 97%, 98%, 99%, or 100% identity to SEQ ID NO: 16.

In some embodiments, a levansucrase fiber-synthesizing enzyme has an amino acid sequence according to SEQ ID NO: 17 (UniProt Accession No. Q97181), a levansucrase enzyme expressed by *Clostridium acetobutylicum*, and/or a levansucrase enzyme encoded by *Clostridium acetobutylicum* sacB. In various embodiments, a fiber-synthesizing enzyme has at least 80% identity to SEQ ID NO: 17, e.g., at least 80%, 85%, 90%, 95%, 96%, 97%, 98%, 99%, or 100% identity to SEQ ID NO: 17.

In some embodiments, a levansucrase fiber-synthesizing enzyme has an amino acid sequence according to SEQ ID NO: 18 (UniProt Accession No. P05655), a levansucrase enzyme expressed by *Bacillus Subtilis* natto or *Bacillus Subtilis* PY79, and/or a levansucrase enzyme encoded by *Bacillus Subtilis* natto sacB and/or *Bacillus Subtilis* PY79 sacB. In various embodiments, a fiber-synthesizing enzyme has at least 80% identity to SEQ ID NO: 18, e.g., at least 80%, 85%, 90%, 95%, 96%, 97%, 98%, 99%, or 100% identity to SEQ ID NO: 18.

The present disclosure further includes nucleic acid sequences encoding a levansucrase fiber-synthesizing enzyme. In certain embodiments, a nucleic acid sequence encoding a levansucrase fiber-synthesizing enzyme is a sequence engineered for expression in *B. subtilis*, e.g., a nucleic acid sequence having at least 80% identity to SEQ ID NO: 19, e.g., at least 80%, 85%, 90%, 95%, 96%, 97%, 98%, 99%, or 100% identity to SEQ ID NO: 19. Those of skill in the art will appreciate that fiber-synthesizing enzymes of the present disclosure are effective to produce fiber when provided with enzyme substrate as disclosed herein. Accordingly, at least because as those of skill in the art will appreciate many bacteria are able to process monosaccharides and/or disaccharides into modified forms, constituent monosaccharides, and/or other substrate carbohydrates those of skill will appreciate that a variety of carbohydrate sources may be decreased in the gut and consumed directly or indirectly by enzymes or by cells of the present disclosure that express such fiber-synthesizing enzymes. In general, it is to be appreciated that any of, for example, glucose, sucrose, or fructose may be modified and/or processed to provide enzyme substrate carbohydrates for the production of any of a wide variety of fibers as disclosed herein, including particular fibers produced by particular enzymes as disclosed herein. Accordingly, in certain embodiments, fiber-synthesizing enzymes of the present disclosure can directly utilize gut carbohydrate and in certain embodiments can utilize modified and/or processed forms.

In some embodiments, fiber produced by a composition or method of the present disclosure is soluble levan fiber. Levan is a naturally occurring fructan present in certain plant and microorganism species. Rare fibers such as levan can favor a healthy and/or healthily balanced microbiome or microbiome composition, e.g., by stimulating the growth and/or increasing the concentration and/or amount of various beneficial types of gut microbiome constituent microbes such as Bifidobacteria, *Roseburia*, and/or *Eubacterium* rectale. For at least these reasons, increasing levan can increase the concentration or amount of beneficial molecules such as butyrate and propionate. Fructans such as levan can be synthesized from sucrose. Levan is known to be abundantly produced when the bacterium *Bacillus subtilis* sp. *Natto* (*B.s. Natto*) is cultured on soy beans and *B.s. natto* can be used to make the food 'Natto' (for which the bacterial strain is named). *B.s. natto* likely originated from the soil and is not a commensal of the human gut.

Levan fiber polymer is made up of fructose, a monosaccharide, conjugated in 2,6 beta glycosidic linkages. In some embodiments of the present disclosure, levan fiber is enzymatically synthesized by a process and/or enzyme that utilizes a fructose molecule liberated by enzymatic digestion of sucrose (which includes two monosaccharide moieties, one glucose and one fructose). In some embodiments, the present disclosure includes a levansucrase enzyme that synthesizes levan from sucrose. In various embodiments, a levansucrase enzyme can cleave sucrose into constituent monosaccharide moieties and incorporate the fructose monosaccharide moiety into levan. Accordingly, without wishing to be bound by theory, a levansucrase enzyme can convert 50% of the carbohydrate biomass and/or monosaccharide moieties, and/or 100% of the fructose biomass and/or fructose moieties, generated by levansucrase cleavage of sucrose to soluble fiber.

In various embodiments a fiber-synthesizing enzyme of the present disclosure can synthesize fiber from substrates including carbohydrate (e.g., monosaccharides and/or disaccharides) within or across a pH range of (e.g., in an environment characterized by a pH that is in the range of) 5.7 to 8.5 In certain embodiments, a fiber-synthesizing enzyme of the present disclosure can synthesize fiber at pH 5.7, pH 6.0, pH 7.4, and/or pH 8.5. In certain embodiments, a fiber-synthesizing enzyme of the present disclosure can synthesize fiber within or across a pH range of 5.7 to 6.0, 6.0 to 7.4, and/or 7.4 to 8.5, or within or across a range having a lower bound selected from about 5.5, 5.6, 5.7, 5.8, 5.9, 6.0, 6.1, 6.2, 6.3, 6.4, 6.5, 6.6, 6.7, 6.8, 6.9, and 7.0 and an upper bound selected from about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. Without wishing to be bound by any particularly scientific theory, the human gastrointestinal tract pH typically gradually increases in the small intestine from about pH 6 to about pH 7.4 in the terminal ileum, drops to about 5.7 in the caecum, and again gradually increases through the colon, reaching about pH 6.7 in the rectum. Those of skill in the art will appreciate that various established techniques can be used to modify polypeptide pH and/or peptidase resistance. In various embodiments, a fiber-synthesizing enzyme of the present disclosure is secluded and/or protected within a fiber matrix that prevents larger peptidases from engaging in degradation of the enzyme (while still allowing agents for fiber synthesis, such as carbohydrate, e.g., sucrose, to contact the enzyme). Those of skill in the art will further appreciate that coding sequences encoding a fiber-synthesizing enzyme of the present disclosure can be modified to reflect codon usage of a cell in which the enzyme is expressed.

In various embodiments, a polypeptide of the present disclosure (e.g., an enzyme, e.g., a levansucrase enzyme) is operably linked with a secretion polypeptide. Identification of secretion polypeptides is common in the art, e.g., by synthesis of a fusion polypeptides including signaling polypeptides of interest and screening the fusion polypeptides for secretion from an exemplary cell. Exemplary signal sequences can include, without limitation, those provided in Table 2.

TABLE 2

Secretion polypeptides

| Name | Amino Acid Sequence |
|---|---|
| sacB | MNIKKFAKQATVLTFTTALLAGGATQAFA (SEQ ID NO: 55) |
| yvcE | MRKSLITLGLASVIGTSSFLIPFTSKTASA (SEQ ID NO: 56) |
| yoqM | MKLRKVLTGSVLSLGLLVSASPAFA (SEQ ID NO: 57) |
| yuaB | MKRKLLSSLAISALSLGLLVSAPTASFAAE (SEQ ID NO: 58) |
| pel | MKKVMLATALFLGLTPAGANA (SEQ ID NO: 59) |
| pelB | MKRLCLWFTVFSLFLVLLPGKALG (SEQ ID NO: 60) |
| yoaW | MKKMLMLAFTFLLALTIHVGEASA (SEQ ID NO: 61) |
| yqxI | MFKKLLLATSALTFSLSLVLPLDGHAKA (SEQ ID NO: 62) |
| lipA | MKFVKRRIIALVTILMLSVTSLFALQPSAKAA (SEQ ID NO: 63) |
| lipB | MKKVLMAFIICLSLILSVLAAPPSGAKA (SEQ ID NO: 64) |
| yoqH | MKRFILVLSFLSIIVAYPIQTNA (SEQ ID NO: 65) |
| ybfO | MKRMIVRMTLPLLIVCLAFSSFSASARA (SEQ ID NO: 66) |
| sacB | MNIKKFAKQTVLTFTTALLAGGATQAFA (SEQ ID NO: 67) |
| bglS | MPYLKRVLLLLVTGLFMSLFAVTATASA (SEQ ID NO: 68) |
| yddT | MRKKRVITCVMAASLTLGSLLPAGYASA (SEQ ID NO: 69) |
| yobB | MKIRKILLSSALSFGMLISAVPALA (SEQ ID NO: 70) |

Those of skill in the art will further appreciate that further signal sequences are present in the *Bacillus subtilis* genome and can be included in transgene and enzymes of the present disclosure. Of the three known secretory routes in *B. subtilis*, the Sec pathway directs the majority of secretory proteins into the growth medium. Alternatively, a small number of exoproteins with specific functions are secreted via the Tat pathway or ABC. Export by the Sec pathway can be achieved by inclusion in a polypeptide of a hydrophobic secretion polypeptide at the N-terminus of the secreted polypeptide, which secretion polypeptide can be about 20 amino acids in length and can include, in some examples, 3 regions: a positively charged amino terminal, a hydrophobic core, and a polar carboxyl-terminal. A commercial kit (Takara Bio) is available to test with limited effort 173 distinct secretion polypeptides. In certain Examples provided herein, a fusion polypeptide includes a levansucrase enzyme operatively linked to a secretion polypeptide derived from a sequence naturally associated with SacB.

Expression of a fiber-synthesizing enzyme engineered to include a secretion polypeptide (also known in the art as a secretion signal) can result in secretion of the enzyme (e.g., secretion from cells including a transgene encoding the fiber-synthesizing enzyme, e.g., into gut of a subject to which the cells were administered). The present disclosure includes the recognition that, in various embodiments, synthesis of fiber from carbohydrate in the gut can advantageously occur extracellularly with respect to administered engineered cells of the present disclosure. For example, extracellular synthesis of fiber by a fiber-synthesizing enzyme delivered to the gut by engineered cells of the present disclosure can obviate the need to import sucrose across the cell membrane into the cytosol of engineered cells, resulting in higher enzyme activity than would be achieved by intracellular expression of enzyme, and therefore faster and/or greater consumption of sugar and/or synthesis of fiber. Moreover, because comparatively higher sucrose concentrations can cause production of comparatively higher molecular weight fiber molecules, synthesis of fiber in the gut where carbohydrate concentration is maximal can increase average fiber molecular weight.

Various methods are known in the art for selecting a secretion polypeptide for pairing (e.g., fusing or otherwise operably linking) with a polypeptide or nucleic acid sequence encoding the polypeptide. For example, various commercial kits such as that from Takara Bio (3380—*B. subtilis* Secretory Protein Expression System) are available for rapid screening of secretion polypeptides. Those of skill in the art will further appreciate that laboratory methods can be used to select or evolve (e.g., by random evolution) variants of fusion polypeptides that include a fiber-synthesizing enzyme of the present disclosure and a secretion polypeptide, where the variants can have increased stability and/or expression as compared to a reference fusion polypeptide (e.g., fusion polypeptide prior to section or evolution). In various embodiments, a secretion polypeptide of the present disclosure can be selected based on the cell type in which an engineered polypeptide (e.g., a fusion polypeptide) is expressed.

In various embodiments, a fiber-synthesizing enzyme of the present disclosure is not secreted. Accordingly, in some embodiments a fiber-synthesizing enzyme is engineered for secretion such that the enzyme acts directly on substrates present in the gut, and in some embodiments a fiber-synthesizing enzyme is engineered such that it is not secreted and acts on substrates internalized by a cell that expresses a fiber-synthesizing enzyme. Exemplary secreted enzymes can include a sucrose isomerase, trehalulose synthase, inulinsucrase, levanosucrase, beta-galactosidas, or b-D-Galactosidase. Accordingly, certain such secreted fiber-synthesizing enzymes can utilize substrate present in gut and decrease the concentration or amount of that substrate in gut (e.g., the substrate sucrose for sucrose isomerase, trehalulose synthase, inulinsucrase, or levanosucrase, or the substrate lactose for beta-galactosidas, or b-D-Galactosidase). Exemplary fiber-sythensizing enzymes that in various embodiments are not secreted and synthesize fiber at or in cells of the present disclosure (e.g., through cytosolic or membrane activity) can include a 1,3-beta-glucan synthase, 1,3;1,4-beta-D-glucan synthase, 1,3-beta-glucan synthase, 1,6-beta-glucan synthase, Trehalose-6-phosphate synthase, 1,6-alpha-galactosyltransferase, α-1,4-galactosyltransferase, Alpha-1,2-fucosyltransferase, cellulose synthase, maltose synthase, starch synthase, Starch-branching enzyme, Glycogen synthase, galacturonosyltransferase, or Chitinoligosaccharide synthase. Accordingly, various non-secreted fiber-synthesizing enzymes present in the cytosol or membranes of cells of the present disclosure can act on substrates internalized by cells and optionally modified by cells prior to use as a substrate in fiber synthesis by the enzyme. Fiber-synthesizing enzymes such as 1,3-beta-glucan synthase, 1,3;1,4-beta-D-glucan synthase, 1,3-beta-glucan synthase, 1,6-beta-glucan synthase, Trehalose-6-phosphate synthase, cellulose synthase, maltose synthase, starch synthase, and Starch-branching enzyme can utilize UDP-glucose as a substrate where activity of the enzyme decreases the amount or concentration of glucose, sucrose, and/or fructose in gut, in that glucose, sucrose, and/or fructose carbohydrates taken up by cells are naturally converted to UDP-glucose that provide a substrate for the fiber-synthesizing enzyme. Fiber-synthesizing enzymes such as Glycogen synthase can utilize ADP-α-D-glucose as a substrate where activity of the enzyme decreases the amount or concentration of glucose, sucrose, and/or fructose in gut, in that glucose, sucrose, and/or fructose carbohydrates taken up by cells are naturally converted to ADP-α-D-glucose that provides a substrate for the fiber-synthesizing enzyme. Fiber-synthesizing enzymes such as α-1,4-galactosyltransferase can utilize UDP-galactose as a substrate where activity of the enzyme decreases the amount or concentration of lactose in gut, in that lactose carbohydrates taken up by cells are naturally converted to UDP-galactose that provides a substrate for the fiber-synthesizing enzyme. Fiber-synthesizing enzymes such as Alpha-1,2-fucosyltransferase can utilize UDP-galactose and/or UDP-fucose as a substrate where activity of the enzyme decreases the amount or concentration of lactose in gut, in that lactose carbohydrates taken up by cells are naturally converted to utilize UDP-galactose and/or UDP-fucose that provide a substrate for the fiber-synthesizing enzyme. Fiber-synthesizing enzymes such as 1,6-alpha-galactosyltransferase can utilize lactose and/or galactinol as a substrate where activity of the enzyme decreases the amount or concentration of lactose in gut, in that lactose carbohydrates taken up by cells are naturally converted to lactose and/or galactinol that provide a substrate for the fiber-synthesizing enzyme. Fiber-synthesizing enzymes such galacturonosyltransferase can utilize various molecules as a substrate where activity of the enzyme decreases the amount or concentration of glucose, sucrose, and/or fructose in gut, in that glucose, sucrose, and/or fructose carbohydrates taken up by cells are naturally converted to substrates of the fiber-synthesizing enzyme. Fiber-synthesizing enzymes such Chitinoligosaccharide synthase can utilize UDP-N-acetyl-alpha-D-glucosamine as a substrate where activity of the enzyme decreases the amount or concentration of glucose, sucrose, and/or fructose in gut, in that glucose, sucrose, and/or fructose carbohydrates taken up by cells are naturally converted to UDP-N-acetyl-alpha-D-glucosamine that provide sa substrate for the fiber-synthesizing enzyme.

The present disclosure generally includes, among other things, the innovation of administering to a subject an engineered cells that encodes and/or expresses a fiber-synthesizing enzyme of the present disclosure. Those of skill in the art will further appreciate that, in various embodiments, a nucleic acid sequence encoding a fiber-synthesizing enzyme of the present disclosure can be operably linked with a regulatory nucleic acid sequence that controls expression of the enzyme in the cell. Moreover, as those of skill in the art will appreciate, a wide variety of regulatory nucleic acid sequences for operable linkage to coding sequences and/or for expression of encoded polypeptides are known in the art.

In some embodiments, a regulatory nucleic acid can be a constitutive promoter and/or cause constitutive expression of a polypeptide encoded by an operably linked coding sequence, e.g., in bacteria (e.g., in *B. subtilis*). In some embodiments, a regulatory nucleic acid can be a conditional promoter and/or cause conditional expression of a polypeptide encoded by an operably linked coding sequence, e.g., in bacteria (e.g., in *B. subtilis*). In various embodiments, a bacterial regulatory nucleic acid sequence can be a promoter selected from T7, T7lac, Sp6, araBAD, trp, lac, Ptac, or pL. In some embodiments a regulatory nucleic acid sequence can be a *B. subtilis* promoter is selected from Pveg, PserA, PymdA, PfbaA, Pzwf, PfoleA, Ppgi, PlepA, or PrelA, e.g., as set forth in Guiziou (2016 *Nucl. Acids Res.* 44(15): 7495-7508), which is herein incorporated by reference with respect to *B. subtilis* promoters and in its entirety.

In various embodiments, an exemplary regulatory nucleic acid can be based on regulator nucleic acid sequence(s) associated with expression of, e.g., flagellar machinery. Such regulatory nucleic acid sequences have been previously adapted for constitutive and/or robust expression of polypeptide encoded by an operably linked coding nucleic acid sequence. Various bacteria (e.g., *B. subtilis*) regulate expression of a flagellin gene locus (in some systems referred to as hag) by a regulatory system that includes positive and negative control. Removal and/or reduction of negative regulation of flagellin gene locus expression and/or addition of or increased positive regulation of flagellin gene locus expression can be utilized to increase expression from a flagellin promoter. Typically, without wishing to be bound by any particular scientific theory, expression of the flagellin gene locus is positively controlled by a sigma factor, SigD, which is repressed by the FlgM protein. Deletion of flgM and/or reduction of FlgM expression significantly enhances expression and/or activity of SigD, and consequently results in increased and/or constitutive expression of the flagellin gene locus. Typically, without wishing to be bound by any particular scientific theory, expression of flagellar subunits can be negatively, post-transcriptionally controlled by binding of a protein referred to as CsrA to a ribosome binding site present in flagellin gene locus transcripts. Deletion of csrA and/or reduction of CsrA expression significantly enhances expression of flagellar subunits. Deletion and/or reduction of one or more CsrA binding sites in flagellin gene regulatory nucleic acid sequence(s) can additionally or laternatively significantly increases expression of flagellar subunits. In various embodiments, certain point mutations in a CsrA binding site can reduce and/or abrogate negative control of flagellar subunit expression by CsrA. Accordingly, in various embodiments, expression of a nucleic acid operably linked with a flagellin gene regulatory nucleic acid sequence (e.g., a flagellin promoter, e.g., a hag promoter) can be increased by either or both of (i) deleting the flgM gene and/or (ii) a point mutation in the CsrA-binding site, e.g., in *B. subtilis*. Those of skill in the art will therefore appreciate that, if the coding nucleic acid sequence of the flagellin gene is replaced with a nucleic acid sequence encoding a fiber-synthesizing enzyme (e.g., a levansucrase enzyme) such that the fiber-synthesizing enzyme is operably linked to flagellin gene regulatory sequence(s) (e.g., including the hag promoter), the fiber-synthesizing enzyume can be expressed at high and/or constitutive levels. In various embodiments, the fiber-synthesizing enzyme includes a secretion polypeptide.

In certain embodiments, a transgene of the present disclosure includes a nucleic acid sequence that encodes a levansucrase enzyme operably linked with a flagellin gene regulatory nucleic acid sequence, e.g., a flagellin gene promoter. In certain embodiments, a transgene of the present disclosure can include a nucleic acid sequence that encodes a levansucrase enzyme is operably linked with a hag promoter. In various embodiments, the levansucrase enzyme includes a secretion polypeptide.

Those of skill in the art will appreciate that endogenous sacB loci can include regulatory elements that repress sacB expression in the absence of sucrose. In the digestive tract, residence time of digesta can be shorter than the time required for induction of expression by consumed carbohydrate (e.g., sucrose), as the residence time can be less than 20 minutes. Moreover, endogenous gut enzymes can also breakdown carbohydrates. The present disclosure therefore includes embodiments in which fiber-synthesizing enzyme is constitutively expressed to increase the overlap of digesta residence in gut and fiber-synthesizing enzyme activity in gut. Constitutive expression of fiber-synthesizing enzyme in gut can result in accumulation of fiber-synthesizing enzyme available for synthesis of fiber from carbohydrate, e.g., digestion during consumption and digestion.

The present disclosure further includes nucleic acid vectors that include transgenes of the present disclosure. Those of skill in the art will appreciate that a wide variety of vectors, such as plasmids, are available for introduction of heterologous nucleic acids into target cells, e.g., bacterial target cells disclosed herein, e.g., with integration of a heterologous nucleic acid sequence into the genome of target cells. Exemplary vectors can include plasmids and viral vectors. In various embodiments vectors include a selectable marker and/or counter-selectable marker. In some embodiments, a vector is engineered for integration of heterologous nucleic acid sequence into a target cell genome by homologous recombination. In some embodiments, a vector is engineered for unstable integration of a heterologous nucleic acid sequence into a target cell genome (e.g., in some embodiments, by production of merodiploid cells). In some embodiments, a vector is engineered to integrate into a host cell genome by a single crossover event subsequently resolved by subsequent double-crossover resulting in loss of plasmid DNA, such as those made from pminiMAD or pMAD plasmids.

Engineered Cells

The present disclosure includes cells (e.g., spores) that include a heterologous nucleic acid sequence that includes a transgene that encodes and/or expresses a fiber-synthesizing enzyme of the present disclosure (such cells referred to herein as engineered cells). Those of skill in the art will appreciate that any of a wide variety of cells and/or spores can be engineered to produce, and/or used in, a composition, e.g., for administration to a subject, e.g., a human subject.

In various embodiments, engineered cells of the present disclosure can be vegetative cells and/or non-spore forming. Many cell preparations for administration to human subjects, e.g., as probiotics, include bacteria that are not capable of forming spores and/or are administered as vegetative cells (e.g., in lyophilized preparations). Common examples of non-spore forming cells that can be administered as vegetative cells include lactobacilli and bifidobacteria. *Lactobacillus* cells are commonly used. Examples of non-spore forming cells that can be administered as vegetative cells include but are not limited to members of the Bacteroidetes family (e.g. *Bacteroides unformis, Bacteroides thetaiotaomicron, Bacteroides fragilis, Bacteroides ovatus, Bacteroides vulgatus, Bacteroides caccae, Bacteroides eggerthii, Bacteroides vulgatus,* and *Parabacteroides distasonis*) and members of the Lactobacillae family (e.g., *Lactobacillus paracasei, Lactobacillus brevis, Lactobacillus casei, Lactobacillus delbrueckii, Lactobacillus gasseri, Lactobacillus rhamnosus, Lactobacillus reuteri, Lactobacillus plantarum,* and, *Lactobacillus johnsonii*).

In various embodiments, cells of the present disclosure include commensal bacteria such as Lactobacilli, clostridia, or *bacteroides*, or other cells recognized as edible in live form, such as *Saccharomyces cerevisiae*.

In various embodiments a cell is a probiotic microorganism that is safe for ingestion by an animal, e.g., a human. Probiotic microorganisms include, without limitation, from *Bacillus*, *Bifidobacterium*, *Enterococcus*, *Escherichia coli*, *Lactobacillus*, *Leuconostoc*, *Pediococcus* and *Streptococcus*. The present disclosure includes use of bacteria of the genus *Bacillus*, e.g., *B. subtilis*. In certain embodiments, the microorganism is not a eukaryote. For example, the microorganism is not a eukaryote used for fermentation of alcoholic beverages, such as *Saccharomyces*.

In certain embodiments, a cell is a bacterial cell that can form a spore. A spore can be a resilient form of a cell. Bacterial spores can be dormant living forms that can exist in a desiccated and/or dehydrated state for significant periods of time and/or indefinitely. Without wishing to be bound by any particular scientific theory, the natural life cycle of various spore forming bacteria can includes germination of the spore in the presence of environmental nutrients and/or factors, proliferation of germinated cells, and re-sporulation in the event of environmental nutrient exhaustion. In various embodiments, a spore can germinate and/or proliferate after administration to a subject, e.g., in the gut of a subject, e.g., in the intestine of a subject. Various spore-forming bacteria are known in the art and can be engineered to include, e.g., a heterologous nucleic acid including a transgene of the present disclosure. In various embodiments, an engineered cell is a cell that is in a spore state. Exemplary engineered spores of the present disclosure include engineered spores of *Bacillus* species, e.g., for administration to a subject.

A spore can be a useful cell form in the context of the present disclosure at least in part because spores can retain ability to germinate and/or porliferate after a period of storage, e.g., a long period of storage, e.g., at room temperature, and for at least this reason spores are considered to have a long useful shelf life. Shelf-life can be an important factor in safety, satisfaction, and price point for consumer products making it a valuable asset both for the provider and consumer. Additionally, the resilient spore form allows the live organism to traverse the environment of the stomach which is widely known to inactivate enzymes and active molecules not otherwise formulated to withstand traversal of the stomach. Spore form therefore enables formulation of engineered cells in forms that are pleasing to consumers. For example, while methods exist for formulating pills to enable purified and formulated therapeutic molecules to traverse the stomach, formulations such as liquid formulations (e.g., based at least in part by use of engineered spores) can also be produced and may be preferred by some consumers. Administration of spores obviates the need for certain costly formulation steps. Additionally, administration of spores can provide a staggered release of active cells from a dormant state. Thus, the present disclosure provides, among other things, compositions and methods for extended release of a therapeutic agent in the gut, where the composition includes an engineered cell, e.g., a spore form of an engineered cell. Due to their small size and resilience to heat, spores can also facilitate and/or enable lyophilization at a faster rate than comparable non-spore cells could be lyophilized with a comparable cell survival.

Those of skill in the art will appreciate that germination from spores can follow exponential decay, e.g., modelled by a constant percentage of spores germinating per minute and defined by the availability of nutrient triggers. Germination can results in a steady release of active live cells over a number of hours, which can further contribute to the period of time over which a dose is effective and/or delivers fiber-synthesizing enzyme to gut. Furthermore, active cells can re-enter a spore state in the absence of sufficient nutrients. Properties of germination and re-sporulation individual and together can allow administered cells to reside in the gut in a resilient spore form until contacted with digesta.

Spore forming bacteria and spores thereof include, for example, *Bacillus subtilis* PY79 and spores thereof. Other spore forming microbes and spores thereof include but are not limited to *Bacillus subtilis* group members (e.g. *Bacillus subtilis* subsp. *subtilis* str. 168, and *Bacillus subtilis* subsp. Natto), *Bacillus* group members (e.g. *Bacillus coagulans*, *Bacillus amyloliquefaciens*, *Bacillus lichenformis*, *Bacillus* sp., *Bacillus megatarium*, and *Bacillus subtilis* subsp. *Spizizenii*), Clostridiaceae family members (e.g., *Clostridium butyricum*, *Clostridium acetobutylicum*, *Clostridium arbusti*, *Clostridium aurantibutyricum*, *Clostridium beijerinckii*, *Clostridium cellulovorans*, *Clostridium cellulolyticum*, *Clostridium thermocellum*, *Clostridium thermobutyricum*, *Clostridium pasteurianum*, *Clostridium kluyveri*, *Clostridium novyi*, *Clostridium saccharobutylicum*, *Clostridium thermosuccinogenes*, *Clostridium thermopalmarium*, *Clostridium saccharolyticum*, *Clostridium saccharoperbutylacetonicum*, *Clostridium tyrobutyricum*, *Clostridium tetanomorphum*, *Clostridium magnum*, *Clostridium ljungdahlii*, *Clostridium autoethanogenum*, *Clostridium butyricum*, *Clostridium puniceum*, *Clostridium diolis*, *Clostridium* 5 *homopropionicum* and/or *Clostridium roseum*), and various edible yeasts such as *Saccharomyces cerevisiae*, and spores thereof.

In various embodiments, spore forming microbes and spores thereof include but are not limited to *Bacillus subtilis* group members *Bacillus subtilis* A29, *Bacillus subtilis* Abs3, *Bacillus subtilis* AP254, *Bacillus subtilis* At2, *Bacillus subtilis* B2, *Bacillus subtilis* B7-s, *Bacillus subtilis* BEST7003, *Bacillus subtilis* BEST7613, *Bacillus subtilis* BSn5, *Bacillus subtilis* E1, *Bacillus subtilis* gtP20b, *Bacillus subtilis* Hal1, *Bacillus subtilis* HJ5, *Bacillus subtilis* J22, *Bacillus subtilis* J23, *Bacillus subtilis* J24, *Bacillus subtilis* J25, *Bacillus subtilis* J26, *Bacillus subtilis* J27, *Bacillus subtilis* KCTC 1028=ATCC 6051a, *Bacillus subtilis* LX-8, *Bacillus subtilis* MB73/2, *Bacillus subtilis* Miyagi-4, *Bacillus subtilis* Miyagi-4100, *Bacillus subtilis* PRO 1, *Bacillus subtilis* PS216, *Bacillus subtilis* PTS-394, *Bacillus subtilis* PY79, *Bacillus subtilis* QB928, *Bacillus subtilis* QH-1, *Bacillus subtilis* S1-4, *Bacillus subtilis* SPZ1, *Bacillus subtilis* str. 10, *Bacillus subtilis* strain DY, *Bacillus subtilis* sub sp. *amylosacchariticus*, *Bacillus subtilis* subsp. *chungkookjang*, *Bacillus subtilis* subsp. *endophyticus*, *Bacillus subtilis* subsp. *globigii*, *Bacillus subtilis* subsp. *inaquosorum*, *Bacillus subtilis* subsp. *inaquosorum* KCTC 13429, *Bacillus subtilis* subsp. *krictiensis*, *Bacillus subtilis* subsp. *lactipan*, *Bacillus subtilis* subsp. *natto*, *Bacillus subtilis* subsp. natto BEST195, *Bacillus subtilis* subsp. *natto* HSF 1410, *Bacillus subtilis* subsp. *niger*, *Bacillus subtilis* subsp. *qingdao*, *Bacillus subtilis* subsp. *sadata*, *Bacillus subtilis* sub sp. *spizizenii*, *Bacillus subtilis* sub sp. *spizizenii* ATCC 6633, *Bacillus subtilis* subsp. *spizizenii* DV1-B-1, *Bacillus subtilis* subsp. *spizizenii* JCM2499, *Bacillus subtilis* subsp. *spizizenii* RFW-GIA3, *Bacillus subtilis* subsp. *spizizenii* RFWGIA4, *Bacillus subtilis* subsp. *spizizenii* RFWG4C10, *Bacillus subtilis* subsp. *spizizenii* RFWG5BJ5, *Bacillus subtilis* subsp. *spizizenii* str. W23, *Bacillus subtilis* subsp. *spizizenii* TU-B-10, *Bacillus subtilis* subsp. *stercoris*, *Bacillus subtilis* subsp. *subtilis*, *Bacillus subtilis* subsp. *subtilis* NCIB 3610 ATCC 6051, *Bacillus subtilis* subsp. *subtilis* 6051-HGW, *Bacillus subtilis* subsp. *subtilis* str. 168, *Bacillus subtilis* sub sp.

*subtilis* str. L170, *Bacillus subtilis* sub sp. *subtilis* str. N170, *Bacillus subtilis* subsp. *subtilis* str. AG1839, *Bacillus subtilis* subsp. *subtilis* str. AUSI98, *Bacillus subtilis* subsp. *subtilis* str. B2, *Bacillus subtilis* subsp. *subtilis* str. BAB-1, *Bacillus subtilis* subsp. *subtilis* str. BSP1, *Bacillus subtilis* subsp. *subtilis* str. JH642, *Bacillus subtilis* subsp. *subtilis* str. JH642 substr. AG174, *Bacillus subtilis* subsp. *subtilis* str. MP11, *Bacillus subtilis* subsp. *subtilis* str. MP9, *Bacillus subtilis* subsp. *subtilis* str. OH 131.1, *Bacillus subtilis* subsp. *subtilis* str. R0179, *Bacillus subtilis* subsp. *subtilis* str. RO-NN-1, *Bacillus subtilis* subsp. *subtilis* str. SC-8, *Bacillus subtilis* subsp. *subtilis* str. SMY, *Bacillus subtilis* TO-A, *Bacillus subtilis* TPK 210909, *Bacillus subtilis* UCMB5014, *Bacillus subtilis* XF-1, and *Bacillus subtilis* YF001.

In various embodiments, spore forming microbes and spores thereof include but are not limited to *Bacillus subtilis* group members *Bacillus subtilis* Group:*Bacillus amyloliquefaciens, Bacillus amyloliquefaciens* AB01, *Bacillus amyloliquefaciens* AP143, *Bacillus amyloliquefaciens* AP193, *Bacillus amyloliquefaciens* AP71, *Bacillus amyloliquefaciens* AP79, *Bacillus amyloliquefaciens* CC178, *Bacillus amyloliquefaciens* DC-12, *Bacillus amyloliquefaciens* DSM 7=ATCC 23350, *Bacillus amyloliquefaciens* EBL11, *Bacillus amyloliquefaciens* EGD-AQ14, *Bacillus amyloliquefaciens* GGI-18, *Bacillus amyloliquefaciens* HB-26, *Bacillus amyloliquefaciens* IT-45, *Bacillus amyloliquefaciens* KHG19, *Bacillus amyloliquefaciens* LFB112, *Bacillus amyloliquefaciens* LL3, *Bacillus amyloliquefaciens* Lx-11, *Bacillus amyloliquefaciens* PGK1, *Bacillus amyloliquefaciens* TA208, *Bacillus amyloliquefaciens* UASWS BA1, *Bacillus amyloliquefaciens* UCMB5007, *Bacillus amyloliquefaciens* UCMB5140, *Bacillus amyloliquefaciens* UMAF6614, *Bacillus amyloliquefaciens* UMAF6639, *Bacillus amyloliquefaciens* XH7, *Bacillus amyloliquefaciens* Y2, *Bacillus siamensis, Bacillus siamensis* KCTC 13613, *Bacillus velezensis, Bacillus velezensis* A3, *Bacillus velezensis* AS43.3, *Bacillus velezensis* At1, *Bacillus velezensis* CAU B946, *Bacillus velezensis* FZB42, *Bacillus velezensis* M27, *Bacillus velezensis* NAU-B3, *Bacillus velezensis* NJN-6, *Bacillus velezensis* SK19.001, *Bacillus velezensis* SQR9, *Bacillus velezensis* TrigoCor1448, *Bacillus velezensis* UCMB5033, *Bacillus velezensis* UCMB5036, *Bacillus velezensis* UCMB5113, *Bacillus velezensis* variant polyfermenticus, *Bacillus velezensis* YAU B9601-Y2, *Bacillus atrophaeus, Bacillus atrophaeus* 1013-1, *Bacillus atrophaeus* 1013-2, *Bacillus atrophaeus* 1942, *Bacillus atrophaeus* BACI051-E, *Bacillus atrophaeus* BACI051-N, *Bacillus atrophaeus* C89, *Bacillus atrophaeus* Detrick-1, *Bacillus atrophaeus* Detrick-2, *Bacillus atrophaeus* Detrick-3, *Bacillus atrophaeus* NBRC 15539, *Bacillus atrophaeus* str. Dugway, *Bacillus atrophaeus* subsp. *globigii, Bacillus atrophaeus* ATCC 49822, *Bacillus atrophaeus* ATCC 9372, *Bacillus atrophaeus* UCMB-5137, *Bacillus licheniformis, Bacillus licheniformis* 10-1-A, *Bacillus licheniformis* 5-2-D, *Bacillus licheniformis* CG-B52, *Bacillus licheniformis* CGMCC 3963, *Bacillus licheniformis* DSM 13=ATCC 14580, *Bacillus licheniformis* F1-1, *Bacillus licheniformis* F2-1, *Bacillus licheniformis* KRB2009, *Bacillus licheniformis* LMG 17339, *Bacillus licheniformis* LMG 6934, *Bacillus licheniformis* LMG 7559, *Bacillus licheniformis* MKU3, *Bacillus licheniformis* S 16, *Bacillus licheniformis* WX-02, *Bacillus mojavensis* subgroup, *Bacillus halotolerans, Bacillus mojavensis, Bacillus mojavensis* RO-H-1=KCTC 3706, *Bacillus mojavensis* RRC 101, *Bacillus paralicheniformis, Bacillus paralicheniformis* ATCC 9945a, *Bacillus paralicheniformis* G-1, *Bacillus sonorensis, Bacillus sonorensis* L12, *Bacillus sonorensis*

NBRC 101234=KCTC 13918, *Bacillus subtilis, Bacillus subtilis* A29, *Bacillus subtilis* Abs3, *Bacillus subtilis* AP254, *Bacillus subtilis* At2, *Bacillus subtilis* B2, *Bacillus subtilis* B7-s, *Bacillus subtilis* BEST7003, *Bacillus subtilis* BEST7613, *Bacillus subtilis* BSn5, *Bacillus subtilis* E1, *Bacillus subtilis* gtP20b, *Bacillus subtilis* Hal1, *Bacillus subtilis* HJ5, *Bacillus subtilis* J22, *Bacillus subtilis* J23, *Bacillus subtilis* J24, *Bacillus subtilis* J25, *Bacillus subtilis* J26, *Bacillus subtilis* J27, *Bacillus subtilis* KCTC 1028=ATCC 6051a, *Bacillus subtilis* LX-8, *Bacillus subtilis* MB73/2, *Bacillus subtilis* Miyagi-4, *Bacillus subtilis* Miyagi-4100, *Bacillus subtilis* PRO 1, *Bacillus subtilis* PS216, *Bacillus subtilis* PTS-394, *Bacillus subtilis* PY79, *Bacillus subtilis* QB928, *Bacillus subtilis* QH-1, *Bacillus subtilis* S 1-4, *Bacillus subtilis* SPZ1, *Bacillus subtilis* str. 10, *Bacillus subtilis* strain DY, *Bacillus subtilis* subsp. *amylosacchariticus, Bacillus subtilis* subsp. *chungkookjang, Bacillus subtilis* subsp. *endophyticus, Bacillus subtilis* subsp. *globigii, Bacillus subtilis* subsp. *inaquosorum, Bacillus subtilis* subsp. *inaquosorum* KCTC 13429, *Bacillus subtilis* subsp. *krictiensis, Bacillus subtilis* subsp. *lactipan, Bacillus subtilis* subsp. *natto, Bacillus subtilis* subsp. *natto* BEST195, *Bacillus subtilis* subsp. natto HSF 1410, *Bacillus subtilis* subsp. *niger, Bacillus subtilis* subsp. *qingdao, Bacillus subtilis* subsp. sadata, *Bacillus subtilis* subsp. *spizizenii, Bacillus subtilis* subsp. *spizizenii* ATCC 6633, *Bacillus subtilis* subsp. *spizizenii* DV1-B-1, *Bacillus subtilis* subsp. *spizizenii* JCM 2499, *Bacillus subtilis* subsp. *spizizenii* RFWG1A3, *Bacillus subtilis* subsp. *spizizenii* RFWG1A4, *Bacillus subtilis* subsp. *spizizenii* RFWG4C10, *Bacillus subtilis* subsp. *spizizenii* RFWG5B15, *Bacillus subtilis* subsp. *spizizenii* str. W23, *Bacillus subtilis* subsp. *spizizenii* TU-B-10, *Bacillus subtilis* subsp. *stercoris, Bacillus subtilis* subsp. *subtilis, Bacillus subtilis* subsp. *subtilis* NCIB 3610=ATCC 6051, *Bacillus subtilis* subsp. *subtilis* str. 168, *Bacillus subtilis* subsp. *subtilis* str. AG1839, *Bacillus subtilis* subsp. *subtilis* str. AUSI98, *Bacillus subtilis* subsp. *subtilis* str. B2, *Bacillus subtilis* subsp. *subtilis* str. BAB-1, *Bacillus subtilis* subsp. *subtilis* str. BSP1, *Bacillus subtilis* subsp. *subtilis* str. JH642, *Bacillus subtilis* subsp. *subtilis* str. MPP11, *Bacillus subtilis* subsp. *subtilis* str. MP9, *Bacillus subtilis* subsp. *subtilis* str. OH 131.1, *Bacillus subtilis* subsp. *subtilis* str. R0179, *Bacillus subtilis* subsp. *subtilis* str. RO-NN-1, *Bacillus subtilis* subsp. *subtilis* str. SC-8, *Bacillus subtilis* subsp. *subtilis* str. SMY, *Bacillus subtilis* TO-A, *Bacillus subtilis* TPK 210909, *Bacillus subtilis* UCMB5014, *Bacillus subtilis* XF-1, *Bacillus subtilis* YF001, *Bacillus tequilensis, Bacillus tequilensis* KCTC 13622, *Bacillus vallismortis, Bacillus vallismortis* DV1-F-3, *Bacillus vallismortis* NRRL B-14890, *Bacillus* sp. AB01, *Bacillus* sp. AP102, *Bacillus* sp. AP143, *Bacillus* sp. AP183, *Bacillus* sp. AP189, *Bacillus* sp. AP193, *Bacillus* sp. AP215, *Bacillus* sp. AP218, *Bacillus* sp. AP219, *Bacillus* sp. AP295, *Bacillus* sp. AP301, *Bacillus* sp. AP303, *Bacillus* sp. AP305, *Bacillus* sp. AP71, *Bacillus* sp. AP77, *Bacillus* sp. AP79, *Bacillus* sp. D10(2019), *Bacillus* sp. D9(2019), *Bacillus* sp. GeS7V, *Bacillus* sp. LiF4a, *Bacillus* sp. LJF-10, *Bacillus* sp. LJF-11, *Bacillus* sp. LJF-2, *Bacillus* sp. LJF-5, *Bacillus* sp. LJF-8, *Bacillus* sp. LJF-9, *Bacillus* sp. M1(2010), *Bacillus* sp. M100(2010), *Bacillus* sp. M101(2010), *Bacillus* sp. M103(2010), *Bacillus* sp. M110(2010), *Bacillus* sp. M112(2010), *Bacillus* sp. M14 (2010), *Bacillus* sp. M2(2010), *Bacillus* sp. M21(2010), *Bacillus* sp. M22(2010), *Bacillus* sp. M25(2010), *Bacillus* sp. M29(2010), *Bacillus* sp. M30(2010), *Bacillus* sp. M35 (2010), *Bacillus* sp. M38(2010), *Bacillus* sp. M4(2010b), *Bacillus* sp. M40(2010), *Bacillus* sp. M5(2010), *Bacillus* sp. M63(2010), *Bacillus* sp. M64(2010), *Bacillus* sp. M67

(2010), *Bacillus* sp. M68(2010), *Bacillus* sp. M88(2010), *Bacillus* sp. M90(2010), *Bacillus* sp. M94(2010), *Bacillus* sp. M95(2010), *Bacillus* sp. M98(2010), *Bacillus* sp. SE-54, *Bacillus* sp. TT106(2010), *Bacillus* sp. TT45(2010), *Bacillus* sp. TT46(2010), *Bacillus* sp. TT53(2010), *Bacillus* sp. TT80(2010), *Bacillus* sp. ZYJ-1, *Bacillus* sp. ZYJ-10, *Bacillus* sp. ZYJ-11, *Bacillus* sp. ZYJ-12, *Bacillus* sp. ZYJ-13, *Bacillus* sp. ZYJ-15, *Bacillus* sp. ZYJ-16, *Bacillus* sp. ZYJ-17, *Bacillus* sp. ZYJ-18, *Bacillus* sp. ZYJ-19, *Bacillus* sp. ZYJ-2, *Bacillus* sp. ZYJ-20, *Bacillus* sp. ZYJ-21, *Bacillus* sp. ZYJ-22, *Bacillus* sp. ZYJ-23, *Bacillus* sp. ZYJ-24, *Bacillus* sp. ZYJ-26, *Bacillus* sp. ZYJ-27, *Bacillus* sp. ZYJ-28, *Bacillus* sp. ZYJ-3, *Bacillus* sp. ZYJ-32, *Bacillus* sp. ZYJ-33, *Bacillus* sp. ZYJ-34, *Bacillus* sp. ZYJ-35, *Bacillus* sp. ZYJ-36, *Bacillus* sp. ZYJ-37, *Bacillus* sp. ZYJ-38, *Bacillus* sp. ZYJ-39, *Bacillus* sp. ZYJ-4, *Bacillus* sp. ZYJ-40, *Bacillus* sp. ZYJ-43, *Bacillus* sp. ZYJ-44, *Bacillus* sp. ZYJ-5, *Bacillus* sp. ZYJ-6, *Bacillus* sp. ZYJ-7, *Bacillus* sp. ZYJ-8, *Bacillus* sp. ZYJ-9, *Bacillus subtilis* group sp., and *Nocardia* sp. KY2-1.

In various embodiments, spore forming microbes and spores thereof include but are not limited to *Bacillus coagulans* bacterium, optionally selected from *Bacillus coagulans* 2-6, *Bacillus coagulans* 36D1, *Bacillus coagulans* CSIL1, *Bacillus coagulans* DSM 1=ATCC 7050, *Bacillus coagulans* H-1, *Bacillus coagulans* P38, *Bacillus coagulans* XZL4, and *Bacillus coagulans* XZL9. In various embodiments, spore forming microbes and spores thereof include but are not limited to a *Lactobacillus* bacterium, optionally selected from *Lactobacillus paracasei*, *Lactobacillus brevis*, *Lactobacillus casei*, *Lactobacillus delbrueckii*, *Lactobacillus gasseri*, *Lactobacillus rhamnosus*, *Lactobacillus reuteri*, *Lactobacillus plantarum*, and *Lactobacillus johnsonii*. In various embodiments, spore forming microbes and spores thereof include but are not limited to a *Lactobacillus* bacterium, optionally selected from *Lactobacillus paracasei* (*Lactobacillus paracasei* ATCC 334, *Lactobacillus paracasei* COM0101, *Lactobacillus paracasei* N1115, *Lactobacillus paracasei* NRIC 0644, *Lactobacillus paracasei* NRIC 1917, *Lactobacillus paracasei* NRIC 1981, *Lactobacillus paracasei* subsp. *paracasei*, *Lactobacillus paracasei* subsp. *paracasei* 8700:2, *Lactobacillus paracasei* subsp. *paracasei* ATCC 25302, *Lactobacillus paracasei* subsp. *paracasei* BGSJ2-8, *Lactobacillus paracasei* subsp. *paracasei* CNCM I-2877, *Lactobacillus paracasei* subsp. *paracasei* CNCM I-4270, *Lactobacillus paracasei* subsp. *paracasei* CNCM I-4648, *Lactobacillus paracasei* subsp. *paracasei* CNCM I-4649, *Lactobacillus paracasei* subsp. *paracasei* DSM 5622, *Lactobacillus paracasei* subsp. *paracasei* JCM 8130, *Lactobacillus paracasei* subsp. *paracasei* Lpp120, *Lactobacillus paracasei* subsp. *paracasei* Lpp122, *Lactobacillus paracasei* subsp. *paracasei* Lpp123, *Lactobacillus paracasei* subsp. *paracasei* Lpp125, *Lactobacillus paracasei* subsp. *paracasei* Lpp126, *Lactobacillus paracasei* subsp. *paracasei* Lpp14, *Lactobacillus paracasei* subsp. *paracasei* Lpp17, *Lactobacillus paracasei* subsp. *paracasei* Lpp189, *Lactobacillus paracasei* subsp. *paracasei* Lpp219, *Lactobacillus paracasei* subsp. *paracasei* Lpp22, *Lactobacillus paracasei* subsp. *paracasei* Lpp221, *Lactobacillus paracasei* subsp. *paracasei* Lpp223, *Lactobacillus paracasei* subsp. *paracasei* Lpp225, *Lactobacillus paracasei* subsp. *paracasei* Lpp226, *Lactobacillus paracasei* subsp. *paracasei* Lpp227, *Lactobacillus paracasei* subsp. *paracasei* Lpp228, *Lactobacillus paracasei* subsp. *paracasei* Lpp229, *Lactobacillus paracasei* subsp. *paracasei* Lpp230, *Lactobacillus paracasei* subsp. *paracasei* Lpp37, *Lactobacillus paracasei* subsp. *paracasei* Lpp41, *Lactobacillus paracasei* subsp. *paracasei* Lpp43, *Lactobacillus paracasei* subsp. *paracasei* Lpp46, *Lactobacillus paracasei* subsp. *paracasei* Lpp48, *Lactobacillus paracasei* subsp. *paracasei* Lpp49, *Lactobacillus paracasei* subsp. *paracasei* Lpp7, *Lactobacillus paracasei* subsp. *paracasei* Lpp70, *Lactobacillus paracasei* subsp. *paracasei* Lpp71, *Lactobacillus paracasei* subsp. *paracasei* Lpp74, *Lactobacillus paracasei* subsp. *tolerans*, *Lactobacillus paracasei* subsp. *tolerans* DSM 20258, *Lactobacillus paracasei* subsp. *tolerans* Lp114, *Lactobacillus paracasei* subsp. *tolerans* Lp17, *Lactobacillus paracasei* TXW), *Lactobacillus brevis* (*Lactobacillus brevis* AG48, *Lactobacillus brevis* ATCC 14869=DSM 20054, *Lactobacillus brevis* ATCC 367, *Lactobacillus brevis* BSO 464, *Lactobacillus brevis* EW, *Lactobacillus brevis* KB290, *Lactobacillus brevis* subsp. *coagulans*, *Lactobacillus brevis* subsp. *gravesensis*, *Lactobacillus brevis* subsp. *gravesensis* ATCC 27305), *Lactobacillus casei* (*Lactobacillus casei* 12A, *Lactobacillus casei* 21/1, *Lactobacillus casei* 32G, *Lactobacillus casei* 5b, *Lactobacillus casei* A2-362, *Lactobacillus casei* BD-II, *Lactobacillus casei* BL23, *Lactobacillus casei* CRF28, *Lactobacillus casei* DN-114001, *Lactobacillus casei* DSM 20011=JCM 1134=ATCC 393, *Lactobacillus casei* Lc-10, *Lactobacillus casei* LC2W, *Lactobacillus casei* LcA, *Lactobacillus casei* LcY, *Lactobacillus casei* LOCK919, *Lactobacillus casei* Lpc-37, *Lactobacillus casei* M36, *Lactobacillus casei* str. Zhang, *Lactobacillus casei* T71499, *Lactobacillus casei* UCD174, *Lactobacillus casei* UW1, *Lactobacillus casei* UW4, *Lactobacillus casei* W56), *Lactobacillus delbrueckii* (*Lactobacillus delbrueckii* subsp. *bulgaricus*, *Lactobacillus delbrueckii* subsp. *bulgaricus* 2038, *Lactobacillus delbrueckii* subsp. *bulgaricus* ATCC 11842=JCM 1002, *Lactobacillus delbrueckii* subsp. *bulgaricus* ATCC BAA-365, *Lactobacillus delbrueckii* subsp. *bulgaricus* CNCM I-1519, *Lactobacillus delbrueckii* subsp. *bulgaricus* CNCM I-1632, *Lactobacillus delbrueckii* subsp. *bulgaricus* ND02, *Lactobacillus delbrueckii* subsp. *bulgaricus* PB2003/044-T3-4, *Lactobacillus delbrueckii* subsp. *delbrueckii*, *Lactobacillus delbrueckii* subsp. *delbrueckii* DSM 20074=JCM 1012, *Lactobacillus delbrueckii* subsp. *indicus*, *Lactobacillus delbrueckii* subsp. *indicus* DSM 15996, *Lactobacillus delbrueckii* subsp. *jakobsenii*, *Lactobacillus delbrueckii* subsp. *jakobsenii* ZN7a-9=DSM 26046, *Lactobacillus delbrueckii* subsp. *lactis*, *Lactobacillus delbrueckii* subsp. *lactis* CRL581, *Lactobacillus delbrueckii* subsp. *lactis* DSM 20072, *Lactobacillus delbrueckii* subsp. *sunkii*), *Lactobacillus gasseri* (*Lactobacillus gasseri* 130918, *Lactobacillus gasseri* 2016, *Lactobacillus gasseri* 202-4, *Lactobacillus gasseri* 224-1, *Lactobacillus gasseri* ADH, *Lactobacillus gasseri* ADL-351, *Lactobacillus gasseri* ATCC 33323=JCM 1131, *Lactobacillus gasseri* CECT 5714, *Lactobacillus gasseri* DSM 14869, *Lactobacillus gasseri* EX336960VC01, *Lactobacillus gasseri* EX336960VC02, *Lactobacillus gasseri* EX336960VC03, *Lactobacillus gasseri* EX336960VC06, *Lactobacillus gasseri* EX336960VC07, *Lactobacillus gasseri* EX336960VC10, *Lactobacillus gasseri* EX336960VC13, *Lactobacillus gasseri* EX336960VC15, *Lactobacillus gasseri* MV-22, *Lactobacillus gasseri* SJ-9E-US, *Lactobacillus gasseri* SV-16A-US), *Lactobacillus rhamnosus* (*Lactobacillus rhamnosus* 2166, *Lactobacillus rhamnosus* 51B, *Lactobacillus rhamnosus* ATCC 21052, *Lactobacillus rhamnosus* ATCC 8530, *Lactobacillus rhamnosus* BPL15, *Lactobacillus rhamnosus* CASL, *Lactobacillus rhamnosus* CRL1505, *Lactobacillus rhamnosus* DSM 14870, *Lactobacillus rhamnosus* DSM 20021=JCM 1136=NBRC 3425, *Lactobacillus rhamnosus* E800, *Lactobacillus rhamnosus* GG, *Lactobacillus rhamno-*

*sus* HN001, *Lactobacillus rhamnosus* K32, *Lactobacillus rhamnosus* L31, *Lactobacillus rhamnosus* L33, *Lactobacillus rhamnosus* L34, *Lactobacillus rhamnosus* L35, *Lactobacillus rhamnosus* Lc 705, *Lactobacillus rhamnosus* LMG 25859, *Lactobacillus rhamnosus* LMG 27229, *Lactobacillus rhamnosus* LMS2-1, *Lactobacillus rhamnosus* LOCK900, *Lactobacillus rhamnosus* LOCK908, *Lactobacillus rhamnosus* LR231, *Lactobacillus rhamnosus* LRHMDP2, *Lactobacillus rhamnosus* LRHMDP3, *Lactobacillus rhamnosus* MSUIS1, *Lactobacillus rhamnosus* MTCC 5462, *Lactobacillus rhamnosus* PEL5, *Lactobacillus rhamnosus* PEL6, *Lactobacillus rhamnosus* R0011), *Lactobacillus reuteri* (*Lactobacillus reuteri* 100-23, *Lactobacillus reuteri* 1063, *Lactobacillus reuteri* ATCC 53608, *Lactobacillus reuteri* CF48-3A, *Lactobacillus reuteri* DSM 20016, *Lactobacillus reuteri* F275, *Lactobacillus reuteri* I5007, *Lactobacillus reuteri* JCM 1112, *Lactobacillus reuteri* lpuph, *Lactobacillus reuteri* mlc3, *Lactobacillus reuteri* MM2-2, *Lactobacillus reuteri* MM2-3, *Lactobacillus reuteri* MM4-1A, *Lactobacillus reuteri* SD2112, *Lactobacillus reuteri* T D1), *Lactobacillus plantarum* (*Lactobacillus plantarum* 16, *Lactobacillus plantarum* 19L3, *Lactobacillus plantarum* 2025, *Lactobacillus plantarum* 2165, *Lactobacillus plantarum* 4_3, *Lactobacillus plantarum* 80, *Lactobacillus plantarum* AY01, *Lactobacillus plantarum* CMPG5300, *Lactobacillus plantarum* DOMLa, *Lactobacillus plantarum* EGD-AQ4, *Lactobacillus plantarum* IPLA88, *Lactobacillus plantarum* JDM1, *Lactobacillus plantarum* LP91, *Lactobacillus plantarum* ST-III, *Lactobacillus plantarum* subsp. *argentoratensis, Lactobacillus plantarum* subsp. *argentoratensis* DSM 16365, *Lactobacillus plantarum* subsp. *plantarum, Lactobacillus plantarum* subsp. *plantarum* ATCC 14917=JCM 1149=CGMCC 1.2437, *Lactobacillus plantarum* subsp. *plantarum* KCA-1, *Lactobacillus plantarum* subsp. *plantarum* NC8, *Lactobacillus plantarum* subsp. *plantarum* P-8, *Lactobacillus plantarum* subsp. *plantarum* R0403, *Lactobacillus plantarum* subsp. *plantarum* ST-III, *Lactobacillus plantarum* UCMA 3037, *Lactobacillus plantarum* WCFS1, *Lactobacillus plantarum* WHE 92, *Lactobacillus plantarum* WJL, *Lactobacillus plantarum* ZJ316), *Lactobacillus johnsonii* (*Lactobacillus johnsonii* 135-1-CHN, *Lactobacillus johnsonii* 16, *Lactobacillus johnsonii* ATCC 33200, *Lactobacillus johnsonii* DPC 6026, *Lactobacillus johnsonii* FI9785, *Lactobacillus johnsonii* N6.2, *Lactobacillus johnsonii* NCC 533, and *Lactobacillus johnsonii* pf01.

Cells administered to a subject, e.g., spores and/or non-spore cells administered to a subject and/or delivered to the intestine of a subject, can express and/or deliver a fiber-synthesizing enzyme to the subject. In various embodiments, a cell administered to a subject expresses a fiber-synthesizing enzyme in and/or delivers a fiber-synthesizing enzyme to ascending colon, traverse colon, and/or descending colon. In various embodiments, a cell administered to a subject colonizes the gut. In various embodiments, a cell administered to a subject expresses a fiber-synthesizing enzyme in gut and/or delivers a fiber-synthesizing enzyme to gut before, during, and/or after the cell has colonized the gut. In some embodiments, a cell administered to a subject is non-colonizing and can pass through the entire digestive tract, e.g., while expressing and/or delivering a fiber-synthesizing enzyme of the present disclosure. In various embodiments, an engineered cell is a cell that is able to pass through a subject's gastrointestinal tract without persisting in the microbiome of the subject (orthogonal to the microbiome), optionally wherein the cell is an engineered *B. subtilis* cell.

In various embodiments, the engineered cell is of a cell type that has been designated by a governmental regulatory authority, such as the United States Food and Drug Administration or an equivalent body of another country, as safe, or is a cell of a cell type that is otherwise known to be or regarded as safe by those of skill in the art.

In various embodiments, a cell of the present disclosure is a cell that can be fermented in large batches, e.g., using minimal media, e.g., in a 30-3,000 L fermenter. In various embodiments, a cell of the present disclosure is a cell that can be purified as a biomass product including vegetative cells or spores, optionally wherein the cells of the biomass product can be readily purified and/or wherein the biomass product can be stabilized (e.g., by filtering and/or lyophilization, e.g., to facilitate shipping). For example, rapid spore formation upon nutrient starvation enables large fermentation batches to convert to spores at the end of growth. Spores can be readily stored, transported and/or purified from vegetative cells by heating the growth medium and removing the supernatant.

Various methods are known for the preparation and/or purification of spores. To provide one example, spores (e.g., *Bacillus subtilis* spores) can be prepared by a technique that includes growing cells to high density in a nutrient limited medium to stimulate sporulation, followed by a step of purifying spores. In one example, cells can be grown in Difco Sporulation Medium (0.8% Nutrient Broth, 0.1% KCl, 0.012% $MgSO_4 \cdot 7H_2O$, 0.5 mM NaOH, 1 mM $Ca(NO_3)_2$ 0.01 mM $MnCl_2$, 1 uM $FeSO_4$) at 37° C. for 24-48 hours, with 250 rpm shaking to provide oxygen. The resulting mixture of cell debris and spores can be heated to 80° C. to kill and lyse vegetative cells followed by pelleting and rinsing three times with distilled water to remove cell debris and purify the spore layer. Spores prepared in this manner can be stable in water for more than a year.

In certain embodiments, a transgene of the present disclosure is introduced into a cell that includes a sequence having significant homology to the transgene, e.g., where the transgene has at least 80% identity (e.g., at least 80%, 85%, 90%, 95%, 96%, 97%, 98%, 99%, or 100% identity) with a sequence of the cell (e.g., a sequence of at least 50 nucleotides, e.g., at least 50, 75, 100, 150, 200, 250, 300, 350, 400, 450, 500, 1,000, 2,000, 3,000, 4,000, or 5,000 nucleotides). In various such instances, homology-based interaction of the cell nucleic acid sequence and transgene can compete for and/or inhibit integration of the transgene at a different target locus. Moreover, integration of the transgene (e.g., at a target locus not homologous to the transgene) can in various instances result in genome instability and/or loss of transgene function. For at least these reasons, in various embodiments, a homologous endogenous nucleic acid sequence of a cell is modified or deleted from the cell genome (e.g., by knockout) prior to introduction of the transgene nucleic acid sequence.

Isolated Fiber-Synthesizing Enzymes

In various embodiments, the present disclosure includes isolated fiber-synthesizing enzymes and compositions including the same. For the avoidance of doubt, while the present disclosure provides various engineered cells useful for administration to subjects such that the cells deliver to the subject a fiber-synthesizing enzyme, isolated fiber-synthesizing enzymes of the present disclosure need not be derived, isolated from such cells. To the contrary, the present disclosure includes fiber-synthesizing enzymes isolated from any source. In various embodiments, a fiber-synthesizing enzyme of the present disclosure is produced by and/or isolated from a plant or bacterium in which the fiber-synthesizing enzyme is naturally expressed. In various embodiments, a fiber-synthesizing enzyme of the present disclosure is produced by and/or isolated from a plant, bacterium, or animal (e.g., a rat, mouse, cow, pig, or horse) engineered to express a fiber-synthesizing enzyme of the present disclosure, e.g., using standard techniques of molecular biology known to those of skill in the art.

Fiber-synthesizing enzymes of the present disclosure can be isolated by any means known to those of skill in the art. Those of skill in the art will appreciate that isolation of proteins is a well-established practice with a wide variety of known techniques at the disposal of those of skill in the art for that purpose. Methods of isolating fiber-synthesizing enzymes can include, e.g., expressing fiber-synthesizing enzymes in cell culture (e.g., bacterial cell culture or mammalian cell culture, e.g., *E. coli* cell culture), tagging fiber-synthesizing enzymes with an affinity tag to facilitate isolation (e.g., by engineering and expressing a nucleic acid sequence encoding a fiber-synthesizing enzyme and an affinity tag), and/or isolating fiber-synthesizing enzyme by methods such as chromatography (e.g., high performance liquid chromatography (HPLC) or reversed-phase chromatography) or enzyme-linked immunosorbent assay (ELISA) or other immunoaffinity methods. In various embodiments, isolated fiber-synthesizing enzyme can be processed, e.g., by lyophilization or ultrafiltration.

The present disclosure includes that methods and compositions including isolated fiber-synthesizing enzymes disclosed herein can be delivered to subjects and can provide various health benefits disclosed herein.

Formulations and Applications

The present disclosure includes fiber-synthesizing enzyme formulations, e.g., where the fiber-synthesizing enzyme formulation can be or include one or more engineered cells of the present disclosure (e.g., in a spore form) and/or isolated fiber-synthesizing enzyme of the present disclosure. Enzymes (e.g., isolated fiber-synthesizing enzymes) and cells of the present disclosure can be delivered to a subject in any of a variety of formulations. The present disclosure includes, for example, formulation of isolated fiber-synthesizing enzymes and/or engineered cells of the present disclosure in any manner known for use in administration of probiotics. The present disclosure includes administration of a fiber-synthesizing enzyme formulation to a subject. In various embodiments, the present disclosure includes pharmaceutically acceptable fiber-synthesizing enzyme formulations that include a pharmaceutically acceptable carrier or excipient.

In some embodiments, a fiber-synthesizing enzyme formulation can be formulated as a dietary supplements. In some embodiments, a fiber-synthesizing enzyme formulation can be formulated in a freeze-dried powder form. In some embodiments, a fiber-synthesizing enzyme formulation can be formulated as a powder in stick packaging or sachets.

In some embodiments, a fiber-synthesizing enzyme formulation can be formulated in an oral dosage form such as a capsule or tablet (e.g., chewable tablets). In some embodiments, a fiber-synthesizing enzyme formulation can be formulated as a gummy (e.g., including ingredients such as one or more of sugar and gelatin). The present disclosure includes administration of a fiber-synthesizing enzyme formulation formulated in a delayed release oral dosage form, e.g., an enterically coated oral dosage form.

Many foods and/or ingredients can be, or be utilized as vehicles for delivery of, a fiber-synthesizing enzyme formulation, including without limitation chocolate, crackers, cereal, yogurt, natto, kombucha, or flour. Accordingly, the present disclosure includes a fiber-synthesizing enzyme formulation formulated in or as a food product and/or food ingredient such as chocolate, crackers, cereal, yogurt, natt6, kombucha, or flour. In various embodiments, a fiber-synthesizing enzyme formulation is formulated in or as a food product or food ingredient that is a liquid such as a juice or drink. In various embodiments, spores can be formulated in a suspension. In various embodiments, a unit dose or dosage form of a food product or food ingredient of the present disclosure has volume of between about 0.05 mL and 500 mL, e.g., between about 0.5 mL and about 50 mL or between about 2.5 mL and 15 mL. In various embodiments, a unit dose or dosage form of a food product or food ingredient of the present disclosure has volume that has a lower bound of, e.g., 0.05 mL, 0.5 mL, 1 mL, 10 mL, 15 mL, 20 mL, 25 mL, 50 mL, or 100 mL and an upper bound of, e.g., 50 mL, 100 mL, 150 mL, 200 mL, 250 mL, 300 mL, 350 mL, 400 mL, 450 mL, or 500 mL.

The present disclosure further includes a fiber-synthesizing enzyme formulation that is a sachet including one or more engineered cells of the present disclosure (e.g., in a spore form) and/or isolated fiber-synthesizing enzyme of the present disclosure. In various embodiments, a sachet is formulated for use of the one or more engineered cells of the present disclosure (e.g., in a spore form) and/or isolated fiber-synthesizing enzyme of the present disclosure with a food product for consumption, e.g., by combination of the food product with the fiber-synthesizing enzyme formulation, e.g., by mixing with the food product and/or distribution onto or into the food product (e.g., by sprinkling).

In various embodiments, a fiber-synthesizing enzyme formulation is included in or added to a food product (e.g., a food ingredient) prior to administration to and/or consumption of the food product by a subject. In various embodiments a food product is a food product for human consumption. In various embodiments the food product is a food for animals, such as animal feed or biscuits. In various embodiments, a fiber-synthesizing enzyme formulation is included for activity after administration and/or consumption of the food product and/or food ingredient, e.g., in the gut of a subject. monosaccharides and/or disaccharides and increase concentration or amount of fiber in the food product and/or food ingredient prior to consumption by a subject.

Various formulations can be stored at ambient conditions for extend periods of time, e.g., at least 1 week, 2 weeks, 3 weeks, 1 month, 2 months, 3 months, 6 months, or 1 year, e.g., up to 1 month, 2 months, 3 months, 6 months, or 1 year.

In various embodiments, a unit dose or dosage form of a formulation that includes an engineered cell of the present disclosure includes a number of colony-forming units (CFU) that is between 1E+04 and 1E+14 (e.g., about 1E+04, 1E+05, 1E+06, 1E+07, 1E+08, 1E+09, 1E+10, 1E+11, 1E+12, 1E+13, or 1E+14 CFU, or within a range having a lower bound of about 1E+04, 1E+05, 1E+06, 1E+07, 1E+08, 1E+09, or 1E+10 CFU and an upper bound of about 1E+08, 1E+09, 1E+10, 1E+11, 1E+12, 1E+13, or 1E+14 CFU). In certain embodiments, a unit dose or dosage form includes 1E+11 CFU of engineered cells (e.g., spores). Various examples of live cell formulation administration are known in the art. For example, in one study, 2.25E+11 CFU was found to be a tolerable dose with no observable adverse effects. Natt6, a food made through fermentation with *Bacillus subtilis* can contain as much as 1E+09 CFU per gram and a typical consumed portion of nattō (~90-100 g) can include 1E+11 CFU. Some recommendations for consumption of *Bacillus coagulans* recommend a daily dosage of 1E+11-

2E+11 CFU. Animal studies support safety and efficacy of CFU dosage levels provided herein, e.g., demonstrating that 7E+12 and 9E+12 as a safe dosages, e.g., for a 70 kg human.

In various embodiments, a fiber-synthesizing enzyme formulation of the present disclosure is administered to a subject in need thereof. In various embodiments, administration of a fiber-synthesizing enzyme formulation of the present disclosure causes production (e.g., in a 1, 3, 6, 12 or 24 hour period) of at least 1 g soluble fiber, e.g., at least 1 g, 2 g, 3 g, 4 g, 5 g, 10 g, 15 g, 20 g, 25 g, 30 g, 35 g, or 40 g. In various embodiments, administration of a fiber-synthesizing enzyme formulation of the present disclosure causes production (e.g., in a 1, 3, 6, 12 or 24 hour period) of at least 5 g soluble fiber. In various embodiments, administration of a fiber-synthesizing enzyme formulation of the present disclosure causes production (e.g., in a 1, 3, 6, 12 or 24 hour period) of at least 10 g soluble fiber. In various embodiments, administration of a fiber-synthesizing enzyme formulation of the present disclosure causes production (e.g., in a 1, 3, 6, 12 or 24 hour period) of an amount of soluble fiber that is in a range having a lower bound of 1 g, 2 g, 3 g, 4 g, or 5 g and an upper bound of 5 g, 10 g, 15 g, 20 g, 25 g, 30 g, 35 g, or 40 g. In various embodiments, production of fiber is caused by administration of a single dose or dosage form of a fiber-synthesizing enzyme formulation of the present disclosure. Those of skill in the art will appreciate that, in various embodiments, a recommended total amount of daily fiber (e.g., by consumption and/or synthesis by isolated fiber-synthesizing enzymes and/or engineered cells of the present disclosure) is 25 to 30 g per day, including 6 g to 8 g per day soluble fiber (about 1 total fiber).

In various embodiments, administration of a fiber-synthesizing enzyme formulation of the present disclosure causes incorporation into fiber (e.g., in a 1, 3, 6, 12 or 24 hour period) of at least 1 g carbohydrate, e.g., at least 1 g, 2 g, 3 g, 4 g, 5 g, 10 g, 15 g, 20 g, 25 g, 30 g, 35 g, or 40 g. In various embodiments, administration of a fiber-synthesizing enzyme formulation of the present disclosure causes incorporation into fiber (e.g., in a 1, 3, 6, 12 or 24 hour period) of at least 5 g carbohydrate. In various embodiments, administration of a fiber-synthesizing enzyme formulation of the present disclosure causes incorporation into fiber (e.g., in a 1, 3, 6, 12 or 24 hour period) of at least 10 g carbohydrate. In various embodiments, administration of a fiber-synthesizing enzyme formulation of the present disclosure causes incorporation into fiber (e.g., in a 1, 3, 6, 12 or 24 hour period) of an amount of carbohydrate that is in a range having a lower bound of 1 g, 2 g, 3 g, 4 g, or 5 g and an upper bound of 5 g, 10 g, 15 g, 20 g, 25 g, 30 g, 35 g, or 40 g. In various embodiments, production of fiber is caused by administration of a single dose or dosage form of a fiber-synthesizing enzyme formulation of the present disclosure. Those of skill in the art will appreciate that, in various embodiments, typical daily consumption of carbohydrates can include, e.g., about 45 g-77 g sucrose.

In various embodiments, administration of a fiber-synthesizing enzyme formulation of the present disclosure causes cleavage of (e.g., in a 1, 3, 6, 12 or 24 hour period) of at least 1 g substrate carbohydrate, e.g., at least 1 g, 2 g, 3 g, 4 g, 5 g, 10 g, 15 g, 20 g, 25 g, 30 g, 35 g, or 40 g. In various embodiments, administration of a fiber-synthesizing enzyme formulation of the present disclosure causes cleavage of (e.g., in a 1, 3, 6, 12 or 24 hour period) of at least 5 g substrate carbohydrate. In various embodiments, administration of a fiber-synthesizing enzyme formulation of the present disclosure causes cleavage of (e.g., in a 1, 3, 6, 12 or 24 hour period) of at least 10 g substrate carbohydrate. In various embodiments, administration of a fiber-synthesizing enzyme formulation of the present disclosure causes cleavage of (e.g., in a 1, 3, 6, 12 or 24 hour period) of an amount of substrate carbohydrate that is in a range having a lower bound of 1 g, 2 g, 3 g, 4 g, or 5 g and an upper bound of 5 g, 10 g, 15 g, 20 g, 25 g, 30 g, 35 g, or 40 g.

Accordingly, administration of a fiber-synthesizing enzyme formulation of the present disclosure that includes an engineered cell of the present closure can dramatically impact ratio of substrate carbohydrate to a synthesized fiber type in gut. As an example, if 60 g of sucrose and 4 g of soluble fiber are consumed by a subject, the weight ratio of soluble fiber:sucrose is about 6.7%. If sucrose is utilized as a substrate for fiber synthesis by a fiber-synthesizing enzyme expressed by an engineered cell, such that 5 g of fiber (e.g., levan) is produced, the total simple sugar content is decreased to 55 g and the total soluble fiber is increased to 9 g, fiber:sucrose ratio becomes 16%. It is likely that many consumers have an intake of soluble fiber significantly lower than 4 g a day which would make the impact of administration of a fiber-synthesizing enzyme formulation of the present disclosure even more dramatic.

Various means of measuring carbohydrate (e.g., consumed and/or gut carbohydrate, e.g., monosaccharides and/or disaccharides) and/or fiber (e.g., consumed and/or gut fiber) are known in the art. However, those of skill in the art will appreciate that direct sampling of the gut (e.g., human intestinal tract) is not always possible. Accordingly, those of skill in the art will appreciate that activity and/or efficacy of a fiber-synthesizing enzyme formulation can be demonstrated by a variety of in vivo or ex vivo alternative assays that do not require direct sampling of the gut. For example, synthesis of fiber from fructose generated by cleavage of sucrose can be measured by cognate release of glucose. In certain embodiments, engineered cells are cultured in growth media together with sucrose and change in the amount of glucose in media can be quantified, e.g., by a variety of enzymatic assays and/or by direct high pressure liquid chromatography measurement. Other methods include detection of fiber-synthesizing enzyme in stool, e.g., where the fiber-synthesizing enzyme is secreted in gut by engineered cells. Samples can be derived from excrement or through invasive or other means. Another method of measuring soluble fiber production includes chromatography and/or NMR of stool. This method can be particularly effective for rarely consumed fibers such as levan. Microbiome composition itself can also provide an indication of fiber-synthesizing enzyme activity. Microbiome composition can be routinely measured by metagenomics. A decrease in number or ratio of strains associated with simple sugar dysbiosis and/or an increase in strains associated with healthy gut function from a high fiber diet demonstrate therapeutic efficacy.

In various embodiments, a fiber-synthesizing enzyme formulation is administered in a therapeutically effective amount and/or delivers a therapeutically effective amount of fiber-synthesizing enzyme. In various embodiments, isolated fiber-synthesizing enzymes are administered in a therapeutically effective amount (e.g., a therapeutically effective number of cells) and/or deliver a therapeutically effective amount of fiber-synthesizing enzyme. In various embodiments, engineered cells are administered in a therapeutically effective amount (e.g., a therapeutically effective number of cells) and/or deliver a therapeutically effective amount of fiber-synthesizing enzyme. In various embodiments, the engineered cells are non-colonizing cells. In various embodiments the engineered cells are spore-forming cells. In various embodiments, the engineered cells germinate in the gut of a subject, e.g., the gut of a human subject, following administration to the subject. In various embodiments, engineered cells administered to a subject germinate transiently in the gut of the subject. In various embodiments, engineered cells administered to a subject secrete fiber-synthesizing enzyme in the gut of the subject. In various embodiments, engineered cells of a single administered dose of a fiber-synthesizing enzyme formulation, fiber-synthesizing enzyme produced by engineered cells of a single administered dose of a fiber-synthesizing enzyme formulation, and/or isolated fiber-synthesizing enzyme delivered by a single administered dose of a fiber-synthesizing enzyme formulation can be detected in the gut of the subject, e.g., for a period of at least 6 hours (e.g., at least 6, 12, 18, 24, 48, or 72 hours, e.g., for a period of time having a lower bound of 6, 12, 18, or 24 hours and an upper bound of 12, 24, 48, 72, 96, or 120 hours).

In various embodiments, a fiber-synthesizing enzyme formulation the present disclosure is administered to a subject, before (e.g., up to 1, 2, 3, 4, 5, 6, 12, 24, or 48 hours prior to), during, or after (e.g., up to, up to 1, 2, 3, 4, 5, 6, 12, 24, or 48 hours after) consumption of food by the subject, optionally wherein the food includes carbohydrates (e.g., monosaccharides and/or disaccharides, e.g., sucrose). In various embodiments, a fiber-synthesizing enzyme formulation the present disclosure is administered in a dosage regimen, e.g., where a subject is administered a single daily dose, multiple daily doses (e.g., two or three daily doses), or one dose for each period of a certain number of days, e.g., 1, 2, 3, 4, 5, 6, or 7 days. To enable consumers to successfully use this technology it is highly desirable to limit the number of administration events required by a user of a supplement. The present inventors have determined one tablet a day is preferred by consumers and, among other things, is particularly preferable to taking a tablet or other form of administration with each meal. This is partly driven by enabling privacy, wherein meals can be enjoyed under any circumstances without drawing attention to the use of the supplement. In one embodiment, efficacy in a single dose is achieved by delivering the active enzyme in *Bacillus subtilis*, which traverses the intestinal tract in a manner different to that of formulated supplements.

The present disclosure includes the recognition that, in various embodiments, it can be beneficial for the expected time passage of a composition of the present disclosure through a subject's gastrointestinal tract to be longer than the expected time for passage of typical foods through the gastrointestinal tract of the subject, which can be referred to herein as slow passage. One benefit of slow passage is that a single administration of a composition provided herein can express an enzyme of the present disclosure in the subject for a period of time that includes multiple meals and/or a period of time that is at least 3 hours (e.g., at least 3, 6, 9, 12, 18, or 24 hours, e.g., a period of time that is at least 3 to 6 hours, 3 to 9 hours, 3 to 12 hours, 3 to 18 hours, 3 to 24 hours, 6 to 9 hours, 6 to 12 hours, 6 to 18 hours, 6 to 24 hours, 12 to 18 hours, or 12 to 24 hours). In various embodiments, slow passage can be characteristic of compositions that transiently adhere to the lining of the intestine. Those of skill in the art will appreciate that, by contrast, purified enzymes delivered (e.g., using various slow release formulations) pass through the intestine at the same rate as digesta and therefore generally must be administered with or at about the same time as ingested food with respect to which therapeutic effect is desired.

The present disclosure includes the recognition that, in various embodiments, it can be beneficial for a composition of the present disclosure to pass through the stomach of a subject without significant loss of cells (e.g., survival of cells) or cell viability (e.g., capacity to germinate and/or proliferate). In various embodiments, loss of cells or cell viability is less than 50%, e.g., less than 50%, 40%, 30%, 20%, 10%, 5%, 4%, 3%, 2%, or 1%. The present disclosure includes the recognition that, in various embodiments, it can be beneficial for a composition of the present disclosure to pass through the stomach of a subject without significant loss of isolated fiber-synthesizing enzyme activity. In various embodiments, loss of fiber-synthesizing enzyme activity is less than 50%, e.g., less than 50%, 40%, 30%, 20%, 10%, 5%, 4%, 3%, 2%, or 1%.

The present disclosure includes the recognition that, in various embodiments, it can be beneficial for a composition of the present disclosure to pass through the gut within a limited timeframe (gut residency time). Agents that include protective layers can be subject to passage times that vary with the activity of the intestinal tract, which, for example, can increase or decrease depending on eating behaviors of the subject and content consumed. Agents that colonize the gut can provide long-term delivery of an expressed transgene product, but the extended residency of colonizing bacteria can allow time for mutations in the bacteria, e.g., mutations that reduce transgene expression, and proliferation or population size can be difficult to monitor, stabilize, and/or control. An inflammatory and/or immune response against a colonizing bacteria could also arise over time. Colonization can also impact the composition of the microbiome with respect to other microbes, e.g., by causing loss of a similar strain present in the microbiome prior to administration of an agent of the present disclosure. Extended residency associated with colonization can also reveal unexpected characteristics, such as the discovered carcinogenic effects of colibactin produced by the colonizing probiotic *E. coli* Nissile, a strain that had historically been developed for human consumption. In various embodiments, gut residency time of a composition of the present disclosure is less than 10 days, e.g., less than 10, 9, 8, 7, 6, 5, 4, 3, 2, or 1 days. In various embodiments, residency time is measured from administration of a dose of a fiber-synthesizing enzyme formulation of the present disclosure to a time at which the subject includes a number of cells administered with or derived from the cell composition that is no more than 5%, 4%, 3%, 2%, 1%, 0.5%, 0.1%, 0.05%, 0.01%, 0.005%, or 0.001% the total number of cells administered in the dose. In various embodiments, clearance is measured as the inability to detect DNA characteristic of administered cells in DNA samples of the subject, e.g., isolated from stool of the subject. Those of skill in the art will appreciate from the present disclosure will appreciate that the present disclosure includes that a cell composition administered in repeated doses can therefore be advantageous as compared to a colonizing cell composition, e.g., where individual doses have a limited residency time and a plurality of doses over time can be used to extend duration of treatment. In various embodiments, cells of the present disclosure are cells that lack one or more functions required for survival in and/or colonization of the gut, including but not limited to, reliance on oxygen as an electron acceptor, susceptibility to defenses of host microbes, inability to participate in the cross-feeding ecosystem of the established microbiome, and/or lack of offensive self-preservation against host microbiome strains.

Those of skill in the art will appreciate that administration to a subject of a fiber-synthesizing enzyme formulation before, during, or after consumption of carbohydrate (e.g., monosaccharides and/or disaccharides, e.g., sucrose) can decrease concentration or amount of monosaccharides and/or disaccharides in the gut of the subject and/or decrease the rate or amount of fructose absorbed by the intestine of the subject and/or decrease the rate or amount of monosaccharides and/or disaccharides processed by microbiome cells of the subject, and also increase the production of fiber. In some embodiments, for every weight or mole units of fructose utilized as a substrate by a fiber-synthesizing enzyme an equal weight or mole units of fiber can be produced, leading to commensurate beneficial health effects from the increase in the concentration or amount of gut soluble fiber.

In various embodiments, administration of a fiber-synthesizing enzyme formulation in need thereof can treat a condition associated with or caused by consumption of carbohydrate (e.g., monosaccharides and/or disaccharides), e.g., high blood pressure, heart disease, obesity, diabetes, high blood glucose and other health problems. In various embodiments, administration of a fiber-synthesizing enzyme formulation of the present disclosure to a subject in need thereof can treat a condition associated with or caused by low soluble fiber consumption, e.g., high blood cholesterol, heart disease, obesity, diabetes, high blood glucose, and other health problems. In various embodiments, administration of a fiber-synthesizing enzyme formulation of the present disclosure to a subject in need thereof can provide health benefits associated with consumption of soluble fiber, including without limitation reduced risk of high blood cholesterol, heart disease, obesity, diabetes, high blood glucose, and other health problems. In various embodiments, administration of a fiber-synthesizing enzyme formulation of the present disclosure to a subject in need thereof to treat dysbiosis.

In various embodiments, a fiber-synthesizing enzyme formulation is administered to a subject in need thereof, wherein the subject has, has been diagnosed as having, or is at risk of developing one or more of a condition associated with or caused by consumption of carbohydrate (e.g., monosaccharides and/or disaccharides), caused by low soluble fiber consumption, or preventable by soluble fiber consumption, e.g., where the condition is selected from high blood pressure, heart disease, obesity, diabetes, high blood glucose and other health problems.

In various embodiments, a fiber-synthesizing enzyme formulation is administered to a subject for weight management, e.g., for dieting and/or for treatment of obesity. In various embodiments, the subject is overweight or obese. In various embodiments, obesity refers to a condition of having a body mass index equal to or greater than 30. In various conditions, overweight refers to a condition of having a body mass index equal to or greater than 25. Those of skill in the art will appreciate that a fiber-synthesizing enzyme formulation of the present disclosure can also be used by an individual who is neither overweight nor obese (body mass index below 25) for purposes of weight management or for any other purposes provided herein, e.g., for gut health.

In various embodiments, a fiber-synthesizing enzyme formulation is administered to a subject having consumed in the preceding 24 hours an amount of carbohydrate (e.g., an amount of total carbohydrate or monosaccharides and/or disaccharides) that is equal to or greater than about 45 g (e.g., at least about 45 g, 50 g, 55 g, 60 g, 65 g, 70 g, 80 g, 85 g, 90 g, 95 g, 100 g, 105 g, 110 g, 115 g, 120 g, 125 g, 130 g, 135 g, 140 g, 145 g, 150 g, 155 g, 160 g, 165 g, 170 g, 175 g, 180 g, 185 g, 190 g, 195 g, 200 g, or more). In various embodiments, a fiber-synthesizing enzyme formulation is administered to a subject having consumed in the preceding 24 hours an amount of fiber that is equal to or less than about 50 g (e.g., less than about 50 g, 45 g, 40 g, 35 g, 30 g, 25 g, 20 g, 15 g, 10 g, 5 g, or 1 g). In various embodiments, a fiber-synthesizing enzyme formulation is administered to a subject having consumed in the preceding 24 hours an amount of soluble fiber that is equal to or less than about 20 g (e.g., less than about 20 g, 15 g, 10 g, 9 g, 8 g, 7 g, 6 g, 5 g, 4 g, 3 g, 2 g, or 1 g).

In various embodiments, a fiber-synthesizing enzyme formulation is administered to a subject having consumed during at least about 10% (e.g., at least about 10%, 20%, 30%, 40%, 50%, 60%, 70%, 80%, 90%, or 100%) of the preceding 5 or more days (e.g., 5, 7, 10, 14, 28, 42, 50, 100, 150, 200, 250, 300, 350, or 365 days) an amount of carbohydrate (e.g., an amount of total carbohydrate or monosaccharides and/or disaccharides) that is equal to or greater than about 45 g (e.g., at least about 45 g, 50 g, 55 g, 60 g, 65 g, 70 g, 80 g, 85 g, 90 g, 95 g, 100 g, 105 g, 110 g, 115 g, 120 g, 125 g, 130 g, 135 g, 140 g, 145 g, 150 g, 155 g, 160 g, 165 g, 170 g, 175 g, 180 g, 185 g, 190 g, 195 g, 200 g, or more). In various embodiments, a fiber-synthesizing enzyme formulation is administered to a subject having consumed during at least about 10% (e.g., at least about 10%, 20%, 30%, 40%, 50%, 60%, 70%, 80%, 90%, or 100%) of the preceding 5 or more days (e.g., 5, 7, 10, 14, 28, 42, 50, 100, 150, 200, 250, 300, 350, or 365 days) an amount of fiber that is equal to or less than about 50 g (e.g., less than about 50 g, 45 g, 40 g, 35 g, 30 g, 25 g, 20 g, 15 g, 10 g, 5 g, or 1 g). In various embodiments, a fiber-synthesizing enzyme formulation is administered to a subject having consumed during at least about 10% (e.g., at least about 10%, 20%, 30%, 40%, 50%, 60%, 70%, 80%, 90%, or 100%) of the preceding 5 or more days (e.g., 5, 7, 10, 14, 28, 42, 50, 100, 150, 200, 250, 300, 350, or 365 days) an amount of soluble fiber that is equal to or less than about 20 g (e.g., less than about 20 g, 15 g, 10 g, 9 g, 8 g, 7 g, 6 g, 5 g, 4 g, 3 g, 2 g, or 1 g).

In various embodiments, a fiber-synthesizing enzyme formulation is administered to a subject that is a human. In various embodiments, a fiber-synthesizing enzyme formulation is administered to a subject that is an animal, e.g., a domestic animal (e.g., a cat, dog, or other domestic animal), a livestock animal (e.g., a horse, cow, sheep, goat, pig, or other livestock animal), or a zoo animal (e.g., a non-human primate, elephant, hippopotamus, rhinoceros, bear, or other zoo animal).

In various embodiments, treatment achieved by administration of a fiber-synthesizing enzyme formulation is advantageous as compared to direct consumption of fiber. For example, direct consumption of fiber does not prevent an overabundance of purified sugars in the colon. Additionally, a single daily dose of fiber only mediates one bolus passing through the digestive tract and may not affect other food portions containing sugar consumed throughout the day. Large doses of fiber also have physicochemical and biochemical properties that are abnormal for food, leading to changes in osmotic pressure and blooms in bacterial growth with associated negative experiences. Ingesting a large amount of fiber quickly can promote intestinal gas, abdominal bloating and cramping. No attempts have been made, to the knowledge of the present inventors, to decrease sugar after consumption prior to absorption by the intestine or microbiome. Nor, to the knowledge of the present inventors, is there a suitable technology for sustained delivery of therapeutically effective amounts of soluble fiber over, e.g., a period of 12 or 24 hours or longer.

The present disclosure includes the discovery that that solutions to various challenges disclosed herein are solved through the use of a living engineered cells as a delivery vector. In various embodiments, engineered cells temporarily adhere to and/or reside within the mucus layer lining the wall of the intestine. The proximity of the mucus layer to passing digesta allows for rapid interaction of engineered cells and/or fiber-synthesizing enzyme with passing digesta. Engineered bacterial spores and other live cells are known to transit the intestine over a period of greater than 9 hours, allowing for interaction of engineered cells and/or fiber-synthesizing enzyme produced thereby with multiple meals (e.g., two meals consumed within a period of 9 hours). Bacterial spores are extremely robust, with demonstrated ability to survive intact through the environment of the stomach. We were further able to identify, in particular embodiments, a microbial spore former that is active in the intestinal environment but does not colonize the intestine long term. This microbe, *Bacillus subtilis*, has a long history of being consumed in food as an active reagent in fermentation of soy beans, producing the food natt6, and is considered food safe. For at least these reasons, administration of an engineered cell of the present disclosure can provide longer lasting activity than ingestion of purified enzyme. Engineered cells (e.g. spores) of the present disclosure can pass safely pass through the stomach and subsequently express fiber-synthesizing enzyme in intestine. We identified that *B. subtilis* is a preferred candidate engineered cell at least in part because, when administered to a subject, it becomes caught in the mucosa (sticky ball model). *B. subtilis* is therefore exemplary of the limited set of delivery vectors that are food safe, non-colonizing (orthogonal to the microbiome), and spore forming.

REFERENCES

Davis, L. M. G., I. Martinez, J. Walter, and R. Hutkins. 2010. "A Dose Dependent Impact of Prebiotic Galactooligosaccharides on the Intestinal Microbiota of Healthy Adults." *International Journal of Food Microbiology* 144 (2): 285-92.

Desai, Mahesh S., Anna M. Seekatz, Nicole M. Koropatkin, Nobuhiko Kamada, Christina A. Hickey, Mathis Wolter, Nicholas A. Pudlo, et al. 2016. "A Dietary Fiber-Deprived Gut Microbiota Degrades the Colonic Mucus Barrier and Enhances Pathogen Susceptibility." *Cell* 167 (5): 1339-53.e21.

Dong, Yutong, Li Chen, Bernard Gutin, and Haidong Zhu. 2019. "Total, Insoluble, and Soluble Dietary Fiber Intake and Insulin Resistance and Blood Pressure in Adolescents." *European Journal of Clinical Nutrition* 73 (8): 1172-78.

Earle, Kristen A., Gabriel Billings, Michael Sigal, Joshua S. Lichtman, Gunnar C. Hansson, Joshua E. Elias, Manuel R. Amieva, Kerwyn Casey Huang, and Justin L. Sonnenburg. 2015. "Quantitative Imaging of Gut Microbiota Spatial Organization." *Cell Host & Microbe* 18 (4): 478-88.

Kim, H. J., M. Camilleri, S. McKinzie, M. B. Lempke, D. D. Burton, G. M. Thomforde, and A. R. Zinsmeister. 2003. "A Randomized Controlled Trial of a Probiotic, VSL #3, on Gut Transit and Symptoms in Diarrhoea-Predominant Irritable Bowel Syndrome." *Alimentary Pharmacology & Therapeutics* 17 (7): 895-904.

Marlett, J. A., and T. F. Cheung. 1997. "Database and Quick Methods of Assessing Typical Dietary Fiber Intakes Using Data for 228 Commonly Consumed Foods." *Journal of the American Dietetic Association* 97 (10): 1139-48, 1151; quiz 1149-50.

Parnell, Winsome, Noela Wilson, Donnell Alexander, Mark Wohlers, Micalla Williden, Joel Mann, and Andrew Gray. 2008. "Exploring the Relationship between Sugars and Obesity." *Public Health Nutrition* 11 (8): 860-66.

Schmidt, Kristin, Philip J. Cowen, Catherine J. Harmer, George Tzortzis, Steven Errington, and Philip W. J. Burnet. 2015. "Prebiotic Intake Reduces the Waking Cortisol Response and Alters Emotional Bias in Healthy Volunteers." *Psychopharmacology* 232 (10): 1793-1801.

Townsend, Guy E., 2nd, Weiwei Han, Nathan D. Schwalm 3rd, Varsha Raghavan, Natasha A. Barry, Andrew L. Goodman, and Eduardo A. Groisman. 2019. "Dietary Sugar Silences a Colonization Factor in a Mammalian Gut Symbiont." *Proceedings of the National Academy of Sciences of the United States of America* 116 (1): 233-38.

Wei, Q., C. Wolf-Hall, and K. C. Chang. 2001. "Natto Characteristics as Affected by Steaming Time, *Bacillus* Strain, and Fermentation Time." *Journal of Food Science* 66 (1): 167-73.

EXAMPLES

The present Examples demonstrate the construction of transgenes that encode a fiber-synthesizing enzyme. The present Examples further demonstrate production of engineered cells that include and express a transgene encoding fiber-synthesizing enzyme. As will be appreciated by those of skill in the art, engineered cells of the present disclosure are suitable for administration to subjects, including human subjects, and express fiber-synthesizing enzyme. Accordingly, the present Examples illustrate engineered cells representative of compositions disclosed herein and suitable for various applications provided herein, including without limitation applications that include administration to a human subject.

Example 1: Construction and Experimental Validation of Engineered Cells that Express an Enzyme for Synthesis of Soluble Fiber from Carbohydrate Substrate A transgene was constructed for expression of a fiber-synthesizing enzyme. The transgene was produced using standard techniques of molecular biology. The transgene included nucleic acid sequences encoding a fiber-synthesizing enzyme that included a secretion polypeptide. The present example utilizes SacB levansucrase enzyme. The nucleic acid encoding the fiber-synthesizing enzyme was derived from *B.s. Natto* sacB and has the following sequence, with the secretion polypeptide encoding sequence bolded and underlined:

(SEQ ID NO: 20)
atgaacatcaaaaagtttgcaaaacaagcaacagtattaacctttacta ccgcactgctggcaggaggcgcaactcaagcgtttgcgaaagaaacgaa ccaaaagccatataaggaaacatacggcatttcccatattacacgccat gatatgctgcaaatccctgaacagcaaaaaaatgaaaaatatcaagttc ctgaattcgattcgtccacaattaaaaatatctcttctgcaaaaggcct -continued

```
ggacgtttgggacagctggccattacaaaacgctgacggcactgtcgca aactatcacggctaccacatcgtctttgcattagccggagatcctaaaa atgcggatgacacatcgatttacatgttctatcaaaaagtcggcgaaac ttctattgacagctggaaaaacgctggccgcgtctttaaagacagcgac aaattcgatgcaaatgattctatcctaaaagaccaaacacaagaatggt caggttcagccacatttacatctgacggaaaaatccgtttattctacac tgatttctccggtaaacattacggcaaacaaacactgacaactgcacaa gttaacgtatcagcatcagacagctctttgaacatcaacggtgtagagg attataaatcaatctttgacggtgacggaaaaacgtatcaaaatgtaca gcagttcatcgatgaaggcaactacagctcaggcgacaaccatacgctg agagatcctcactacgtagaagataaaggccacaaatacttagtatttg aagcaaacactggaactgaagatggctaccaaggcgaagaatctttatt taacaaagcatactatggcaaaagcacatcattcttccgtcaagaaagt caaaaacttctgcaaagcgataaaaaacgcacggctgagttagcaaacg gcgctctcggtatgattgagctaaacgatgattacacactgaaaaaagt gatgaaaccgctgattgcatctaacacagtaacagatgaaattgaacgc gcgaacgtctttaaaatgaacggcaaatggtacctgttcactgactccc gcggatcaaaaatgacgattgacggcattacgtctaacgatatttacat gcttggttatgtttctaattctttaactggcccatacaagccgctgaac aaaactggccttgtgttaaaaatggatcttgatcctaacgatgtaacct ttacttactcacacttcgctgtacctcaagcgaaaggaaacaatgtcgt gattacaagctatatgacaaacagaggattctacgcagacaaacaatca acgtttgcgccaagcttcctgctgaacatcaaaggcaagaaaacatctg ttgtcaaagacagcatccttgaacaaggacaattaacagttaacaaata a.
```

The protein product SacB has the following amino acid sequence, with the secretion polypeptide sequence bolded and underlined:

```
                                  (SEQ ID NO: 21)
MNIKKFAKQATVLTFTTALLAGGATQAFAKETNQKPYKETYGISHITRH

DMLQIPEQQKNEKYQVPEFDSSTIKNISSAKGLDVWDSWPLQNADGTVA

NYHGYHIVFALAGDPKNADDTSIYMFYQKVGETSIDSWKNAGRVFKDSD

KFDANDSILKDQTQEWSGSATFTSDGKIRLFYTDFSGKHYGKQTLTTAQ

VNVSASDSSLNINGVEDYKSIFDGDGKTYQNVQQFIDEGNYSSGDNHTL

RDPHYVEDKGHKYLVFEANTGTEDGYQGEESLFNKAYYGKSTSFFRQES

QKLLQSDKKRTAELANGALGMIELNDDYTLKKVMKPLIASNTVTDEIER

ANVFKMNGKWYLFTDSRGSKMTIDGITSNDIYMLGYVSNSLTGPYKPLN

KTGLVLKMDLDPNDVTFTYSHFAVPQAKGNNVVITSYMTNRGFYADKQS

TFAPSFLLNIKGKKTSVVKDSILEQGQLTVNK*.
```

The nucleic acid sequence encoding fiber-synthesizing enzyme derived from *B.s. Natto* was operably linked with a nucleic acid sequence encoding a secretion polypeptide, such that the encoded fiber-synthesizing enzyme was a fusion polypeptide including a secretion polypeptide. The nucleic acid sequence encoding the fusion polypeptide was analyzed for secondary structure, at least in part because significant secondary structure can cause translation termination and poor expression. Base pairs that significantly contributed to secondary structure in the nucleic acid sequence were modified by silent modifications of nucleic acid sequence (e.g., non-coding and/or synonymous modifications of nucleic acid sequence) that reduced the contribution to secondary structure.

The nucleic acid sequence encoding the fiber-synthesizing enzyme was transformed into *B. subtilis* PY79 cells and operably linked to hag promoter by homologous recombination at the endogenous hag locus of *B. subtilis* PY79 genome with the addition of a modifying mutation in the promoter sequence by homologous integration as described in U.S. Ser. No. 16/048,147 (published as US 2019/0076489) and PCT/US18/50957 (published as WO 2019/055707) herein incorporated by reference in their entirety and with respect to regulatory sequences and systems disclosed therein.

Figure 1:
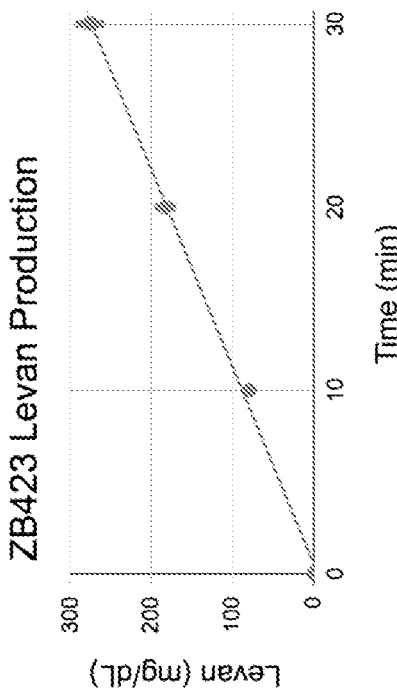
FIG. 1. The rate of production of levan (mg/dL over time (minutes)) in a culture of bacteria (strain ZB423) engineered to express levansucrase. Levan is calculated from glucose release and verified in batch culture by HPAEC and NMR (see FIGS. 3-7).

Fiber-synthesizing enzymatic activity was measured by the following assay. Because levansucrase cleavage of sucrose releases glucose, accumulation of glucose provides a measure of fiber-synthesizing enzyme activity. Accumulation of glucose is directly proportional to the cleavage of sucrose and formation of fructooligosaccharides. Various glucose meters are known in the art and can be standardized for measurement of glucose concentrations in bacterial media. Engineered bacteria of the present Example were cultured in media together with a defined concentration of sucrose. After culture for a defined period, bacteria were pelleted by centrifugation (21×g for 2 minutes) and remaining supernatant was contacted with a glucose meter testing strip. Levan production (mg/dL over time) is shown in FIG. 1.

Controls demonstrated no significant consumption of glucose occurred in the assay, consistent with expectations that glucose consumption due to cell growth would be <0.1% of available glucose. Further controls demonstrated that addition of sucrase to collected supernatant for complete cleavage of remaining sucrose resulted in a final yield of glucose equal to the starting amount of sucrose.

Figure 3:
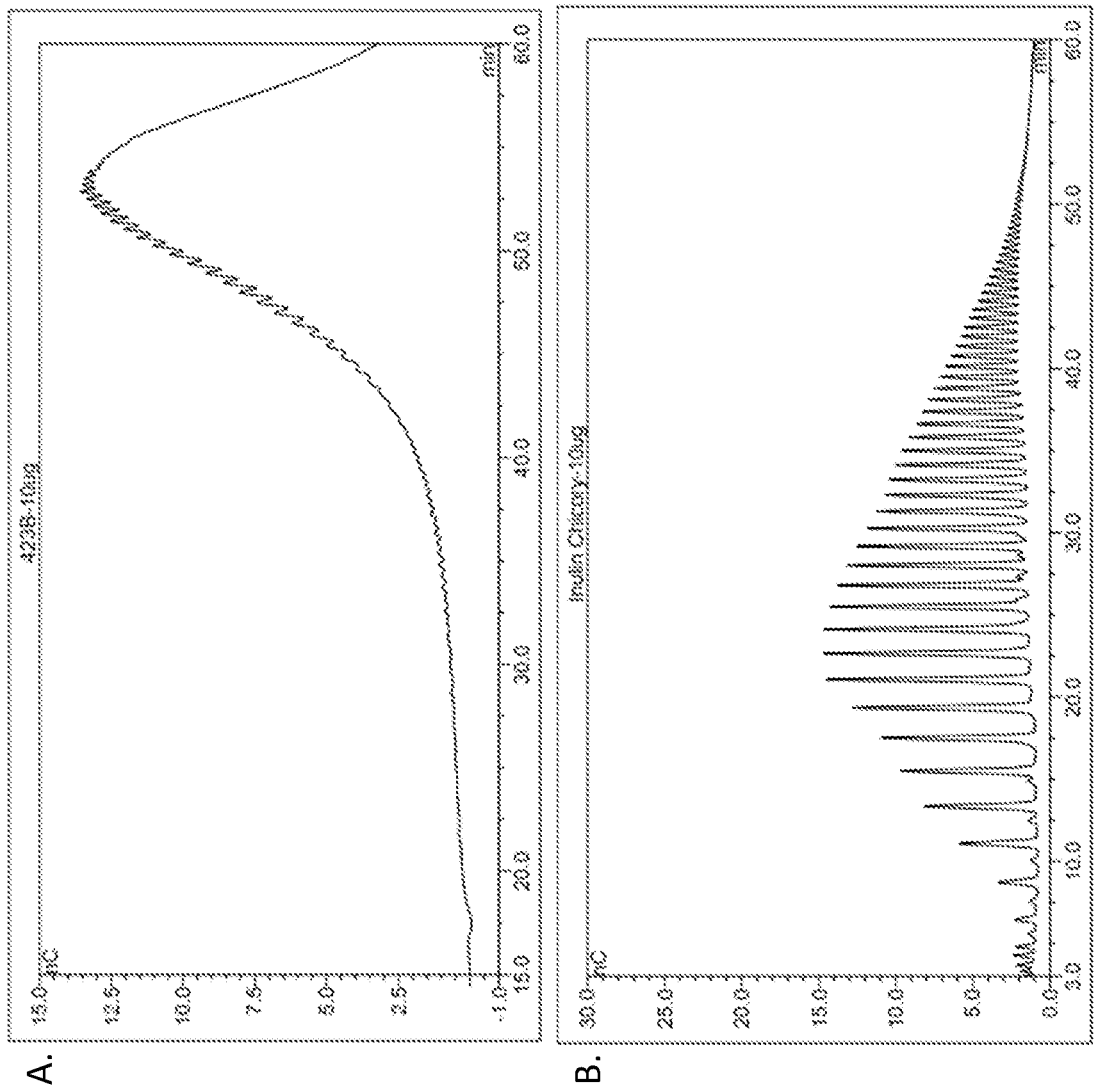
FIG. 3 High Performance Anion Exchange Chromatog-raphy (HPAEC) data for Levan isolated from ZB423 culture.

Fructose polymer formation was confirmed by addition of xylose isomerase to collected supernatant. Xylose isomerase can convert glucose to fructose, and addition of xylose isomerase equilibrates free, non-polymerized fructose with free glucose. If fructooligosaccharide fibers have formed, then the level of free, non-polymerized fructose would be significantly lower than glucose, such that xylose isomerase would catalyze conversion of glucose into fructose causing the glucose level of the supernatant to drop. If fructooligosaccharides have not formed, then the level of free, non-polymerized fructose would be comparable or higher than that of glucose, in which case xylose isomerase would not catalyze conversion of glucose to fructose and the level of glucose would rise or remain unchanged. Results demonstrated that addition of xylose isomerase catalyzed conversion of glucose into fructose causing the glucose level of the supernatant to drop, indicative of fructooligosaccharide fiber formation. Those of skill in the art will appreciate that a variety of alternative methods are readily available for quantification (e.g., of the amount and/or concentration) of glucose, fructose, fructooligosaccharide, and the like, including without limitation HPLC and HPAEC. To confirm that Levan is produced from ZB423 the strain was cultured in productive media (Per Liter in water: 2.5 g yeast extract, 1.5 g NH4SO4, 7.2 g K2HPO4, 0.2 g MgSO4.7H2O, and 200 g sucrose) for 72 hours. The cell culture was then pelleted to remove cells and cold ethanol (1:1.5) was added to the supernatant. A white precipitate was observed, collected by centrifugation, and further purified by twice repeating dissolution in water and precipitation in cold ethanol followed by centrifugation to collect the pellet. The pellet was dried under vacuum for 24 hours before analysis, becoming clear, hard, and brittle after drying. A strain of *Bacillus subtilis* PY79 that was not engineered to express SacB did not produce a precipitate or pellet from the supernatant and could not be analyzed. The pellet was analyzed by High Performance Anion Exchange Chromatography (HPAEC) [FIG. 3.] to confirm the degree of polymerization, and by 1H-NMR [FIG. 4], 13C-NMR [FIG. 5], and HSQC-NMR [FIG. 6] to confirm the structure of the polymer as Levan. A comparison of 13C-NMR chemical shifts to those previously measured in literature shows that they closely correlate with known values for Levan [FIG. 7].

Figure 2:
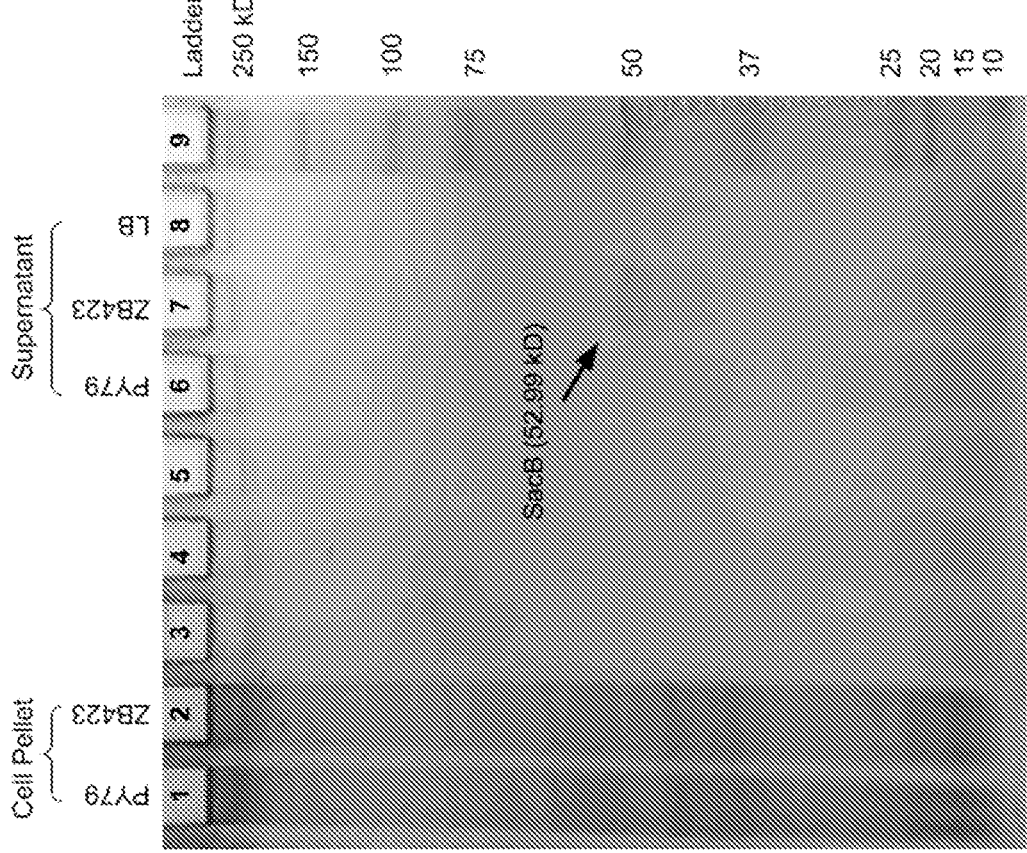
FIG. 2 is an SDS-PAGE gel showing accumulation of secreted levansucrase enzyme in supernatant. Lanes 1 and 2 are cell pellet lysates from strains not encoding SacB (PY79) or engineered to encode SacB (ZB423) respectively. Lanes 6 and 7 are cell culture supernatant from strains not encoding SacB (PY79) or engineered to encode SacB (ZB423) respec-tively. Lanes 3, 4, and 5 are supernatant from other *Bacillus subtilis* strains not relevant to this study. Lane 8 contains cell culture media only as a control reference. Lane 9 contains the protein ladder with bands corresponding to 10, 15, 20, 25, 37, 50, 75, 100, 150, 250 kDa from bottom to top. The supernatant fraction of ZB423 clearly shows a band adjacent to the 50 kDa ladder marker, matching the expected size of 52.99 kDa for SacB protein.

Secretion of fiber-synthesizing enzyme by engineered cells was assayed in LB media. Engineered cells were cultured for 18 hours, after which period sucrose was added to media and glucose accumulation was measured periodically as described above. Additionally, a gel of the supernatant shows protein of the correct size in supernatant and not in cell fractions. Results are shown in FIG. 2.

The present Example demonstrated that transgene encoding a fiber-synthesizing enzyme derived from F1-sacB of *B. subtilis* sp. natto expressed a highly active fiber-synthesizing enzyme.

The present disclosure further includes the recognition that levansucrase (SacB) derived from B.s. Natto has certain exemplary qualities that confirm the utility of SacB expression in gut. The optimum pH range for levansucrase activity of sacB is 6-7 which matches that of the small intestine. SacB enzyme is naturally secreted and therefore stable outside of the engineered cell, amenable to secretion through a gram positive cell envelope.

Example 2: Engineered Cells for Increased Efficiency of Transgene Integration The present Example demonstrated engineering of target cells to increase the efficiency of transformation of the target cells with a transgene including a nucleic acid sequence encoding a fiber-synthesizing enzyme, where the nucleic acid sequence that encodes the fiber-synthesizing enzyme has at least 80% identity to an endogenous sequence of a target cell type. The present Example provides in particular a transgene as set forth in Example 1, encoding F1-SacB, and target cells that are *B. subtilis* PY79 cells. The transgene was flanked by homology regions (often referred to as "homology arms") of about 800 bp designed to target the transgene for integration at the *B. subtilis* PY79 hag locus by homologous recombination. The transgene included a sequence of about 1400 bp having significant (greater than 80%) identity with *B. subtilis* PY79 sacB gene. Because of the 1400 bp region of significant identity between the transgene and the endogenous sacB gene, homologous recombination between the transgene and the endogenous sacB gene can complete with homologous recombination between the homology arms and the endogenous hag locus. Due it's large size, the 1400 bp region may be more likely to recombine with the endogenous genome than the desired homology arms. To reduce and/or obviate recombination between the transgene and the endogenous SacB gene, the corresponding sequence of the endogenous sacB gene was knocked out by deletion using standard molecular biology techniques.

Example 3: Engineered Cells for Constitutive Expression of Fiber-Synthesizing Enzyme While those of skill in the art will appreciate that any of a variety of promoters are known to cause constitutive expression of an operably linked coding sequence, the present Example provides an exemplary demonstration of cells engineered for constitutive expression of a transgene-encoded fiber-synthesizing enzyme. The present Example includes a transgene that includes a flagellin gene promoter operably linked to a nucleic acid sequence encoding a fiber-synthesizing enzyme. Many bacteria have a flagellin gene homolog. Flagellin genes go by many names, some examples of which are: hag in *B. subtilis*; fliC in *Escherichia coli, Bacillus thuringiensis*, and several *lactobacillus* species; and flaA or flaB C/D E/F etc. in *Legionella* species, *Vibrio* species, and *Campylobacter* species. Various embodiments including a hag promoter operably linked to a nucleic acid sequence encoding a fiber-synthesizing enzyme are disclosed, and at least one representative embodiment thereof is exemplified. The disclosures of U.S. Ser. No. 16/048,147 (published as US 2019/0076489) and PCT/US18/50957 (published as WO 2019/055707) are herein incorporated by reference in their entirety and with respect to regulatory sequences and systems disclosed therein. Those of skill in the art will appreciate that the flagellin gene expression system disclosed herein is merely one of many expression systems available for expression (e.g., constitutive expression) of coding sequences in in bacteria, and that the flagellin system disclosed herein was used as a matter of experimental convenience based on available reagents.

In the present Example, flagellar regulatory machinery of *B. subtilis* was adapted to accomplish constitutive and robust expression of a fiber-synthesizing enzyme, levansucrase. Various bacteria, including *B. subtilis*, regulate motility, at least in part, by a sophisticated system involving several positive and negative regulators. The constitutive expression strategy of this Example includes removing negative regulators of the highly expressed *B. subtilis* flagellin gene, called hag.

The gene encoding the flagellar subunit of *B. subtilis* flagellin is hag, and the protein it encodes is expressed in hundreds of thousands of copies in a single bacterium in the right conditions, using a transcriptional promoter and a ribosome binding site that are both robust. Transcription is mediated by a sigma factor, SigD, which is repressed by the FlgM protein. Inactivation (e.g., by deletion or mutation) of flgM expression greatly enhances constitutive expression and activity of SigD, and consequently results in higher and more constitutive transcription of the flagellar operon and specifically the hag gene. Translation of transcripts generated from the hag gene is enabled by a highly robust ribosome binding site that is bound and repressed post-transcriptionally by a protein called CsrA. However, a single point mutation in the CsrA binding site abrogates its binding and results in increased constitutive translation of the Hag protein.

Using the combination of inactivation the flgM gene and making the single point mutation in the CsrA-binding site can achieve extremely high levels of Hag protein expression constitutively during the *B. subtilis* life cycle. Similarly, if the hag gene is replaced with a heterologous gene encoding a protein of interest, that gene can be transcribed and translated constitutively at high levels. Thus, replacement of the hag gene with a gene encoding a fiber-synthesizing enzyme, inactivation of expression of the flgM gene, and introduction of a single point mutation at the CsrA binding site of the hag promoter can result in robust and constitutive expression of fiber-synthesizing enzyme in *B. subtilis*.

Accordingly, in certain embodiments provided herein, bacteria include a point mutation in the binding site of CsrA in combination with a mutation that inactivates flgM expression. By making these two mutations, constitutive expression from any SigD-based or flagellin promoter system is increased. Without wishing to be limited by any particular scientific theory, it is believed that mutation of a CsrA binding site is distinct from simple deletion of CsrA because CsrA is a pluripotent regulator in many bacterial species and its deletion could have many other potentially undesirable phenotypic effects on a cell. By making a point mutation only in the binding site, the mutation reduces or precludes CsrA repression of the hag promoter specifically and/or uniquely, rather than removing CsrA repression from any other targets it may have.

Certain nucleic acids disclosed herein thus include a transgene comprising a flagellin gene transcription regulatory sequence (e.g., a flagellin gene promoter, e.g., a hag promoter) operatively linked with a heterologous nucleic acid sequence encoding a fiber-synthesizing enzyme. In certain embodiments, the hag promoter comprises genetic alterations such that, upon transcription of an mRNA from the hag promoter, CsrA inhibition of mRNA translation is reduced or repressed compared to a reference with wild-type or canonical CsrA binding sites.

In certain embodiments, the flagellin gene promoter is a hag gene promoter. The flagellin homolog is hag in *Bacillus*, e.g., *B. subtilis*. In another embodiment, the flagellin gene promoter is native to the cell in which the subject protein is to be expressed. For example, this can be the case when the expression construct is located in a bacterial chromosome.

As used herein, the term "Hag" (or "hag" or "hag") can refer to the protein (or gene encoding such protein) annotated as "Hag" in *B. subtilis* or any homolog in the same or other genus, species, or strain, which is the structural subunit also known more generically as "flagellin" used to assemble a flagellum. It is known by several other names in other genera, species, and strains. *B. subtilis* Hag is encoded by the following sequence:

```
                                    (SEQ ID NO: 22)
atgagaattaaccacaatattgcagcgcttaacacactgaaccgtttgt cttcaaacaacagtgcgagccaaaagaacatggagaaactttcttcagg tcttcgcatcaaccgtgcgggagatgacgcagcaggtcttgcgatctct gaaaaaatgagaggacaaatcagaggtcttgaaatggcttctaaaaact ctcaagacggaatctctcttatccaaacagctgagggtgcattaactga aactcatgcgatccttcaacgtgttcgtgagctagttgttcaagctgga aacactggaactcaggacaaagcaactgatttgcaatctattcaagatg aaatttcagctttaacagatgaaatcgatggtatttcaaatcgtacaga attcaatggtaagaaattgctcgatggcacttacaaagttgacacagct actcctgcaaatcaaaagaacttggtattccaaatcggagcaaatgcta cacagcaaatctctgtaaatattgaggatatgggtgctgacgctcttgg
```

-continued
```
aattaaagaagctgatggttcaattgcagctcttcattcagttaatgat cttgacgtaacaaaattcgcagataatgcagcagatactgctgatatcg gtttcgatgctcaattgaaagttgttgatgaagcgatcaaccaagtttc ttctcaacgtgctaagcttggtgcggtacaaaatcgtctagagcacaca attaacaacttaagcgcttctggtgaaaacttgacagctgctgagtctc gtatccgtgacgttgacatggctaaagagatgagcgaattcacaaagaa caacattctttctcaggcttctcaagctatgcttgctcaagcaaaccaa cagccgcaaaacgtacttcaattattacgttaa.
```

As used herein, the term "hag promoter" refers to a naturally occurring flagellin gene promoter cognate from genus *Bacillus* and promoters having sequences substantially identical (e.g., at least 80%, e.g., 80%, 85%, 90%, 95%, 96%, 97%, 98%, 99%, or 100% identical) thereto or hybridizing specifically thereto. In *B. subtilis*, the hag promoter is comprised in a 273 base-pair sequence 5' of the start codon of the hag gene, having the nucleic acid sequence:

```
                                    (SEQ ID NO: 23)
ggaattgacgccccaaagcatattgatattcacaggaaagaaatttact tgaccattcaggaagaaaataaccgtgcagcagcgttatccagcgatgt gatctccgcattatcctcacaaaaaaagtgaggatttttttatttttgt attaacaaaatcagagacaatccgatattaatgatgtagccgggaggag gcgcaaaagactcagccagttacaaaataagggcacaaggacgtgcctt aacaacatattcagggaggaacaaaaca(ATG)
```

(where "ATG" represents the start codon of hag). The sequence in bold beginning with TTAA (underlined) through the start codon ATG is sufficient to promote expression of an operably linked coding sequence.

In particular, the hag promoter includes a SigD recognition sequence defined by a "ttaa" sequence (underlined), which is the −35 SigD RNA polymerase binding site and a "tccgatat" sequence (underlined), which is the −10 SigD RNA polymerase binding site. In addition, hag has two CsrA binding sites defined by the sequences "gcacaaggacgt" (SEQ ID NO: 24) (high-affinity binding site 1, or "BS1") (underlined) and "attcagggaggaa" (SEQ ID NO: 25) (low-affinity binding site 2, or "BS2") (underlined). The hag promoter also includes a Shine-Dalgarno sequence: agggagga (SEQ ID NO: 26).

As used herein, the term "CsrA" ("Carbon storage regulator A") refers to the protein (or gene encoding such protein) annotated as "CsrA" in *B. subtilis*—or any homolog or ortholog in another genus or species, or paralog in the same species. CsrA is homologously referred to as RsmA in some species. CsrA protein binds to a stem-loop RNA motif having the consensus sequence AGGA in the loop, thereby inhibiting translation into polypeptide of a nucleic acid sequence incorporated in an mRNA comprising the consensus sequence. CsrA can inhibit expression of an mRNA transcribed from the hag promoter either directly by binding to the RNA and preventing translation or indirectly by binding to another RNA that encodes a protein that otherwise regulates flagellar expression. CsrA is encoded in *B. subtilis* by the sequence:

```
                                          (SEQ ID NO: 27)
atgctagttttatcgcggaaaataaacgaagcgattcaaataggtgctg atattgaagtaaaagtgattgcggttgaaggggatcaagtgaagcttgg aattgacgccccaaagcatattgatattcacaggaaagaaatttacttg accattcaggaagaaaataaccgtgcagcagcgttatccagcgatgtga tctccgcattatcctcacaaaaaagtga.
```

In certain embodiments, transgenes of the present disclosure include genetic modifications in a flagellin gene promoter that, upon transcription from the promoter into a transcript, such as mRNA, reduce and/or repress CsrA inhibition of mRNA translation. The present disclosure contemplates several genetic modifications to a flagellin gene promoter, and, in particular, to a hag promoter, to reduce and/or repress CsrA inhibition of mRNA translation. In some embodiments, genetic modifications to hag to inhibit CsrA repression of translation can comprise an alteration of a stem and loop structure in either or both of BS1 or BS2. In some embodiments, the genetic modification is an insertion or a deletion of one or more nucleotides. A genetic modification can include one or more point mutations to CsrA BS1 (binding site 1P. BS1 can be modified by altering one or a plurality (e.g., two, three, or four) nucleotides in the CsrA recognition sequence, AGGA. For example, the AGGA binding motif of BS1 can be modified to AGAA. Alternatively, the genetic modification can include one or more mutations in the 12-base-pair BS1 binding site or in the surrounding bases on either side of the nucleotides that form the stem of the stem-loop secondary structure of BS1. This includes, for example, modification of one or a plurality of nucleotides (e.g., at least 2, at least 3, at least 4, at least 5, at least 6, at least 7, at least 8, at least 9, at least 10, at least 11, or at least 12 nucleotides) of the BS1 binding site, gcacaaggacgt (SEQ ID NO: 24). Alternatively, a genetic modification can disrupt the stem and loop structure of BS1 by eliminating complementarity that allows hydrogen bonding. Such alterations can be made as one or a plurality of mutations in the sequence taagggcacaaggacgtgcctta (SEQ ID NO: 28) involved in hydrogen bonding, for example, to eliminate one, two, three, four or more hydrogen bond pairs. In one embodiment, the modified BS1 has the nucleotide sequence GCACAAGAACGT (SEQ ID NO: 29). A genetic modification can also or alternatively include one or more point mutations to CsrA BS2 (binding site 2). This includes, for example, modification of one or a plurality of nucleotides (e.g., at least 2, at least 3, at least 4, at least 5, at least 6, at least 7, at least 8, at least 9, at least 10, at least 11, at least 12, or at least 13 nucleotides) of the 13-base-pair BS2 binding site or in the surrounding bases on either side of the binding site that form the stem of the stem-loop secondary structure of BS2. Alternatively, a genetic modification can disrupt the stem and loop structure of BS2 by eliminating complementarity that allows hydrogen bonding. For example, the modified BS2 can have the nucleotide sequence ATTTAGGGAGGAA (SEQ ID NO: 30). In certain embodiments, the modification does not include an alteration of nucleotides in the Shine-Dalgarno sequence agggagga (SEQ ID NO: 26).

It will be recognized that the genetic modification, while inhibiting CsrA binding, is selected to allow the mRNA to retain ribosome binding activity and to permit translation.

Sigma factors, such as SigD and its homologs, initiate flagellin synthesis. FlgM and its homologs function as repressors of Sigma factor activity. This disclosure provides for de-repression of Sigma factor activity by disruption (e.g. inactivation) of expression and/or activity of Sigma factor repressors such as FlgM.

As used herein, the term "FlgM" can refer to the protein (or the gene encoding such protein) annotated as "FlgM" in *B. subtilis*, or any homolog in another genus or species, which inhibits the sigma factor responsible for recruiting RNA polymerase to late flagellar genes for transcription. This inhibited sigma factor is called SigD in *B. subtilis*, FliA in *E. coli*, or potentially other names such as sigma 28 in other genera and species in which said sigma factor has a homolog. FlgM is defined in *B. subtilis* by the sequence:

```
                                          (SEQ ID NO: 31)
atgaaaatcaatcaatttggaacacaatccgttaatccatatcaaaaaa attatgataagcaagcggtgcaaaaaactgttgcacaacctcaagataa aattgaaatttcatcacaggctaaagaaatgcaacatgcatccgacgca gtcactggttcacgacaggaaaaaattgcgcagcttaaagcgcaaattg aaaacgggtcatacaaagtagacgcaaatcatattgcgaaaaatatgat taatttttataaaaagcaataa.
```

As used herein, the term "SigD" can refer to the sigma factor (or the gene encoding it) in *B. subtilis* responsible for, among other things, recruiting the RNA polymerase to late flagellar genes for transcription. "SigD" furthermore refers to homologs in other species, such as FliA in *E. coli*, or the broader denotation of sigma-28 in several species. SigD is defined in *B. subtilis* by the sequence:

```
                                          (SEQ ID NO: 32)
atgcaatccttgaattatgaagatcaggtgctttggacgcgctggaaag agtggaaagatcctaaagccggtgacgacttaatgcgccgttacatgcc gcttgtcacatatcatgtaggcagaatttctgtcggactgccgaaatca gtgcataaagacgatcttatgagccttggtatgcttggtttatatgatg cccttgaaaaatttgaccccagccgggacttaaaatttgatacctacgc ctcgtttagaattcgcggcgcaatcatagacgggcttcgtaaagaagat tggctgcccagaacctcgcgcgaaaaaacaaaaaaggttgaagcagcaa ttgaaaagcttgaacagcggtatcttcggaatgtatcgcccgcggaaat tgcagaggaactcggaatgacggtacaggatgtcgtgtcaacaatgaat gaaggttttttgcaaatctgctgtcaattgatgaaaagctccatgatc aagatgacggggaaaacattcaagtcatgatcagagatgacaaaaatgt tccgcctgaagaaaagattatgaaggatgaactgattgcacagcttgcg gaaaaaattcacgaactctctgaaaaagaacagctggttgtcagtttgt tctacaaagaggagttgacactgacagaaatcggacaagtattaaatct ttctacgtcccgcatatctcagatccattcaaaggcattatttaaatta aagaatctgctggaaaaagtgatacaataa.
```

FlgM can bind to SigD via several residues, the majority of which are located in the 4th helix at the C-terminal end of the FlgM protein. Targets for inactivation would be mutation of the highly conserved residues in the 3rd and 4th helices corresponding to I-58, K-62, I-65, G-68, D-73, A-78 of the *B. subtilis* FlgM. More broadly, any one or combination of the 26 residues directly involved in binding to SigD (as identified in PMID: 15068809) could be mutated to potentially generate a protein with reduced or null activity. Alternatively, any mutation or combination of mutations that disrupted the secondary or tertiary structure—in particular the 4 helices that define the secondary structure—could potentially successfully reduce or attenuate the ability of FlgM to inhibit SigD.

In various embodiments, a cell includes a genetic modification that reduces the ability FlgM to inhibit SigD activity. For example, one such genetic modification can be partial or complete deletion of the FlgM gene to reduce or eliminate its biological activity. Partial deletion can include deletion of part of the gene encoding at least 25% of the C-terminus of the protein.

Other genetic modifications include, for example, frameshift mutations producing an inactive FlgM protein, or disruption of the FlgM promoter. Alternatively, FlgM could be rendered inactive by a point mutation that renders it functionally inactive or otherwise inhibits its ability to bind to or otherwise repress SigD. Indirectly, FlgM could be disrupted by making it insensitive to activators such as ComK or DegU, or by making it overly sensitive to repressors such as ScoC or proteases Epr and Wpr.

A heterologous nucleic acid sequence such as a transgene encoding a fiber-synthesizing enzyme can be operably linked with a flagellin promoter by any method known in the art. For example, a heterologous nucleic acid sequence can be integrated into the bacterial chromosome. Alternatively, a heterologous nucleic acid sequence can be attached to a flagellin promoter in a plasmid that is introduced into the microorganism. A heterologous nucleic acid sequence can be targeted to the hag promoter by, for example, homologous recombination, as described, for example, in PMID: 4994568. Another useful method involves transposon technology. Transposons can target specific sequences in a chromosome and insert an attached nucleic acid sequence at a target locus. Various transposon systems are known in the art.

The present Example provides engineered cells that express a fiber-synthesizing enzyme, where the cells are PY79 strain cells that include an inactivation deletion of flgM (ΔflgM), a deletion of endogenous sacB (ΔsacB), and a modified hag promoter ("Pso3") engineered to reduce binding of CsrA to transcripts (Δhag, the engineering including a mutation referred to alternatively as "sow3" or "so3") operably linked to a nucleic acid sequence encoding a fiber-synthesizing enzyme, where the nucleic acid sequence encoding the fiber-synthesizing enzyme has the following structure: Pso3::nucleic acid sequence encoding secretion polypeptide::nucleic acid sequence encoding sacB. These engineered cells were assayed for enzymatic activity in vitro. A unit dose of 1E+09 engineered spore form cells was found to produce 10.4 mg of glucose through cleavage of sucrose for incorporation into fiber per hour. Scaled to an exemplary therapeutic unit dose of 1E11 CFU of spore form cells, a single unit dose of 1E11 engineered cells yields at least 1.04 g glucose from cleavage of sucrose for incorporation into fiber per hour, or at least about 25 g of glucose from cleavage of sucrose for incorporation into fiber per day. These engineered cells produce a stoichiometric amount of fiber in the reaction, and a single unit dose of 1E11 engineered cells therefore synthesizes 25 g of fiber per day.

Example 4: Engineered Cells for Conversion of Lactose to Human Milk Oligosaccharide Prebiotic Fibers Genetically modified *Bacillus subtilis* strains were engineered to express transgenes encoding Human Milk Oligosaccharide-synthesizing enzymes. Transgenes and bacterial strains were produced using standard techniques of molecular biology. Each transgene included a nucleic acid sequence encoding a lactose-degrading/oligosaccharide-synthesizing enzymes. In particular, four engineered strains, each including a distinct transgene, were produced. The strains respectively included transgenes for expression of LacZ (*E. coli*), YesZ (*Bacillus subtilis*), GanA (*Bacillus subtilis*), and LacZ (*Bacillus coagulans*) beta-galactosidase enzymes in accordance with the following sequence information:

Nucleic acid sequence encoding LacZ (*E. coli*):

(SEQ ID NO: 71)

```
atgaccatgattacggattcactggccgtcgtttacaacgtcgtgact gggaaaaccctggcgttacccaacttaatcgccttgcagcacatccccc tttcgccagctggcgtaatagcgaagaggcccgcaccgatcgcccttcc caacagttgcgcagcctgaatggcgaatggcgctttgcctggtttccgg caccagaagcggtgccggaaagctggctggagtgcgatcttcctgaggc cgatactgtcgtcgtcccctcaaactggcagatgcacggttacgatgcg cccatctacaccaacgtgacctatcccattacggtcaatccgccgtttg ttcccacggagaatccgacgggttgttactcgctcacatttaatgttga tgaaagctggctacaggaaggccagacgcgaattattttttgatggcgtt aactcggcgtttcatctgtggtgcaacgggcgctgggtcggttacggcc aggacagtcgtttgccgtctgaatttgacctgagcgcatttttacgcgc cggagaaaaccgcctcgcggtgatggtgctgcgctggagtgacggcagt tatctggaagatcaggatatgtggcggatgagcggcattttccgtgacg tctcgttgctgcataaaccgactacacaaatcagcgatttccatgttgc cactcgctttaatgatgatttcagccgcgctgtactggaggctgaagtt cagatgtgcggcgagttgcgtgactacctacgggtaacagtttctttat ggcagggtgaaacgcaggtcgccagcggcaccgcgcctttcggcggtga aattatcgatgagcgtggtggttatgccgatcgcgtcacactacgtctg aacgtcgaaaacccgaaactgtggagcgccgaaatcccgaatctctatc gtgcggtggttgaactgcacaccgccgacggcacgctgattgaagcaga agcctgcgatgtcggtttccgcgaggtgcggattgaaaatggtctgctg ctgctgaacggcaagccgttgctgattcgaggcgttaacgtcacgagc atcatcctctgcatggtcaggtcatggatgagcagacgatggtgcagga tatcctgctgatgaagcagaacaactttaacgccgtgcgctgttcgcat tatccgaaccatccgctgtggtacacgctgtgcgaccgctacggcctgt atgtggtggatgaagcaatattgaaacccacggcatggtgccaatgaa tcgtctgaccgatgatccgcgctggctaccggcgatgagcgaacgcgta acgcgaatggtgcagcgcgatcgtaatcacccgagtgtgatcatctggt cgctggggaatgaatcaggccacggcgctaatcacgacgcgctgtatcg ctggatcaaatctgtcgatccttcccgcccggtgcagtatgaaggcggc ggagccgacaccacggccaccgatattatttgcccgatgtacgcgcgcg tggatgaagaccagcccttcccggctgtgccgaaatggtccatcaaaaa atggctttcgctacctggagagacgcgcccgctgatcctttgcgaatac
```

-continued

```
gcccacgcgatgggtaacagtcttggcggtttcgctaaatactggcagg cgtttcgtcagtatccccgtttacagggcggcttcgtctgggactgggt ggatcagtcgctgattaaatatgatgaaaacggcaacccgtggtcggct tacggcggtgattttggcgatacgccgaacgatcgccagttctgtatga acggtctggtctttgccgaccgcacgccgcatccagcgctgacggaagc aaaacaccagcagcagtttttccagttccgtttatccgggcaaaccatc gaagtgaccagcgaatacctgttccgtcatagcgataacgagctcctgc actggatggtggcgctggatggtaagccgctggcaagcggtgaagtgcc tctggatgtcgctccacaaggtaaacagttgattgaactgcctgaacta ccgcagccggagagcgccgggcaactctggctcacagtacgcgtagtgc aaccgaacgcgaccgcatggtcagaagccgggcacatcagcgcctggca gcagtggcgtctggcggaaaacctcagtgtgacgctccccgccgcgtcc cacgccatcccgcatctgaccaccagcgaaatggattttttgcatcgagc tgggtaataagcgttggcaatttaaccgccagtcaggctttctttcaca gatgtggattggcgataaaaaacaactgctgacgccgctgcgcgatcag ttcacccgtgcaccgctggataacgacattggcgtaagtgaagcgaccc gcattgaccctaacgcctgggtcgaacgctggaaggcggcgggccatta ccaggccgaagcagcgttgttgcagtgcacggcagatacacttgctgat gcggtgctgattacgaccgctcacgcgtggcagcatcaggggaaaacct tatttatcagccggaaaacctaccggattgatggtagtggtcaaatggc gattaccgttgatgttgaagtggcgagcgatacaccgcatccggcgcgg attggcctgaactgccagctggcgcaggtagcagagcgggtaaactggc tcggattagggccgcaagaaaactatcccgaccgccttactgccgcctg ttttgaccgctgggatctgccattgtcagacatgtataccccgtacgtc ttcccgagcgaaaacggtctgcgctgcgggacgcgcgaattgaattatg gcccacaccagtggcgcggcgacttccagttcaacatcagccgctacag tcaacagcaactgatggaaaccagccatcgccatctgctgcacgcgaa gaaggcacatggctgaatatcgacggtttccatatggggattggtggcg acgactcctggagcccgtcagtatcggcggaattccagctgagcgccgg tcgctaccattaccagttggtctggtgtcaaaaataa..
```

LacZ (*E. coli*) amino acid sequence (encoded by SEQ ID NO: 71):

(SEQ ID NO: #72)
```
MTMITDSLAVVLQRRDWENPGVTQLNRLAAHPPFASWRNSEEARTDRPS

QQLRSLNGEWRFAWFPAPEAVPESWLECDLPEADTVVVPSNWQMHGYDA

PIYTNVTYPITVNPPFVPTENPTGCYSLTFNVDESWLQEGQTRIIFDGV

NSAFHLWCNGRWVGYGQDSRLPSEFDLSAFLRAGENRLAVMVLRWSDGS

YLEDQDMWRMSGIFRDVSLLHKPTTQISDFHVATRFNDDFSRAVLEAEV

QMCGELRDYLRVTVSLWQGETQVASGTAPFGGEIIDERGGYADRVTLRL

NVENPKLWSAEIPNLYRAVVELHTADGTLIEAEACDVGFREVRIENGLL
```

-continued
```
LLNGKPLLIRGVNRHEHHPLHGQVMDEQTMVQDILLMKQNNFNAVRCSH

YPNHPLWYTLCDRYGLYVVDEANIETHGMVPMNRLTDDPRWLPAMSERV

TRMVQRDRNHPSVIIWSLGNESGHGANHDALYRWIKSVDPSRPVQYEGG

GADTTATDIICPMYARVDEDQPFPAVPKWSIKKWLSLPGETRPLILCEY

AHAMGNSLGGFAKYWQAFRQYPRLQGGFVWDWVDQSLIKYDENGNPWSA

YGGDFGDTPNDRQFCMNGLVFADRTPHPALTEAKHQQQFFQFRLSGQTI

EVTSEYLFRHSDNELLHWMVALDGKPLASGEVPLDVAPQGKQLIELPEL

PQPESAGQLWLTVRVVQPNATAWSEAGHISAWQQWRLAENLSVTLPAAS

HAIPHLTTSEMDFCIELGNKRWQFNRQSGFLSQMWIGDKKQLLTPLRDQ

FTRAPLDNDIGVSEATRIDPNAWVERWKAAGHYQAEAALLQCTADTLAD

AVLITTAHAWQHQGKTLFISRKTYRIDGSGQMAITVDVEVASDTPHPAR

IGLNCQLAQVAERVNWLGLGPQENYPDRLTAACFDRWDLPLSDMYTPYV

FPSENGLRCGTRELNYGPHQWRGDFQFNISRYSQQQLMETSHRHLLHAE

EGTWLNIDGFHMGIGGDDSWSPSVSAEFQLSAGRYHYQLVWCQK*,
```

Nucleic acid sequence encoding YesZ (*Bacillus subtilis*):

(SEQ ID NO: 73)
```
atgagaaaactgtatcatggcgcttgctattatccggaattatgggatg aagagacgattcagcaggacattgacatcatgcgtgaagttggcgtaaa tgttgtgcggatcggcgaatttgcctggtcagtcatggaacctgaagaa ggaaaaattgacgtcggtttttttcaaagaaatcatcgcccggctgtatg atagcgggatcgaaacgattatgtgcacgccgacgcctaccccgccgat ttggttctcacatggccggcccgaacgcatgcatgccaatgaaaaaaga gagatcatgggcatggctcccgtcagcatgcctgtacgaacaacccgt atttccgaaaaaaagccgccatcatcaccacagccatcgccaaggagct tggccggctcccgggggctgatcggatggcagctagacaatgagtttaaa tgccatgttgcagaatgcatgtgtgagacatgcttgcgcctatggcatg actggctcaaaaatcgctacggggtaattgagcgcttgaatgaagcttg gggaaccgatgtgtggagcgagacctatcagacgtttgagcaagtcccg cagccgggaccggccccgtttctgcatcatgcctctctacgcactatgt atcagctgttttcgatggagatgatcgcttcgtttgcggatgaacaggc caaaatcatccgctgctattcagatgcgccgatcacgcataacggatca gtcatgttcagcgtggacaatgagcgaatgtttcagaatctcgattttg cctcctatgacacgtacgcttcgcaggaaaacgcctctgcctttttatt gaactgtgatttatggagaaatctgaaacaagggcgcccgttttggatt ttggaaacgagtccgtcgtatgccgcctcgcttgaaagctccgcttacc cgcacgcagacgggtatttgcaggccgaagccgtatcgtcctacgcctt agggagccaggggttttgctactggctatggcgacagcagcgttcaggc agcgagatttcccacggttcggttctcagtgcctggggcgaacccacca tcggctatcaaaatgtgctggcggttgagcgggcaagaaaggaaatcga gcctattattctatcgactgaacccgttcaagccgaggcggcgatgact
```

-continued

```
tactctgacagagcaaaagcatttattaaaactgagcctcaccggggac tccggcatcgttcgcttgtgacgcattttttatgaacgtattctcaacac gggggattcaccgtgaccttattccggaaggcgctccactggacggctat cgcttgctgtttacgccatttgtgccgtatttgtcttctgaatttatca aaaaagcttcggcattcgctgaagcgggcggcatctggatcaccgggcc gctgacaggaggacgcacatgcgagcataccattcataccgattgcgga cttggcgaacttgagaaaacgtcagggatcaaaacacttttttacctttc cgatgaatgagaacgtgaatacaggaaaagcgtttggcatcacggcgcc gctcggactgtggagcgcggtgtttgacacagagagcggaaacaccctt ggcacggttgaagcaggaccggggggggccatgctttttctgacggaacg gaattacggcgaggggaaaattgtcatgctgggctcgcttccatccggg aaagaaggggatgcgatgctggaagcgctcgtcaggcattatgcggagg aagctgttatttccagccggtcggatgtgacaccggcacgatcgttgc cccgcgtataggcgaaaacggccttgtgtggatcgttgtgaatatggat ggaaaaggcgggagcgtgacattgccggaatcgggaacggatttgttga cgcaccgcttggaaaaggcggggagactggcggtcggaccgcatgaata ccgtgtgattcaatttgacaatcacagctga
```

YesZ (*Bacillus subtilis*) amino acid sequence (encoded by SEQ ID NO: 73):

```
                                         (SEQ ID NO: 74
MRKLYHGACYYPELWDEETIQQDIDIMREVGVNVVRIGEFAWSVMEPEE

GKIDVGFFKEIIARLYDSGIETIMCTPTPTPPIWFSHGRPERMHANEKR

EIMGHGSRQHACTNNPYFRKKAAIITTAIAKELGRLPGLIGWQLDNEFK

CHVAECMCETCLRLWHDWLKNRYGVIERLNEAWGTDVWSETYQTFEQVP

QPGPAPFLHHASLRTMYQLFSMEMIASFADEQAKIIRCYSDAPITHNGS

VMFSVDNERMFQNLDFASYDTYASQENASAFLLNCDLWRNLKQGRPFWI

LETSPSYAASLESSAYPHADGYLQAEAVSSYALGSQGFCYWLWRQQRSG

SEISHGSVLSAWGEPTIGYQNVLAVERARKEIEPIILSTEPVQAEAAMT

YSDRAKAFIKTEPHRGLRHRSLVTHFYERILNTGIHRDLIPEGAPLDGY

RLLFTPFVPYLSSEFIKKASAFAEAGGIWITGPLTGGRTCEHTIHTDCG

LGELEKTSGIKTLFTFPMNENVNTGKAFGITAPLGLWSAVFDTESGNTL

GTVEAGPGAGHAFLTERNYGEGKIVMLGSLPSGKEGDAMLEALVRHYAE

EAVISSRSDVTPGTIVAPRIGENGLVWIVVNMDGKGGSVTLPESGTDLL

THRLEKAGRLAVGPHEYRVIQFDNHS*
```

Nucleic acid sequence encoding GanA (*Bacillus subtilis*):

```
                                         (SEQ ID NO: 75)
atgtcaaagcttgaaaaaacgcacgtaacaaaagcaaaatttatgctcc atgggggagactacaaccccgatcagtggctggatcggcccgatatttt agctgacgatatcaaactgatgaagctttctcatacgaatacgtttct gtcggcattttttgcatggagcgcacttgagccggaggagggcgtatatc aatttgaatggctggatgatattttttgagcggattcacagtataggcgg
```

-continued

```
ccgggtcatattagcaacgccgagcggagcccgtccggcctggctgtcg caaacctatccggaagttttgcgcgtcaatgcctcccgcgtcaaacagc tgcacggcggaaggcacaaccactgcctcacatctaaagtctaccgaga aaaaacacggcacatcaaccgcttattagcagaacgatacggacatcac ccggcgctgttaatgtggcacatttcaaacgaatacggggggagattgcc actgtgatttatgccagcatgctttccgggagtggctgaaatcgaaata tgacaacagcctcaagacattgaaccatgcgtggtggaccccttttttgg agccatacgttcaatgactggtcacaaattgaaagcccttcgccgatcg gtgaaaatggcttgcatggcctgaatttagattggcgccggttcgtcac cgatcaaacgatttcgtttttatgaaaatgaaatcattccgctgaaagaa ttgacgcctgatatccctatcacaacgaattttatggctgacacaccgg atttgatcccgtatcagggcctcgactacagcaaatttgcaaagcatgt cgatgccatcagctgggacgcttatcctgtctggcacaatgactgggaa agcacagctgatttggcgatgaaggtcggctttatcaatgatctgtacc gaagcttgaagcagcagcccttcttattaatggagtgtacgccaagcgc ggtcaattggcataacgtcaacaaggcaaagcgcccgggcatgaatctg ctgtcatccatgcaaatgattgcccacggctcggacagcgttctctatt tccaataccgcaaatcacgggggtcatcagaaaaattacacggagcggt tgtggatcatgacaatagcccgaagaaccgcgtctttcaagaagtggcc aaggtaggcgagacattggaacggctgtccgaagttgtcggaacgaaga ggccggctcaaaccgcgattttatatgactgggaaaatcattgggcgct cgaggatgctcaggggtttgcgaaggcgacaaaacgttatccgcaaacg cttcagcagcattaccgcacattctgggaacacgatatccctgtcgacg tcatcacgaaagaacaagacttttcaccatataaactgctgatcgtccc gatgctgtatttaatcagcgaggacaccgtttcccgtttaaaagcgttt acggctgacggcggcaccttagtcatgacgtatatcagcggggttgtga atgagcatgacttaacatacacaggcggatggcatccggatcttcaagc tatatttggagttgagcctcttgaaacggacaccctgtatccgaaggat cgaaacgctgtcagctaccgcagccaaatatatgaaatgaaggattatg caaccgtgattgatgtaaagacagcttcagtggaagcggtgtatcaaga agattttttatgcgcgcacgccagcggtcacaagccatgagtatcagcag ggcaaggcgtattttatcggcgcgcgtttggaggatcaatttcagcgtg atttctatgagggtctgatcacagacctgtctctctctccagttttttcc ggttcggcacggaaaaggcgtctccgtacaagcgaggcaggatcaggac aatgattatatttttgtcatgaatttcacggaagaaaaacagctggtca cgtttgatcagagtgtgaaggacataatgacaggagacatattgtcagg cgacctgacgatggaaaagtatgaagtgagaattgtcgtaaacacacat tag
```

GanA (*Bacillus subtilis*) amino acid sequence (encoded by SEQ TD NO: 75):

```
                                          (SEQ ID NO: 76)
MSKLEKTHVTKAKFMLHGGDYNPDQWLDRPDILADDIKLMKLSHTNTFS

VGIFAWSALEPEEGVYQFEWLDDIFERIHSIGGRVILATPSGARPAWLS

QTYPEVLRVNASRVKQLHGGRHNHCLTSKVYREKTRHINRLLAERYGHH

PALLMWHISNEYGGDCHCDLCQHAFREWLKSKYDNSLKTLNHAWWTPFW

SHTFNDWSQIESPSPIGENGLHGLNLDWRRFVTDQTISFYENEIIPLKE

LTPDIPITTNFMADTPDLIPYQGLDYSKFAKHVDAISWDAYPVWHNDWE

STADLAMKVGFINDLYRSLKQQPFLLMECTPSAVNWHNVNKAKRPGMNL

LSSMQMIAHGSDSVLYFQYRKSRGSSEKLHGAVVDHDNSPKNRVFQEVA

KVGETLERLSEVVGTKRPAQTAILYDWENHWALEDAQGFAKATKRYPQT

LQQHYRTFWEHDIPVDVITKEQDFSPYKLLIVPMLYLISEDTVSRLKAF

TADGGTLVMTYISGVVNEHDLTYTGGWHPDLQAIFGVEPLETDTLYPKD

RNAVSYRSQIYEMKDYATVIDVKTASVEAVYQEDFYARTPAVTSHEYQQ

GKAYFIGARLEDQFQRDFYEGLITDLSLSPVFPVRHGKGVSVQARQDQD

NDYIFVMNFTEEKQLVTFDQSVKDIMTGDILSGDLTMEKYEVRIVVNT

H*
```

Nucleic acid sequence encoding LacZ (*Bacillus coagulans*):

```
                                          (SEQ ID NO: 77)
atgctcaaaaagcacgaaaagttctactatggcggtgattataatcctg aacaatgggacgaaagcgtctggaaagaggatatgcgcttgatgaagaa agcaggtgttaactatgtatccataaacatttctcttgggcacgtctc caacctgatgaagaaacatatgattttctacgcttgataaaataatgg atatgctggctgaaaacggaattggtgctgacctggctaccgccacggc tgctccgccggcctggctgtcacgtaagtatcctgattctttgccggtc gacaaagatggctcccggttcctgccgggatctcgccaacactactgtc cgaactctaaagactatgctagactcgcagctaaattggtgagaaagat cgctgagcgctataaaagtcacccagcattagttatgtggcatgaaac aacgaatacggctgccacatatctgaatgctactgcgataattgtaaaa agggtttttcaaacgtggctcaaggagaaatatggaacgatcgagaactt gaataagagctggagtaccgatttctggtcacagcgctactatgagtgg gaagaaatttgcctccctggaaaaacacctacctttgcgaatccaatgc agcagctcgattataaggcctttatggatgatagcctgttagcactgta taaaatggagcgtgacatactgaaaacttatacgccagacgtcccagtc atgacgaatttaatggggcttcataaaccagtggacggctttcactggg ctaaggagatggatttggttacctgggacgcgtatcctgatcctttcga ggacatcccgtacgctcagttcatggcgcacgatctgacacgcagcttg aagaaacaacctttcttctcatggaacaggccgcgggggccgtaaatt ggcgcgcacagaacgctgttaaggcgccaggggttatgcgtttatggtc
```

```
atacgaagcagcggcgcatggtgctgacggtataatgttttttcaatgg cgggcaagtcaaggaggcgcggaaaaatttcatagcgggatggtaccgc attcaggagatgaggagtctcggaattttcgggaggtcgtacagttagg aaatgaacttaagaatttggaaaaagtaacgggaagtgcgtacgcgtcc gacgtagcaatagttttttgattggaaaaactggtgggcgttggaactgg acagtaagccgagctctctggtcacttatatataaaacaactcctcccgtt ctatcgggttttgcacacgcagaacataggtgtcgactttatccatcca gatgaagctatggatcgctacaaggtggttttcgctccggcgagctacc gggtgacaaagacgtttgcagataaggtcaaggcatacgtagagaacgg aggatatttcgcgacaaacttcttcagcgggatagctgatgagaatgaa cgtgtgtaccttggaggttacccaggcgcttaccgtgacattttgggta tatatgtggaagagtttgccccgatgaaaaaaggagcggtacatcagat ccggactggatacggagatgctgcgatacgcgtgtgggaagagaaaatt catttgaaaggcgccgaggcactcgcgtggtttaaggatggttatctgg ccggctcaccggcggtgaccgcacatcactgtggcaaaggcaaagcata ctatattggcacacagccagatgagcaatacttatcctcactgctgaag gaaattctcaaggaggctgacgttcgcccggccctcgatgctccgcgtg gagtagaagtcgcggttcgcaaaaacggtcatgaaaaatttctcttctt actgaaccatacagatcaggtgcaattcgtagatgccggcggtacttat ccagaactgatttacggtcgcaccgaagccgaaaccgtgagactctcac cacgcgacgtgaaaatccttcaggtcatagagaaataa
```

LacZ (*Bacillus coagulans*) amino acid sequence (encoded by SEQ ID NO: 77):

```
                                          (SEQ ID NO: 78)
MLKKHEKFYYGGDYNPEQWDESVWKEDMRLMKKAGVNYVSINIFSWARL

QPDEETYDFSTLDKIMDMLAENGIGADLATATAAPPAWLSRKYPDSLPV

DKDGSRFLPGSRQHYCPNSKDYARLAAKLVRKIAERYKSHPALVMWHVN

NEYGCHISECYCDNCKKGFQTWLKEKYGTIENLNKSWSTDFWSQRYYEW

EEICLPGKTPTFANPMQQLDYKAFMDDSLLALYKMERDILKTYTPDVPV

MTNLMGLHKPVDGFHWAKEMDLVTWDAYPDPFEDIPYAQFMAHDLTRSL

KKQPFLLMEQAAGAVNWRAQNAVKAPGVMRLWSYEAAAHGADGIMFFQW

RASQGGAEKFHSGMVPHSGDEESRNFREVVQLGNELKNLEKVTGSAYAS

DVAIVFDWKNWWALELDSKPSSLVTYIKQLLPFYRVLHTQNIGVDFIHP

DEAMDRYKVVFAPASYRVTKTFADKVKAYVENGGYFATNFFSGIADENE

RVYLGGYPGAYRDILGIYVEEFAPMKKGAVHQIRTGYGDAAIRVWEEKI

HLKGAEALAWFKDGYLAGSPAVTAHHCGKGKAYYIGTQPDEQYLSSLLK

EILKEADVRPALDAPRGVEVAVRKNGHEKFLFLLNHTDQVQFVDAGGTY

PELIYGRTEAETVRLSPRDVKILQVIEK*.
```

In the case of expressing yesZ or ganA constructs in *Bacillus subtilis*, endogenous sequences encoding corresponding sequences were deleted using standard molecular biology techniques, to prevent undesirable recombination. The present Example further includes the insight that, while not required, fiber synthesis can be increased by genetic modification of cells to increase transport of Lactose across the cell membrane. Accordingly, strains were additionally, optionally engineered to express one or more lactose transporters. In the case of cells engineered to express LacZ (*E. coli*), cells were further modified to express a heterologous nucleic acid sequence encoding polar linked lacY transporter, the heterologous nucleic acid sequence including the following sequence:

(SEQ ID NO: 79)

```
atgtactatttaaaaaacacaaacttttggatgttcggtttattctttt
tcttttacttttttatcatgggagcctacttcccgttttttcccgatttg
gctacatgacatcaaccatatcagcaaaagtgatacgggtattatttttt
gccgctatttctctgttctcgctattattccaaccgctgtttggtctgc
tttctgacaaactcgggctgcgcaaatacctgctgtggattattaccgg
catgttagtgatgtttgcgccgttctttattttttatcttcgggccactg
ttacaatacaacattttagtaggatcgattgttggtggtatttatctag
gcttttgttttaacgccggtgcgccagcagtagaggcatttattgagaa
agtcagccgtcgcagtaatttcgaatttggtcgcgcgcggatgtttggc
tgtgttggctgggcgctgtgtgcctcgattgtcggcatcatgttcacca
tcaataatcagtttgttttctggctgggctctggctgtgcactcatcct
cgccgttttactcttttttcgccaaaacggatgcgccctcttctgccacg
gttgccaatgcggtaggtgccaaccattcggcatttagccttaagctgg
cactggaactgttcagacagccaaaactgtggtttttgtcactgtatgt
tattggcgtttcctgcacctacgatgtttttgaccaacagtttgctaat
ttctttacttcgttctttgctaccggtgaacagggtacgcgggtatttg
gctacgtaacgacaatgggcgaattacttaacgcctcgattatgttctt
tgcgccactgatcattaatcgcatcggtgggaaaaacgccctgctgctg
gctggcactattatgtctgtacgtattattggctcatcgttcgccacct
cagcgctggaagtggttattctgaaaacgctgcatatgtttgaagtacc
gttcctgctggtgggctgctttaaatatattaccagccagtttgaagtg
cgtttttcagcgacgatttatctggtctgtttctgcttctttaagcaac
tggcgatgattttttatgtctgtactggcgggcaatatgtatgaaagcat
cggtttccagggcgcttatctggtgctgggtctggtggcgctgggcttc
accttaatttccgtgttcacgcttagcggcccccggcccgctttccctgc
tgcgtcgtcaggtgaatgaagtcgcttaa
``` which encodes the following amino acid sequence:

(SEQ ID NO: 80)

```
MYYLKNTNFWMFGLFFFFYFFIMGAYFPFFPIWLHDINHISKSDTGIIF
AAISLFSLLFQPLFGLLSDKLGLRKYLLWIITGMLVMFAPFFIFIFGPL
LQYNILVGSIVGGIYLGFCFNAGAPAVEAFIEKVSRRSNFEFGRARMFG
CVGWALCASIVGIMFTINNQFVFWLGSGCALILAVLLFFAKTDAPSSAT
VANAVGANHSAFSLKLALELFRQPKLWFLSLYVIGVSCTYDVFDQQFAN
FFTSFFATGEQGTRVFGYVTTMGELLNASIMFFAPLIINRIGGKNALLL
```

-continued

```
AGTIMSVRIIGSSFATSALEVVILKTLHMFEVPFLLVGCFKYITSQFEV
RFSATIYLVCFCFFKQLAMIFMSVLAGNMYESIGFQGAYLVLGLVALGF
TLISVFTLSGPGPLSLLRRQVNEVA*
```

In the case of cells engineered to express LacZ (*B. coagulans*), cells were further modified to express a heterologous nucleic acid sequence lacY (*B. megatarium*), the heterologous nucleic acid sequence including the following sequence:

(SEQ ID NO: 81)

```
atgaaaagtagtaagtcactctactggaagctttctgcgtatttcttct
ttttcttctttacctggagctctagttactctctgttttccatttggtt
gggacaggagataaagctgaatggctcagccacggggctcatatttagt
gtcaacgccatattcgctctttgtatgcaaccattatacggatatatct
ccgacagaatcggcctcaagaagcatattttatttttttataagttgcct
tcttgtatttgttgggccattctacatatttgtgtatgggccgttattg
cagtataatgtgctcataggtgccattattggtggcctgtacttgggcg
tggcattttttggcaggaataggcgcgatagaaacgtatattgagaaggt
atctcgcaagtacaagttcgagtatggaaagtctcggatgtgggggagt
cttggttgggccgccgcgacgtttttgcgggccaacttttcaatatca
acccgcacatcaatttttgggtggccagcgtatccgctgttatacttat
ggctataatcttctcagtaaaagttgaaatgagctcttatgaaatggag
aaggcagaatcagtgcgtctccgtgatgtaggtaacttgttcctcttaa
aggaattctggttttttcatgatctatgtcgtaggtgtaacatgtgtcta
tggggtgtacgaccaacagttcccaatatactatgcgtctttattccca
accgagtcaatcggtaatcaagtgttcggttatctcaatagtttccaag
tctttctcgaggcagggatgatgttcgccgcgccatttattgttaacaa
aataggcgcgaagaattccttaatcctggctggtttcctcatgggctttt
agaattattggttccgggttggttgtgggtcctataggaatcagttcta
tgaagcttatacacgcgcttgaacttcctataatgctcatagccatttt
taagtacctcgccgcgaattttgatacaagattatcatctattttgtac
ctggttggcttccaatttgccagtcagattggcgcctctgtcctctccc
ctatcgccggtggcttgtatgactcagtcggatttagtcgcacttatct
gatcatgggtgggatggtacttgtttttaatgttatttcaatgttcaca
ttgttgaatagcaaaaagcataaatttatccggaaggacgttcaagaaa
agactcagataatt
``` which encodes the following amino acid sequence:

(SEQ ID NO: 82)

```
MKSSKSLYWKLSAYFFFFFTWSSSYSLFSIWLGQEIKLNGSATGLIFS
VNAIFALCMQPLYGYISDRIGLKKHILFFISCLLVFVGPFYIFVYGPLL
QYNVLIGAIIGGLYLGVAFLAGIGAIETYIEKVSRKYKFEYGKSRMWGS
LGWAAATFFAGQLFNINPHINFWVASVSAVILMAIIFSVKVEMSSYEME
```

-continued

```
KAESVRLRDVGNLFLLKEFWFFMIYVVGVTCVYGVYDQQFPIYYASLFP

TESIGNQVFGYLNSFQVFLEAGMMFAAPFIVNKIGAKNSLILAGFLMGF

RIIGSGLVVGPIGISSMKLIHALELPIMLIAIFKYLAANFDTRLSSILY

LVGFQFASQIGASVLSPIAGGLYDSVGFSRTYLIMGGMVLVFNVISMFT

LLNSKKHKFIRKDVQEKTQII
``` fiber synthesis by various strains of the present Example was measured by release of glucose as has been established in literature, where release of glucose corresponds to degradation of lactose. In brief, a suspension of active cells was mixed with Lactose and incubated. Periodically an aliquot was taken, the cells were removed from the aliquot by centrifugation, and the glucose content of the remaining sample of aliquot was assayed by glucose meter. Glucose is released upon degradation of Lactose and galactose is concurrently incorporated into transgalactosylation reactions depending on the reaction conditions and enzyme present. A culture of *B. subtilis* engineered to express LacZ (ZB420) was capable of degrading Lactose at a rate of 163 uM/min, 13-fold faster than probiotic *Lactobacillus acidophilus* (FIG. 8).

Example 5: Construction and Experimental Validation of Engineered Cells that Express an Enzyme for Synthesis of Soluble Trehalulose Fiber from Carbohydrate Substrate A transgene was constructed for expression of a trehalulose disaccharide fiber-synthesizing enzyme. The transgene was produced using standard techniques of molecular biology. The transgene included nucleic acid sequences encoding a fiber-synthesizing enzyme that included a secretion polypeptide. The present example utilizes mutB trehalulose synthase enzyme. The nucleic acid encoding the fiber-synthesizing enzyme was derived from *Pseudomonas mesoacidophila* and has the following sequence, with the secretion polypeptide encoding sequence bolded and underlined:

(SEQ ID NO: 83)
atgaacattaagaagttcgccaagcaagcaacggtgttaacgtttacaa cagcactgctggcaggcggagcgacacaggcttttgcattgatgaaag attgttcgcggcctcattaatgctcgcgttctcctctgtgtcgtccgtt cgcgcggaagaggccgtgaagccgggagcaccatggtggaaatctgctg tgttttatcaggtgtacccgcggtctttcaaggatacgaacgggatgg aattggagactttaagggtctcacggaaaagctggattaccttaagggg ctgggcattgacgccatatggataaaccctcattacgctagtccgaaca ccgataatggttacgatatctcagactatcgggaagtaatgaaagagta tggcactatggaagactttgaccggcttatggcagaattgaagaagaga ggcatgaggctgatggtggacgtggtaatcaaccactcaagcgatcagc acgaatggtttaagtcttctagggcatccaaagacaaccttaccgtga ctactacttctggcgcgacggtaaagatggccatgaaccgaacaattac ccgtcattcttcggcgcgatcggcttgggagaaggacccggtaactgcc agtattatcttcactacttcggtaggcagcaaccggatttgaactggga -continued cacacctaagttgcgtgaggagttatacgcgatgctcagattctggctg gacaaaggtgtgtctggcatgcgttttgacaccgtagcaacctactcta agacaccgggattcccggatcttactcctgaacagatgaagaattttgc ggaagcatacactcagggtcctaacctgcaccgatacttacaagaaatg cacgaaaaggtctttgatcactacgacgctgtcacggcgggagagatct tcggtgccctctcaaccaagtaccgcttttcatcgacagtcgccggaa ggaattagatatggccttcactttcgacttaataagatacgatcgtgct cttgacagatggcacaccattccgaggacattagctgatttccgtcaaa caatcgataaagttgacgcgattgcaggcgagtacgggtggaacacctt cttcttaggaaaccatgacaaccctagagcagtgtcacatttcggcgac gaccgcccacaatggagagaggcaagtgcgaaggcgctggctaccgtga ctttaacacagcggggaacaccgttcatcttccagggagacgagcttgg aatgaccaattacccatttaagacactgcaagactttgatgacatcgag gttaagggcttctttcaagactacgtcgagactggtaaggccacagccg aggaattactgacaaacgtggccttgactagtcgtgacaatgcgagaac gcctttccaatgggatgactcagctaacgctggattcacaaccggcaag ccttggctcaaggtcaatcctaactacacagaaataaacgctgcgcgcg agattggggatcccaagtcagtctactccttctatcgcaacctgatctc gatccgccatgagactcctgccctttcgaccggatcgtatagagatata gaccccagtaatgcagatgtatacgcctatacgcgctcccaagacggag aaacctacttggtggtggtcaatttcaaagccgagcctaggagtttcac cttaccagacggtatgcatatcgccgagacccttattgagtcttctagt ccagctgcgcctgctgccggtgcagcgagcttagagttacaaccgtggc aatcgggcatctacaaggtgaagtag.

The protein product MutB has the following amino acid sequence, with the secretion polypeptide sequence bolded and underlined:

(SEQ ID NO: 84)
MNIKKFAKQATVLTFTTALLAGGATQAFALMKRLFAASLMLAFSSVSSV

RAEEAVKPGAPWWKSAVFYQVYPRSFKDTNGDGIGDFKGLTEKLDYLKG

LGIDAIWINPHYASPNTDNGYDISDYREVMKEYGTMEDFDRLMAELKKR

GMRLMVDVVINHSSDQHEWFKSSRASKDNPYRDYYFWRDGKDGHEPNNY

PSFFGGSAWEKDPVTGQYYLHYFGRQQPDLNWDTPKLREELYAMLRFWL

DKGVSGMRFDTVATYSKTPGFPDLTPEQMKNFAEAYTQGPNLHRYLQEM

HEKVFDHYDAVTAGEIFGAPLNQVPLFIDSRRKELDMAFTFDLIRYDRA

LDRWHTIPRTLADFRQTIDKVDAIAGEYGWNTFFLGNHDNPRAVSHFGD

DRPQWREASAKALATVTLTQRGTPFIFQGDELGMTNYPFKTLQDFDDIE

VKGFFQDYVETGKATAEELLTNVALTSRDNARTPFQWDDSANAGFTTGK

PWLKVNPNYTEINAAREIGDPKSVYSFYRNLISIRHETPALSTGSYRDI

DPSNADVYAYTRSQDGETYLVVVNFKAEPRSFTLPDGMHIAETLIESSS

PAAPAAGAASLELQPWQSGIYKVK*

The nucleic acid sequence encoding fiber-synthesizing enzyme derived from *P. mesoacidophila* was operably linked with a nucleic acid sequence encoding a secretion polypeptide, such that the encoded fiber-synthesizing enzyme was a fusion polypeptide including a secretion polypeptide. The nucleic acid sequence encoding the fusion polypeptide was analyzed for secondary structure, at least in part because significant secondary structure can cause translation termination and poor expression. Base pairs that significantly contributed to secondary structure in the nucleic acid sequence were modified by silent modifications of nucleic acid sequence (e.g., non-coding and/or synonymous modifications of nucleic acid sequence) that reduced the contribution to secondary structure.

The nucleic acid sequence encoding the fiber-synthesizing enzyme was transformed into *B. subtilis* PY79 cells and operably linked to hag promoter by homologous recombination at the endogenous hag locus of *B. subtilis* PY79 genome with the addition of a modifying mutation in the promoter sequence by homologous integration as described in U.S. Ser. No. 16/048,147 (published as US 2019/0076489) and PCT/US18/50957 (published as WO 2019/055707) herein incorporated by reference in their entirety and with respect to regulatory sequences and systems disclosed therein.

Fiber-synthesizing enzymatic activity was measured by the following assay. Because trehalulose synthase rearranges sucrose into trehalulose it renders the sucrose inaccessible for sucrase. The accumulation of glucose after treatment with sucrase reveals remaining sucrose only, as trehalulose is not cleaved and does not release glucose. The glucose released by sucrase is directly proportional to the amount of sucrose remaining, which when subtracted from the amount of sucrose at the beginning of the reaction, yields the amount of trehalulose synthesized. Various glucose meters are known in the art and can be standardized for measurement of glucose concentrations in bacterial media. Engineered bacteria of the present Example were cultured in media to a defined density of 1E9 cells per ml (Optical Density of 1). The cells were then removed by centrifugation (21×g for 2 minutes) and the supernatant, containing secreted enzyme, was assayed by the addition of a defined amount of sucrose. At the beginning of the assay and at the conclusion of 18 hours the level of sucrose in the reaction was measured by cleavage to glucose using sucrase and the difference in sucrose concentration relative to a control strain lacking trehalulose synthase is directly proportional to trehalulose produced. Trehalulose production (g/L) using supernatant containing secreted enzyme or using whole cell broth is shown in FIG. 9 and FIG. 10. Those of skill in the art will appreciate that a small fraction of isomaltulose can also be produced, but that such production would not reduce or negate the advantages or utility of disclosed embodiments.

Those of skill in the art will appreciate that a variety of alternative methods are readily available for quantification (e.g., of the amount and/or concentration) of glucose, disaccharide trehalulose, and the like, including without limitation HPLC and HPAEC.

The present Example demonstrated that a transgene encoding a fiber-synthesizing enzyme derived from F1-mutB of *P. mesoacidophila* expressed a highly active fiber-synthesizing enzyme.

The present disclosure further includes the recognition that trehalulose synthase (mutB) derived from *P. mesoacidophila* has certain exemplary qualities that confirm the utility of MutB expression in gut. The optimum pH range for trehalulose synthase activity of MutB is 5.5-6.5 which matches that of the small intestine. MutB enzyme is naturally secreted and therefore stable outside of the engineered cell, amenable to secretion through a gram positive cell envelope.

Other Embodiments

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

---

SEQUENCE LISTING

```
SEQ ID NO: 1
MNTDQQPYQGQTDYTQGPGNGQSQEQDYDQYGQPLYPSQADGYYDPNVAAGTEADMYGQQPPNESYD
QDYTNGEYYGQPPNMAAQDGENFSDFSSYGPPGTPGYDSYGGQYTASQMSYGEPNSSGTSTPIYGNYDPN
AIAMALPNEPYPAWTADSQSPVSIEQIEDIFIDLTNRLGFQRDSMRNMFDHFMVLLDSRSSRMSPDQALLSL
HADYIGGDTANYKKWYFAAQLDMDDEIGFRNMSLGKLSRKARKAKKKNKKAMEEANPEDTEETLNKIE
GDNSLEAADFRWKAKMNQLSPLERVRHIALYLLCWGEANQVRFTAECLCFIYKCALDYLDSPLCQQRQEP
MPEGDFLNRVITPIYHFIRNQVYEIVDGRFVKRERDHNKIVGYDDLNQLFWYPEGIAKIVLEDGTKLIELPLE
ERYLRLGDVVWDDVFFKTYKETRTWLHLVTNFNRIWVMHISIFWMYFAYNSPTFYTHNYQQLVDNQPLA
AYKWASCALGGTVASLIQIVATLCEWSFVPRKWAGAQHLSRRFWFLCIIFGINLGPIIFVFAYDKDTVYSTA
AHVVAAVMFFVAVATIIFFSIMPLGGLFTSYMKKSTRRYVASQTFTAAFAPLHGLDRWMSYLVWVTVFAA
KYSESYYFLVLSLRDPIRILSTTAMRCTGEYWWGAVLCKVQPKIVLGLVIATDFILFFLDTYLWYIIVNTIFS
VGKSFYLGISILTPWRNIFTRLPKRIYSKILATTDMEIKYKPKVLISQVWNAIIISMYREHLLAIDHVQKLLYH
QVPSEIEGKRTLRAPTFFVSQDDNNFETEFFPRDSEAERRISFFAQSLSTPIPEPLPVDNMPTFTVLTPHYAERI
LLSLREIIREDDQFSRVTLLEYLKQLHPVEWECFVKDTKILAEETAAYEGNENEAEKEDALKSQIDDLPFYCI
GFKSAAPEYTLRTRIWASLRSQTLYRTISGFMNYSRAIKLLYRVENPEIVQMFGGNAEGLERELEKMARRK
FKFLVSMQRLAKFKPHELENAEFLLRAYPDLQIAYLDEEPPLTEGEEPRIYSALIDGHCEILDNGRRRPKFRV
QLSGNPILGDGKSDNQNHALIFYRGEYIQLIDANQDNYLEECLKIRSVLAEFEELNVEQVNPYAPGLRYEEQ
TTNHPVAIVGAREYIFSENSGVLGDVAAGKEQTFGTLFARTLSQIGGKLHYGHPDFINATFMTTRGGVSKA
QKGLHLNEDIYAGMNAMLRGGRIKHCEYYQCGKGRDLGFGTILNFTTKIGAGMGEQMLSREYYYLGTQL
PVDRFLTFYYAHPGFHLNNLFIQLSLQMFMLTLVNLSSLAHESIMCIYDRNKPKTDVLVPIGCYNFQPAVD
WVRRYTLSIFIVFWIAFVPIVVQELIERGLWKATQRFFCHLLSLSPMFEVFAGQIYSSALLSDLAIGGARYIST
FLDYRDYIRWLSRGNNQYHRNSWIGYVRMSRARITGFKRKLVGDESEKAAGDASRAHRTNLIMAEIIPCAI
YAAGCFIAFTFINAQTGVKTTDDDRVNSVLRIIICTLAPIAVNLGVLFFCMGMSCCSGPLFGMCCKKTGSVM
AGIAHGVAVIVHIAFFIVMWVLESFNFVRMLIGVVTCIQCQRLIFHCMTALMLTREFKNDHANTAFWTGK
WYGKGMGYMAWTQPSRELTAKVIELSEFAADFVLGHVILICQLPLIIIPKIDKFHSIMLFWLKPSRQIRPPIYS
LKQTRLRKRMVKKYCSLYFLVLAIFAGCIIGPAVASAKIHKHIGDSLDGVVHNLFQPINTTNNDTGSQMSTY
QSHYYTHTPSLKTWSTIK
```

-continued

SEQUENCE LISTING

SEQ ID NO: 2
ATGAATACGGACCAACAACCATATCAAGGCCAAACAGACTACACGCAAGGTCCTGGGAACGGGCAAT
CCCAGGAACAAGACTACGATCAGTATGGCCAGCCATTGTATCCGAGCCAGGCCGATGGGTATTATGAT
CCGAATGTGGCAGCGGGAACGGAGGCAGATATGTACGGACAACAACCCCCGAATGAGTCGTATGATC
AAGACTATACTAATGGCGAATACTATGGCCAACCGCCTAATATGGCGGCGCAGGATGGCGAAAATTTT
TCGGACTTTTCAAGTTACGGTCCGCCGGGCACACCGGGGTACGATTCATATGGCGGCCAATATACCGC
AAGCCAAATGTCTTATGGCGAGCCGAACAGCTCAGGCACATCAACCCCGATTTACGGAAATTACGACC
CTAACGCAATTGCCATGGCTCTGCCGAATGAACCATATCCCGCATGGACGGCTGATAGCCAGAGTCCG
GTCAGTATTGAACAAATTGAAGATATTTTTATTGATTTGACGAACCGGTTAGGATTTCAGCGGGATAG
CATGCGGAATATGTTTGATCATTTTATGGTTCTGCTTGACTCACGGTCCAGCAGAATGTCACCTGATCA
AGCCTTATTATCATTACACGCCGACTACATTGGAGGAGATACAGCAAACTACAAAAAGTGGTATTTCG
CGGCGCAGTTAGATATGGATGATGAGATCGGGTTTCGTAATATGTCTCTCGGAAAACTGAGCAGGAAA
GCAAGGAAGGCAAAAAAAGAATAAAAAGGCGATGGAGGAGGCGAATCCGGAAGATACAGAGGA
GACACTGAATAAGATCGAAGGCGACAATTCTTTAGAAGCCGCAGATTTCCGTTGGAAGGCAAAAATG
AACCAGTTGAGTCCACTGGAACGAGTTCGACATATCGCGCTGTATCTTTTATGCTGGGGTGAGGCTAA
CCAAGTCCGGTTCACCGCCGAATGTTTATGTTTTATTTACAAATGTGCCTTAGACTACCTTGACTCTCCT
CTGTGCCAACAACGCCAGGAACCGATGCCCGAAGGCGACTTCTTAAACCGCGTGATTACGCCGATTTA
TCATTTCATTCGCAATCAAGTGTATGAAATCGTTGATGGACGTTTTGTTAAACGCGAACGCGATCATAA
TAAAATCGTTGGCTACGATGATCTCAACCAACTTTTTTGGTACCCGGAAGGTATTGCTAAAATTGTATT
AGAAGACGGCACGAAACTCATTGAGTTACCGTTGGAGGAAAGATACTTACGCCTTGGCGACGTGGTCT
GGGACGATGTTTTTTTTAAAACCTACAAAGAAACACGTACGTGGTTACATCTTGTAACGAATTTTAACA
GAATTTGGGTAATGCATATCTCCATTTTTTGGATGTACTTTGCCTACAATAGCCCTACCTTTTATACACA
TAACTACCAGCAGTTAGTCGACAATCAACCGCTGGCCGCATACAAATGGCGTCCTGTGCTTTAGGGG
GCACAGTTGCGAGCTTAATACAGATCGTAGCAACACTGTGCGAATGGAGCTTCGTTCCGAGAAAATGG
GCGGGCGCTCAGCATTTGTCACGCCGTTTCTGGTTTCTTTGTATCATCTTCGGTATCAACCTGGGTCCG
ATTATATTTGTTTTTGCTTACGACAAAGATACCGTCTATTCTACTGCAGCCCATGTAGTTGCAGCAGTA
ATGTTCTTTGTGGCGGTAGCGACTATTATTTTTTTTTTCAATCATGCCTCTGGGCGGCCTGTTCACCTCGT
ATATGAAGAAATCGACACGACGCTATGTAGCATCGCAAACATTTACAGCCGCGTTTGCCCCGCTGCAT
GGGCTTGACCGTTGGATGTCATATCTGGTCTGGGTGACCGTATTCGCAGCCAAATATTCCGAAAGTTAT
TACTTTCTTGTCTTATCTTTGCGAGATCCGATTCGTATCTTAAGTACGACAGCAATGAGATGTACGGGG
GAGTATTGGTGGGGCGCCGTTCTTTGTAAAGTTCAGCCGAAAATCGTCTTGGGACTGGTGATTGCGAC
AGACTTTATTTTATTTTTTCTTGATACATATTTGTGGTATATTATCGTGAATACTATTTTTTCTGTTGGAA
AATCATTTTATCTGGGAATCTCGATTCTGACGCCTTGGCGCAACATCTTTACACGCCTTCCTAAAAGAA
TCTATAGTAAAATTTTGGCCACAACCGATATGGAAATCAAATATAAACCGAAGGTGCTTATTAGTCAG
GTGTGGAATGCTATTATTATATCGATGTATCGCGAACATCTTTTAGCAATCGACCATGTTCAAAAGTTG
CTGTATCACCAGGTTCCTTCAGAGATCGAAGGAAAGAGGACGTTGAGGGCGCCCACCTTTTTCGTGAG
TCAAGATGATAACAACTTTGAAACAGAATTTTTTCCAAGGGACTCCGAGGCCGAAAGACGGATTTCTT
TTTTTGCACAATCTTTATCTACACCAATCCCGGAACCTCTTCCAGTCGACAATATGCCGACGTTTACAG
TGCTCACACCCCACTATGCCGAAAGAATCCTCTTAAGCCTGAGGGAAATAATCCGAGAGGATGATCAG
TTTTCTGTGTTACGCTGCTGGAGTATTTAAAACAATTACATCCTGTTGAGTGGGAGTGCTTCGTGAAG
GATACGAAAATTTTGGCAGAAGAGACGGCTGCTTATGAAGGCAATGAAAACGAAGCTGAAAAGAAG
ACGCGCTCAAGTCACAGATAGATGATCTCCCTTTTTATTGCATAGGCTTTAAATCTGCGGCCCCGGAAT
ATACGCTTCGCACAAGAATATGGGCATCTTTAAGATCCCAAACGTTATACCGGACCATTAGTGGATTT
ATGAACTATTCTCGGGCAATTAAACTTTTGTATAGAGTGGAAAACCCGGAAATTGTACAAATGTTCGG
CGGAAATGCTGAAGGCCTGGAGAGGGAACTCGAAAAAATGGCTCGCAGGAAATTTAAATTTCTGGTTT
CCATGCAACGCCTTGCGAAATTCAAACCCCATGAATTAGAGAATGCCGAATTTCTGTTGAGGGCATAT
CCGGACTTGCAAATAGCATACCTTGATGAAGAACCGCCACTGACGGAAGGTGAAGAGCCGAGAATAT
ATTCTGCACTTATTGACGGACACTGCGAGATCCTTGACAATGGCCGACGTAGGCCTAAATTTAGAGTC
CAACTTTCTGGAAACCCGATTCTTGGTGATGGAAAGTCTGATAATCAAAACCATGCGTTGATCTTCTAT
CGGGGAGAATATATTCAACTTATAGATGCAAATCAGGATAACTATCTTGAGGAGTGCCTGAAAATTCG
GTCTGTTCTGGCTGAGTTTGAGGAACTTAACGTTGAACAGGTGAATCCCTACGCACCGGGACTCAGAT
ATGAGGAACAGACAACCAACCACCCAGTCGCTATCGTAGGCGCAGAATACATATTCTCAGAGAA
TTCCGGTGTATTAGGCGACGTCGCCGCCGGTAAAGAACAAACGTTCGGCACCTTGTTTGCGCGGACGC
TCTCTCAAATTGGGGGAAAACTGCATTACGGACATCCTGATTTTATTAATGCAACGTTTATGACAACGC
GAGGAGGAGTGAGTAAAGCTCAGAAAGGCCTTCATTTAAATGAAGACATTTATGCCGGCATGAATGC
GATGTTGAGGGGCGGCAGAATAAAACATTGTGAATATTATCAGTGTGGAAAAGGTCGGGATTTAGGA
TTCGGAACAATCCTTAATTTTACGACCAAAATCGGCGCTGGTATGGGCGAGCAAATGTTATCACGAGA
GTATTATTATCTTGGAACGCAATTACCGGTTGATCGATTCTTGACCTTTTACTATGCTCATCCGGGTTTT
CATCTTAACAATCTGTTTATTCAACTGTCCCTGCAAATGTTCATGCTGACGCTTGTAAATTTGTCATCTC
TGGCCCATGAATCGATCATGTGTATCTACGATCGCAATAAACCAAAGACAGATGTGCTGGTACCGATC
GGCTGCTATAATTTCCAACCGGCTGTGGACTGGGTAAGACGATATACACTTTCCATATTTATTGTCTTC
TGGATCGCTTTTGTACCCATTGTCGTTCAGGAGCTTATTGAACGCGGCTTGTGGAAAGCGACTCAAAG
ATTCTTTTGCCATCTTTTATCCCTCTCTCCAATGTTTGAGGTCTTCGCGGGTCAAATTTATTCTTCAGCG
CTGCTTAGCGACTTGGCTATTGGCGGCGCGAGGTATATCTCAACAGGTCGCGGGTTTGCTACGTCCCGT
ATACCTTTTTCGATCCTCTATTCAAGATTTGCAGGCAGCGCTATTTACATGGCGCACGATCTATGTTA
ATGTTGTTATTTGGAACAGTTGCTCATTGGCAGGCGCCACTTCTTTGGTTCTGGGCATCCTTGTCATCAT
TAATCTTCGCGCCGTTCGTTTTTAATCCGCATCAATTTGCCTGGGAAGATTTTTTTTTAGATTATCGGGA
TTACATTCGCTGGCTGAGCCGAGGAAATAACCAGTATCATCGTAATTCATGGATTGGTTACGTACGAA
TGTCTCGTGCCCGTATTACAGGCTTTAAAAGAAAGCTCGTCGGCGACGAATCCGAAAAAGCAGCGGGA
GATGCAAGCCGAGCCCATCGTACTAACCTGATCATGGCTGAAATTATCCCGTGCGCTATCTATGCGGC
AGGGTGTTTCATAGCGTTCACGTTTATAAACGCTCAGACAGGCGTAAAGACAACCGACGATGACCGCG
TCAATTCGGTTCTGAGGATCATCATATGTACCCTTGCACCGATTGCCGTGAATTGGGGAGTGCTTTTCT
TTTGTATGGGTATGTCATGCTGCAGCGGTCCTTTATTCGGTATGTGTTCAAGAAGACAGGCTCCGTTA
TGGCTGGTATTGCACACGGTGTTGCTGTGATTGTTCATATTGCGTTCTTTATCGTGATGTGGGTACTGG
AGTCTTTCAATTTTGTTCGCATGCTTATTGGTGTGGTGACATGTATTCAGTGTCAGCGCTTGATCTTTCA
CTGCATGACGGCACTGATGCTGACTCGAGAATTTAAAAACGACCACGCGAATACAGCCTTTTGGACGG

SEQUENCE LISTING

```
GCAAATGGTATGGCAAAGGAATGGGATATATGGCCTGGACCCAGCCGAGTAGAGAATTGACGGCAAA
AGTCATTGAACTTAGTGAATTTGCAGCAGATTTCGTATTGGGTCACGTTATTCTGATCTGTCAGTTACC
ACTGATCATCATCCCCAAAATCGACAAGTTTCACTCAATTATGCTCTTCTGGCTGAAACCATCACGTCA
GATCCGTCCCCCTATCTATAGTCTCAAACAAACGAGATTGAGAAAAGAATGGTTAAAAAATATTGCA
GCCTTTACTTTTTGGTCTTGGCCATTTTTGCGGGGTGTATCATCGGCCCCGCTGTAGCATCAGCCAAGA
TCCATAAACACATCGGTGATTCCTTAGATGGAGTCGTACATAATCTTTTCCAACCGATAAATACCACAA
ACAATGACACGGGCAGTCAGATGTCAACTTACCAGAGTCACTACTATACTCATACGCCGTCCTTAAAA
ACCTGGTCCACAATTAAGTAA
```

SEQ ID NO: 3
```
MAQRREPDPPPPQRRILRTQTVGSLGEAMLDSEVVPSSLVEIAPILRVANEVEASNPRVAYLCRFYAFEKAH
RLDPTSSGRGVRQFKTALLQRLERENETTLAGRQKSDAREMQSFYQHYYKKYIQALLNAADKADRAQLT
KAYQTAAVLFEVLKAVNQTEDVEVADEILETHNKVEEKTQIYVPYNILPLDPDSQNQAIMRLPEIQAAVAA
LRNTRGLPWTAGHKKKLDEDILDWLQSMFGFQKDNVLNQREHLILLLANVHIRQFPKPDQQPKLDDRALT
IVMKKLFRNYKKWCKYLGRKSSLWLPTIQQEVQQRKLLYMGLYLLIWGEAANLRFMPECLCYIYHHMAF
ELYGMLAGSVSPMTGEHVKPAYGGEDEAFLQKVVTPIYQTISKEAKRSRGGKSKHSVWRNYDDLNEYFW
SIRCFRLGWPMRADADFFCQTAEELRLRERSEIKSNSGDRWMGKVNFVEIRSFWHIFRSFDRLWSFYILCLQA
MIVIAWNGSGELSAIFQGDVFLKVLSVFITAAILKLAQAVLDIALSWKARHSMSLYVKLRYVMKVGAAAV
WVVVMAVTYAYSWKNASGFSQTIKNWFGGHSHNSPSLFIVAILIYLSPNMLSALLFLFPFIRRYLERSDYKI
MMLMMWWSQPRLYIGRGMHESALSLFKYTMFWIVLLISKLAFSYYAEIKPLVGPTKDIMRIHISVYSWHEF
FPHAKNNLGVVIALWSPVILVYFMDTQIWYAIVSTLVGGLNGAFRRLGEIRTLGMLRSRFQSIPGAFNDCLV
PQDNSDDTKKKRFRATFSRKFDQLPSSKDKEAARFAQMWNKIISSFREEDLISDREMELLLVPYWSDPDLD
LIRWPPFLLASKIPIALDMAKDSNGKDRELKKRLAVDSYMTCAVRECYASFKNLINYLVVGEREGQVINDIF
SKIDEHIEKETLITELNLSALPDLYGQFVRLIEYLLENREEDKDQIVIVLLNMLELVTRDIMEEEVPSLLETAH
NGSYVKYDVMTPLHQQRKYFSQLRFPVYSQTEAWKEKIKRLHLLLTVKESAMDVPSNLEARRRLTFFSNS
LFMDMPPAPKIRNMLSFSVLTPYFSEDVLFSIFGLEQQNEDGVSILFYLQKIFPDEWTNFLERVKCGNEEEELR
AREDLEEEELRLWASYRGQTLTKTVRGMMYYRKALELQAFLDMAKDEELLKGYKALELTSEEASKSGGSL
WAQCQALADMKFTFVVSCQQYSIHKRSGDQRAKDILRLMTTYPSIRVAYIDEVEQTHKESYKGTEEKIYYS
ALVKAAPQTKPMDSSESVQTLDQLIYRIKLPGPAILGEGKPENQNHAIIFTRGEGLQTIDMNQDNYMEEAFK
MRNLLQEFLEKHGGVRCPTILGLREHIFTGSVSSLAWFMSNQENSFVTIGQRVLASPLKVRFHYGHPDIFDR
LFHLTRGGICKASKVINLSEDIFAGFNSTLREGNVTHHEYIQVGKGRDVGLNQISMFEAKIANGNGEQTLSR
DLYRLGHRFDFFRMLSCYFTTIGFYFSTMLTVLTVYVFLYGRLYLVSGLEEGLSSQRAFRNNKPLEAALAS
QSFVQIGFLMALPMMMEIGLERGFHNALIEFVLMQLQLASVFFTFQLGTKTHYYGRTLFHGGAEYRGTGR
GFVVFHAKFAENYRFYSRSHFVKGIELMILLLVYQIFGQSYRGVVTYILITVSIWFMVVTWLFAPFLFNPSGF
EWQKIVDDWTDWNKWIYNRGGIGVPPEKSWESWWEKELEHLRHSGVRGITLEIFLALRFFIFQYGLVYHL
STFKGKNQSFWVYGASWFVILFILLIVKGLGVGRRRFSTNFQLLFRIIKGLVFLTFVAILITFLALPLITIKDLFI
CMLAFMPTGWGMLLIAQACKPLIQQLGIWSSVRTLARGYEIVMGLLLFTPVAFLAWPFVSEFQTRMLFNQ
AFSRGLQISRILGGQRKDRSSKNKE
```

SEQ ID NO: 4
```
ATGGCACAACGCAGGGAACCGGACCCGCCACCCCCGCAGCGTAGAATATTGCGGACGCAAACGGTTG
GCTCTCTGGGAGAAGCCATGCTTGATTCTGAGGTCGTTCCTTCATCACTTGTCGAAATAGCGCCAATTT
TACGCGTCGCAAACGAAGTAGAAGCTTCAAATCCGCGTGTCGCTTACTTATGTAGATTCTACGCATTTG
AAAAAGCTCACCGACTTGATCCAACCTCTTCAGGCCGCGGAGTTAGACAATTTAAGACGGCATTGCTT
CAACGGTTAGAGCGTGAGAACGAAACCACATTGGCGGGAAGACAAAAAGCGACGCGCGAGAGATG
CAAAGTTTTTACCAGCATTACTACAAAAAATACATTCAAGCGTTACTGAATGCAGCGGACAAGGCAGA
TCGGGCGCAACTTACAAAAGCGTACCAGACAGCTGCAGTCCTTTTTGAAGTGCTTAAAGCTGTCAATC
AGACTGAAGACGTCGAAGTTGCCGATGAAATTCTGGAGACACACAATAAAGTCGAGGAGAAAACGCA
GATTTATGTGCCTTATAACATTCTTCCCTTAGATCCTGACAGCCAAAATCAGGCCATTATGCGTCTTGCC
AGAAATTCAGGCGGCTGTCGCCGCACTGCGCAACACTCGTGGTTTACCTTGGACAGCAGGACACAAAA
AGAAATTGGATGAGGATATTCTTGATTGGCTGCAATCGATGTTCGGTTTTCAAAAAGATAATGTGCTC
AATCAAAGAGAACATCTGATTTTGCTTCTGGCTAACGTTCATATCCGCCAATTCCCGAAGCCTGATCAG
CAGCCAAAACTTGACGACCGGGCTCTTACGATTGTAATGAAAAAGTTATTTCGGAATTACAAGAAGTG
GTGCAAGTATCTTGGTCGCAAGTCATCCCTTTGGCTCCCTACAATTCAACAGGAAGTGCAACAGCGTA
AATTACTTTATATGGGGCTCTACTTGTTAATATGGGGAGAAGCCGCGAATCTTCGCTTTATGCCGGAAT
GTCTGTGCTATATCTATCACCATATGGCATTCGAGTTGTATGGGATGTTAGCAGGCAGCGTGTCTCCGA
TGACTGGCGAACACGTTAAGCCTGCATATGGAGGGGAGGACGAAGGCCTTTTTACAGAAGGTCGTCACG
CCAATTTATCAAACTATTTCTAAAGAAGCAAAAAGATCAAGAGGAGGAAAAAGCAAACATAGCGTGT
GGCGGAACTATGATGATCTCAATGAGTATTTTTGGAGTATTCGGTGTTTTCGGCTTGGCTGGCCCATGC
GCGCGGATGCTGATTTTTTTTGTCAAACAGCTGAAGAATTGAGGTTAGAGAGAAGCGAGATTAAATCG
AATAGCGGGGATCGTTGGATGGGGAAAGTAAACTTTGTAGAGATTAGATCATTTTGGCACATTTTTAG
ATCTTTTGATAGATTGTGGTCCTTTTACATACTGTGCTTGCAAGCGATGATTGTAATCGCTTGGAATGG
CTCGGGTGAATTGTCGGCGATTTTTTCAAGGAGATGTATTTTTGAAGGTGCTCTCTGTCTTTATTACCGC
GGCGATCCTGAAGCTGGCGCAAGCCGTTCTCGATATTGCCCTGTCCTGGAAGGCGCGTCATTCGATGA
GCCTGTATGTTAAACTTCGTTACGTCATGAAAGTGGGTGCTGCGGCAGTTTGGGTCGTCGTTATGGCGG
TAACATACGCATATTCATGGAAAAACGCGTCTGGCTTCTCCCAGACCATTAAGAACTGGTTCGGCGGA
CATTCACATAATTCCCCGTCACTCTTTATTGTGGCTATCCTGATTTATCTGAGCCCTAACATGTTGTCAG
CACTTCTTTTTCTCTTCCCGTTTATCCGTCGGTATTTGGAACGATCTGATTACAAAATCATGATGCTTAT
GATGTGGTGGTCCCAGCCACGACTGTATATCGGAAGGGGGGATGCATGAATCAGCTCTGTCTCTGTTTA
AATACACTATGTTTTGGATTGTTCTGCTGATTTCGAAACTTGCCTTTTCGTATTACGCGGAAATTAAAC
CCCTCGTAGGCCCGACAAAAGACATTATGCGAATTCATATTAGTGTTTATTCGTGGCATGAGTTTTTTTC
CACATGCAAAAAACAATCTGGGTGTAGTCATTGCACTTTGGTCACCCGTCATCCTGGTATATTTCATGG
ACACACAAATTTGGTACGCTATCGTCTCCACCCTGGTGGGAGGCTTAAACGGTGCTTTTAGACGTTTAG
GGGAGATCAGAACCATTAGGTATGTTACGTTCGCGCTTCCAGAGTATCCCAGGTGCATTTAATGATTGTC
TTGTCCCGCAGGACAACTCCGACGACACTAAAAAAAAGCGCTTTAGAGCAACTTTTAGTCGGAAATTT
GATCAGCTTCCATCATCAAAGGACAAAGAGGCGGCAAGATTCGCACAAATGTGGAATAAAATCATTTC
AAGTTTTCGTGAAGAAGACCTGATTTCAGACCGGGAAATGGAACTTTTGCTTGTACCTTACTGGAGTG
```

SEQUENCE LISTING

```
ATCCTGATTTGGACCTGATCAGGTGGCCGCCGTTTTTATTAGCATCCAAAATTCCTATCGCGCTGGACA
TGGCTAAAGACTCTAACGGTAAGGACCGTGAACTCAAAAAGAGACTCGCCGTTGATTCCTATATGACC
TGTGCAGTCCGTGAATGCTACGCGTCTTTCAAAAATTTAATTAATTATTTAGTTGTTGGAGAACGCGAA
GGGCAAGTCATTAATGATATCTTTTCAAAGATCGATGAACATATAGAAAAAGAGACCTTAATTACAGA
ACTTAATTTGAGCGCGCTGCCCGATTTATACGGACAATTCGTGAGACTTATTGAATATCTGCTGGAAAA
TCGGGAAGAGGATAAAGATCAGATTGTTATAGTCTTATTAAATATGCTGGAATTGGTAACGCGGGACA
TTATGGAGGAAGAAGTTCCGTCTTTGTTAGAAACGGCTCATAATGGATCTTACGTTAAGTATGATGTG
ATGACACCACTCCATCAGCAGCGTAAATATTTTAGTCAACTGCGGTTTCCGGTTTACAGCCAAACGGA
GGCGTGGAAAGAGAAATCAAACGACTGCATTTGCTGTTGACGGTCAAAGAATCGGCAATGGACGTA
CCGTCAAACTTGGAAGCGCGAAGAAGATTAACCTTCTTTTCTAATTCACTGTTCATGGATATGCCTCCT
GCACCGAAAATTCGTAATATGTTATCATTTTCAGTCTTAACTCCGTATTTCTCTGAAGATGTCCTTTTTA
GCATCTTCGGCCTTGAACAGCAGAATGAAGATGGAGTGTCCATTCTTTTCTATCTTCAAAAAATTTTTC
CGGATGAATGGACCAATTTTTTAGAGCGGGTCAAATGCGGCAATGAGGAAGAACTGCGGGCCCGTGA
AGATCTTGAAGAAGAATTGCGACTTTGGGCCTCATATAGAGGTCAAACACTGACAAAAACAGTACGTG
GGATGATGTATTATAGAAAAGCTCTGGAACTGCAGGCATTTTTAGACATGGCTAAAGATGAAGAATTA
TTAAAAGGTTACAAAGCTCTGGAGCTTACATCCGAGGAAGCGAGTAAGAGCCGGAGGTTCTTTGTGGGC
TCAATGTCAAGCGTTGGCTGACATGAAGTTCACCTTCGTTGTTTCTTGCCAACAATATAGTATTCATAA
GCGTAGCGGTGATCAAAGAGCGAAGGATATCCTTCGGTTGATGACAACGTATCCGAGCATCCGAGTTG
CATATATAGACGAGGTAGAGCAAACGCACAAAGAGTCCTATAAAGGCACGGAAGAAAGATATATTA
CTCTGCTCTTGTGAAAGCCGCTCCACAGACAAAGCCGATGGATTCTTCAGAAAGCGTACAAACATTGG
ATCAGTTGATTTACCGTATCAAACTTCCGGGGCCAGCAATCCTGGGAGAAGGCAAACCGGAAAATCAG
AATCACGCAATCATTTTCACAAGAGGCGAAGGCCTTCAAACAATCGATATGAATCAGGATAATTATAT
GGAAGAAGCTTTCAAAATGCGCAATCTGTTACAGGAATTCCTTGAAAAACATGGAGGCGTTAGATGCC
CTACAATCCTGGGCCTTCGCGAACACATTTTTACTGGCAGTGTCAGCTCTTTAGCGTGGTTTATGTCCA
ACCAAGAAAACTCATTTGTCACTATAGGCCAGAGAGTCTTAGCGAGCCCTCTGAAAGTACGCTTTCAC
TATGGTCATCCGGATATTTTTGATAGATTGTTTCACCTTACCAGGGGTGGGATTGTAAAGCCTCTAAG
GTCATCAACCTCAGCGAAGACATCTTTGCTGGCTTTAACAGCACACTTCGCGAAGGCAATGTCACCCA
CCATGAATATATTCAAGTTGGTAAGGGACGTGATGTGGGGTTGAATCAAATCTCGATGTTTGAAGCGA
AAATTGCCAATGGCAATGGAGAACAAACCTTGTCCCGGGATCTTTACCGGTTGGGTCATCGTTTCGATT
TCTTTCGTATGCTTTCTTGCTATTTTACCACGATTGGGTTTTATTTTTCTACCATGTTGACCGTCCTGACT
GTATACGTCTTCCTGTATGGGCGGCTGTATCTTGTCCTGAGCGGTCTGGAAGAAGGACTTAGCTCCCAA
CGGGCCTTTCGCAACAACAAGCCTTTAGAAGCCGCACTTGCATCACAAAGTTTTGTTCAGATCGGATTT
TTAATGGCATTGCCTATGATGATGGAAATTGGGCTCGAAAGGGGTTTTCACAATGCTTTAATAGAATTT
GTGCTTATGCAATTGCAGCTTGCATCCGTATTCTTTACTTTTCAATTAGGAACCAAGACTCACTACTAT
GGAAGGACATTATTTCACGGCGGAGCAGAGTATAGAGGCACAGGCCGTGGATTTGTCGTGTTTCATGC
GAAATTTGCCGAAAATTATCGGTTCTATTCTAGGTCTCATTTTGTCAAAGGCATCGAGCTGATGATCCT
TCTTTTGGTCTATCAAATCTTCGGTCAATCATATAGGGGTGTAGTGACATACATCCTTATCACTGTAAG
CATATGGTTTATGGTTGTGACGTGGCTGTTTGCGCCTTTTCTGTTTAACCCCAGTGGATTTGAATGGCA
GAAGATCGTGGATGACTGGACCGATTGGAACAAATGGATCTATAATCGCGGCGGCATTGGGGTTCCAC
CGGAGAAATCTTGGGAGTCATGGTGGGAAAAAGAACTGGAACACCTCCGCCATAGCGGAGTCCGGGG
AATTACATTGGAAATTTTCCTTGCGCTTCGCTTTTTCATCTTTCAGTACGGGCTTGTCTACCATCTCAGC
ACATTTAAAGGCAAAAACCAGTCATTTTGGGTCTACGGGGCCTCATGGTTTGTCATTCTGTTTATTTTG
TTAATTGTAAAAGGTTTGGGCGTTGGACGGCGCCGCTTTTCTACTAATTTCCAGCTGCTTTTCCGCATC
ATTAAAGGTCTCGTTTTCTTAACGTTCGTTGCAATTCTGATTACTTTTCTGGCACTGCCGCTGATAACCA
TAAAGGATTTATTTATCTGTATGCTTGCATTTATGCCTACGGGGTGGGGTACTTCTTCTGATAGCTCAGG
CGTGCAAACCGCTGATCCAGCAACTGGGAATCTGGTCTTCCGTCAGAACCTTAGCACGGGGGTACGAA
ATCGTTATGGGCCTGTTACTGTTTACCCCAGTGGCATTTCTTGCGTGGTTTCCGTTTGTAAGCGAATTCC
AAACGCGCATGCTGTTTAATCAGGCGTTTTCTCGCGGGTTGCAAATTAGCCGCATTTTAGGCGGCCAAC
GGAAGGATAGGAGCAGCAAAAATAAGGAG
```

SEQ ID NO: 5
```
MAPAVAGGGGRRNNEGVNGNAAAPACVCGFPVCACAGAAAVASAASSADMDIVAAGQIGAVNDESWV
AVDLSDSDDAPAAGDVQGALDDRPVFRTEKIKGVLLHPYRVLIFVRLIAFTLFVIWRIEHKNPDAMWLWVT
SIAGEFWFGFSWLLDQLPKLNPINRVPDLAVLRRRFDHADGTSSLPGLDIFVTTADPIKEPILSTANSILSILAA
DYPVDRNTCYLSDDSGMLLTYEAMAEAAKFATLWVPFCRKHAIEPRGPESYFELKSHPYMGRAQEEFVND
RRRVRKEYDDFKARINGLEHDIKQRSDSYNAAAGVKDGEPRATWMADGSQWEGTWIEQSENHRKGDHA
GIVLVLLNHPSHARQLGPPASADNPLDFSGVDVRLPMLVYVAREKRPGCNHQKKAGAMNALTRASAVLS
NSPFILNLDCDHYINNSQALRAGICFMLGRDSDTVAFVQFPQRFEGVDPTDLYANHNRIFFDGTLRALDGLQ
GPIYVGTGCLFRRITLYGFEPPRINVGGPCFPRLGGMFAKNRYQKPGFEMTKPGAKPVAPPPAATVAKGKH
GFLPMPKKAYGKSDAFADTIPRASHPSPYAAEEAAVAADEAAIAEAVMVTAAAYEKKTGWGSDIGWVYGT
VTEDVVTGYRMHIKGWRSRYCSIYPHAFIGTAPINLTERLFQVLRWSTGSLEIFFSRNNPLFGSTFLHPLQRV
AYINITTYPFTALFLIFYTTVPALSFVTGHFIVQRPTTMFYVYLAIVLGTLLILAVLEVKWAGVTVFEWFRNG
QFWMTASCSAYLAAVLQVVTKVVFRRDISFKLTSKLPAGDEKKDPYADLYVVRWTWLMITPIIIILVNIIGS
AVAFAKVLDGEWTHWLKVAGGVFFNFWVLFHLYPFAKGILGKHGKTPVVVLVWWAFTFVITAVLYINIP
HIHGPGRHGAASPSHGHHSAHGTKKYDFTYAWP
```

SEQ ID NO: 6
```
ATGGCGCCGGCTGTCGCGGGAGGCGGTGGCCGTCGAAATAATGAAGGAGTCAACGGCAACGCCGCAG
CTCCAGCCTGCGTATGCGGCTTTCCGGTTTGCGCATGCGCCGGGGCTGCCGCTGTTGCTAGTGCGGCCT
CTTCCGCTGATATGGACATTGTGGCGGCCGGCCAGATCGGCGCGGTCAACGACGAATCATGGGTCGCC
GTCGATCTGAGCGATAGTGACGACGCCCGGCGGCGGGTGATGTACAAGGCGCTCTCGATGACCGTCC
GGTGTTTAGAACAGAGAAAATTAAAGGCGTTCTCCTTCACCCGTATAGAGTGCTTATTTTTGTACGGCT
GATCGCGTTTACGCTTTTCGTCATCTGGAGGATAGAGCATAAGAACCCGGATGCGATGTGGCTGTGGG
TTACATCGATAGCAGGTGAATTTTGGTTTGGTTTTTCTTGGCTTCTTGATCAGCTCCCGAAACTTAATCC
TATAAACAGAGTTCCAGACTTGGCTGTATTGCGGAGACGATTCGATCATGCGGATGGTACTTCGTCATT
ACCCGGACTGGATATCTTCGTTACAACAGCTGATCCAATTAAAGAGCCTATTTTGAGCACTGCGAACA
GTATCCTGTCAATTTTAGCTGCCGATTATCCGGTTGATCGGAACACATGTTATCTTAGCGATGATTCAG
```

SEQUENCE LISTING

```
GAATGCTGCTCACATATGAAGCAATGGCTGAGGCAGCTAAATTTGCCACATTATGGGTGCCGTTTTGT
CGTAAACATGCTATTGAGCCGAGGGGACCGGAAAGCTATTTTGAATTAAAATCTCATCCTTATATGGG
TAGGGCACAGGAAGAATTTGTTAACGATCGTCGAAGGGTAAGGAAAGAATATGATGATTTTAAAGCA
CGGATTAACGGCTTAGAACACGATATCAAACAACGCTCAGATTCATACAACGCGGCAGCAGGTGTTAA
AGACGGGGAACCACGTGCTACATGGATGGCAGATGGCTCACAGTGGGAAGGGACATGGATCGAACAA
TCGGAAAATCATCGAAAAGGCGATCACGCAGGTATAGTGCTTGTTCTGTTAAATCATCCTTCACATGC
ACGTCAATTAGGACCACCGGCAAGCGCAGATAATCCTTTGGACTTTTCCGGAGTTGACGTTAGGTTAC
CTATGCTTGTATACGTAGCCCGTGAAAAACGGCCCGGATGCAACCACCAAAAAAAAGCGGGAGCAAT
GAACGCGTTGACGCGCGCTTCCGCGGTCCTCAGCAATTCTCCGTTTATACTTAATCTGGACTGCGATCA
CTACATTAACAACTCACAAGCGCTTCGTGCAGGGATATGCTTTATGTTGGGACGTGATAGTGACACAG
TGGCTTTCGTGCAATTTCCGCAAAGATTTGAAGGCGTAGATCCGACCGACCTGTACGCAAACCACAAT
AGAATTTTTTTTGATGGTACCCTGAGAGCTTTAGATGGGTTACAGGGGCCGATTTATGTTGGTACGGGC
TGCTTGTTTAGACGCATAACCTTATATGGTTTCGAACCGCCGAGAATCAATGTTGGTGGCCCCTGCTTT
CCTCGCCTCGGTGGGATGTTTGCCAAGAATCGGTATCAGAAGCCTGGCTTCGAGATGACTAAGCCGGG
AGCGAAACCCGTTGCACCTCCACCGGCTGCTACAGTAGCCAAGGGGAAGCATGGCTTTTTACCGATGC
CGAAAAAAGCGTATGGGAAAAGCGACGCATTTGCGGATACAATTCCTAGAGCGTCACACCCTAGTCC
GTATGCCGCCGAAGCAGCTGTTGCCGCCGACGAGGCTGCAATTGCCGAAGCGGTGATGGTCACAGCTG
CCGCTTATGAGAAAAAGACGGGTTGGGGGTCAGACATCGGCTGGGTTTACGGAACAGTTACAGAGGA
TGTCGTTACTGGATATAGAATGCACATCAAAGGCTGGCGGTCACGCTACTGTAGCATCTACCCGCATG
CATTCATCGGTACCGCTCCGATTAATTTGACAGAACGACTGTTTCAAGTCTTACGCTGGAGCACAGGAT
CTTTGGAAATCTTCTTCTCTAGAAATAATCCGTTATTCGGTAGCACATTCCTCCATCCATTGCAGAGGG
TTGCGTATATTAATATCACCACCTATCCATTTACTGCACTGTTTCTTATTTTTTATACAACAGTCCCGGC
GCTGTCTTTTGTCACGGGTCACTTCATTGTACAACGCCCGACAACGATGTTTTACGTGTATCTCGCAAT
AGTACTGGGCACGCTGCTGATCTTAGCCGTCTTAGAAGTTAAGTGGGCTGGGGTAACGGTATTCGAAT
GGTTCCGCAACGGACAATTTTGGATGACGGCATCTTGTTCAGCTTATTTAGCTGCTGTCCTTCAAGTCG
TTACGAAGGTTGTGTTTCGCCGGGACATTTCGTTTAAACTGACATCGAAATTGCCCGCTGGGGATGAA
AAGAAAGATCCATATGCGGATCTTTACGTCGTGCGGTGGACCTGGTTAATGATTACGCCGATCATTAT
CATCCTCGTTAACATCATCGGCTCTGCAGTCGCGTTCGCTAAAGTGCTTGATGGAGAATGGACCCATTG
GTTAAAAGTGGCGGGCGGCGTCTTTTTTAACTTCTGGGTCTTGTTTCATTTATACCCTTTCGCAAAGGG
AATTTTAGGCAAGCATGGGAAAACGCCTGTTGTGGTCCTGGTTTGGTGGGCTTTCACCTTTGTTATTAC
AGCGGTTCTTTACATCAACATCCCTCATATCCATGGGCCGGGAAGACATGGCGCCGCAAGCCCGTCTC
ATGGACATCATTCTGCACATGGCACAAAAAAAATATGATTTCACGTACGCATGGCCATAA

SEQ ID NO: 7
MRLQRNSIICALVFLVSFVLGDVNIVSPSSKATFSPSGGTVSVPVEWMDNGAYPSLSKISTFTFSLCTGPNNN
IDCVAVLASKITPSELTQDDKVYSYTAEFASTLTGNGQYYIQVFAQVDGQGYTIHYTPRFQLTSMGGVTAY
TYSATTEPTPQTSIQTTTTNNAQATTIDSRSFTVPYTKQTGTSRFAPMQMQPNTKVTATTWTRKFATSAVTY
YSTFGSLPEQATTITPGWSYTISSGVNYATPASMPSDNGGWYKPSKRLSLSARKINMRKV

SEQ ID NO: 8
ATGCGGCTTCAACGTAACAGTATCATTTGTGCCTTAGTTTTTTTAGTATCTTTTGTCTTGGGTGATGTCA
ACATTGTGTCGCCGTCAAGCAAAGCTACATTTTCTCCAAGTGGCGGCACAGTGTCCGTTCCTGTCGAAT
GGATGGACAACGGAGCTTATCCGAGCCTTTCAAAAATTTCTACATTTACATTTAGTCTGTGCACGGGTC
CAAATAATAATATTGATTGTGTTGCTGTCCTGGCAAGTAAAATAACGCCTAGCGAATTAACTCAGGAT
GACAAAGTTTATTCTTATACGGCTGAATTTGCTTCAACGTTGACCGGGAATGGTCAATACTATATCCAA
GTATTTGCCCAGGTAGATGGCCAAGGCTACACAATCCATTACACGCCGCGGTTCCAGCTCACGTCAAT
GGGGGGCGTGACAGCGTACACATATAGTGCAACGACCGAACCTACACCCCAGACTAGTATTCAAACA
ACAACGACAAATAATGCGCAGGCAACTACCATAGATTCCCGGTCCTTCACAGTCCCTTATACTAAACA
AACGGGCACTTCACGCTTTGCGCCTATGCAGATGCAGCCGAATACTAAAGTGACCGCGACAACGTGGA
CGAGGAAATTCGCCACCTCAGCAGTTACCTATTACTCTACTTTTGGATCGTTGCCTGAACAAGCAACAA
CAATTACACCCGGCTGGTCGTATACTATATCAAGCGGGGTAAACTATGCGACACCTGCTAGTATGCCT
AGCGATAACGGAGGTTGGTATAAGCCAAGCAAACGATTGAGCCTTTCAGCGCGGAAAATTAACATGC
GAAAAGTTTGA

SEQ ID NO: 9
MLMKRLFAASLMLAFSSVSSVRAEEAVKPGAPWWKSAVFYQVYPRSFKDTNGDGIGDFKGLTEKLDYLK
GLGIDAIWINPHYASPNTDNGYDISDYREVMKEYGTMEDFDRLMAELKKRGMRLMVDVVINHSSDQHEW
FKSSRASKDNPYRDYYFWRDGKDGHEPNNYPSFFGGSAWEKDPVTGQYYLHYFGRQQPDLNWDTPKLRE
ELYAMLRFWLDKGVSGMRFDTVATYSKTPGFPDLTPEQMKNFAEAYTQGPNLHRYLQEMHEKVFDHYD
AVTAGEIFGAPLNQVPLFIDSRRKELDMAFTFDLIRYDRALDRWHTIPRTLADFRQTIDKVDAIAGEYGWNT
FFLGNHDNPRAVSHFGDDRPQWREASAKALATVTLTQRGTPPIFQGDELGMTNYPFKTLQDFDDIEVKGFF
QDYVETGKATAEELLTNVALTSRDNARTPFQWDDSANAGFTTGKPWLKVNPNYTEINAAREIGDPKSVYS
FYRNLISIRHETPALSTGSYRDIDPSNADVYAYTRSQDGETYLVVVNFKAEPRSFTLPDGMHIAETLIESSSPA
APAAGAASLELQPWQSGIYKVK

SEQ ID NO: 10
ATGCTGATGAAGAGATTATTCGCGGCCAGCTTAATGCTGGCCTTCAGTTCAGTATCAAGTGTTAGAGC
AGAGGAAGCAGTAAAACCTGGAGCGCCGTGGTGGAAGTCAGCAGTTTTTTATCAAGTTTATCCTAGGA
GTTTTAAGGATACAAATGGTGATGGGATTGGCGACTTTAAGGGTCTTACGGAGAAACTTGACTATCTT
AAAGGCCTTGGAATCGATGCGATCTGGATAAATCCTCATTATGCATCCCCTAACACGGATAATGGCTA
TGATATTAGCGACTATCGTGAAGTAATGAAAGAGTATGGGACGATGGAGGATTTCGACCGGCTGATGG
CGGAGCTGAAAAAACGCGGCATGCGCCTTATGGTAGATGTAGTGATCAACCATTCATCTGATCAGCAC
GAATGGTTCAAATCCTCTCGTGCCAGTAAAGATAATCCGTATCGTGATTACTATTTTTGGCGTGATGGA
AAAGACGGTCATGAACCTAATAATTATCCTTCTTTCTTCGGCGGCTCAGCATGGGAAAAGGATCCGGT
TACCGGGCAATACTATCTCCATTACTTCGGAAGACAGCAGCCAGACTTGAACTGGGATACACCGAAAC
TGCGGGAGGAGCTGTATGCGATGCTTCGTTTCTGGCTGGATAAAGGCGTCTCTGGAATGCGGTTTGAT
ACGGTGGCCACATATTCTAAAACGCCGGGATTTCCGGACCTGACGCCTGAGCAGATGAAAAACTTTGC
```

-continued

SEQUENCE LISTING

```
CGAAGCTTATACCCAGGGTCCGAACCTCCACCGGTATCTGCAAGAAATGCATGAAAAAGTGTTTGATC
ATTATGACGCGGTCACCGCTGGGGAGATTTTTGGCGCGCCGCTTAACCAAGTTCCGCTGTTTATTGATT
CAAGAAGAAAAGAGCTTGATATGGCTTTCACTTTCGACTTGATTAGATACGACCGTGCTTTAGACCGG
TGGCATACAATTCCGCGCACGTTAGCTGATTTCCGTCAGACGATCGACAAGGTGGATGCCATAGCCGG
CGAATACGGCTGGAATACATTTTTCTTGGGGAACCATGACAACCCTCGCGCAGTGAGCCATTTTGGTG
ACGATAGACCTCAGTGGAGAGAAGCGAGCGCTAAAGCACTCGCCACAGTCACGCTGACCCAGCGCGG
CACGCCTTTTATTTTTCAAGGGGATGAATTAGGGATGACGAATTACCCTTTTAAAACGCTTCAGGATTT
TGATGACATCGAAGTCAAAGGATTCTTCCAAGACTATGTTGAAACAGGGAAAGCTACTGCTGAAGAGC
TTTTGACAAACGTTGCGCTTACGTCAAGGGATAATGCCCGAACGCCTTTTCAATGGGACGATAGTGCA
AATGCGGGATTTACCACCGGCAAGCCATGGCTGAAAGTTAACCCGAATTACACCGAAATCAATGCCGC
GCGTGAAATTGGAGATCCCAAGAGCGTCTATAGCTTTTATAGAAACCTGATTTCTATACGTCACGAAA
CACCGGCGTTGTCAACTGGGTCCTATCGAGACATTGATCCTAGCAACGCCGATGTGTACGCGTATACG
CGGTCACAGGACGGAGAGACATATTTGGTAGTCGTTAATTTTAAGGCAGAGCCCCGGTCTTTTACCTT
ACCGGATGGTATGCATATTGCGGAAACACTGATTGAGTCCTCTTCCCCGGCGGCTCCGGCAGCCGGCG
CAGCCTCTCTGGAGCTCCAGCCGTGGCAGAGTGGTATTTACAAGGTTAAATAA
```

SEQ ID NO: 11
```
MLENKNHKKISLSGKSLLMGTLSTAAIVLSASTANAATINADNVNENQTVEVTASSVNNENNKQVTEKDS
ADKSTSDVAEDANTKKSNENTETTEKNTQTVVTNAPVSDVKNTNTVTAETPVDKVVNNSDQKTTNAATT
DTKKDDVKQVEKKDSVDKTNAEENKDSSVKPAENATKAELKGQVKDIVEESGVDTSKLTNDQINELNKIN
FSKEAKSGTQLTYNDFKKIAKTLIEQDARYAIPFFNASKIKNMPAAKTLDAQSGKVEDLEIWDSWPVQDAK
TGYVSNWNGYQLVIGMMGVPNVNDNHIYLLYNKYGDNDFNHWKNAGPIFGLGTPVIQQWSGSATLNKD
GSIQLYYTKVDTSDNNTNHQKLASATVYLNLEKDQDKISIAHVDNDHIVFEGDGYHYQTYDQWKETNKG
ADNIAMRDAHVIDDDNGNRYLVFEASTGTENYQGDDQIYQWLNYGGTNKDNLGDFFQILSNSDIKDRAK
WSNAAIGIIKLNDDVKNPSVAKVYSPLISAPMVSDEIERPDVVKLGNKYYLFAATRLNRGSNDDAWMATN
KAVGDNVAMIGYVSDNLTHGYVPLNESGVVLTASVPANWRTATYSYYAVPVEGRDDQLLITSYITNRGEV
AGKGMHATWAPSFLLQINPDNTTTVLAKMTNQGDWIWDDSSENPDMMGVLEKDAPNSAALPGEWGKPV
DWDLIGGYNLKPHQPVTPIPNVPTTPETPTTPDKPEVPTTPEVPTTPETPTPEAPKNPVKKTSQSKLPKAGDK
NSFAAVVLGAVSSILGAVGLTGVSKRKRNN
```

SEQ ID NO: 12
```
ATGTTAGAAAACAAGAATCATAAGAAGATTAGCCTTAGTGGAAAATCACTTTTGATGGGAACTTTATC
AACAGCCGCTATTGTACTGAGCGCCAGCACAGCAAACGCTGCAACAATTAATGCAGATAACGTTAACG
AAAATCAAACCGTTGAAGTAACGGCATCCTCCGTGAATAACGAAAATAATAAGCAGGTGACTGAAAA
AGATAGCGCGGATAAATCAACTTCAGACGTTGCCGAGGACGCCAACACAAAAAAATCTAATGAAAAC
ACAGAAACGACAGAGAAAAATACACAAACTGTTGTAACAAACGCTCCGGTGAGTGATGTAAAGAACA
CGAATACGGTTACAGCAGAAACACCGGTTGATAAGGTGGTTAACAACTCTGACCAGAAAACAACTAA
TGCAGCGACAACAGATACAAAAAAAGACGACGTGAAACAAGTAGAGAAAAAAGATTCCGTGGATAA
GACCAACGCTGAAGAAAATAAGGACTCCTCAGTAAAGCCTGCTGAAAACGCTACAAAGGCAGAATTG
AAAGGGCAGGTAAAAGATATCGTTGAGGAAAGCGGAGTCGACACGAGTAAACTTACCAATGATCAAA
TTAACGAGCTGAACAAAATTAACTTTAGCAAAGAGGCAAAAAGCGGAAAGTGGAAGATCTTGAA
TTTTAAAAAGATCGCCAAAACCCTTATTGAACAAGATGCCCGCTATGCCATCCCTTTTTTTAATGCAAG
TAAAATTAAAAATATGCCAGCAGCTAAAACACTCGACGCACAAAGCGGCAAAGTGGAAGATCTTGAA
ATTTGGGATTCTTGGCCGGTGCAGGACGCGAAAACGGGCTACGTGAGTAACTGGAATGGGTACCAGCT
GGTCATTGGAATGATGGGAGTTCCGAATGTCAACGATAATCATATTTTACCTCCTGTATAATAAATATG
GTGACAACGACTTTAATCATTGGAAAAACGCGGGCCCTATTTTCGGCCTGGGAACACCAGTGATCCAA
CAATGGTCCGGATCAGCCACTTAATAAAGACGGATCGATACAGCTTTACTACACTAAGGTAGACAC
AAGCGATAATAATACAAATCATCAAAAACTGGCCAGTGCTACAGTCTACTTAAATTTGGAAAAAGATC
AAGACAAGATAAGTATTGCACACGTGGATAATGACCACATCGTGTTTGAAGGAGACGGTTACCACTAT
CAGACATACGATCAATGGAAGGAAACCAATAAAGGCGCAGACAATATCGCAATGCGCGATGCACACG
TCATAGACGACGATAACGGGAATCGCTATCTCGTGTTCGAAGCGAGTACCGGAACAGAAAACTATCA
GGGTGATGACCAGATTTATCAATGGTTGAATTATGGAGGCACTAACAAAGATAACCTTGGTGACTTTT
TTCAAATCTTAAGCAACTCAGATATCAAAGATCGCGCAAAATGGTCCAATGCAGCCATCGGCATCATT
AAATTAAATGATGATGTCAAGAATCCTTCTGTCGCCAAGGTCTATTCACCGTTGATTTCAGCGCCTATG
GTATCTGATGAGATCGAACGGCCGGATGTCGTGAAGTTAGGAAATAAATATTATCTGTTTGCTGCCAC
GCGGTTAAACAGAGGCAGCAACGATGATGCTTGGATGGCAACAAACAAAGCAGTGGGGGACAATGTG
GCAATGATTGGGTATGTATCTGACAACCTTACCCATGGCTATGTACCGCTTAATGAATCTGGAGTAGTC
CTTACCGCGTCAGTTCCTGCGAATTGGCGCACGGCCACCTACTCTTATTATGCGGTCCCTGTCGAAGGG
CGCGATGATCAATTGCTGATCACATCTTATATTACCAATAGAGGTGAGGTTGCCGGTAAAGGAATGCA
TGCCACGTGGGCACCCAGCTTTTTGCTTCAGATCAACCCGGACAATACGACCACAGTTCTGGCAAAGA
TGACGAACCAGGGGGACTGGATATGGGACGATAGCAGTGAAAACCCTGACATGATGGGCGTATTAGA
AAAAGACGCCCCTAATTCAGCAGCACTCCCGGGCGAGTGGGGCAAACCAGTTGACTGGGATCTGATTG
GTGGGTACAACCTCAAACCACATCAACCTGTCACACCTATACCGAACGTGCCAACTACGCCGGAAACA
CCTACAACGCCTGATAAACCAGAAGTACCAACTACCCCAGAAGTCCCGACAACACCGGAAACACCGA
CCCCCGGAAGCCCCTAAAAACCCTGTCAAAAAGACGTCACAGTCGAAACTTCCTAAAGCGGGTGATAA
GAATTCTTTTGCCGCGGTTGTTTTAGGGGCAGTCTCAAGCATTCTGGGCGCCGTGGGCCTCACGGGCGT
TTCTAAAAGAAAACGTAACAATTAA
```

SEQ ID NO: 13
```
MAPNLSKAKDDLIGDVVAVDGLIKPPRFTLKGKDLAVDGHPFLLDVPANIRLTPASTLVPNSDVPAAAAGS
FLGFDAPAAKDRHVVPIGKLRDTRFMSIFRFKVWWTTHWVGTNGRDVENETQMMILDQSGTKSSPTGPRP
YVLLLPIVEGPFRACLESGKAEDYVHMVLESGSSTVRGSVFRSAVYLHAGDDPFDLVKDAMRVVRAHLGT
FRLMEEKTPPPIVDKFGWCTWDAFYLKVHPEGVWEGVRRLADGGCPPGLVLIDDGWQSICHDDDDLGSG
AEGMNRTSAGEQMPCRLIKFQENYKFREYKGGMGGFVREMKAAFPTVEQVYVWHALCGYWGGLRPGAP
GLPPAKVVAPRLSPGLQRTMEDLAVDKIVNNGVGLVDPRRARELYEGLHSHLQASGIDGVKVDVIHLLEM
VCEEYGGRVELAKAYFAGLTESVRRHFNGNGVIASMEHCNDFMLLGTEAVALGRVGDDFWCTDPSGDPD
GTFWLQGCHMVHCAYNSLWMGAFIHPDWDMFQSTHPCAAFHAASRAVSGGPVYVSDAVGCHDFDLLRR
```

SEQUENCE LISTING

LALPDGTILRCERYALPTRDCLFADPLHDGKTMLKIWNVNKFSGVLGAFNCQGGGWSREARRNMCAAGF
SVPVTARASPADVEWSHGGGGGDRFAVYFVEARKLQLLRRDESVELTLEPFTYELLVVAPVRAIVSPELGI
GFAPIGLANMLNAGGAVQGFEAARKDGDVAAEVAVKGAGEMVAYSSARPRLCKVNGQDAEFKYEDGIV
TVDVPWTGSSKKLSRVEYFY

SEQ ID NO: 14
ATGGCTCCGAATCTGAGTAAAGCAAAGGACGATTTAATTGGAGACGTCGTCGCAGTGGATGGCCTTAT
CAAACCTCCTCGGTTTACACTCAAAGGAAAAGACCTCGCCGTTGATGGTCACCCGTTTCTGCTGGACGT
GCCGGCGAATATCCGGTTAACACCAGCATCAACTCTTGTCCCAAACTCGGATGTTCCGGCTGCAGCTG
CTGGGAGCTTTCTTGGCTTCGATGCACCCGCGGCAAAAGATCGTCATGTCGTTCCGATTGGGAAACTG
CGCGATACAAGATTTATGTCTATCTTTCGTTTTAAAGTCTGGTGGACGACACATTGGGTTGGGACAAAT
GGACGGGATGTAGAGAACGAGACCCAGATGATGATCTTGGATCAGTCCGGAACAAAGTCTAGCCCGA
CTGGACCGCGCCCGTATGTTCTGCTTCTTCCGATCGTCGAAGGCCCGTTTAGAGCCTGTTTAGAATCGG
GGAAAGCCGAAGATTATGTCCATATGGTGCTGGAAAGTGGGTCTAGCACCGTACGTGGTTCAGTGTTT
AGAAGCGGCTGTGTATCTTCATGCTGGCGATGACCCTTTTGATTTGGTGAAAGATGCAATGCGCGTCGTA
CGTGCGCATTTAGGAACGTTCCGGTTGATGGAGGAAAAGCACCGCCTCCGATCGTTGATAAGTTTGG
CTGGTGCACCTGGGATGCCTTTTATTTAAAGGTACATCCAGAAGGAGTGTGGGAAGGAGTACGGAGAT
TAGCAGATGGCGGCTGCCCACCGGGGCTGGTATTAATTGACGATGGATGGCAATCGATTTGCCATGAT
GATGACGATCTTGGCTCAGGAGCTGAAGGAATGAACAGAACAAGCGCGGGCGAGCAAATGCCTTGTA
GGCTTATTAAATTTCAGGAAAACTATAAATTCAGGGAATACAAAGGTGGCATGGGAGGCTTCGTGCGT
GAGATGAAAGCAGCATTTCCGACCGTGGAGCAAGTCTATGTTTGGCACGCACTGTGCGGATATTGGGG
AGGTCTCCGTCCGGGTGCACCGGGTCTGCCGCCAGCAAAGTGGTAGCACCGCGATTGTCCCCGGGCT
TACAGCGGACGATGGAAGATCTTGCGGTAGATAAAATTGTTAACAATGGCGTGGGCCTTGTGGATCCT
CGCAGAGCTAGAGAACTGTATGAAGGCCTTCATTCCCACCTCCGTGACGGCCAGCGGTATAGATGGAGTGAA
AGTAGATGTTATACACCTTCTTGAGATGGTTTGCGAGGAATACGGGGGGGAGAGTAGAATTGGCTAAAG
CGTATTTCGCAGGACTCACTGAGTCAGTTCGGAGGCATTTTAACGGAAATGGTGTCATTGCGTCAATG
GAGCACTGCAACGATTTTATGCTGCTGGGTACAGAAGCTGTAGCATTAGGCCGGGTGGGAGATGATTT
CTGGTGTACAGATCCGTCTGGTGACCCAGATGGTACGTTCTGGTTTACAGGGATGCCCACATGGTACACT
GTGCGTATAATAGTTTATGGATGGGCGCCTTTATACATCCGGACTGGGACATGTTTCAATCTACACACC
CCTGCGCGGCGTTCCATGCTGCGAGCAGAGCCGTCTCCGGTGGACCAGTCTATGTATCAGATGCGGTT
GGCTGCCATGATTTCGATCTGCTTCGTAGGCTCGCACTGCCGGATGGCACAATTTTGCGTTGCGAACGC
TATGCACTGCCGACAAGAGATTGTCTTTTTGCGGATCCCTTGCATGATGGCAAAACAATGTTGAAAAT
ATGGAACGTAAACAAATTTTCAGGAGTTTTAGGAGCATTTAATTGCCAGGGCGGAGGATGGTCACGCG
AAGCTCGTCGCAACATGTGCGCGGCTGGTTTTAGTGTTCCGGTGACTGCTCGGGCTTCACCTGCAGACG
TTGAGTGGTCACACGGAGGCGGTGGTGGAGATCGTTTTGCCGTTTATTTCGTGGAGGCTCGCAAACTTC
AATTACTGCGTCGCGACGAAAGCGTGGAACTGACATTAGAACCGTTTACATATGAGCTGTTAGTCGTG
GCCCCCGTGAGAGCTATCGTGTCACCAGAATTAGGTATCGGCTTCGCACCGATTGGCCTCCGCTAATAT
GCTGAACGCCGGCGGGGCGGTTCAGGGTTTTGAAGCCGCCCGTAAGGATGGAGATGTGGCTGCTGAG
GTGGCTGTCAAAGGGGCGGGTGAAATGGTCGCATACTCTAGTGCGAGACCAAGGTTATGCAAGGTAA
ACGGACAGGACGCCGAATTTAAATATGAAGACGGAATTGTCACAGTAGACGTCCCTTGGACAGGATC
CTCCAAAAAACTTAGCAGGGTAGAATATTTCTATTAG

SEQ ID NO: 15
MAHVRRKVATLNMALAGSLLMVLGAQSALAQGNFSRQEAARMAHRPGVMPRGGPLFPGRSLAGVPGFP
LPSIHTQQAYDPQSDFTARWTRADALQIKAHSDATVAAGQNSLPAQLTMPNIPADFPVINPDVWVWDTWT
LIDKHADQFSYNGWEVIFCLTADPNAGYGFDDRHVHARIGFFYRRAGIPASRRPVNGGWTYGGHLFPDGA
SAQVYAGQTYTNQAEWSGSSRLMQIHGNTVSVFYTDVAFNRDANANNITPPQAIITQTLGRIHADFNHVW
FTGFTAHTPLLQPDGVLYQNGAQNEFFNFRDPFTFEDPKHPGVNYMVFEGNTAGQRGVANCTEADLGFRP
NDPNAETLQEVLDSGAYYQKANIGLAIATDSTLSKWKFLSPLISANCVNDQTERPQVYLHNGKYYIFTISHR
TTFAAGVDGPDGVYGFVGDGIRSDFQPMNYGSGLTMGNPTDLNTAAGTDFDPSPDQNPRAFQSYSHYVM
PGGLVESFIDTVENRRGGTLAPTVRVRIAQNASAVDLRYGNGGLGGYGDIPANRADVNIAGFIQDLFGQPT
SGLAAQASTNNAQVLAQVRQFLNQ

SEQ ID NO: 16
MLNKAGIAEPSLWTRADAMKVHTDDPTATMPTIDYDFPVMTDKYWVWDTWPLRDINGQVVSFQGWSVI
FALVADRTKYGWHNRNDGARIGYFYSRGGSNWIFGGHLLKDGANPRSWEWSGCTIMAPGTANSVEVFFT
SVNDTPSESVPAQCKGYIYADDKSVWFDGFDKVTDLFQADGLYYADAYAENNFWDFRDPHVFINPEDGKT
YALFEGNVAMERGTVAVGEEEIGPVPPKTETPDGARYCAAAIGIAQALNEARTEWKLLPPLVTAFGVNDQ
TERPHVVFQNGLTYLFTISHHSTYADGLSGPDGVYGFVSENGIFGPYEPLNGSGLVLGNPSSQPYQAYSHYV
MTNGLVTSFIDTIPSSDPNVYRYGGTLAPTIKLELVGHRSFVTEVKGYGYIPPQIEWLAEDESSNSAAALSLL
NK

SEQ ID NO: 17
MNKLKIVKCILIGSMICSGIITQQTFASTNDMNYKETYGVSHITRYNMSKIPMEQNDLKFKVPQFNASTLKNI
ASAKGYDKNGNLIDLDVWDSWPLQNGDGTVANYHGYHIVFALAGDPKNQDDTSIYMFYQKIGENSIDSW
KNAGKVFKDSDKYVANDPYLKYQTQEWSGSATLTSDGQVRLFYTDFSGVAKDGGTDASNQVITTTQVNL
SQPDSNTINIDSVSDHKSVFDGGNGTIYQNVQQFIDEGKWSSGDNHTLRDPHYVEDNGRKYLVFEANTGTN
DGYQGDTSLLNKAFYGRSQSFFKTEKDQLLIDTNKKHDASLANGALGIIELNNDYTLKKEMKPLIASNTVT
DEIERANVFKMNGRWYLFTDSRGSKMTINGISSKDIYMLGFSSNSLTGPYKPLNKTGLVLNLNLDPTDLTFT
YSHFAVPQTNGKNVVITSYITNRGMYSDHHSSFAPSFLLNIKGTKTSVISNSILQQGQLTIDNY

SEQ ID NO: 18
MNIKKFAKQATVLTFTTALLAGGATQAFAKETNQKPYKETYGISHITRHDMLQIPEQQKNEKYQVPEFDSS
TIKNISSAKGLDVWDSWPLQNADGTVANYHGYHIVFALAGDPKNADDTSIYMFYQKVGETSIDSWKNAG
RVFKDSDKFDANDSILKDQTQEWSGSATFTSDGKIRLFYTDFSGKHYGKQTLTTAQVNVSASDSSLNINGV
EDYKSIFDGDGKTYQNVQQFIDEGNYSSGDNHTLRDPHYVEDKGHKYLVFEANTGTEDGYQEESLFNKA
YYGKSTSFFRQESQKLLQSDKKRTAELANGALGMIELNDDYTLKKVMKPLIASNTVTDEIERANVFKMNG

-continued

SEQUENCE LISTING

KWYLFTDSRGSKMTIDGITSNDIYMLGYVSNSLTGPYKPLNKTGLVLKMDLDPNDVTFTYSHFAVPQAKG
NNVVITSYMTNRGFYADKQSTFAPSFLLNIKGKKTSVVKDSILEQGQLTVNK

SEQ ID NO: 19
ATGAACATAAAGAAGTTTGCGAAGCAGGCGACAGTATTAACGTTCACCACGGCACTCTTGGCTGGGGG
CGCAACCCAGGCTTTTGCTAAAGAGACCAACCAGAAGCCGTATAAGGAAACGTATGGGATTTCCCACA
TTACAAGACATGATATGCTGCAGATCCCAGAACAACAGAAAAACGAAAAATACCAAGTCCCGGAATT
TGATTCTTCGACCATTAAAAACATTTCCTCAGCTAAAGGGCTGGACGTATGGGATTCTTGGCCCCTTCA
GAATGCAGATGGAACTGTTGCCAATTACCATGGCTATCATATTGTCTTTGCGCTGGCGGGGGATCCGA
AAAACGCAGATGATACGTCCATCTACATGTTTTACCAAAAAGTAGGGGAAACAAGCATTGATTCCTGG
AAAAACGCTGGCCGCGTCTTCAAGGATTCAGACAAATTTGATGCGAATGATAGTATACTGAAAGATCA
GACGCAAGAGTGGAGCGGTTCCGCAACTTTCACGAGCGACGGAAAAATCCGTCTGTTCTACACCGATT
TTAGCGGCAAGCATTACGGGAAGCAGACTCTGACGACGGCCCAAGTCAATGTATCTGCATCGGACTCT
TCCCTGAATATTAACGGAGTTGAAGATTACAAATCTATATTTGACGGTGATGGCAAAACCTACCAAAA
CGTCCAGCAGTTCATAGACGAAGGCAATTATAGTTCAGGGGACAATCATACTTTACGTGACCCACATT
ATGTCGAAGATAAAGGACATAAATATCTGGTTTTTGAGGCGAACACTGGCACAGAGGACGGGTATCA
GGGGGAAGAGTCCCTGTTCAATAAAGCTTATTACGGCAAGTCAACATCTTTTTTTCGCCAAGAATCAC
AAAAGCTGCTGCAATCAGATAAGAAAAGGACTGCTGAGTTAGCGAACGGCGCATTAGGCATGATTGA
ACTGAATGACGACTACACACTTAAAAAAGTTATGAAACCATTAATTGCGTCGAACACCGTTACTGATG
AAATTGAAAGGGCGAATGTTTTTAAGATGAACGGGAAATGGTATCTCTTTACGGATAGTCGCGGATCA
AAGATGACCATCGATGGTATCACGTCCAATGACATTTACATGCTTGGATATGTTAGCAATTCCTTAACT
GGACCTTATAAACCGCTTAACAAAACAGGCTTGGTACTGAAAATGGATTTGGATCCAAATGACGTCAC
ATTTACATACTCTCATTTCGCTGTTCCGCAGGCAAAGGGCAACAATGTTGTGATTACATCTTATATGAC
CAACCGCGGCTTTTATGCGGATAAGCAATCAACCTTCGCACCATCATTCCTGCTTAACATCAAGGGCA
AAAAAACGAGCGTAGTCAAAGATTCTATCTTGGAACAGGGTCAGCTGACGGTCAACAAATAA

SEQ ID NO: 20
ATGAACATCAAAAAGTTTGCAAAACAAGCAACAGTATTAACCTTTACTACCGCACTGCTGGCAGGAGG
CGCAACTCAAGCGTTTGCGAAAGAAACGAACCAAAAGCCATATAAGGAAACATACGGCATTTCCCAT
ATTACACGCCATGATATGCTGCAAATCCCTGAACAGCAAAAAAATGAAAAATATCAAGTTCCTGAATT
CGATTCGTCCACAATTAAAAATATCTCTTCTGCAAAAGGCCTGGACGTTTGGGACAGCTGGCCATTAC
AAAACGCTGACGGCACTGTCGCAAACTATCACGGCTACCACATCGTCTTTGCATTAGCCGGAGATCCT
AAAAATGCGGATGACACATCGATTTACATGTTCTATCAAAAAGTCGGCGAAACTTCTATTGACAGCTG
GAAAAACGCTGGCCGCGTCTTTAAAGACAGCGACAAATTCGATGCAAATGATTCTATCCTAAAAGACC
AAACACAAGAATGGTCAGGTTCAGCCACATTTACATCTGACGGAAAAATCCGTTTATTCTACACTGAT
TTCTCCGGTAAACATTACGGCAAACAAACACTGACAACTGCACAAGTTAACGTATCAGCATCAGACAG
CTCTTTGAACATCAACGGTGTAGAGGATTATAAATCAATCTTTGACGGTGACGGAAAAACGTATCAAA
ATGTACAGCAGTTCATCGATGAAGGCAACTACAGCTCAGGCGACAACCATACGCTGAGAGATCCTCAC
TACGTAGAAGATAAAGGCCACAAATACTTAGTATTTGAAGCAAACACTGGAACTGAAGATGGCTACC
AAGGCGAAGAATCTTTATTTAACAAAGCATACTATGGCAAAAGCACATCATTCTTCCGTCAAGAAAGT
CAAAAACTTCTGCAAAGCGATAAAAAACGCACGGCTGAGTTAGCAAACGGCGCTCTCGGTATGATTG
AGCTAAACGATGATTACACACTGAAAAAAGTGATGAAACCGCTGATTGCATCTAACACAGTAACAGA
TGAAATTGAACGCGCGAACGTCTTTAAAATGAACGGCAAATGGTACCTGTTCACTGACTCCCGCGGAT
CAAAAATGACGATTGACGGCATTACGTCTAACGATATTTACATGCTTGGTTATGTTTCTAATTCTTTAA
CTGGCCCATACAAGCCGCTGAACAAAACTGGCCTTGTGTTAAAAATGGATCTTGATCCTAACGATGTA
ACCTTTACTTACTCACACTTCGCTGTACCTCAAGCGAAAGGAAACAATGTCGTGATTACAAGCTATATG
ACAAACAGAGGATTCTACGCAGACAAACAATCAACGTTTGCGCCAAGCTTCCTGCTGAACATCAAAGG
CAAGAAAACATCGTTGTCAAAGACAGCATCCTTGAACAAGGACAATTAACAGTTAACAAATAA

SEQ ID NO: 21
MNIKKFAKQATVLTFTTALLAGGATQAFAKETNQKPYKETYGISHITRHDMLQIPEQQKNEKYQVPEFDSS
TIKNISSAKGLDVWDSWPLQNADGTVANYHGYHIVFALAGDPKNADDTSIYMFYQKVGETSIDSWKNAG
RVFKDSDKFDANDSILKDQTQEWSGSATFTSDGKIRLFYTDFSGKHYGKQTLTTAQVNVSASDSSLNINGV
EDYKSIFDGDGKTYQNVQQFIDEGNYSSGDNHTLRDPHYVEDKGHKYLVFEANTGTEDGYQGEESLFNKA
YYGKSTSFFRQESQKLLQSDKKRTAELANGALGMIELNDDYTLKKVMKPLIASNTVTDEIERANVFKMNG
KWYLFTDSRGSKMTIDGITSNDIYMLGYVSNSLTGPYKPLNKTGLVLKMDLDPNDVTFTYSHFAVPQAKG
NNVVITSYMTNRGFYADKQSTFAPSFLLNIKGKKTSVVKDSILEQGQLTVNK

SEQ ID NO: 22
ATGAGAATTAACCACAATATTGCAGCGCTTAACACACTGAACCGTTTGTCTTCAAACAACAGTGCGAG
CCAAAAGAACATGGAGAAACTTTCTTCAGGTCTTCGCATCAACCGTTGCGGGGATGATGACGCAGGTC
TTGCGATCTCTGAAAAAATGAGAGGACAAATCAGAGGTCTTGAAATGGCTTCTAAAAACTCTCAAGAC
GGAATCTCTCTTATCCAAACAGCTGAGGGTGCATTAACTGAAACTCATGCGATCCTTCAACGTGTTCGT
GAGCTAGTTGTTCAAGCTGGAAACACTGGAACTCAGGACAAAGCAACTGATTTGCAATCTATTCAAGA
TGAAATTTCAGCTTTAACAGATGAAATCGATGGTATTTCAAATCGTACAGAATTCAATGGTAAGAAAT
TGCTCGATGGCACTTACAAAGTTGACACAGCTACTCCTGCAAATCAAAAGAACTTGGTATTCCAAATC
GGAGCAAATGCTACACAGCAAATCTCTGTAAATATTGAGGATATGGGTGCTGACGCTCTTGGAATTAA
AGAAGCTGATGGTTCAATTGCAGCTCTTCATTCAGTTAATGATCTTGACGTAACAAAATTCGCAGATA
ATGCAGCAGATACTGCTGATATCGGTTTCGATGCTCAATTGAAAGTTGTTGATGAAGCGATCAACCAA
GTTTCTTCTCAACGTGCTAAGCTTGGTGCGGTACAAAATCGTCTAGAGCACACAATTAACAACTTAAG
CGCTTCTGGTGAAAACTTGACAGCTGCTGAGTCTCGTATCCGTGACGTTGACATGGCTAAAGAGATGA
GCGAATTCACAAAGAACAACATTCTTTCTCAGGCTTCTCAAGCTATGCTTGCTCAAGCAAACCAACAG
CCGCAAAACGTACTTCAATTATTACGTTAA

SEQ ID NO: 23
GGAATTGACGCCCCAAAGCATATTGATATTCACAGGAAAGAAATTTACTTGACCATTCAGGAAGAAAA
TAACCGTGCAGCAGCGTTATCCAGCGATGTGATCTCCGCATTATCCTCACAAAAAAAGTGAGGATTTT

-continued

---

SEQUENCE LISTING
---

TTTATTTTTGTATTAACAAAATCAGAGACAATCCGATATTAATGATGTAGCCGGGAGGAGGCGCAAAA
GACTCAGCCAGTTACAAAATAAGGGCACAAGGACGTGCCTTAACAACATATTCAGGGAGGAACAAAA
CA

SEQ ID NO: 24
GCACAAGGACGT

SEQ ID NO: 25
ATTCAGGGAGGAA

SEQ ID NO: 26
AGGGAGGA

SEQ ID NO: 27
ATGCTAGTTTTATCGCGGAAAATAAACGAAGCGATTCAAATAGGTGCTGATATTGAAGTAAAAGTGAT
TGCGGTTGAAGGGGATCAAGTGAAGCTTGGAATTGACGCCCCAAAGCATATTGATATTCACAGGAAA
GAAATTTACTTGACCATTCAGGAAGAAAATAACCGTGCAGCAGCGTTATCCAGCGATGTGATCTCCGC
ATTATCCTCACAAAAAAGTGA

SEQ ID NO: 28
TAAGGGCACAAGGACGTGCCTTA

SEQ ID NO: 29
GCACAAGAACGT

SEQ ID NO: 30
ATTTAGGGAGGAA

SEQ ID NO: 31
ATGAAAATCAATCAATTTGGAACACAATCCGTTAATCCATATCAAAAAAATTATGATAAGCAAGCGGT
GCAAAAACTGTTGCACAACCTCAAGATAAAATTGAAATTTCATCACAGGCTAAAGAAATGCAACAT
GCATCCGACGCAGTCACTGGTTCACGACAGGAAAAAATTGCGCAGCTTAAAGCGCAAATTGAAACG
GGTCATACAAAGTAGACGCAAATCATATTGCGAAAAATATGATTAATTTTTATAAAAAGCAATAA

SEQ ID NO: 32
ATGCAATCCTTGAATTATGAAGATCAGGTGCTTTGGACGCGCTGGAAAGAGTGGAAAGATCCTAAAGC
CGGTGACGACTTAATGCGCCGTTACATGCCGCTTGTCACATATCATGTAGGCAGAATTTCTGTCGGACT
GCCGAAATCAGTGCATAAAGACGATCTTATGAGCCTTGGTATGCTTGGTTTATATGATGCCCTTGAAA
AATTTGACCCCAGCCGGGACTTAAAATTTGATACCTACGCCTCGTTTAGAATTCGCGGCGCAATCATA
GACGGGCTTCGTAAAGAAGATTGGCTGCCCAGAACCTCGCGCGAAAAAACAAAAAAGGTTGAAGCAG
CAATTGAAAAGCTTGAACAGCGGTATCTTCGGAATGTATCGCCCGCGGAAATTGCAGAGGAACTCGGA
ATGACGGTACAGGATGTCGTGTCAACAATGAATGAAGGTTTTTTTGCAAATCTGCTGTCAATTGATGA
AAAGCTCCATGATCAAGATGACGGGGAAAACATTCAAGTCATGATCAGAGATGACAAAAATGTTCCG
CCTGAAGAAAGATTATGAAGGATGAACTGATTGCACAGCTTGCGGAAAAAATTCACGAACTCTCTGA
AAAAGAACAGCTGGTTGTCAGTTTGTTCTACAAAGAGGAGTTGACACTGACAGAAATCGGACAAGTAT
TAAATCTTTCTACGTCCCGCATATCTCAGATCCATTCAAAGGCATTATTTAAATTAAAGAATCTGCTGG
AAAAAGTGATACAATAA

SEQ ID NO: 33
MSRLVVVSNRIAPPDEHAASAGGLAVGILGALKAAGGLWFGWSGETGNEDQPLKKVKKGNITWASFNLS
EQDLDEYYNQFSNAVLWPAFHYRLDLVFQRPAWDGYLRVNALLADKLLPLLQDDDIIWIHDYHLLPFAH
ELRKRGVNNRIGFFLHIPFPTPEIFNALPTYDTLLEQLCDYDLLGFQTENDRLAFLDCLSNLTRVTTRSAKSH
TAWGKAFRTEVYPIGIEPKEIAKQAAGPLPPKLAQLKAELKNVQNIFSVERLDYSKGLPERFLAYEALLEKY
PQHHGKIRYTQIAPTSRGDVQAYQDIRHQLENEAGRINGKYGQLGWTPLYYLNQHFDRKLLMKIFRYSDV
GLVTPLRDGMNLVAKEYVAAQDPANPGVLVLSQFAGAANELTSALIVNPYDRDEVAAALDRALTMSLAE
RISRHAEMLDVIVKNDINHWQECFISDLKQIVPRSAESQQRDKVATFPKLA

SEQ ID NO: 34
ATGTCCCGTTTAGTAGTGGTGTCCAATCGTATCGCGCCGCCGGACGAACATGCTGCCTCAGCTGGCGG
CCTGGCCGTAGGAATCCTGGGCGCCCTCAAGGCAGCTGGAGGATTATGGTTCGGCTGGTCTGGCGAGA
CAGGAAATGAGGATCAACCACTTAAGAAAGTGAAAAAAGGCAATATCACATGGGCTTCCTTCAACCT
CAGCGAGCAAGACCTGGATGAGTATTATAACCAGTTTAGCAATGCTGTGCTTTGGCCGGCTTTTCATTA
CAGGTTAGATTTGGTTCAGTTTCAAAGACCCGCATGGGATGGATACCTCCGAGTGAATGCGTTGTTGG
CAGATAAACTTCTCCCGCTCCTTCAGGATGATGATATTATCTGGATTCATGACTACCATCTTCTCCCTTT
CGCCCACGAATTGCGCAAACGGGGCGTGAACAATAGGATAGGTTTTTTTTTGCACATTCCTTTTCCCAC
ACCGGAAATTTTCAACGCGCTTCCGACATACGATACTTTACTTGAACAGCTGTGTGATTACGATCTTCT
CGGCTTCCAAACTGAAAATGACAGACTTGCCTTTTTGGATTGCCTCTCAAATTTGACGAGGGTTACGAC
TAGAAGTGCCAAGAGCCATACAGCGTGGGGAAAAGCATTCAGGACAGAAGTTTATCCTATTGGGATC
GAGCCTAAGGAATTGCGAAACAAGCGGCAGGGCCATTACCTCCGAAACTTGCGCAACTCAAAGCGG
AATTAAAGAACGTACAAAACATTTTTAGCGTCGAAAGACTTGATTATTCTAAGGGTCTCCCGGAAAGA
TTCTTAGCCTACGAGGCATTGCTTGAAAAAATATCCACAGCATCATGGGAAAATTCGTTATACGCAAAT
CGCTCCGACTAGCAGAGGCGACGTCCAAGCGTATCAGGACATACGCCACCAACTTGAAAATGAAGCG
GGTAGAATCAATGGCAAATATGGACAACTGGGGTGGACACCTCTTTATTACTTGAATCAACATTTCGA
TAGAAAATTGTTGATGAAATCTTTCGTTATTCTGACGTCGGACTGGTGACACCGCTGAGAGATGGCA
TGAACTTAGTTGCCAAGGAATATGTAGCTGCGCAAGACCCTGCTAATCCGGGAGTACTGGTGCTCTCA
CAATTTGCAGGGGCCGCGAATGAACTTACATCAGCTCTCATCGTTAATCCGTATGACAGGGATGAAGT
CGCAGCGGCGCTTGACCGGGCTCTTACAATGTCCTTAGCGGAGAGAATTAGCAGACATGCTGAAATGC

SEQUENCE LISTING

TGGATGTGATTGTGAAGAACGATATCAATCATTGGCAAGAATGTTTCATTTCTGACTTAAAGCAAATT
GTCCCGCGTTCAGCTGAGTCACAGCAACGGGATAAAGTCGCCACATTTCCCAAACTGGCATAA

SEQ ID NO: 35
MDIVFAADDNYAAYLCVAAKSVEAAHPDTEIRFHVLDAGISEANRAAVAANLRGGGNIRFIDVNPEDFAG
FPLNIRHISITTYARLKLGEYIADCDKVLYLDIDVLVRDSLKPLWDTDLGDNWLGACIDLFVERQNAYKQKI
GMADGEYYFNAGVLLINLKKWRQHDIFKMACEWVEQYKDVMQYQDQDILNGLFKGGVCYANSRFNFMP
TNDAFMANRFASRHTDPLYRDRTYTAMPVAVSHYCGPAKPWHRDCTAWGAERFTELAGSLTSVPEEWRG
KLAVPHRVFPTKRMLQRWRRKLSARFLRKIY

SEQ ID NO: 36
ATGGATATTGTATTTGCGGCAGATGATAATTATGCTGCGTATCTCTGTGTTGCCGCCAAATCCGTGGAA
GCCGCTCACCCCGATACAGAGATCCGGTTCCATGTACTTGACGCTGGCATTTCCGAAGCAAACCGGGC
AGCAGTTGCAGCCAATCTCCGCGGTGGCGGTAATATTCGTTTTATAGATGTGAACCCGGAAGACTTTG
CCGGCTTTCCATTGAATATTCGCCATATTAGTATAACAACTTACGCACGTCTGAAACTTGGGGAGTACA
TTGCGGATTGTGACAAGGTACTTTATCTCGATATAGATGTACTTGTGCGTGATAGTCTTAAACCGTTAT
GGGATACAGATCTTGGAGATAATTGGCTTGGTGCATGCATCGACTTATTTGTAGAGAGACAAAACGCT
TATAAGCAAAAAATTGGCATGGCTGACGGTGAATATTACTTTAACGCAGGGGTGCTCCTGATTAACCT
TAAGAAGTGGCGGCAACACGATATCTTCAAAATGGCTTGCGAATGGGTTGAGCAGTATAAGGATGTA
ATGCAGTACCAGGACCAAGACATCCTGAATGGATTATTTAAAGGTGGAGTGTGTTACGCTAATAGCAG
ATTCAATTTCATGCCGACCAATGATGCTTTCATGGCAAACCGGTTTGCTTCACGCCATACGGACCCATT
GTATAGAGATAGAACGTATACAGCAATGCCTGTGGCCGTTTCGCATTATTGTGGTCCGGCGAAACCGT
GGCATCGCGATTGCACAGCATGGGGCGCAGAAAGATTTACAGAACTTGCAGGAAGTCTGACATCAGTT
CCGGAGGAATGGCGCGGAAAACTTGCGGTGCCTCATCGGGTGTTCCCGACTAAACGTATGCTGCAAAG
ATGGAGACGCAAACTCTCCGCTCGATTTCTGAGAAAAATCTATTGA

SEQ ID NO: 37
MIIVHLCGGLGNQMFQYAAGLAAAHRIGSEVKFDTHWFDATCLHQGLELRRVFGLELPEPSSKDLRKVLG
ACVHPAVRRLLAGHFLHGLRPKSLVIQPHFHYWTGFEHLPDNVYLEGYWQSERYFSNIADIIRQQFRFVEPL
DPHNAALMDEMQSGVSVSLHIRRGDYFNNPQMRRVHGVDLSEYYPAAVATMIEKTNAERFYVFSDDPQW
VLEHLKLPVSYTVVDHNRGAASYRDMQLMSACRHHIIANSTFSWWGAWLNPRPDKVVIAPRHWFNVDVF
DTRDLYCPGWIVL

SEQ ID NO: 38
ATGATTATTGTGCACCTTTGCGGTGGTTTAGGAAACCAGATGTTCCAATATGCGGCAGGCCTTGCCGCG
GCGCACAGAATTGGCAGCGAAGTTAAATTCGATACGCATTGGTTCGATGCGACATGTCTGCATCAGGG
TTTAGAGTTGCGCAGAGTTTTTGGTTTGGAGCTTCCGGAACCCAGTTCCAAGGACCTGAGAAAAGTTTT
AGGCGCTTGCGTTCATCCTGCAGTGAGACGGCTTTTGGCTGGTCACTTTCTGCATGGCTTACGGCCGAA
GTCGCTCGTTATCCAACCCCATTTTCACTACTGGACGGGCTTTGAACATTTACCGGACAACGTATACTT
AGAGGGCTACTGGCAGTCTGAAAGATACTTTTCAAATATTGCTGATATTATAAGCAACAGTTTCGTTT
TGTCGAACCGTTAGATCCGCATAATGCGGCCCTCATGGATGAAATGCAGTCCGGGGTTAGTGTTTCAC
TTCATATTCGCCGTGGAGACTACTTCAACAACCCGCAAATGCGTCGTGTCCACGGCGTAGACTTGAGC
GAGTACTACCCGGCGGCAGTCGCGACGATGATCGAAAAAACCAACGCAGAACGGTTTTACGTGTTTTC
AGATGACCCACAGTGGGTATTGGAACATCTGAAACTGCCTGTTTCTTACACCGTGGTGGACCATAACC
GAGGCGCTGCCTCGTATAGGGATATGCAACTTATGTCTGCTTGCCGACACCATATCATTGCGAATTCAA
CATTCAGCTGGTGGGGAGCTTGGCTTAACCCTCGGCCGGACAAGGTCGTGATCGCTCCACGCCATTGG
TTTAACGTAGATGTATTCGACACACGCGATTTATATTGCCCAGGGTGGATAGTACTGTAA

SEQ ID NO: 39
MNVLSSICYGGDYNPEQWPEEIWYEDAKLMQKAGVNLVSLGIFSWSKIEPSDGVFDFEWLDKVIDILYDHG
VYINLGTATATTPAWFVKKYPDSLPIDESGVILSFGSRQHYCPNHPQLITHIKRLVRAIAERYKNHPALKMW
HVNNEYACHVSKCFCENCAVAFRKWLKERYKTIDELNERWGTNFWGQRYNHWDEINPPRKAPTFINPSQE
LDYYRFMNDSILKLFLTEKEILREVTPDIPVSTNFMGSFKPLNYFQWAQHVDIVTWDSYPDPREGLPIQHAM
MNDLMRSLRKGQPFILMEQVTSHVNWRDINVPKPPGVMRLWSYATIARGADGIMFFQWRQSRAGAEKFH
GAMVPHFLNENNRIYREVTQLGQELKKLDCLVGSRIKAEVAIIFDWENWWAVELSSKPHNKLRYIPIVEAY
YRELYKRNIAVDFVRPSDDLTKYKVVIAPMLYMVKEGEDENLRQFVANGGTLIVSFFSGIVDENDRVHLG
GYPGPLRDILGIFVEEFVPYPETKVNKIYSNDGEYDCTTWADIIRLEGAEPLATFKGDWYAGLPAVTRNCYG
KGEGIYVGTYPDSNYLGRLLEQVFAKHHINPILEVAENVEVQQRETDEWKYLIIINHNDYEVTLSLPEDKIY
QNMIDGKCFRGGELRIQGVDVAVLREHDEAGKV

SEQ ID NO: 40
ATGAACGTTTTGTCGTCTATTTGCTACGGTGGGGATTATAACCCGGAGCAATGGCCGGAGGAGATCTG
GTATGAAGATGCTAAATTAATGCAAAAAGCGGGGGTCAATTTAGTGAGCTTAGGCATTTTTTCTTGGT
CTAAAATCGAACCGTCTGATGGGGTTTTTGACTTTGAATGGTTAGATAAAGTCATTGATATCCTTTACG
ATCACGGCGTGTATATTAATCTGGGAACAGCGACGGCTACTACTCCGGCGTGGTTTGTAAAAAAGTAT
CCTGATTCACTCCCGATCGATGAATCCGGCGTCATCTTATCTTTTGGTTCTCGGCAACATTATTGCCCG
AACCACCCTCAATTGATCACACATATTAAACGTCTTGTTCGGGCTATCGCCGAACGCTATAAAAACCA
TCCAGCGCTTAAGATGTGGCACGTCAATAACGAGTATGCATGTCATGTGTCAAAATGCTTTTGCGAGA
ATTGTGCTGTGGCGTTTCGAAATGGTTAAAAGAACGTTATAAAACAATCGACGAACTTAACGAAAGA
TGGGGGACTAATTTCTGGGGCCAGAGATATAATCACTGGGACGAAATTAACCCGCCGCGAAAGCAC
CGACATTCATCAATCCTAGCCAAGAACTTGACTATTATCGATTTATGAAGGTGACACCTGACATCCCTGTCTCAACAAATTTCATGGGA
AGCTTCAAGCCGTTGAACTATTTTCAATGGGCACAACACGTGGATATTGTTACGTGGGATTCTTATCCG
GACCCTCGCGAAGGTCTTCCGATCCAACATGCCATGATGAATGATTTAATGCGTTCACTCAGGAAGGG
CCAACCGTTTATTCTGATGGAGCAGGTAACAAGCCATGTGAATTGGAGAGATATCAACGTCCCTAAAC
CGCCAGCGTAATGAGGCTGTGGTCCTATGCAACTATTGCGCGGGGAGCAGATGGCATTATGTTTTTT
CAGTGGCGTCAATCACGAGCTGGGGCTGAAAAATTTCACGGAGCGATGGTGCCGCATTTTTTAAATGA

-continued

---

SEQUENCE LISTING

---

```
AAACAATAGAATTTATCGCGAAGTTACACAGCTTGGACAGGAACTGAAGAAACTTGATTGTTTGGTCG
GGTCACGTATAAAAGCCGAAGTCGCGATAATATTTGATTGGGAAAACTGGTGGGCCGTAGAGTTATCC
TCGAAACCACACAACAAACTCCGATACATTCCCATTGTTGAAGCATACTATCGCGAACTGTATAAAAG
AAATATTGCAGTGGATTTTGTGCGGCCATCTGATGACTTGACGAAGTATAAGGTTGTGATCGCACCAA
TGTTATATATGGTAAAAGAAGGCGAAGATGAAAACTTACGACAATTCGTGGCTAATGGAGGCACATTG
ATCGTCTCATTCTTTAGCGGAATTGTGGACGAAAACGATCGCGTTCATTTAGGCGGTTATCCTGGCCCT
CTCCGCGATATCCTTGGCATATTTGTTGAGGAGTTTGTACCTTACCCAGAAACTAAGGTGAATAAAATT
TATTCCAACGATGGGGAATATGACTGTACAACATGGGCGGACATTATTCGTTTAGAAGGTGCGGAGCC
GTTAGCTACCTTTAAAGGCGATTGGTATGCGGGCCTGCCAGCGGTCACGAGGAATTGCTATGGTAAAG
GCGAAGGTATTTATGTGGGCACTTACCCTGATAGCAATTATTTAGGCAGACTGTTGGAACAAGTGTTT
GCCAAACATCACATTAATCCTATCCTCGAAGTGGCGGAGAATGTCGAAGTCCAACAGAGGGAAACAG
ATGAATGGAAATATCTGATTATTATTAACCACAACGATTATGAAGTAACCCTGTCCTTACCGGAAGAT
AAGATCTACCAAATATGATAGACGGAAATGTTTTAGGGCGGAGAGCTGCGTATCCAAGGGGTGG
ACGTTGCAGTCTTACGGGAACACGACGAAGCAGGAAAAGTTTAA
```

SEQ ID NO: 41
```
MKKAISCVFLISALILSSFQVPVQGQAMSKTTSAAGNSVSYDGERRVNFNENWRFQRETNGSIAGAQNPGF
DDSSWRKLNLPHDWSIELDFNKNSLATHEGGYLDGGIGWYRKTFTIPESMKGKRISLDFDGVYMNSTTYL
NGEVLGTYPFGYNAFSYDISDKLYKDGRANVLVVKVNNTQPSSRWYSGSGIYRNVYLTVTDPIHVARYGT
FVTTPNLEKSIKEDRADVNIKTKISNDAAEAKQVKIKSTIYDGAGNTVQTVETEEKTAAAGTVTPFEQNTVI
KQPKLWSIDKPYRYNLVTEVIVGGQTVDTYETKFGVRYFKFDENEGFSLNGEYMKLHGVSMHHDLGALG
AATNARGVERQMQIMKDMGVNAIRVTHNPASPELLEAANKLGLFIIEEAFDSWAQSKKPYDYGRFFNAW
AEHDIKEMVDRGKNEPAIIMWSIGNEIYDTTNAAGVETARNLVGWVKEIDTTRPTTIGEDKTRGDKVNVTP
INSYIKEIFNIVDVVGLNYSENNYDGYHKQNPSWKLYGSETSSATRSRGVYTHPYQYNQSTKYADLQQSSY
DNDYVGWGRTAEDAWKYDRDLKHIAGQFIWTGFDYIGEPTPYYNSYPAKSSYFGAVDTAGFPKDIFYYYQ
SQWKKEPMVHLLPHWNWKEGEKVRVLAYTNASKVELVLNGESLGEKNYDNKQTSWGAPYKETKDGKT
YLEWAVPFKPGKLEAVAKDENGKVIARDQVVTAGEPASVRLTADRKVVKADGTDLSFITADIVDSKGIVV
PDADHLITFNVTGQGELAGVDNGNASSVERYKDNKRKAFSGKALAIVQSSKLSGKITVHASVAGLSSDSTS
VFTVTPADHDKKIVAGIDDVNLTVDVNEAPKLPSEIKVYYSDESAAAKNVTWDEVDPKQYSTVGEFTVEG
SVEGTSLKAKAFVIVKGIVAVKPYSTATKVGVQPVLPEKATLLYSDGTTKGATVTWDEIPEDKLAKEGRFT
VEGSVEGTDLKANVYVRVTNEVKSVNIMLQEQGSAYPKLEATFTNPADNLQHLNDGIKSYTNNPVNRWT
NWTRTPRDAGDSITVNFGKKHVINNLDLFVFTDSGTVVPEKAEVQYWDGTAWKDVENLTQPSPYVVEKN
ELTFDAVATEKLKFHLTPSVKGKFLALTEAEVYADQIVMGETAKLQSITVNGKALEGFDHAKKNYELVLP
YGGSELPKIEAAAADNATVTILPAFSYPGTAKLFVTSEDGKVTTEYSIGVSTEEPKLVSAELSADKTNVMEDD
IIDLKVIGLFESKEKIDVTDSQPTYEFDQQIIKIEGNKLYALETGNVKVKVTVTYKGVSVTTPALEFTIAKNPA
PKYITSLEPVTVVVKKGEAPELPATVVAHYNRGIPRDVKVKWERINPSKYQQLGEFTVSGMVEGTDIKAQA
KVIVKGAVAVEDIRMAVLLKQMPQLPGKVTVYYSDGAEEQRAVKWEEIPQEELENVGEFKVKGDVNGVK
LKATATIRVTDEVGGEQNISRAKNGYEYPKAEASFTNNGPGSSDRIEAINDDVISYEANPHNRWTNWQPVP
RAGDWVSITFGDYEPTEYDVDSMEIHWFADHGTSYPERFQIEYKSGDSWKEVTSLKSDPASPALGKANVY
SFDRVKTSAIRVKMTAQAGKSLAITELKVFSKWPKAGTEPEVTDIKVGGKSILEDFEQKGDHYEVTIDAGD
ANVMPKINVKAKDQTSITIVPAVTSPSTAKVIAKSEDGKKVKVYSIHYK
```

SEQ ID NO: 42
```
ATGAAGAAAGCGATCAGCTGCGTTTTTCTGATATCTGCACTCATCTTAAGCAGCTTTCAAGTACCGGTG
CAGGGGCAAGCGATGTCTAAAACTACGTCAGCGGCCGGAAACAGCGTTTCATACGATGGTGAACGGA
GAGTTAATTTCAATGAAAATTGGCGGTTCCAGCGGGAAACCAATGGTAGCATTGCAGGTGCACAAAAT
CCAGGGTTTGATGACTCTTCCTGGAGAAAGCTTAATTTACCGCATGACTGGAGCATAGAACTTGATTTC
AATAAAAACTCATTGGCGACGCACGAAGGGGGGTATTTGGACGGCGGCATCGGGTGGTACCGAAAAA
CGTTCACCATACCTGAATCAATGAAAGGCAAAAGAATCTCTCTGGATTTCGATGGTGTATATATGAAC
TCAACAACATATTTAAACGGGGAGGTATTAGGTACATATCCGTTTGGCTATAACGCCTTTTCTTACGAC
ATTTCCGATAAACTGTATAAAGATGGAAGAGCGAACGTGCTTGTAGTGAAGGTCAATAATACGCAACC
ATCTAGTCGATGGTATTCAGGAAGCGGCATATATCGTAATGTGTATTTAACTGTAACGGATCCCATTCA
TGTTGCGCGGTATGGCACATTTGTCACAACACCTAACTTGGAGAAATCAATTAAAGAAGATCGGGCAG
ACGTCAACATTAAAACGAAAATTTCTAACGATGCGGCGGAAGCAAAACAAGTCAAAATCAAATCAAC
AATATATGACGGAGCTGGTAACACAGTACAGACGGTTGAAACGGAGGAAAAAACAGCAGCAGCAGGT
ACCGTAACCCCGTTTGAGCAAAACACGGTAATAAAACAGCCTAAACTGTGGTCCATCGACAAACCGTA
CCGTTATAACCTGGTAACGGAGGTTATTGTTGGCGGCCAAACGGTGGATACTTATGAAACTAAATTCG
GAGTCAGGTATTTTAAGTTTGACGAGAATGAGGGGTTTTCTCTGAACGGAGAGTACATGAAGCTTCAT
GGCGTCTCCATGCATCACGATTTAGGAGCTTTAGGCGCGGCGACAAACGCTAGAGGGGTTGAAAGGC
AGATGCAGATTATGAAAGACATGGGAGTCAATGCCATCAGAGTAACACATAACCCGGCAAGCCCTGA
ACTTCTGGAAGCCGCGAACAAGCTCGGCCTGTTTATTATTGAGGAAGCTTTTGATTCGTGGGCTCAGA
GTAAGAAACCCTATGACTATGGAAGATTTTTCAATGCGTGGGCGGAGCACGATATAAAAGAAATGGTT
GACAGAGGGAAAAACGAACCCGCAATCATCATGTGGAGTATTGGGAATGAAATCTATGATACGACTA
ATGCAGCGGGCGTGGAAACCGCGAGGAATCTTGTGGGCTGGGTCAAAGAAATTGACACTACACGGCC
CACAACAATCGGCGAAGACAAGACTAGGGGCGACAAAGTAAACGTGACGCCAATTAACAGTTATATC
AAAGAAATTTTCAACATTGTTGACGTAGTTGGGCTGAACTACTCGGAAAACAATTATGGTGACATATCA
CAAACAGAATCCCTCTTGGAAACTGTATGGATCCGAAACAAGCAGTGCGACAAGATCAAGGGGTGTTT
ATACACACCCATATCAGTATAACCAATCTACAAAATACGCCGATCTGCAACAATCCTCTTATGACAAC
GACTATGTTGGCTGGGGTAGAACAGCGGAAGACGCGTGGAAGTACGACAGAGATTTGAAACATATCG
CGGGACAGTTTATTTGGACGGGATTCGATTACATTGGTGAACCAACCCCGTACTATAATAGCTATCCTG
CGAAAAGCAGCTACTTCGGAGCAGTGGATACAGCTGGATTCCCTAAAGATATCTTTTACTATTATCAG
TCGCAATGGAAAAAGGAGCCGATGGTACATCTTCTTCCGCATTGGAACTGGAAGGAAGGAGAGAAGG
TCAGAGTACTGGCCTACACCAATGCTAGCAAAGTCGAACTTGTACTGAATGGCGAATCCCTCGGAGAG
AAAAATTATGATAATAAACAAACGTCCTGGGGAGCTCCTTATAAGGAAACAAAAGACGGAAAGACAT
ATCTGGAATGGGCGGTCCCTTTCAAGCCTGGCAAACTGGAAGCCGTGGCAAAAGATGAAAACGGCAA
GGTAATTGCAAGAGATCAAGTAGTGACGGCGGGAGAGCCCGCTAGCGTTAGATTGACAGCTGATAGG
AAAGTTGTGAAAGCAGATGGAACAGATTTAAGCTTTATTACCGCAGATATCGTAGATTCTAAGGGCAT
```

```
                            SEQUENCE LISTING
TGTTGTCCCGGATGCTGATCATTTGATTACATTCAATGTGACTGGACAAGGAGAACTGGCTGGAGTAG
ATAATGGTAATGCATCATCCGTTGAACGGTACAAAGATAATAAAAGAAAGGCCTTTTCAGGTAAGGCC
TTGGCAATCGTACAGTCATCAAAACTTAGCGGTAAAATCACCGTACACGCCTCGGTTGCAGGTCTTTC
ATCCGATAGTACAAGTGTCTTCACAGTCACACCGGCGGATCACGATAAAAAAATTGTAGCAGGTATTG
ACGATGTGAACCTTACGGTTGACGTCAACGAAGCGCCAAAACTTCCGTCTGAAATTAAAGTCTATTAT
TCAGACGAATCTGCGGCCGCGAAAAATGTTACATGGGATGAAGTGGACCCTAAACAGTATTCTACAGT
TGGCGAGTTTACAGTCGAAGGCTCGGTTGAGGGCACAAGCTTAAAGGCGAAAGCGTTTGTCATAGTTA
AAGGTATCGTCGCCGTTAAACCCTATTCTACGGCGACCAAAGTTGGAGTTCAACCTGTTTTACCTGAGA
AAGCAACATTACTTTATAGCGATGGCACTACTAAAGGGGCCACAGTGACATGGGATGAAATCCCAGA
AGATAAATTGGCGAAAGAGGGCCGGTTTACGGTAGAAGGTTCAGTAGAGGGCACAGACTTGAAAGCG
AATGTTTATGTGCGAGTTACGAATGAGGTAAAGTCTGTTAACATTATGCTTCAGGAGCAGGGCAGCGC
ATATCCAAAGCTTGAGGCGACCTTTACAAATCCGGCGGACAATCTGCAGCACCTGAATGATGGTATCA
AATCTTATACAAACAATCCGGTGAATAGATGGACGAATTGGACAAGAACACCAAGGGACGCGGGAGA
CAGTATCACGGTGAACTTTGGGAAAAAACACGTAATCAACAATCTTGACCTTTTTGTATTTACAGATA
GTGGTACGGTTGTCCCTGAGAAAGCTGAAGTTCAATATTGGGATGGAATCTGCTGGAAAGACGTAGAG
AATTTAACACAGCCTTCACCGTACGTTGTGGGAAAAAAACGAGTTGACTTTCGATGCAGTCGCGACAGA
AAAATTAAAATTTCATCTGACACCGTCTGTCAAAGGTAAATTTCTGGCCCTGACAGAAGCAGAAGTAT
ACGCAGACCAGATTGTAATGGGAGAAACAGCTAAACTCCAGTCCATAACGGTCAATGGTAAGGCACT
CGAAGGGTTTGATCATGCGAAAAAGAATTATGAGCTCGTACTGCCGTACGGGTCCGAATTGCCTAAGA
TTGAAGCAGCTGCGGCTGACAATGCTACCGTGACGATTTTACCTGCCTTTTCTTATCCAGGAACGGCGA
AGTTGTTCGTAACAAGTGAGGACGGAAAAGTTACAACCGAATATAGCATTGGCGTTTCGACTGAAGAG
CCAAAGCTGGTCTCAGCTGAGTTGAGCGCAGATAAGACCAATGTCATGGAAGATGATATAATTGACCT
GAAAGTGATAGGCCTCTTTGAGAGCAAGGAAAAGATTGACGTCACAGACAGCCAACCAACCTACGAG
TTCGACCAGCAAATTATAAAGATCGAAGGAAATAAATTGTATGCGCTGGAAACCGGTAATGTCAAAGT
AAAGGTCACCGTTACTTATAAAGGAGTCTCTGTTACGACACCAGCCCTTGAATTCACGATCGCGAAGA
ATCCTGCTCCGAAATATATTACATCGCTCGAGCCAGTCACAGTAGTTGTGAAAAAAGGCGAAGCTCCC
GAACTCCCTGCGACTGTTGTCGCTCATTATAACCGCGGTATCCCGCGGGATGTTAAAGTTAAATGGGA
ACGGATAAATCCATCAAAGTACCAACAATTAGGCGAATTTACCGTTTCGGGAATGGTGGAAGGAACTG
ATATTAAAGCCCAAGCTAAAGTGATAGTGAAAGGAGCAGTTGCAGTAGAGGATATTAGAATGGCAGT
CCTTTTGAAGCAAATGCCTCAGTTACCTGGAAAGGTTACGGTATACTATAGTGATGGTGCGGAAGAAC
AACGAGCTGTTAAATGGGAGGAGATACCGCAAGAAGAACTTGAAAACGTGGGAGAATTTAAGGTGAA
AGGAGATGTTAATGGTGTTAAGCTGAAAGCAACCGCGACCATCCGGGTAACGGATGAAGTGGGGGGA
GAACAGAATATTTCGCGGGCAAAAAATGGCTATGAGTACCCGAAGGCTGAGGCTAGTTTTACAAATA
ATGGGCCGGGGTCTAGCGACCGTATTGAGGCTATCAATGACGACGTTATCTCATACGAAGCAAATCCG
CACAACAGGTGGACCAACTGGCAGCCGGTGCCTAGAGCTGGCGACTGGGTCTCCATTACCTTTGGTGA
TTATGAACCAACAGAATACGACGTTGACTCGATGGAAATCATTGGTTTGCGGACCACGGAACCTCTT
ACCCAGAGAGGTTTCAGATCGAATATAAAAGCGGAGACTCGTGGAAAGAAGTCACGAGCCTGAAGAG
TGACCCGGCCTCTCCAGCCCTGGGAAAAGCTAATGTTTATTCATTCGACCGTGTGAAGACCTCTGCTAT
TAGGGTAAAAATGACAGCTCAGGCGGGTAAAAGTCTTGCTATTACGGAATTAAAAGTCTTTTCAAAAT
GGCTAAAGCAGGCACCGAACCTGAGGTCACCGATATCAAGGTTGGCGGCAAATCTATCCTCGAAGAT
TTTGAACAAAAAGGCGACCATTATGAAGTGACAATTGATGCGGGTGATGCGAATGTAATGCCGAAAA
TCAATGTGAAAGCGAAGGATCAAACGTCTATCACAATCGTCCCGGCGGTTACTAGTCCGTCAACGGCA
AAAGTGATCGCTAAATCGGAAGATGGCAAAAAAGTGAAAGTATATTCAATACATTATAAATAA

SEQ ID NO: 43
MPEVRSSTQSESGMSQWMGKILSIRGAGLTIGVFGLCALIAATSVTLPPEQQLIVAFVCVVIFFIVGHKPSRR
SQIFLEVLSGLVSLRYLTWRLTETLSFDTWLQGLLGTMLLVAELYALMMLFLSYFQTIAPLHRAPLPLPPNP
DEWPTVDIFVPTYNEELSIVRLTVLGSLGIDWPPEKVRVHILDDGRRPEFAAFAAECGANYIARPTNEHAKA
GNLNYAIGHTDGDYILIFDCDHVPTRAFLQLTMGWMVEDPKIALMQTPHHFYSPDPFQRNLSAGYRTPPEG
NLFYGVVQDGNDFWDATFFCGSCAILRRTAIEQIGGFATQTVTEDAHTALKMQRLGWSTAYLRIPLAGGL
ATERLILHIGQRVRWARGMLQIFRIDNPLFGRGLSWGQRLCYLSAMTSFLFAVPRVIFLSSPLAFLFFGQNIIA
ASPLALLAYAIPHMFHAVGTASKINKGWRYSFWSEVYETTMALFLVRVTIVTLLSPSRGKFNVTDKGGLLE
KGYFDLGAVYPNIILGLIMFGGLARGVYELSFGHLDQIAERAYLLNSAWAMLSLIIILAAIAVGRETQQKRN
SHRIPATIPVEVANADGSIIVTGVTEDLSMGGAAVKMSWPAKLSGPTPVYIRTVLDGEELILPARIIRAGNGR
GIFIWTIDNLQQEFSVIRLVFGRADAWVDWGNYKADRPLLSLMDMVLSVKGLFRSSGDIVHRSSPTKPLAG
NALSDDTNNPSRKERVLKGTVKMVSLLALLTFASSAQAASAPRAVAAKAPAHQPEASDLPPLPALLPATSG
AAQAGAGDAGANGPGSPTGQPLAADSADALVENAENTSDTATVHNYTLKDLGAAGSITMRGLAPLQGIEF
GIPSDQLVTSARLVLSGSMSPNLRPETNSVTMTLNEQYIGTLRPDPAHPTFGPMSFEINPIFFVSGNRLNFNFA
SGSKGCSDITNDTLWATISQNSQLQITTIALPPRRLLSRLPQPFYDKNVRQHVTVPMVLAQTYDPQILKSAGI
LASWFGKQTDFLGVTFPVSSTIPQSGNAILIGVADELPTSLGRPQVNGPAVLELPNPSDANATILVVTGRDRD
EVITASKGIAFASAPLPTDSHMDVAPVDIAPRKPNDAPSFIAMDHPVRFGDLVTASKLQGTGFTSGVLSVPF
RIPPDLYTWRNRPYKMQVRFRSPAGEAKDVEKSRLDVGINEVYLHSYPLRETHGLVGAVLQGVGLARPAS
GMQVHDLDVPPWTVFGQDQLNFYFDAMPLARGICQSGAANNAFHLGLDPDSTIDFSRAHHIAQMPNLAY
MATVGFPFTTYADLSQTAVVLPEHPNAATVGAYLDLMGFMGAATWYPVAGVDIVSADHVSDVADRNLL
VISTLATSGEIAPLLSRSSYEVADGHLRTVSHASALDNAIKAVDDPLTAFRDRDSKPQDVDTPLTGGVGAMI
EAESPLTAGRTVLALLSSDGAGLNNLLQMLGERKKQANIQGDLVVAHGEDLSSYRTSPVYTIGTLPLWLW
PDWYMHNRPVRVLLVGLLGCILIVSVLARALARHATRRFKQLEDERRKS

SEQ ID NO: 44
ATGCCAGAGGTCCGATCTTCGACGCAGTCAGAGAGCGGGATGTCCCAGTGGATGGGAAAAATCTTATC
AATAAGAGGGGCAGGACTGACGATAGGAGTATTTGGCCTCTGTGCTCTTATAGCCGCGACAAGCGTTA
CACTTCCACCTGAACAACAACTTATTGTGGCGTTCGTCTGTGTTGTAATCTTTTTTTATCGTCGGACACA
AGCCATCACGGAGATCGCAAATCTTTCTGGAAGTACTTTCCGGACTTGTCTCTCTTCGCTACCTTACCT
GGCGGTTAACGGAGACCCTGTCCTTTGATACCTGGTTACAGGGTCTTCTGGGCACGATGTTACTGGTCG
CGGAATTATATGCCCTGATGATGTTATTCTTGTCATACTTCCAGACAATAGCACCGCTGCATAGAGCGC
CCCTCCCACTCCCCCCGAATCCTGATGAATGGCCTACAGTAGATATATTCGTCCCGACTACAATGAG
GAACTTTCAATCGTAAGACTGACAGTTTTGGGGAGTTTGGGAATAGATTGGCCGCCGGAAAAAGTTAG
```

SEQUENCE LISTING

```
AGTACATATCCTTGACGATGGGAGGCGTCCAGAATTTGCCGCCTTTGCAGCCGAGTGCGGAGCAAACT
ATATTGCTAGACCTACAAATGAGCATGCGAAAGCTGGAAATTTAAATTATGCGATTGGCCATACAGAC
GGGGACTATATATTAATTTTTGATTGTGACCACGTACCAACACGCGCTTTCCTGCAGCTTACCATGGGA
TGGATGGTTGAAGATCCAAAAATCGCGCTTATGCAAACTCCGCATCACTTTTACAGCCCTGACCCATTC
CAACGCAATTTGTCTGCGGGGTATAGAACTCCGCCTGAAGGCAACTTATTTTACGGCGTAGTGCAGGA
TGGAAATGATTTCTGGGATGCTACTTTCTTCTGCGGTAGCTGCGCTATTCTTAGACGGACAGCCATAGA
ACAAATTGGGGGATTCGCGACGCAGACCGTAACGGAGGACGCTCATACAGCCCTTAAAATGCAAAGA
CTTGGTTGGTCAACAGCGTATTTGAGAATACCATTGGCAGGTGGTCTTGCGACGGAAAGATTAATCCT
GCATATCGGACAACGCGTTCGTTGGGCACGGGGCATGCTGCAAATCTTTCGCATAGATAACCCGCTCT
TTGGACGCGGCTTATCATGGGGGCAGAGGTTGTGTTATTTAAGTGCCATGACCTCCTTTCTTTTTGCCG
TGCCGCGTGTTATTTTTTTAAGTTCACCTCTGGCCTTTCTGTTTTTTGGACAAAACATAATTGCTGCAAG
CCCCTTGGCTTTACTGGCTTATGCGATCCCCCATATGTTTCACGCCGTTGGAACTGCATCTAAGATCAA
TAAAGGTTGGCGTTATTCGTTCTGGAGTGAAGTGTACGAGACTACAATGGCGCTGTTCCTGGTGCGTGT
GACCATTGTCACACTGCTCTCTCCTAGCAGAGGCAAGTTTAATGTGACAGACAAAGGGGGTCTGCTCG
AAAAAGGTTACTTTGATCTTGGAGCGGTATATCCTAATATCATTCTTGGCTTGATCATGTTTGGAGGGT
TGGCGCGTGGAGTATACGAATTGTCGTTTGGACATCTTGATCAAATCGCCGAACGTGCTTATTTGCTGA
ATTCAGCGTGGGCAATGTTATCACTTATAATCATCTTAGCTGCGATTGCGGTAGGCAGGGAGACACAA
CAGAAAAGAAATTCTCACAGGATTCCGGCCACAATTCCGGTCGAGGTCGCCAATGCTGACGGAAGCAT
AATTGTCACAGGAGTCACAGAAGATTTGTCTATGGGTGGAGCGGCAGTTAAAATGAGCTGGCCGGCG
AAGCTGTCCGGCCCTACGCCGGTTTATATTAGAACAGTACTGGATGGGGAGGAATTAATCCTTCCCGC
GAGGATCATTAGGGCTGGGAACGGCCGAGGCATTTTTATCTGGACGATTGACAATTTGCAGCAAGAAT
TTTCTGTCATCCGTCTGGTATTCGGGCGTGCCGATGCGTGGGTTGACTGGGGAAACTACAAAGCAGAT
CGTCCGCTGCTGTCCTTAATGGATATGGTGCTCTCGGTTAAAGGACTTTTTCGTTCCAGCGGCGATATT
GTTCATCGATCTTCTCCTACAAAACCGTTAGCGGGGAATGCCTTGAGTGACGATACAAATAACCCTAG
CAGAAAAGAACGTGTTTTGAAAGGAACGGTGAAGATGGTATCACTGCTTGCACTGTTGACATTCGCAA
GCTCGGCACAGGCCGCTTCCGCTCCTAGAGCGGTGGCAGCTAAGGCTCCGGCTCATCAACCGGAAGCT
TCCGATCTGCCCCCGCTGCCTGCCTTACTTCCGGCGACAAGCGGAGCAGCACAAGCAGGCGCCGGAGA
CGCGGGAGCAAATGGACCGGGGTCTCCAACCGGACAACCCCTTGCGGCAGATTCCGCAGATGCGCTTG
TTGAGAATGCCGAGAACACGTCCGATACGGCCACAGTTCACAATTACACACTTAAGGACCTGGGAGCT
GCTGGCTCCATTACTATGAGGGGACTGGCACCCCTGCAGGGAATTGAGTTCGGCATCCCAAGCGATCA
ACTGGTAACCTCGGCTCGCCTGGTACTTTCAGGAAGCATGTCACCTAACCTCCGACCGGAAACGAATT
CTGTTACAATGACCCTCAACGAGCAATATATTGGTACATTGAGACCTGACCCAGCACACCCGACGTTT
GGGCCAATGAGTTTCGAAATCAATCCGATTTTTTTTGTGTCTGGAAACAGATTAAATTTCAATTTCGCT
TCGGGGTCAAAAGGCTGCTCTGACATTACTAATGACACGCTCTGGGCAACAATCTCGCAAAATAGTCA
ACTCCAGATAACAACAATTGCCCTTCCCCCGAGAAGATTGTTAAGCAGGCTGCCCCAACCTTTCTATG
ATAAAAATGTACGGCAACATGTCACGGTCCCTATGGTACTTGCCCAGACCTATGATCCCCAGATTCTTA
AGAGCGCAGGCATTCTCGCTTCTTGGTTTGGCAAGCAGACAGACTTTCTTGGTGTAACGTTTCCGGTTT
CTTCAACGATCCCGCAGTCCGGAAACGCGATCCTTATCGGGGTGGCGGATGAATTACCGACAAGCTTG
GGCAGGCCTCAAGTTAACGGTCCGGCAGTACTGGAATTGCCGAATCCTTCCGATGCTAACGCCACAAT
CCTTGTTGTGACCGGGCGTGATCGAGATGAAGTAATTACAGCCAGCAAAGGGATCGCTTTTGCCTCGG
CACCGCTTCCTACGGATAGCCATATGGATGTCGCGCCAGTTGATATCGCCCCACGTAAGCCTAATGAT
GCGCCCAGTTTTATCGCAATGGATCATCCTGTACGGTTTGGAGACCTCGTTACAGCATCCAAATTACAA
GGCACAGGGTTTACGTCAGGCGTTTTGAGCGTTCCATTCCGGATCCCTCCTGACTTATACACCTGGCGG
AATCGTCCTTACAAAATGCAAGTTCGCTTTCGTTCACCAGCGGGCGAAGCGAAAGATGTGGAAAAATC
TCGGCTTGATGTCGGAATCAACGAAGTTTATTTGCATAGTTATCCCTTACGAGAGACACACGGCCTGGT
CGGTGCCGTTTTACAAGGGGTTGGCCTTGCTAGACCAGCATCTGGTATGCAAGTGCACGACCTGGATG
TCCCTCCATGGACCGTGTTTGGACAAGATCAATTAAATTTTTATTTTGATGCGATGCCGCTTGCTCGGG
GGATTTGTCAGTCCGGAGCAGCAAATAATGCGTTCCATCTGGGATTGGACCCAGACTCTACTATAGAC
TTTTCTCGGGCCCATCATATAGCGCAGATGCCTAACCTTGCGTACATGGCAACCGTTGGCTTCCCATTT
ACTACCTATGCCGATTTGAGCCAGACAGCTGTCGTCCTGCCGGAGCATCCCAATGCGGCAACAGTTGG
AGCTTATCTTGACCTGATGGGGTTTATGGGCGCGGCCACATGGTATCCGGTGGCGGGTGTGGATATTG
TCAGTGCGGATCACGTTAGCGATGTCGCGGACCGGAATCTCCTTGTTATTTCTACACTGGCTACATCTG
GTGAGATCGCACCGCTTCTTTCTCGTTCCAGCTATGAGGTAGCTGACATTTGCGTACCGTTAGCC
ATGCTAGCGCGTTAGATAACGCTATTAAGGCAGTGGATGATCCTTTAACCGCCTTTAGAGACCGGGAC
TCAAAACCACAAGACGTGGATACGCCACTTACTGGCGGGGTCGGTGCTATGATCGAAGCAGAATCACC
GCTCACCGCTGGACGTACGGTGTTAGCCCTTTTGTCATCCGATGGCGCTGGCCTGAATAATCTCTTGCA
GATGCTGGGCGAAAGGAAAAAGCAGGCCAATATACAAGGGGATCTTGTTGTAGCCCACGGAGAAGAT
TTGTCATCCTACCGTACATCTCCGGTCTATACCATCGGCACGCTGCCATTATGGCTGTGGCCGGACTGG
TACATGCACAATCGGCCAGTGAGGGTACTTCTTGTGGGGCTTCTGGGTTGCATTCTCATAGTTTCCGTG
CTTGCGCGCGCTTTAGCTAGACATGCGACTAGACGGTTTAAACAACTGGAGGACGAGAGACGCAAATC
GTAA
```

SEQ ID NO: 45
```
MATPSAVGAACLLLARAAWPAAVGDRARPRRLQRVLRRRCVAELSREGPAPRPLPPALLAPPLVPGFLAPP
AEPTGEPASTPPPVPDAGLGDLGLEPEGIAEGSIDNTVVVASEQDSEIVVGKEQARAKVTQSIVFVTGEASPY
AKSGGLGDVCGSLPVALAARGHRVMVVMPRYLNGTSDKNYANAFYTEKHIRIPCFGGEHEVTFFHEYRDS
VDWVFVDHPSYHRPGNLYGDKFGAFGDNQFRYTLLCYAACEAPLILELGGYIYGQNCMFVVNDWHASLV
PVLLAAKYRPYGVYKDSRSILVIHNLAHQGVEPASTYPDLGLPPEWYGALEWVFPEWARRHALDKGEAV
NPLKGAVVTADRIVTVSKGYSWEVTTAEGGQGLNELLSSRKSVLNGIVNGIDINDWNPATDKCIPCHYSVD
DLSGKAKCKGALQKELGLPIRPDVPLIGFIGRLDYQKGIDLIQLIIPDLMREDVQFVMLGSGDPELEDWMRS
TESIFKDKFRGWVGFSVPVSHRITAGCDILLMPSRFEPCGLNQLYAMQYGTVPVVHATGLRDTVENFNPF
GENGEQGTGWAFAPLTTENMLWTLRTAISTYREHKSSWEGLMKRGMSKDFTWDHAAEQYEQIFQWAFID
RPYVM
```

SEQ ID NO: 46
```
ATGGCGACCCCGTCCGCAGTGGGCGCAGCCTGCCTTTTATTAGCGCGCGCAGCTTGGCCGGCAGCCGT
TGGAGACAGGGCAAGACCGCGGCGATTACAACGCGTGTTGCGGCGGAGATGTGTAGCAGAACTTTCT
```

-continued

---

SEQUENCE LISTING

---

```
CGTGAAGGGCCAGCACCGAGGCCTTTACCTCCTGCCTTGCTTGCCCCCCCGTTAGTACCTGGTTTTCTG
GCACCCCCAGCGGAACCAACAGGCGAACCAGCGAGCACGCCTCCGCCGGTTCCGGACGCTGGACTTG
GCGACTTGGGATTAGAACCTGAAGGAATCGCGGAAGGTTCAATCGATAATACCGTCGTGGTGGCTTCT
GAACAGGATAGTGAGATCGTAGTTGGGAAAGAGCAGGCTCGCGCAAAAGTAACGCAATCAATTGTAT
TCGTAACCGGCGAGGCAAGCCCCTATGCGAAATCTGGAGGCCTGGGCGATGTTTGCGGAAGCCTTCCG
GTTGCGTTAGCTGCCAGAGGACATCGAGTCATGGTCGTCATGCCGCGGTATCTGAACGGAACGTCAGA
TAAAAATTATGCCAATGCCTTCTATACCGAGAAGCATATCCGGATCCCTTGCTTTGGTGGCGAACACG
AAGTGACTTTTTTTCATGAATATCGTGACTCAGTCGACTGGGTTTTTGTCGACCACCCGAGCTATCATA
GACCGGGTAACCTGTACGGGGATAAATTTGGAGCGTTTGGCGATAATCAATTCCGGTATACCTTGCTG
TGTTATGCCGCATGCGAAGCCCCTCTCATCTTGGAACTCGGAGGCTATATTTATGGACAAAACTGTATG
TTCGTAGTAAACGATTGGCACGCATCACTCGTACCAGTACTTCTCGCAGCGAAATATAGACCGTATGG
CGTTTACAAAGATTCCAGATCAATTTTAGTTATTCACAACTTAGCTCACCAAGGCGTAGAACCGGCGTC
CACATATCCAGATCTTGGATTGCCGCCAGAGTGGTATGGAGCGCTTGAATGGGTCTTTCCTGAATGGG
CTCGTCGACATGCGCTGGATAAAGGTGAAGCTGTCAATTTTCTCAAAGGTGCTGTGGTCACTGCCGAC
AGAATTGTAACAGTGAGCAAAGGCTATTCCTGGGAAGTTACCACCGCTGAGGGTGGCCAAGGGCTCA
ATGAATTGCTGAGCAGCCGTAAAAGTGTTTTGAATGGTATAGTGAATGGTATCGACATCAATGATTGG
AACCCGGCAACAGACAAATGTATCCCCTGTCATTACTCCGTCGACGACCTTTCGGGAAAAGCAAAGTG
TAAAGGCGCGCTTCAAAAAGAGTTGGGCTTGCCGATTAGACCGGATGTGCCTCTTATTGGATTCATTG
GCCGGTTGGATTATCAGAAGGGAATTGATCTGATCCAGCTGATTATTCCGGACTTGATGAGAGAAGAT
GTCCAGTTTGTGATGTTGGGCTCCGGCGATCCAGAACTTGAAGATTGGATGCGGAGCACCGAATCAAT
CTTTAAGGATAAATTTAGAGGATGGGTCGGGTTCTCTGTGCCTGTCTCACATCGCATTACGGCGGGCTG
CGATATCCTCCTTATGCCTTCTCGGTTCGAACCGTGTGGTTTAAATCAACTTTATGCGATGCAGTACGG
CACTGTGCCGGTTGTTCACGCGACTGGAGGGCTGCGAGATACTGTTGAGAATTTTAATCCGTTTGGAG
AGAACGGTGAACAAGGAACAGGATGGGCCTTCGCACCCACTGACTACGGAGACAATGCTGTGGACACT
TAGAACGGCCATCTCTACGTATAGGGAGCACAAGTCCTCGTGGGAGGGACTCATGAAACGGGGAATG
AGTAAAGATTTCACCTGGGATCACGCTGCAGAACAATATGAGCAAATCTTTCAGTGGGCGTTTATCGA
TCGCCCCTACGTTATGTGA
```

SEQ ID NO: 47
```
MVSLSNQTRFSFHPNNLVVSEKRRLGISGVNFPRKIKLKITCFAAERPRQEKQKKKSQSQSTSDAEAGVDPV
GFLTRLGIADRIFAQFLRERHKALKDLKDEIFKRHFDFRDFASGFELLGMHRHMEHRVDFMDWGPGSRYG
AIIGDFNGWSPTENAAREGLFGHDDYGYWFIILEDKLREGEEPDELYFQQYNYVDDYDKGDSGVSAEEIFQ
KANDEYWEPGEDRFIKNRFEVPAKLYEQMFGPNSPQTLEELGDIPDAETRYKQWKEEHKDDPPSNLPPCDII
DKGQGKPYDIFNVVTSPEWTKKFYEKEPPIPYWLETRKGRKAWLQKYIPAVPHGSKYRLYFNTPDGPLERV
PAWATYVQPEDEGKQAYAIHWEPSPEAAYKWKYSKPKVPESLRIYECHVGISGSEPKVSTFEEFTKKVLPH
VKRAGYNAIQLIGVPEHKDYFTVGYRVTNFFAASSRYGTPDDFKRLVDEAHGLGLLVFLDIVHSYAAADQ
MVGLSLFDGSNDCYFHYGKRGHHKHWGTRMFKYGDLDVLHFLISNLNWWITEYQVDGYQFHSLASMIYT
HNGFASFNNDLDDYCNQYVDRDALMYLILANEILHVQHPNIITIAEDATYYPGLCEPVSQGGLGFDYYVNL
SASEMWVSLLDNVPDNEWSMSKIVSTLVANKEYADKMLSYAENHNQSISGGRSFAEILFGGVDNGSPGGK
ELLDRGISLHKMIRLITFTSGGRAYLNFMGNEFGHPERVEFPTQSNNFSFSLANRRWDLLESGVHHHLFSFD
KELMDLDKSKGILSRGLPSIHHVNDANMVISFSRGPFLFIFNFHPSNSYEKYDVGVEEAGEYTMILNSDEVK
YGGQGIVTEDHYLQRSISKRIDGQRNCLEVFLPSRTAQVYKLTRILRI
```

SEQ ID NO: 48
```
ATGGTCTCTTTGTCGAATCAGACTAGATTTTCTTTCCATCCGAATAACCTGGTCGTGAGTGAGAAACGA
CGTTTAGGAATCTCGGGCGTTAACTTCCCTCGAAAGATTAAATTAAAAATTACATGCTTTGCAGCGGA
GAGACCGCGCCAAGAAAAGCAGAAGAAAAAGTCACAATCTCAAAGCACGTCCGATGCGGAAGCAGG
AGTAGACCCGGTGGGCTTTTTAACACGCTTGGGCATAGCGGATAGGATTTTTGCACAATTTCTTAGAG
AAAGACATAAGGCTCTTAAAGACCTTAAGGACGAAATATTTAAACGCATTTTGATTTTCGGGATTTT
GCATCAGGCTTCGAACTGTTAGGAATGCACAGGCATATGGAGCATCGGGTTGATTTTATGGATTGGGG
ACCGGGATCACGGTACGGCGCAATTATTGGTGATTTTAACGGATGGTCTCCAACGGAGAATGCTGCGC
GCGAAGGCCTCTTTGGCCATGATGACTATGGTTATTGGTTTATTATACTTGAAGATAAATTGAGAGAA
GGAGAGGAGCCGGACGAGTTGTATTTTCAACAATAAACTATGTTGATGACTATGATAAAGGTGACTC
AGGCGTGTCGGCTGAAGAAATTTTCCAAAAAGCAAATGATGAATATTGGGAGCCGGGTGAAGATAGG
TTTATCAAAAATAGATTTGAAGTGCCGGCTAAATTATATGAGCAAATGTTTGGACCGAATTCACCGCA
AACACTGGAGGAATTAGGTGATATCCCTGACGCGGAAACAAGATACAAGCAGTGGAAAGAAGAGCAT
AAAGATGATCCTCCATCTAACCTGCCGCCTTGCGATATTATTGATAAAGGTCAAGGCAAACCGTATGA
TATCTTTAATGTTGTTACGTCCCCAGAATGGACAAAAAAATTTTATGAGAAAGAACCCCCGATCCCAT
ATTGGCTGGAGACACGTAAAGGCAGAAAGGCGTGGCTCCAGAATATATCCCGGCCGTCCCCCACGG
CTCCAAGTACCGCTTATACTTCAATACCCCGGATGGACCATTAGAAAGGGTTCCGGCTTGGGCGACCT
ACGTACAGCCAGAAGATGAAGGCAAACAGGCCTATGCTATTCATTGGGAACCGAGCCCGGAGGCTGC
CTATAAATGGAAGTACTCAAAACCAAAAGTACCAGAATCTTTACGGATTTATGAATGCCATGTGGGGA
TTAGCGGAAGCGAACCGAAAGTAAGCACTTTTGAAGAGTTTACAAAAAAGGTGCTGCCGCACGTCAA
ACGAGCGGGATATAACGCGATCCAGTTGATCGGCGTGCCTGAGCATAAGGATTATTTTACGGTCGGTT
ATAGAGTGACCAACTTTTTCGCAGCATCTTCCCGCTACGGTACTCCTGACGATTTTAAAAGACTTGTGG
ATGAAGCTCATGGGCTGGGTCTCCTGGTCTTTCTGGATATTGTCCACTCATATGCTGCGGCGGATCGAA
TGGTTGGGCTGAGCTTGTTTGACGGTTCCAACGATTGCTACTTCCACTATGGGAAACGTGGCCATCATA
AACATTGGGGGACCAGAATGTTCAAATATGGCGACCTTGATGTGCTTCACTTTTTAATTTCAAACTTAA
ATTGGTGGATTACAGAATACCAGGTTGACGGATATCAATTCCACAGCTTGGCATCGATGATCTATACA
CATAACGGGTTCGCAAGTTTCAATAATGATTTGGACGATTATTGCAATCAGTATGTAGACCGGGATGC
CCTTATGTACCTGATTCTTGCGAACGAAATCCTTCATGTTCAGCATCCGAACATCATTACTATTGCGGA
AGATGCAACATACTACCCGGGCCTGTGCGAACCAGTTTCCCAAGGCGGACTGGGATTTGATTATTATG
TCAATCTGTCTGCATCCGAAATGTGGGTTAGCTTACTTGATAACGTGCCTGATAATGAGTGGTCAATGT
CAAAAATCGTTAGCACACTCGTTGCAAATAAAGAATACGCTGACAAAATGTTATCCTACGCAGAAAT
CATAATCAGAGTATAAGCGGTGGTCGGTCATTTGCCGAGATCTTATTTGGCGGCGTGGACAACGGCAG
TCCCGGCGGTAAAGAGTTATTAGATAGAGGTATCAGCCTTCACAAGATGATTCGCCTGATTACTTTTAC
AAGTGGCGGAAGAGCTTATTTGAACTTCATGGGAAACGAGTTCGGACATCCTGAAAGAGTAGAATTCC
```

-continued

SEQUENCE LISTING

CAACACAATCCAACAATTTCTCGTTCAGCTTAGCAAACCGGCGATGGGATCTGCTGGAGAGTGGGGTA
CATCATCATTTGTTTTCGTTTGATAAAGAGCTGATGGACCTGGATAAAAGCAAAGGAATTCTGAGCCG
AGGACTTCCGAGCATCCATCATGTTAATGACGCAAATATGGTCATTAGCTTTTCCCGGGGCCCCTTCCT
TTTTATCTTTAATTTTCACCCCTCAAATTCATATGAAAAGTATGATGTCGGCGTCGAGGAGGCGGGTGA
GTATACCATGATCCTCAACTCAGATGAGGTGAAATATGGTGGCCAAGGGATAGTAACCGAAGATCATT
ATTTACAAAGGTCTATAAGCAAGAGGATCGATGGACAGAGAAACTGCTTGGAGGTCTTTTTGCCCAGT
AGGACAGCTCAGGTGTACAAGCTTACACGAATCCTTCGCATTTGA

SEQ ID NO: 49
MKILFAVSECTPFVKSGGLADVAGALPKALARLGNEVAVMLPKYSQIPEPWKKRMKKQAECTVAVGWRQ
QYCGIEHMAENDVNYYFIDNEYYFNRDSLYGHYDDGERFAFFSRAVLEAAKVVNVQADIVHTHDWHTA
MVNYLLKEEYRKHPFYERMKSVLTIHNLQFQGIFPPDVTHDLLGLEMDHFHYERLECNGFVNFMKAGIIAA
DHVTTVSPTYRNEIMTPYYGEQLEQVLQYREDDVTGILNGIDDTFYQPKSDPYIEAQYDSGDLACKLENKT
KLQQRMGLPEKNDIPLISMVTRLTKQKGLDLVRRIMHELLEEQDIQLVVLGTGEREFEDYFRYAEFAFHEK
CRAYIGFDEPLAHQIYAGSDMFLMPSKFEPCGLGQLIALQYGAIPIVRETGGLYDTVRAYQEEEGTGNGFTF
SAFNAHDLKFTIERALSFYCQQDVWKSIVKTAMNADYSWGKSAKEYQRIFEQVTRSGRDVLE

SEQ ID NO: 50
ATGAAGATTTTGTTCGCGGTTAGCGAGTGCACACCTTTCGTAAAATCCGGCGGATTAGCGGACGTTGC
GGGTGCTTTACCGAAAGCCTTAGCGCGCCTTGGAAATGAAGTCGCTGTGATGCTGCCGAAATATAGTC
AAATTCCGGAACCGTGGAAGAAAAGAATGAAAAAACAGGCAGAATGCACAGTTGCGGTCGGCTGGCG
CCAACAGTACTGCGGAATCGAACATATGGCTGAGAATGACGTGAACTATTATTTTATAGATAACGAAT
ATTATTTTAACAGAGATTCTCTGTATGGACACTATGACGATGGAGAGAGGTTTGCGTTTTTTAGCCGGG
CTGTGCTCGAAGCCGCGAAAGTCGTGAATGTGCAGGCTGAATATCGTTCATACGCATGACTGGCATACC
GCGATGGTCAACTATTTGCTGAAAGAAGAATATCGGAAACATCCGTTTTATGAGCGCATGAAAAGCGT
TCTTACGATTCATAATCTCCAATTCCAGGGTATCTTTCCACCCGATGTCACACATGACCTTTTAGGCTTA
GAAATGGATCATTTCCATTACGAACGTTTGGAATGCAACGGTTTCGTGAATTTTATGAAGGCTGGAAT
CATCGCCGCAGATCATGTGACTACGGTCTCTCCTACGTATCGTAATGAATGACGCCATATTATGG
TGAACAGCTGGAGCAGGTTCTTCAGTATCGCGAAGATGATGTCACGGGAATTCTGAACGGCATTGATG
ACACGTTCTACCAACCTAAATCAGACCCATATATTGAAGCGCAGTACGATAGTGGCGATCTTGCCTGC
AAATTAGAAAATAAAACAAAGCTGCAACAACGCATGGGATTACCAGAGAAGAATGATATCCCGTTAA
TTTCAATGGTAACCAGACTTACGAAGCAGAAGGGCCTGGATTTGGTCAGACGGATAATGCATGAACTT
TTAGAAGAGCAGGATATCCAGCTGGTCGTGCTGGGCACCGGAGAAAGAGAATTTGAGGATTACTTTCG
CTACGCTGAATTTGCGTTTCATGAGAAGTGCCGCGCCTACATTGGCTTTGACGAACCCTTAGCGCACCA
GATTTACGCCGGATCAGATATGTTTCTCATGCCGAGCAAGTTTGAACCTTGTGGACTTGGCCAGCTGAT
TGCATTACAATACGGCGCCATTCCTATTGTACAGGGAGACCGGAGGCGTGTATGACACAGTGCGAGCCT
ATCAGGAAGAAGAAGGTACAGGCAATGGCTTTACTTTTAGTGCGTTTAATGCACATGATCTGAAATTC
ACAATAGAAAGAGCTTTAAGCTTTTATTGTCAACAGGATGTCTGGAAATCAATCGTAAAGACCGCTAT
GAATGCCGATTATTCATGGGGTAAATCTGCAAAAGAGTACCAACGTATCTTCGAACAAGTGACACGGT
CTGGGCGCGACGTCCTTGAATAA

SEQ ID NO: 51
MALKRGLSGVNRIRGSGGGSRSVLVLLIFFCVFAPLCFFVGRGVYIDSSNDYSIVSVKQNLDWRERLAMQS
VRSLFSKEILDVIATSTADLGPLSLDSFKKNNLSASWRGTGVDPSFRHSENPATPDVKSNNLNEKRDSISKDS
IHQKVETPTKIHRRQLREKRREMRANELVQHNDDTILKLENAAIERSKSVDSAVLGKYSIWRRENENDNSD
SNIRLMRDQVIMARVYSGIAKLKNKNDLLQELQARLKDSQRVLGEATSDADLPRSAHEKLRAMGQVLAK
AKMQLYDCKLVTGKLRAMLQTADEQVRSLKKQSTFLAQLAAKTIPNPIHCLSMRLTIDYLLSPEKRKFPR
SENLENPNLYHYALFSDNVLAASVVVNSTIMNAKDPSKHVFHLVTDKLNFGAMNMWFLLNPPGKATIHVE
NVDEFKWLNSSYCPVLRQLESAAMREYYFKADHPTSGSSNLKYRNPKYLSMLNHLRFYLPEVYPKLNKIL
FLDDDIIVQKDLTPLWEVNLNGKVNGAVETCGESFHRFDKYLNFSNPHIARNFNPNACGWAYGMNMFDL
KEWKKRDITGIYHKWQNMNENRTLWKLGTLPPGLITFYGLTHPLNKAWHVLGLGYNPSIDKKDIENAAVV
HYNGNMKPWLELAMSKYRPYWTKYIKFDHPYLRRCNLHE

SEQ ID NO: 52
ATGGCCCTTAAGAGGGGGCTGAGTGGAGTGAACCGTATCAGAGGATCAGGAGGAGGCAGCCGTTCAG
TCCTGGTTCTTCTTATCTTTTTTTGCGTGTTCGCACCGTTATGTTTCTTCGTTGGTCGCGGAGTCTATATA
GACAGCTCGAACGACTACTCAATTGTTAGTGTAAAGCAGAATTTAGACTGGAGAGAGCGCCTGGCAAT
GCAATCTGTAAGATCATTATTCTCGAAGGAAATTTTAGATGTGATAGCCACGTCTACGGCAGACTTGG
GGCCGTTATCTTTAGATAGCTTCAAAAAGAACAATTTATCAGCTAGCTGGAGAGGCACGGGCGTTGAC
CCTAGCTTTCGCCACAGCGAAAACCCTGCGACCCCGGATGTTAAGTCAAACAATTTAAATGAAAAAAG
AGATTCTATTTCTAAAGATTCCATCCATCAGAAGGTTGAGACACCGACTAAAATCCACCGACGACAAC
TTCGTGAGAAAAGGAGAGAGATGCGCGCGAATGAACTTGTCCAGCACAACGATGATACAATTTTAAA
GTTGGAGAATGCAGCCATTGAGCGTAGTAAAAGTGTAGATTCTGCAGTATTAGGAAAATACTCAATTT
GGCGCCGGGAAAATGAAATGACAATAGCGATTCTAATATCAGGCTGATGAGGGACCAGGTCATTAT
GGCACGCGTATATTCGGGCATTGCAAAATTAAAAAACAAAAACGACTTACTTCAAGAACTTCAGGCGC
GGCTTAAGGATTCCCAGAGAGTGCTGGGAGAAGCTACATCCGATGCCGATTTGCCAAGGAGCGCGCA
CGAGAAACTTAGAGCGATGGGTCAAGTTTTGGCTAAAGCGAAAATGCAGCTGTATGATTGCAAATTAG
TCACTGGTAAACTGAGAGCAATGTTGCAGACAGCAGATGAGCAGGTACGAAGCTTAAAAAAACAATC
AACGTTTCTTGCACAGCTTGCAGCTAAAACAATACCCAATCCAATCCATTGTTTATCTATGAGATTGAC
CATAGATTATTACCTTTTGTCTCCCGAGAAGAGGAAGTTTCCGCGATCTGAAAATCTGGAAAACCCTA
ATCTGTATCATTACGCTCTGTTTCTCAGACAATGTTTTAGCAGCATCTGTTGTCGTAAATAGCACAATCA
TGAATGCGAAGGACCCGTCTAAACATGTGTTCCATCTTGTCACGGATAAACTTAACTTTGGCGCCATG
AATATGTGGTTTCTTCTGAATCCTCCGGGCAAAGCCACAATCCATGTGGAAAATGTCGACGAATTTAA
ATGGCTTAACTCCTCCTATTGCCCGGTTCTTCGGCAGTTAGAATCAGCTGCTATGAGAGAATACTATTT
TAAAGCGGATCATCCTACGTCCGGCAGCAGCAATTTAAAATACAGAAATCCGAAGTACTTATCTATGC
TTAACCATTTAAGATTTTATTTACCGGAAGTTTATCCGAAACTTAATAAAATCCTGTTTCTCGACGATG
ACATTATTGTTCAAAAAGATTTGACTCCGCTTTGGGAAGTGAACTTAAATGGCAAAGTCAATGGGGCC

SEQUENCE LISTING

```
GTGGAGACTTGCGGGGAGTCATTTCATAGATTTGACAAGTACTTAAACTTTTCTAACCCGCACATTGCA
CGTAATTTCAACCCAAATGCATGTGGATGGGCGTATGGTATGAATATGTTTGACTTAAAAGAATGGAA
AAAACGCGATATAACAGGAATTTATCATAAGTGGCAAAACATGAACGAAAACAGGACACTGTGGAAA
CTGGGAACGTTGCCGCCTGGACTTATTACGTTTTATGGGTTGACGCACCCGCTTAATAAAGCCTGGCAT
GTTTTAGGACTGGGATATAATCCTAGCATTGACAAGAAAGATATTGAAAACGCGGCGGTAGTGCATTA
TAATGGGAATATGAAACCGTGGCTTGAACTGGCTATGTCTAAATATAGACCGTACTGGACGAAATACA
TTAAATTTGACCATCCGTATTTACGACGGTGCAACCTGCATGAATAG

SEQ ID NO: 53
MSVVDVIGLLATAAYVTLASAYKVVQFINVSSVTDVAGLESDALPLTPRVDVIVPTFNENSSTLLECVASIC
AQDYRGPITIVVVDDGSTNKTSFHAVCDKYASDERFIFVELDQNKGKRAAQMEAIRRTDGDLILNVDSDTV
IDKDVVTKLASSMRAPNVGGVMGQLVAKNRERSWLTRLIDMEYWLACNEERIAQSRFGSVMCCCGPCAM
YRRSAITPLLAEYEHQTFLGRPSNFGEDRHLTILMLKAGFRTGYVPGAVARTLVPDGLAPYLRQQLRWARS
TYRDTALALRIKKNLSKYITFEICAQNLGTALLLVMTMISLSLTTSGSQTPVIILGVVVGMSIIRCCSVALIAK
DFRFLYFIVHSALNVLILTPLKLYALLTIRDSRWLSRESS

SEQ ID NO: 54
ATGTCAGTGGTCGACGTAATTGGCCTTCTGGCCACCGCCGCCTATGTGACCCTGGCTTCCGCGTACAAA
GTAGTCCAATTTATCAATGTCTCTAGCGTGACTGACGTAGCAGGCCTTGAGAGTGATGCCCTCCCGCTT
ACACCGCGCTAGATGTAATCGTCCCACGTTTAATGAAAATTCTTCCACGCTGTTAGAATGCGTCGC
AAGCATTTGTGCGCAAGACTACAGAGGCCCAATCACCATTGTGGTGGTAGACGACGGCTCGACTAATA
AAACTAGCTTTCACGCAGTTTGCGACAAATATGCGTCGGATGAGCGCTTCATCTTCGTCGAACTTGATC
AGAACAAGGGGAAACGCGCTGCACAGATGGAGGCAATTCGCCGGACGGACGGCGATCTTATCTTGAA
TGTCGATTCTGATACCGTGATCGACAAGGATGTTGTTACGAAACTTGCTTCGAGCATGCGCGCACCAA
ACGTGGGTGGAGTGATGGGGCAACTGGTTGCCAAAAATCGGGAACGATCATGGCTCACACGGCTTATC
GATATGGAATATTGGTTAGCTTGTAATGAGGAGCGCATCGCTCAAAGCCGCTTTGGTTCTGTCATGTGC
TGTTGTGGTCCATGCGCGATGTACAGACGTTCTGCAATCACGCCACTTCTGGCGGAATACGAACACCA
GACATTCCTTGGACGACCGTCTAATTTTGGCGAAGATCGGCACTTAACGATTTTAATGTTGAAAGCGG
GATTTCGTACGGGGTATGTCCCAGGCGCAGTAGCTCGTACGTTAGTTCCTGACGGATTGGCTCCTTATT
TGCGTCAACAACTTCGGTGGGCCCGGAGCACATACCGTGATACAGCTCTGGCATTGCGTATTAAAAAG
AACTTATCAAAATATATCACATTTGAAATCTGCGCGCAAATCTGGGTACGGCGCTTTTGCTTGTGATG
ACAATGATTTCGTTATCTCTTACCACATCGGGAAGTCAAACCCCGGTAATCATTCTTGGAGTTGTCGTC
GGCATGTCAATCATTAGATGTTGTTCGGTTGCCCTTATCGCTAAAGATTTTAGATTTCTCTATTTTATTG
TACATTCGGCGCTTAATGTACTGATTCTCACTCCGCTTAAATTGTACGCTCTTCTTACCATTAGAGATA
GCAGATGGTTATCGCGCGAATCAAGCTAG

SEQ ID NOS: 55-70: (see Table 2)

SEQ ID NOs: 71-82: (see Example 4)
```

What is claimed is:

1. A method of decreasing the amount or concentration of a carbohydrate in the gut of a subject comprising delivering to the gut of to the subject a bacterium engineered to express an integrated heterologous nucleic acid sequence encoding a fiber-synthesizing enzyme, wherein the fiber-synthesizing enzyme synthesizes fiber from a carbohydrate substrate, where in the enzyme is not a trehalose-6-phosphate synthase and the fiber is not trehalose.

2. A method of increasing the amount or concentration of a fiber in the gut of a subject comprising delivering to the gut of to the subject a bacterium engineered to express an integrated heterologous nucleic acid sequence encoding a fiber-synthesizing enzyme, wherein the fiber-synthesizing enzyme synthesizes fiber from a carbohydrate substrate, where in the enzyme is not a trehalose-6-phosphate synthase and the fiber is not trehalose.

3. A method of treating a subject in need of decreased amount or concentration of a carbohydrate in the gut or increased amount or concentration of a fiber in the gut comprising delivering to the gut of to the subject a bacterium engineered to express an integrated heterologous nucleic acid sequence encoding a fiber-synthesizing enzyme, wherein the fiber-synthesizing enzyme synthesizes fiber from a carbohydrate substrate, where in the enzyme is not a trehalose-6-phosphate synthase and the fiber is not trehalose.

4. The method of claim 3, wherein the subject is suffering from a condition positively correlated or associated with consumption of carbohydrate.

5. The method of claim 3, wherein the subject is suffering from a condition negatively correlated or associated with consumption of fiber.

6. The method of any one of claims 3-5, wherein the subject is suffering from a condition selected from cardiovascular disease, heart disease, high blood pressure, high blood cholesterol, high blood glucose, diabetes, obesity, dysbiosis of the gut, inflammatory bowel disease, irritable bowel syndrome (IBS), diverticulitis, colorectal cancer, intestinal cancer, bloating, cramping, gas, hemorrhoids, and diarrhea.

7. The method of claim 1, wherein the fiber is a soluble fiber.

8. The method of claim 1, wherein the synthesized fiber comprises glucose, fructose, galacturonic acid, N-acetyl-D-glucosamine, and/or galactose monomers.

9. The method of claim 1, wherein the carbohydrate substrate is selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose.

10. The method of claim 1, wherein the synthesized fiber is a fructooligosaccharide and/or is selected from laminaribiose, callose, curdlan, oat beta-glucan, laminarin, pleuran, lentinan, yeast beta glucan, trehalulose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin.

11. The method of claim 1, wherein the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, an α-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyltransferase, and a chitinoligosaccharide synthase.

12. The method of claim 1, wherein the fiber-synthesizing enzyme is operatively linked with a secretion polypeptide.

13. The method of claim 1, wherein the bacterium is a spore-forming bacterium and/or is in a spore form.

14. The method of claim 1, wherein the bacterium is a probiotic bacterium.

15. The method of claim 1, wherein the bacterium is of a genus selected from *Bacillus, Bifidobacterium, Enterococcus, Escherichia, Lactobacillus, Lactococcus, Leuconostoc, Pediococcus,* and *Streptococcus,* optionally wherein the bacterium is of the genus *Bacillus,* optionally wherein the bacterium is of the species *B. subtilis.*

16. The method of claim 1, wherein the bacterium is of a strain characterized in that it does not colonize the gut.

17. The method of claim 1, wherein the method comprises administering the engineered bacterium to a subject that has consumed carbohydrate and/or the carbohydrate substrate within a preceding period, wherein the preceding period is a period of 24 hours 12 hours, 6 hours, 3 hours, or 1 hour.

18. The method of claim 1, wherein the method comprises administering the engineered bacterium to a subject that has not consumed carbohydrate and/or the carbohydrate substrate.

19. The method of claim 1, wherein the method comprises administering the engineered bacterium to a subject that has not consumed carbohydrate and/or the carbohydrate substrate within a preceding period, wherein the preceding period is a period of 24 hours 12 hours, 6 hours, 3 hours, or 1 hour.

20. The method of claim 1, wherein the subject consumes carbohydrate and/or the carbohydrate substrate during a period subsequent to administration of the engineered bacterium, wherein the subsequent period is a period of 24 hours 12 hours, 6 hours, 3 hours, or 1 hour.

21. The method of claim 1, wherein the method prevents accumulation of sugar in the colon of the subject.

22. The method of claim 1, wherein fiber-synthesizing enzymes and/or enzymes encoded by heterologous nucleic acid sequences comprised by the engineered bacterium consist of the fiber-synthesizing enzyme.

23. The method of claim 1, wherein the administration comprises oral administration of a composition comprising the engineered bacterium.

24. The method of claim 1, wherein the administration comprises administration of about 104 to about 1012 colony forming units of the engineered bacterium.

25. The method of claim 1, wherein the nucleic acid sequence encoding the expression product is operatively linked with a constitutive promoter.

26. The method of claim 1, wherein the nucleic acid sequence encoding the expression product is operatively linked with a flagellin gene promoter.

27. The method of claim 26, wherein the flagellin gene promoter comprises a mutation in a CsrA binding site, wherein the mutation in the CsrA binding site inhibits binding of CsrA to mRNA transcripts encoding the fiber-synthesizing enzyme but does not preclude expression of the fiber-synthesizing enzyme.

28. The method of claim 26, wherein the engineered bacterium comprises a mutation of an endogenous flgM gene that reduces inhibition of a sigma factor by FlgM.

29. The method of claim 27, wherein the engineered bacterium comprises a mutation of an endogenous flgM gene that reduces inhibition of a sigma factor by FlgM.

30. The method of claim 2, wherein the fiber is a soluble fiber.

31. The method of claim 2, wherein the synthesized fiber comprises glucose, fructose, galacturonic acid, N-acetyl-D-glucosamine, and/or galactose monomers.

32. The method of claim 2, wherein the carbohydrate substrate is selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose.

33. The method of claim 2, wherein the synthesized fiber is a fructooligosaccharide and/or is selected from laminaribiose, callose, curdlan, oat beta-glucan, laminarin, pleuran, lentinan, yeast beta glucan, trehalulose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin.

34. The method of claim 2, wherein the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, an α-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyltransferase, and a chitinoligosaccharide synthase.

35. The method of claim 2, wherein the fiber-synthesizing enzyme is operatively linked with a secretion polypeptide.

36. The method of claim 2, wherein the bacterium is a spore-forming bacterium and/or is in a spore form.

37. The method of claim 2, wherein the bacterium is a probiotic bacterium.

38. The method of claim 2, wherein the bacterium is of a genus selected from *Bacillus, Bifidobacterium, Enterococ-*

*cus, Escherichia, Lactobacillus, Lactococcus, Leuconostoc, Pediococcus*, and *Streptococcus*, optionally wherein the bacterium is of the genus *Bacillus*, optionally wherein the bacterium is of the species *B. subtilis*.

39. The method of claim 2, wherein the bacterium is of a strain characterized in that it does not colonize the gut.

40. The method of claim 2, wherein the method comprises administering the engineered bacterium to a subject that has consumed carbohydrate and/or the carbohydrate substrate within a preceding period, wherein the preceding period is a period of 24 hours 12 hours, 6 hours, 3 hours, or 1 hour.

41. The method of claim 2, wherein the method comprises administering the engineered bacterium to a subject that has not consumed carbohydrate and/or the carbohydrate substrate.

42. The method of claim 2, wherein the method comprises administering the engineered bacterium to a subject that has not consumed carbohydrate and/or the carbohydrate substrate within a preceding period, wherein the preceding period is a period of 24 hours 12 hours, 6 hours, 3 hours, or 1 hour.

43. The method of claim 2, wherein the subject consumes carbohydrate and/or the carbohydrate substrate during a period subsequent to administration of the engineered bacterium, wherein the subsequent period is a period of 24 hours 12 hours, 6 hours, 3 hours, or 1 hour.

44. The method of claim 2, wherein the method prevents accumulation of sugar in the colon of the subject.

45. The method of claim 2, wherein fiber-synthesizing enzymes and/or enzymes encoded by heterologous nucleic acid sequences comprised by the engineered bacterium consist of the fiber-synthesizing enzyme.

46. The method of claim 2, wherein the administration comprises oral administration of a composition comprising the engineered bacterium.

47. The method of claim 2, wherein the administration comprises administration of about 104 to about 1012 colony forming units of the engineered bacterium.

48. The method of claim 2, wherein the nucleic acid sequence encoding the expression product is operatively linked with a constitutive promoter.

49. The method of claim 2, wherein the nucleic acid sequence encoding the expression product is operatively linked with a flagellin gene promoter.

50. The method of claim 49, wherein the flagellin gene promoter comprises a mutation in a CsrA binding site, wherein the mutation in the CsrA binding site inhibits binding of CsrA to mRNA transcripts encoding the fiber-synthesizing enzyme but does not preclude expression of the fiber-synthesizing enzyme.

51. The method of claim 49, wherein the engineered bacterium comprises a mutation of an endogenous flgM gene that reduces inhibition of a sigma factor by FlgM.

52. The method of claim 50, wherein the engineered bacterium comprises a mutation of an endogenous flgM gene that reduces inhibition of a sigma factor by FlgM.

53. The method of claim 3, wherein the fiber is a soluble fiber.

54. The method of claim 3, wherein the synthesized fiber comprises glucose, fructose, galacturonic acid, N-acetyl-D-glucosamine, and/or galactose monomers.

55. The method of claim 3, wherein the carbohydrate substrate is selected from one or more of UDP-glucose, UDP-galactose, UDP-fucose, ADP-α-D-glucose, UDP-galacturonic acid, UDP-N-acetyl-alpha-D-glucosamine, galactinol, lactose, glucose, and sucrose and/or wherein the carbohydrate decreased in amount or concentration in the gut is selected from one or more of glucose, galactose, sucrose, fructose, and/or lactose.

56. The method of claim 3, wherein the synthesized fiber is a fructooligosaccharide and/or is selected from laminaribiose, callose, curdlan, oat beta-glucan, laminarin, pleuran, lentinan, yeast beta glucan, trehalulose, inulin, kestose, nystose, levan, raffinose, stachyose, verbascose, globotriose, human milk oligosaccharides (HMOs), cellobiose, cellulose, microcellulose, cotton, maltose, amylose, starch, glycogen, amylopectin, pectin, chitin.

57. The method of claim 3, wherein the fiber-synthesizing enzyme is selected from a sucrase, an inulosucrase, a levansucrase, a 1,3-beta-glucan synthase, a 1,3;1,4-beta-D-glucan synthase, a 1,6-beta-glucan synthase, a sucrose isomerase, a 1,6-alpha-galactosyltransferase, a trehalulose synthase, an α-1,4-galactosyltransferase, an alpha-1,2-fucosyltransferase, a beta-galactosidase, a b-D-Galactosidase, a cellulose synthase, a maltose synthase, a starch synthase, a starch-branching enzyme, a glycogen synthase, a galacturonosyltransferase, and a chitinoligosaccharide synthase.

58. The method of claim 3, wherein the fiber-synthesizing enzyme is operatively linked with a secretion polypeptide.

59. The method of claim 3, wherein the bacterium is a spore-forming bacterium and/or is in a spore form.

60. The method of claim 3, wherein the bacterium is a probiotic bacterium.

61. The method of claim 3, wherein the bacterium is of a genus selected from *Bacillus, Bifidobacterium, Enterococcus, Escherichia, Lactobacillus, Lactococcus, Leuconostoc, Pediococcus*, and *Streptococcus*, optionally wherein the bacterium is of the genus *Bacillus*, optionally wherein the bacterium is of the species *B. subtilis*.

62. The method of claim 3, wherein the bacterium is of a strain characterized in that it does not colonize the gut.

63. The method of claim 3, wherein the method comprises administering the engineered bacterium to a subject that has consumed carbohydrate and/or the carbohydrate substrate within a preceding period, wherein the preceding period is a period of 24 hours 12 hours, 6 hours, 3 hours, or 1 hour.

64. The method of claim 3, wherein the method comprises administering the engineered bacterium to a subject that has not consumed carbohydrate and/or the carbohydrate substrate.

65. The method of claim 3, wherein the method comprises administering the engineered bacterium to a subject that has not consumed carbohydrate and/or the carbohydrate substrate within a preceding period, wherein the preceding period is a period of 24 hours 12 hours, 6 hours, 3 hours, or 1 hour.

66. The method of claim 3, wherein the subject consumes carbohydrate and/or the carbohydrate substrate during a period subsequent to administration of the engineered bacterium, wherein the subsequent period is a period of 24 hours 12 hours, 6 hours, 3 hours, or 1 hour.

67. The method of claim 3, wherein the method prevents accumulation of sugar in the colon of the subject.

68. The method of claim 3, wherein fiber-synthesizing enzymes and/or enzymes encoded by heterologous nucleic acid sequences comprised by the engineered bacterium consist of the fiber-synthesizing enzyme.

69. The method of claim 3, wherein the administration comprises oral administration of a composition comprising the engineered bacterium.

70. The method of claim 3, wherein the administration comprises administration of about 104 to about 1012 colony forming units of the engineered bacterium.

71. The method of claim 3, wherein the nucleic acid sequence encoding the expression product is operatively linked with a constitutive promoter.

72. The method of claim 3, wherein the nucleic acid sequence encoding the expression product is operatively linked with a flagellin gene promoter.

73. The method of claim 72, wherein the flagellin gene promoter comprises a mutation in a CsrA binding site, wherein the mutation in the CsrA binding site inhibits binding of CsrA to mRNA transcripts encoding the fiber-synthesizing enzyme but does not preclude expression of the fiber-synthesizing enzyme.

74. The method of claim 72, wherein the engineered bacterium comprises a mutation of an endogenous flgM gene that reduces inhibition of a sigma factor by FlgM.

75. The method of claim 73, wherein the engineered bacterium comprises a mutation of an endogenous flgM gene that reduces inhibition of a sigma factor by FlgM.

\* \* \* \* \*